United States Patent
Haketa et al.

(10) Patent No.: US 10,170,707 B2
(45) Date of Patent: *Jan. 1, 2019

(54) COMPOUND, MATERIAL FOR ORGANIC ELECTROLUMINESCENCE ELEMENT, ORGANIC ELECTROLUMINESCENCE ELEMENT, AND ELECTRONIC DEVICE

(71) Applicant: IDEMITSU KOSAN CO., LTD., Chiyoda-ku (JP)

(72) Inventors: Tasuku Haketa, Chiba (JP); Masahiro Kawamura, Chiba (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/875,394

(22) Filed: Jan. 19, 2018

(65) Prior Publication Data

US 2018/0145265 A1    May 24, 2018

Related U.S. Application Data

(63) Continuation of application No. 15/502,354, filed as application No. PCT/JP2016/067696 on Jun. 14, 2016.

(30) Foreign Application Priority Data

Jun. 16, 2015  (JP) .................................. 2015-120993
Jul. 13, 2015  (WO) .................. PCT/JP2015/070045
Oct. 28, 2015  (JP) .................................. 2015-212049

(51) Int. Cl.
| | | |
|---|---|---|
| H01L 51/00 | (2006.01) | |
| C07D 209/86 | (2006.01) | |
| C09K 11/02 | (2006.01) | |
| C09K 11/06 | (2006.01) | |
| C07D 403/04 | (2006.01) | |
| H01L 51/50 | (2006.01) | |
| H01L 51/52 | (2006.01) | |

(52) U.S. Cl.
CPC ........ *H01L 51/0072* (2013.01); *C07D 209/86* (2013.01); *C07D 403/04* (2013.01); *C09K 11/025* (2013.01); *C09K 11/06* (2013.01); *H01L 51/0054* (2013.01); *H01L 51/0058* (2013.01); *H01L 51/0085* (2013.01); *H01L 51/50* (2013.01); *C09K 2211/1007* (2013.01); *C09K 2211/1011* (2013.01); *C09K 2211/1029* (2013.01); *C09K 2211/185* (2013.01); *H01L 51/5016* (2013.01); *H01L 51/5056* (2013.01); *H01L 51/5206* (2013.01); *H01L 51/5221* (2013.01)

(58) Field of Classification Search
CPC .... C07D 209/86; C09K 11/025; C09K 11/06; C09K 2211/1007; C09K 2211/1029; C09K 2211/185; H01L 51/0054; H01L 51/0058; H01L 51/0072; H01L 51/0085; H01L 51/5016; H01L 51/5206; H01L 51/5221

See application file for complete search history.

(56) References Cited

U.S. PATENT DOCUMENTS

| | | | |
|---|---|---|---|
| 2012/0223295 | A1 | 9/2012 | Inoue et al. |
| 2014/0048784 | A1 | 2/2014 | Inoue et al. |
| 2014/0312331 | A1 | 10/2014 | Inoue et al. |
| 2015/0133662 | A1 | 5/2015 | Ahn et al. |
| 2015/0155491 | A1 | 6/2015 | Mujica-Fernaud et al. |
| 2015/0179953 | A1 | 6/2015 | Mujica-Fernaud et al. |
| 2015/0236273 | A1* | 8/2015 | Jang .................... H01L 51/0072 257/40 |
| 2015/0243891 | A1 | 8/2015 | Kato et al. |
| 2015/0249219 | A1 | 9/2015 | Inoue et al. |
| 2015/0364692 | A1 | 12/2015 | Kawamura et al. |
| 2017/0222152 | A1* | 8/2017 | Haketa ................ H01L 51/0036 |
| 2017/0229661 | A1* | 8/2017 | Haketa ................ H01L 51/0072 |

FOREIGN PATENT DOCUMENTS

| | | |
|---|---|---|
| EP | 2891648 A1 | 7/2015 |
| JP | 2014-531419 A | 11/2014 |

(Continued)

OTHER PUBLICATIONS

International Search Report dated Aug. 16, 2016 in PCT/JP2016/067696 filed Jun. 14, 2016.
Extended European Search Report dated Nov. 16, 2016 in EP15819013.2 filed Jul. 13, 2015.
Office Action as received in the corresponding Chinese Patent Application No. 201580001554.6 dated May 21, 2018 w/English Translation.
Office Action dated Aug. 28, 2018 in the corresponding Japanese patent application with machine English translation (JP-OA 2016-504820).

(Continued)

*Primary Examiner* — Dawn L Garrett
(74) *Attorney, Agent, or Firm* — Oblon, McClelland, Maier & Neustadt, L.L.P.

(57) ABSTRACT

A compound represented by formula (1):

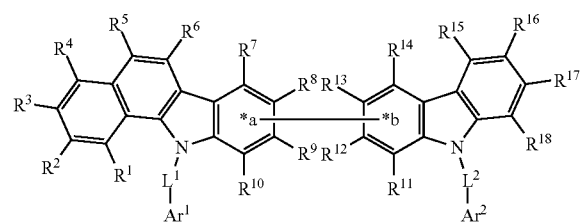

(1)

wherein $R^1$ to $R^6$, $R^7$ to $R^{10}$, $R^{11}$ to $R^{14}$, $R^{15}$ to $R^{18}$, $L^1$, $L^2$, $Ar^1$, and $Ar^2$ are as defined in the description realizes an organic electroluminescence device with long lifetime.

28 Claims, 1 Drawing Sheet

(56) References Cited

FOREIGN PATENT DOCUMENTS

| | | |
|---|---|---|
| KR | 10-2013-0009614 A | 1/2013 |
| KR | 10-2015-0007476 A | 1/2015 |
| KR | 10-2015-0012835 A | 2/2015 |
| WO | 2012/108358 A1 | 8/2012 |
| WO | 2013/187689 A1 | 12/2013 |
| WO | WO 2013/182263 A1 | 12/2013 |
| WO | 2014/015935 A2 | 1/2014 |
| WO | WO 2014/015937 A1 | 1/2014 |
| WO | 2014/034795 A1 | 3/2014 |
| WO | 2014/178434 A1 | 11/2014 |
| WO | WO 2015/041428 A1 | 3/2015 |
| WO | 2015/056965 A1 | 4/2015 |
| WO | 2015/056993 A1 | 4/2015 |
| WO | 2015-082056 A1 | 6/2015 |
| WO | 2015/162912 A1 | 10/2015 |
| WO | 2016/122150 A2 | 8/2016 |

OTHER PUBLICATIONS

Office Action dated Aug. 28, 2018 in the corresponding Japanese patent application with machine English translation (JP-OA 2015-560883).

Office Acton dated Sep. 28, 2018 in connection with Chinese Patent Application No. 201580001555.0 dated Jul. 13, 2015.

Office Action dated Nov. 8, 2018 in European Patent Application No. 15 818 448.1.

Office Action dated Nov. 16, 2018 in European Patent Application No. 15 818 619.7.

\* cited by examiner

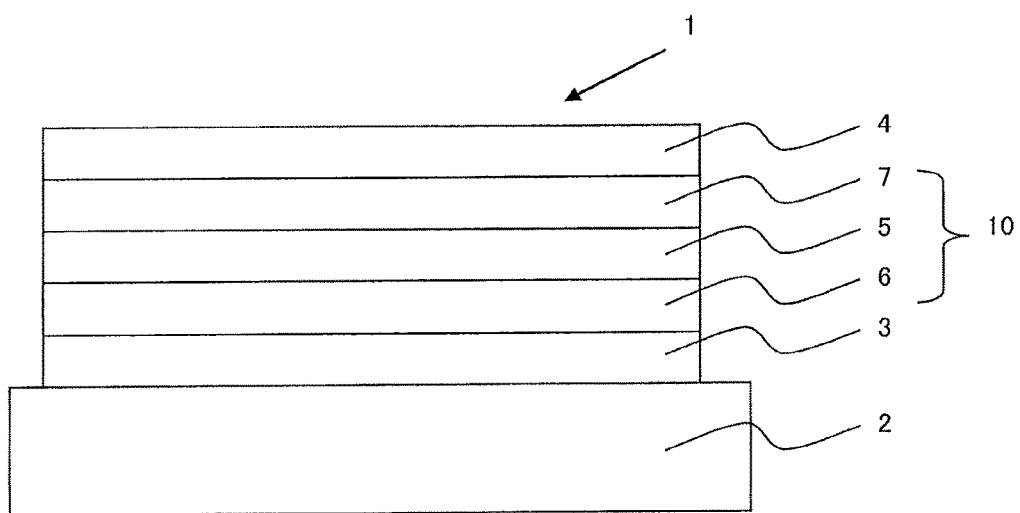

COMPOUND, MATERIAL FOR ORGANIC ELECTROLUMINESCENCE ELEMENT, ORGANIC ELECTROLUMINESCENCE ELEMENT, AND ELECTRONIC DEVICE

CROSS REFERENCE TO RELATED APPLICATIONS

This application is a continuation application of prior U.S. application Ser. No. 15/502,354, filed Feb. 7, 2017, the disclosure of which is incorporated herein by reference in its entirety. U.S. application Ser. No. 15/502,354 in the national stage of PCT/JP2016/067696, filed Jun. 14, 2016, the disclosure of which is incorporated herein by reference in its entirety. U.S. application Ser. No. 15/502,354 claims priority to Japanese Application No. 2015-120993, filed Jun. 16, 2015, to PCT/JP2015/070045, filed Jul. 13, 2015, and Japanese Application No. 2015-212049, filed Oct. 28, 2015, the disclosures of which are incorporated herein by reference in their entireties.

TECHNICAL FIELD

The present invention relates to compounds, materials for organic electroluminescence devices comprising the compound, organic electroluminescence devices comprising the compound, and electronic devices comprising the organic electroluminescence device.

BACKGROUND ART

Organic electroluminescence devices (hereinafter also referred to as "organic EL device") comprising an organic compound are much expected to be useful as inexpensive, large-sized full color display devices of solid state emission type and many developments have been made thereon. An organic EL device is generally constructed from a light emitting layer and a pair of opposite electrodes sandwiching the light emitting layer. When an electric field is applied between the electrodes, electrons are injected from a cathode and holes are injected from an anode into the light emitting layer. The injected electrons recombine with the injected holes in the light emitting layer to form excited states. When the excited state returns to the ground state, the energy is released as light.

Many researches have been made on the applications of organic EL device to display, etc. because of its possibility of a wide selection of emission colors by using various emitting materials in a light emitting layer. Particularly, the research on the materials which emit three primary red, green, and blue colors has been made most actively, and the intensive research has been made to improve their properties.

As a material for organic electroluminescence device, Patent Literature 1 describes a compound having a 3,3'-biscarbazole structure in which a benzene ring is fused to 6,7-position or 5,6-position of one of the carbazole structures and a phenyl group and a 3-fluoranthenyl group are respectively bonded to two nitrogen atoms. Patent Literature 2 describes a compound having a 3,3'-biscarbazole structure in which two benzene rings are fused to 7,8-position of one of the carbazole structures and 7',8'-position of the other and a 1-naphthyl group and a 2-a pyrenyl group are respectively bonded to two nitrogen atoms. Patent Literature 2 further describes a compound in which a benzo[a]carbazole structure is bonded to a phenaleno[1,9-b,c]carbazole structure.

CITATION LIST

Patent Literature

Patent Literature 1: WO 2012/108388 A1
Patent Literature 2: KR 2015-0012835A

SUMMARY OF INVENTION

Technical Problem

To further improve the performance of an organic EL device, it has been required to further develop a material useful for use in an organic EL device. Thus, an object of the invention is to provide an organic EL device with a long lifetime and a compound capable of realizing such an organic EL device.

Solution to Problem

As a result of extensive research in view of achieving the above object, the inventors have found that a compound represented by formula (1) realizes an organic EL device with a long lifetime.

In an aspect of the invention, the following (1) to (4) are provided:
(1) a compound represented by formula (1) (hereinafter also referred to as "compound (1)"):

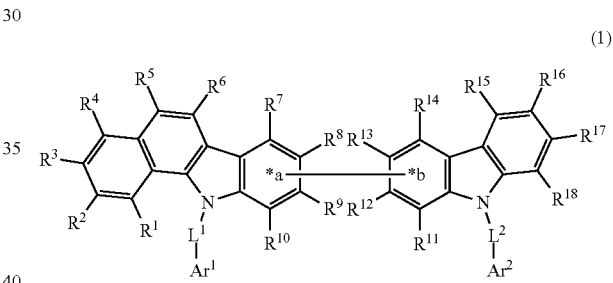

(1)

wherein:
each of $R^1$ to $R^6$ is independently a hydrogen atom, a substituted or unsubstituted alkyl group having 1 to 20 carbon atoms, a substituted or unsubstituted cycloalkyl group having 3 to 10 ring carbon atoms, a substituted or unsubstituted aryl group having 6 to 18 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 18 ring carbon atoms, a halogen atom, or a cyano group;
one of $R^7$ to $R^{10}$ is a single bond bonded to *a and each of the others of $R^7$ to $R^{10}$ is independently a hydrogen atom, a substituted or unsubstituted alkyl group having 1 to 20 carbon atoms, a substituted or unsubstituted cycloalkyl group having 3 to 10 ring carbon atoms, a substituted or unsubstituted aryl group having 6 to 18 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 18 ring carbon atoms, a halogen atom, or a cyano group;
one of $R^{11}$ to $R^{14}$ is a single bond bonded to *b and each of the others of $R^{11}$ to $R^{14}$ is independently a hydrogen atom, a substituted or unsubstituted alkyl group having 1 to 20 carbon atoms, a substituted or unsubstituted cycloalkyl group having 3 to 10 ring carbon atoms, a substituted or unsubstituted aryl group having 6 to 18 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 18 ring carbon atoms, a halogen atom, or a cyano group;

each of $R^{15}$ to $R^{18}$ is independently a hydrogen atom, a substituted or unsubstituted alkyl group having 1 to 20 carbon atoms, a substituted or unsubstituted cycloalkyl group having 3 to 10 ring carbon atoms, a substituted or unsubstituted aryl group having 6 to 18 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 18 ring carbon atoms, a halogen atom, or a cyano group;

each of $L^1$ and $L^2$ is independently a single bond, a substituted or unsubstituted arylene group having 6 to 18 ring carbon atoms, or a substituted or unsubstituted heteroarylene group having 5 to 18 ring atoms; and each of $Ar^1$ and $Ar^2$ is independently a substituted or unsubstituted aryl group having 6 to 18 ring carbon atoms;

provided that at least one selected from $Ar^1$ and $Ar^2$ is a substituted or unsubstituted fluoranthenyl group;

(2) a material for organic electroluminescence devices comprising the compound of item (1);

(3) an organic electroluminescence device comprising a cathode, an anode, and an organic thin film layer between the cathode and the anode, wherein the organic thin film layer comprises one or more layers, the organic thin film layer comprises a light emitting layer, and at least one layer of the organic thin film layer comprises the compound of item (1); and (4) an electronic device comprising the organic electroluminescence device of item (3).

Advantageous Effects of Invention

By using the compound of the invention as a material for organic EL devices, an organic EL device with a long lifetime is obtained.

BRIEF DESCRIPTION OF DRAWINGS

The FIGURE is a schematic view showing the structure of the organic EL device in an aspect of the invention.

DESCRIPTION OF EMBODIMENTS

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ.

The term of "unsubstituted group ZZ" referred to by "substituted or unsubstituted group ZZ" used herein means that no hydrogen atom in the group ZZ is substituted by a substituent.

The definition of "hydrogen atom" used herein includes isotopes different in the neutron numbers, i.e., light hydrogen (protium), heavy hydrogen (deuterium), and tritium.

The number of "ring carbon atoms" referred to herein means, unless otherwise noted, the number of the carbon atoms included in the atoms which are members forming the ring itself of a compound in which a series of atoms is bonded to form a ring (for example, a monocyclic compound, a fused ring compound, a cross-linked compound, a carbocyclic compound, and a heterocyclic compound). If the ring has a substituent, the carbon atom in the substituent is not included in the ring carbon atom. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means, unless otherwise noted, the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

The optional substituent referred to by "substituted or unsubstituted" used herein is at least one selected from the group consisting of an alkyl group having 1 to 20, preferably 1 to 5, and more preferably 1 to 4 carbon atoms; a cycloalkyl group having 3 to 10, preferably 3 to 6, and more preferably 5 or 6 ring carbon atoms; an aryl group having 6 to 18, preferably 6 to 10, and more preferably 6 ring carbon atoms; an aralkyl group having an aryl group having 6 to 18, preferably 6 to 10, and more preferably 6 ring carbon atoms; an alkoxy group having 1 to 20, preferably 1 to 5, and more preferably 1 to 4 carbon atoms; an aryloxy group having 6 to 18, preferably 6 to 10, and more preferably 6 ring carbon atoms; a mono-, di-, or tri-substituted silyl group, wherein the substituent is selected from an alkyl group having 1 to 20, preferably 1 to 5, and more preferably 1 to 4 carbon atoms and an aryl group having 6 to 18, preferably 6 to 10, and more preferably 6 ring carbon atoms; a haloalkyl group having 1 to 20, preferably 1 to 5, and more preferably 1 to 4 carbon atoms; a haloalkoxy group having 1 to 20, preferably 1 to 5, and more preferably 1 to 4 carbon atoms; a halogen atom; a cyano group; and a nitro group. The optional substituent may be a group other than those mentioned above, as long as the effect of the invention is obtained.

The details of the groups mentioned above are described below with respect to $R^1$ to $R^6$.

In the present invention, examples, preferred examples, etc. described with respect to a group may be combined with examples, preferred examples, etc. described with respect to any of other groups. A specific group selected from examples, preferred examples, etc. described with respect to a group may be combined with another specific group selected from examples, preferred examples, etc. described with respect to any of other groups.

The same also applies to the number of atoms, the number of carbon atoms, and other features. In addition, the same also applies to any of the combinations between the groups, the number of atoms, the number of carbon atoms, and other features.

The compound in an aspect of the invention is represented by formula (1):

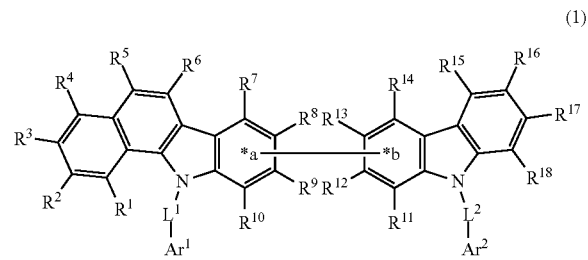

(1)

wherein:

each of $R^1$ to $R^6$ is independently a hydrogen atom, a substituted or unsubstituted alkyl group having 1 to 20 carbon atoms, a substituted or unsubstituted cycloalkyl group having 3 to 10 ring carbon atoms, a substituted or unsubstituted aryl group having 6 to 18 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 18 ring carbon atoms, a halogen atom, or a cyano group;

one of $R^7$ to $R^{10}$ is a single bond bonded to *a and each of the others of $R^7$ to $R^{10}$ is independently a hydrogen atom, a substituted or unsubstituted alkyl group having 1 to 20 carbon atoms, a substituted or unsubstituted cycloalkyl group having 3 to 10 ring carbon atoms, a substituted or unsubstituted aryl group having 6 to 18 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 18 ring carbon atoms, a halogen atom, or a cyano group;

one of $R^{11}$ to $R^{14}$ is a single bond bonded to *b and each of the others of $R^{11}$ to $R^{14}$ is independently a hydrogen atom, a substituted or unsubstituted alkyl group having 1 to 20 carbon atoms, a substituted or unsubstituted cycloalkyl group having 3 to 10 ring carbon atoms, a substituted or unsubstituted aryl group having 6 to 18 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 18 ring carbon atoms, a halogen atom, or a cyano group;

each of $R^{15}$ to $R^{18}$ is independently a hydrogen atom, a substituted or unsubstituted alkyl group having 1 to 20 carbon atoms, a substituted or unsubstituted cycloalkyl group having 3 to 10 ring carbon atoms, a substituted or unsubstituted aryl group having 6 to 18 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 18 ring carbon atoms, a halogen atom, or a cyano group;

each of $L^1$ and $L^2$ is independently a single bond, a substituted or unsubstituted arylene group having 6 to 18 ring carbon atoms, or a substituted or unsubstituted heteroarylene group having 5 to 18 ring atoms: and each of $Ar^1$ and $Ar^2$ is independently a substituted or unsubstituted aryl group having 6 to 18 ring carbon atoms;

provided that at least one selected from $Ar^1$ and $Ar^2$ is a substituted or unsubstituted fluoranthenyl group.

The compound (1) is preferably represented by formula (2):

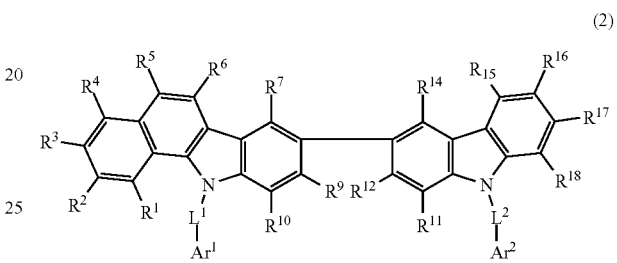

(2)

wherein $R^1$ to $R^7$, $R^9$ to $R^{12}$, $R^{14}$ to $R^{18}$, $L^1$, $L^2$, $Ar^1$, and $Ar^2$ are the same as defined above.

The compound (1) is preferably represented by formula (3):

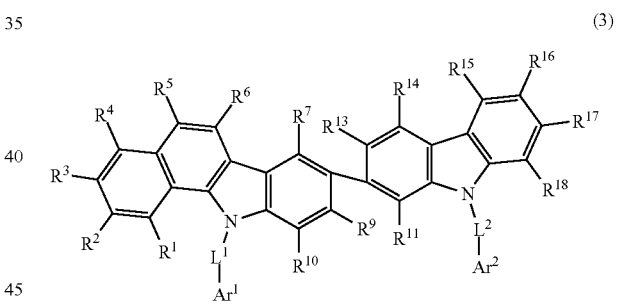

(3)

wherein $R^1$ to $R^7$, $R^9$ to $R^{11}$, $R^{13}$ to $R^{18}$, $L^1$, $L^2$, $Ar^1$, and $Ar^2$ are the same as defined above.

The compound (1) is preferably represented by formula (4):

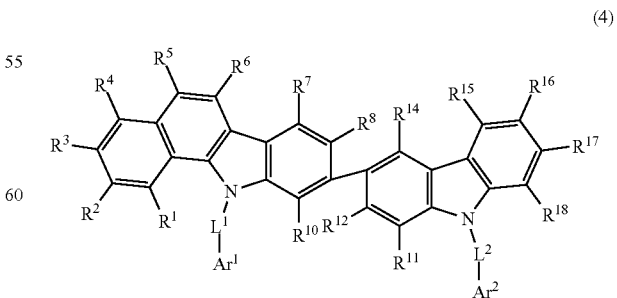

(4)

wherein $R^1$ to $R^8$, $R^{10}$ to $R^{12}$, $R^{14}$ to $R^{18}$, $L^1$, $L^2$, $Ar^1$, and $Ar^2$ are the same as defined above.

The compound (1) is preferably represented by formula (5):

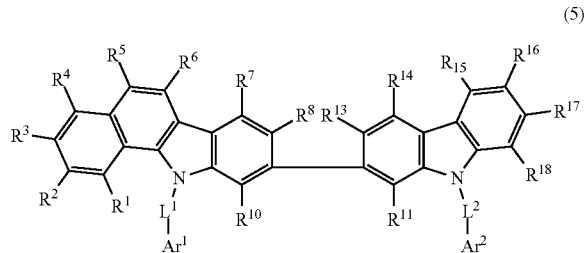

(5)

wherein $R^1$ to $R^8$, $R^{10}$, $R^{11}$, $R^{13}$ to $R^{18}$, $L^1$, $L^2$, $Ar^1$, and $Ar^2$ are the same as defined above.

The compound (1) may be represented by any of formulae (6), (7) and (1a):

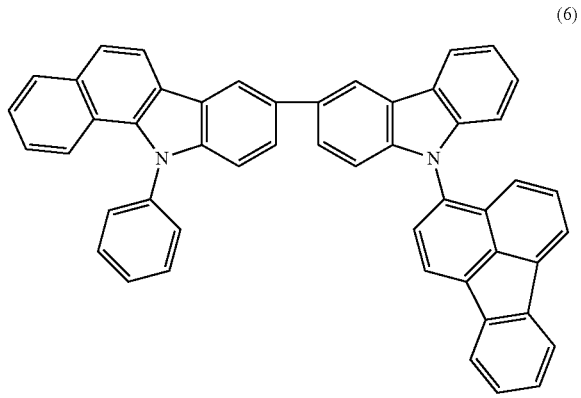

(6)

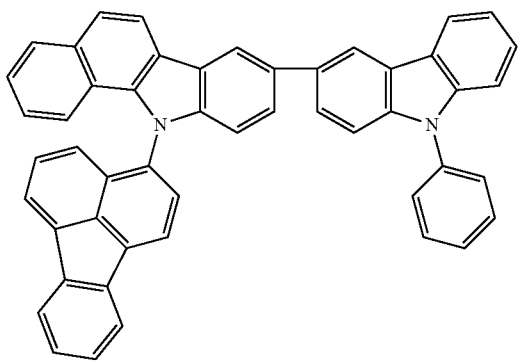

(7)

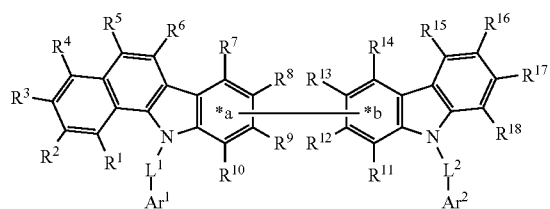

(1a)

wherein $R^1$ to $R^6$, $R^7$ to $R^{10}$, $R^{11}$ to $R^{14}$, $R^{15}$ to $R^{18}$, $L^1$, $L^2$, $Ar^1$, and $Ar^2$ are the same as defined above;

provided that when $R^8$ is a single bond bonded to *a, $R^{13}$ is a single bond bonded to *b, $R^1$ to $R^7$, $R^9$ to $R^{12}$, and $R^{14}$ to $R^{18}$ are all hydrogen atoms, $L^1$ and $L^2$ are both single bonds, and one of $Ar^1$ and $Ar^2$ is a phenyl group, the other of $Ar^1$ and $Ar^2$ is a substituted or unsubstituted fluoranthenyl group selected from the group consisting of a substituted or unsubstituted 1-fluoranthenyl group, a substituted or unsubstituted 2-fluoranthenyl group, a substituted or unsubstituted 3-fluoranthenyl group, a substituted or unsubstituted 7-fluoranthenyl group, and a substituted or unsubstituted 8-fluoranthenyl group.

$R^1$ to $R^6$, $R^7$ to $R^{10}$, $R^{11}$ to $R^{14}$, $R^{15}$ to $R^{18}$, $L^1$, $L^2$, $Ar^1$, $Ar^2$ of formulae (1) to (5) and (1a) are described below in more detail.

Each of $R^1$ to $R^6$ is independently a hydrogen atom; a substituted or unsubstituted alkyl group having 1 to 20, preferably 1 to 5, and more preferably 1 to 4 carbon atoms; a substituted or unsubstituted cycloalkyl group having 3 to 10, preferably 3 to 6, and more preferably 5 or 6 ring carbon atoms; a substituted or unsubstituted aryl group having 6 to 18, preferably 6 to 10, and more preferably 6 ring carbon atoms; a substituted or unsubstituted haloalkyl group having 1 to 20, preferably 1 to 5, and more preferably 1 to 4 carbon atoms; a substituted or unsubstituted alkoxy group having 1 to 20, preferably 1 to 5, and more preferably 1 to 4 carbon atoms; a substituted or unsubstituted haloalkoxy group having 1 to 20, preferably 1 to 5, and more preferably 1 to 4 carbon atoms; a substituted or unsubstituted aryloxy group having 6 to 18, preferably 6 to 10, and more preferably 6 ring carbon atoms; a halogen atom; or a cyano group.

Each of $R^1$ to $R^6$ is independently and preferably selected from the group consisting of a hydrogen atom, a substituted or unsubstituted alkyl group having 1 to 20 carbon atoms, a substituted or unsubstituted aryl group having 6 to 18 ring carbon atoms, a substituted or unsubstituted aryloxy group having 6 to 18 ring carbon atoms, and a cyano group, and more preferably selected from the group consisting of a hydrogen atom, a substituted or unsubstituted alkyl group having 1 to 20 carbon atoms, and a substituted or unsubstituted aryl group having 6 to 18 ring carbon atoms. $R^1$ to $R^6$ may be all hydrogen atoms.

In the substituted or unsubstituted alkyl group having 1 to 20 carbon atoms, examples of the alkyl group having 1 to 20 carbon atoms include a methyl group, an ethyl group, a n-propyl group, an isopropyl group, a n-butyl group, an isobutyl group, as-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups), with a methyl group, an ethyl group, a n-propyl group, an isopropyl group, a n-butyl group, an isobutyl group, a s-butyl group, a t-butyl group, and a pentyl group (inclusive of isomeric groups) being preferred, a methyl group, an ethyl group, a n-propyl group, an isopropyl group, a n-butyl group, an isobutyl group, a s-butyl group, and a t-butyl group being more preferred, and a methyl group and a t-butyl group being still more preferred.

In the substituted or unsubstituted cycloalkyl group having 3 to 10 ring carbon atoms, examples of the cycloalkyl group having 3 to 10 ring carbon atoms include a cyclopropyl group, a cyclobutyl group, a cyclopentyl group, a cyclohexyl group, and a cycloheptyl group, with a cyclopropyl group, a cyclobutyl group, a cyclopentyl group, and a cyclohexyl group being preferred, and a cyclopentyl group and a cyclohexyl group being more preferred.

In the substituted or unsubstituted aryl group having 6 to 18 ring carbon atoms, examples of the aryl group having 6 to 18 ring carbon atoms include a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a triphenylenyl group, a phenalenyl group, a fluorenyl group, a pyrenyl group, a chrysenyl group, a s-indanyl group, an a s-indanyl group, and a fluoranthenyl group, with a phenyl group, a 1-naphthyl group, a 2-naphthyl group, a biphenylyl group, such as a 2-, 3- or 4-biphenylyl group, and a terphenylyl group, such as a 2-p-terphenylyl group, a 4-p-terphenylyl group, a 2'-m-terphenylyl group, and a 5'-m-terphenylyl group being preferred, a phenyl group, a 1-naphthyl group, and a 2-naphthyl group being more preferred, and a phenyl group being still more preferred.

Examples of the substituted aryl group having 6 to 18 ring carbon atoms include a 9,9-dimethylfluorenyl group and a 9,9-diphenylfluorenyl group.

In the substituted or unsubstituted haloalkyl group having 1 to 20 carbon atoms, the haloalkyl group having 1 to 20 carbon atoms is, for example, a group obtained by replacing at least one, preferably 1 to 7 hydrogen atoms, or all the hydrogen atoms of the alkyl group having 1 to 20 carbon atoms mentioned above with a halogen atom selected from the group consisting of a fluorine atom, a chlorine atom, a bromine atom, and an iodine atom, preferably a fluorine atom. Examples thereof include a fluoroalkyl group having 1 to 20 carbon atoms, with a heptafluoropropyl group (inclusive of isomeric groups), a pentafluoroethyl group, a 2,2,2-trifluoroethyl group, and a trifluoromethyl group being more preferred, a pentafluoroethyl group, a 2,2,2-trifluoroethyl group, and a trifluoromethyl group being still more preferred, and a trifluoromethyl group being particularly preferred.

The substituted or unsubstituted alkoxy group having 1 to 20 carbon atoms is represented by —$OR^a$, wherein $R^a$ is the substituted or unsubstituted alkyl group having 1 to 20 carbon atoms mentioned above. The alkoxy group having 1 to 20 carbon atoms is preferably a t-butoxy group, a propoxy group (inclusive of isomeric groups), an ethoxy group, or a methoxy group, more preferably an ethoxy group or a methoxy group, and still more preferably a methoxy group.

The substituted or unsubstituted haloalkoxy group having 1 to 20 carbon atoms is represented by —$OR^b$, wherein $R^b$ is the substituted or unsubstituted haloalkyl group having 1 to 20 carbon atoms and preferably a substituted or unsubstituted fluoroalkyl group having 1 to 20 carbon atoms, each mentioned above. The haloalkoxy group having 1 to 20 carbon atoms is preferably a fluoroalkoxy group, more preferably a heptafluoropropoxy group (inclusive of isomeric groups), a pentafluoroethoxy group, a 2,2,2-trifluoroethoxy group, or a trifluoromethoxy group, still more preferably a pentafluoroethoxy group, a 2,2,2-trifluoroethoxy group, or a trifluoromethoxy group, and particularly preferably a trifluoromethoxy group.

The substituted or unsubstituted aryloxy group having 6 to 18 ring carbon atoms is represented by —$OR^c$, wherein $R^c$ is the substituted or unsubstituted aryl group having 6 to 18 ring carbon atoms mentioned above. Examples of the aryl group having 6 to 18 ring carbon atoms include a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a triphenylenyl group, a phenalenyl group, a fluorenyl group, a pyrenyl group, a chrysenyl group, a s-indanyl group, an as-indanyl group, and a fluoranthenyl group, with a phenyl group, a 1-naphthyl group, a 2-naphthyl group, a biphenylyl group, such as a 2-, 3- or 4-biphenylyl group, and a terphenylyl group, such as a 2-p-terphenylyl group, a 4-p-terphenylyl group, a 2'-m-terphenylyl group, and a 5'-m-terphenylyl group being preferred, a phenyl group, a 1-naphthyl group and a 2-naphthyl group being more preferred, and a phenyl group being still more preferred.

The halogen atom includes a fluorine atom, a chlorine atom, a bromine atom, and an iodine atom, with a fluorine atom being preferred.

One of $R^7$ to $R^{10}$, preferably $R^8$ or $R^9$, is a single bond bonded to *a. Each of the others of $R^7$ to $R^{10}$ is independently a hydrogen atom, a substituted or unsubstituted alkyl group having 1 to 20 carbon atoms, a substituted or unsubstituted cycloalkyl group having 3 to 10 ring carbon atoms, a substituted or unsubstituted aryl group having 6 to 18 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 18 ring carbon atoms, a halogen atom, or a cyano group.

The details of the groups for the others of $R^7$ to $R^{10}$ are the same as those of the corresponding groups mentioned above with respect to $R^1$ to $R^6$.

Each of the others of $R^7$ to $R^{10}$ is independently and preferably selected from the group consisting of a hydrogen atom, a substituted or unsubstituted alkyl group having 1 to 20 carbon atoms, a substituted or unsubstituted aryl group having 6 to 18 ring carbon atoms, a substituted or unsubstituted aryloxy group having 6 to 18 ring carbon atoms, and a cyano group, and more preferably selected from the group consisting of a hydrogen atom, a substituted or unsubstituted alkyl group having 1 to 20 carbon atoms, and a substituted or unsubstituted aryl group having 6 to 18 ring carbon atoms. The others of $R^7$ to $R^{10}$ may be all hydrogen atoms.

One of $R^{11}$ to $R^{14}$, preferably $R^{12}$ or $R^{13}$, is a single bond bonded to *b. Each of the others of $R^{11}$ to $R^{14}$ is independently a hydrogen atom, a substituted or unsubstituted alkyl group having 1 to 20 carbon atoms, a substituted or unsubstituted cycloalkyl group having 3 to 10 ring carbon atoms, a substituted or unsubstituted aryl group having 6 to 18 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 18 ring carbon atoms, a halogen atom, or a cyano group.

The details of the groups for the others of $R^{11}$ to $R^{14}$ are the same as those of the corresponding groups mentioned above with respect to $R^1$ to $R^6$.

Each of the others of $R^{11}$ to $R^{14}$ is independently and preferably selected from the group consisting of a hydrogen atom, a substituted or unsubstituted alkyl group having 1 to 20 carbon atoms, a substituted or unsubstituted aryl group having 6 to 18 ring carbon atoms, a substituted or unsubstituted aryloxy group having 6 to 18 ring carbon atoms, and a cyano group, and more preferably selected from the group consisting of a hydrogen atom, a substituted or unsubstituted alkyl group having 1 to 20 carbon atoms, and a substituted or unsubstituted aryl group having 6 to 18 ring carbon atoms. The others of $R^{11}$ to $R^{14}$ may be all hydrogen atoms.

Each of $R^{15}$ to $R^{18}$ is independently a hydrogen atom, a substituted or unsubstituted alkyl group having 1 to 20 carbon atoms, a substituted or unsubstituted cycloalkyl group having 3 to 10 ring carbon atoms, a substituted or unsubstituted aryl group having 6 to 18 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 18 ring carbon atoms, a halogen atom, or a cyano group.

The details of the groups for $R^{15}$ to $R^{18}$ are the same as those of the corresponding groups mentioned above with respect to $R^1$ to $R^6$.

Each of $R^{15}$ to $R^{18}$ is independently and preferably selected from the group consisting of a hydrogen atom, a substituted or unsubstituted alkyl group having 1 to 20 carbon atoms, a substituted or unsubstituted aryl group having 6 to 18 ring carbon atoms, a substituted or unsubstituted aryloxy group having 6 to 18 ring carbon atoms, and a cyano group, and more preferably selected from the group consisting of a hydrogen atom, a substituted or unsubstituted alkyl group having 1 to 20 carbon atoms, and a substituted or unsubstituted aryl group having 6 to 18 ring carbon atoms. $R^{15}$ to $R^{18}$ may be all hydrogen atoms.

Each of adjacent two groups selected from $R^1$ to $R^6$, adjacent two groups selected from $R^7$ to $R^{10}$, adjacent two groups selected from $R^{11}$ to $R^{14}$, and adjacent two groups selected from $R^{15}$ to $R^{18}$ may be respectively bonded to each other to from a substituted or unsubstituted ring, or may not form a ring. In an embodiment of the invention, adjacent two groups selected from $R^1$ to $R^6$, $R^7$ to $R^{10}$, $R^{11}$ to $R^{14}$, and $R^{15}$ to $R^{18}$ preferably do not form a ring.

Example of the ring to be formed by the adjacent two groups together with two ring carbon atoms to which the adjacent two groups are bonded includes a substituted or unsubstituted hydrocarbon ring, preferably a substituted or unsubstituted aromatic hydrocarbon ring, more preferably a substituted or unsubstituted benzene ring, and still more preferably an unsubstituted benzene ring.

Each of $L^1$ and $L^2$ is independently, a single bond, a substituted or unsubstituted arylene group having 6 to 18, preferably 6 to 10, and more preferably 6 ring carbon atoms, or a substituted or unsubstituted heteroarylene group 5 to 18, preferably 5 to 14, and more preferably 5 to 10 ring atoms, preferably a single bond or a substituted or unsubstituted arylene group having 6 to 18 ring carbon atoms, and more preferably a single bond or an unsubstituted arylene group having 6 to 18 ring carbon atoms.

In the substituted or unsubstituted arylene group having 6 to 18 ring carbon atoms, the arylene group having 6 to 18 ring carbon atoms is a group obtained by removing one hydrogen atom from the aryl group having 6 to 18 ring carbon atoms mentioned above, preferably a group obtained by removing one hydrogen atom from an aryl group selected from the group consisting of a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a triphenylenyl group, a phenalenyl group, a fluorenyl group, a pyrenyl group, a chrysenyl group, a s-indanyl group, an as-indanyl group, and a fluoranthenyl group, more preferably a group selected from the group consisting of a phenylene group, a naphthylene group, and a biphenylylene group, and still more preferably a group selected from the group consisting of an o-phenylene group, a m-phenylene group, a p-phenylene group, a 1,4-naphthalenediyl group, a 1,5-naphthalenediyl group, a 2,6-naphthalenediyl group, a 2,7-naphthalenediyl group, a 2,2'-biphenyldiyl group, a 2,3'-biphenyldiyl group, a 2,4'-biphenyldiyl group, a 3,3'-biphenyldiyl group, a 3,4'-biphenyldiyl group, and a 4,4'-biphenyldiyl group.

In the substituted or unsubstituted heteroarylene group having 5 to 18 ring atoms, the heteroarylene group having 5 to 18 ring atoms comprises 1 to 5, preferably 1 to 3, and more preferably 1 or 2 ring heteroatoms, such as a nitrogen atom, a sulfur atom, and an oxygen atom. Example thereof is a group obtained by removing one hydrogen atom from a heteroaryl group selected from the group consisting of a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzotiophenyl group (benzothienyl group), an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazoly group, a benzisothiazolyl group, a dibenzofuranyl group, a naphthobenzofuranyl group, group (dibenzothienyl group), a naphthobenzotiophenyl group, a N-carbazolyl group, a C-carbazolyl group, a benzo-N-carbazolyl group, a benzo-C-carbazolyl group, a phenanthridinyl group, an acridinyl group, a phenanthrolinyl group, a phenazinyl group, a phenothiazinyl group, a phenoxazinyl group, and a xanthenyl group. Preferred example thereof is a group obtained by removing one hydrogen atom from a heteroaryl group selected from the group consisting of a pyridyl group, a pyrimidinyl group, a pyrazinyl group, a triazinyl group, an imidazolyl group, an oxazolyl group, a thiazolyl group, an isoxazolyl group, an isothiazolyl group, a triazolyl group, an indolyl group, a benzofuranyl group, an isobenzofuranyl group, a benzotiophenyl group (a benzothienyl group), a quinolizinyl group, a quinolyl group, an isoquinolyl group, a quinazolinyl group, a quinoxalinyl group, a benzimidazolyl group, a benzoxazolyl group, a benzothiazolyl group, an indazolyl group, a benzisoxazoly group, a benzisothiazolyl group, a dibenzofuranyl group, a naphthobenzofuranyl group, a dibenzotiophenyl group (a dibenzothienyl group), a naphthobenzotiophenyl group, a N-carbazolyl group, a C-carbazolyl group, a benzo-N-carbazolyl group, a benzo-C-carbazolyl group, a phenanthridinyl group, an acridinyl group, a phenanthrolinyl group, a phenazinyl group, a phenothiazinyl group, a phenoxazinyl group, and a xanthenyl group. More preferred example thereof is a group obtained by removing one hydrogen atom from a heteroaryl group selected from the group consisting of a pyridyl group, a pyrimidinyl group, a triazinyl group, an indolyl group, a quinolizinyl group, a quinolyl group, a quinazolinyl group, a quinoxalinyl group, a benzimidazolyl group, a benzothiazolyl group, a benzisoxazoly group, a benzisothiazolyl group, a dibenzofuranyl group, a naphthobenzofuranyl group, a dibenzotiophenyl group (a dibenzothienyl group), a naphthobenzotiophenyl group, a N-carbazolyl group, a C-carbazolyl group, a benzo-N-carbazolyl group, a benzo-C-carbazolyl group, and a phenanthrolinyl group. Still more preferred example is a group obtained by removing one hydrogen atom from a heteroaryl group selected from the group consisting of a pyridyl group, a pyrimidinyl group, a triazinyl group, a quinazolinyl group, a N-carbazolyl group, and a C-carbazolyl group.

Each of $Ar^1$ and $Ar^2$ is independently a substituted or unsubstituted aryl group having 6 to 18 ring carbon atoms, provided that at least one selected from $Ar^1$ and $Ar^2$ is a substituted or unsubstituted fluoranthenyl group.

In the substituted or unsubstituted aryl group having 6 to 18 ring carbon atoms for $Ar^1$ and $Ar^2$, the aryl group having 6 to 18 ring carbon atoms is selected from the aryl group having 6 to 18 ring carbon atoms mentioned above with respect to $R^1$ to $R^6$.

The aryl group having 6 to 18 ring carbon atoms is preferably selected from the group consisting of a phenyl group, a naphthyl group, a biphenylyl group, a phenanthryl group, and a triphenylenyl group, more preferably selected from the group consisting of a phenyl group, a 1-naphthyl group, a 2-naphthyl group, a 2-biphenylyl group, a 3-biphenylyl group, and a 4-biphenylyl group, and still more preferably a phenyl group.

The substituted or unsubstituted fluoranthenyl group is represented by formula (8):

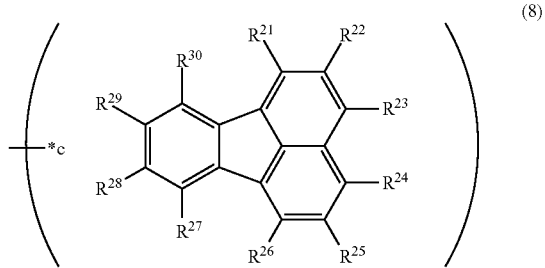

wherein one of $R^{21}$ to $R^{30}$ is a single bond bonded to *c, each of the others of $R^{21}$ to $R^{30}$ is independently a hydrogen atom, a substituted or unsubstituted alkyl group having 1 to 20 carbon atoms, a substituted or unsubstituted cycloalkyl group having 3 to 10 ring carbon atoms, a substituted or unsubstituted aryl group having 6 to 18 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 18 ring carbon atoms, a halogen atom, or a cyano group.

The details of the groups for the others of $R^{21}$ to $R^{30}$ are the same as those of the corresponding groups mentioned above with respect to $R^1$ to $R^6$.

Each of the others of $R^{21}$ to $R^{30}$ is independently and preferably selected from the group consisting of a hydrogen atom, a substituted or unsubstituted alkyl group having 1 to 20 carbon atoms, a substituted or unsubstituted aryl group having 6 to 18 ring carbon atoms, a substituted or unsubstituted aryloxy group having 6 to 18 ring carbon atoms, and a cyano group, and more preferably selected from the group consisting of a hydrogen atom, a substituted or unsubstituted alkyl group having 1 to 20 carbon atoms, and a substituted or unsubstituted aryl group having 6 to 18 ring carbon atoms. The others of $R^{21}$ to $R^{30}$ may be all hydrogen atoms.

In the substituted or unsubstituted fluoranthenyl group, the fluoranthenyl group is selected from the group consisting of a 1-fluoranthenyl group ($R^{21}$ or $R^{26}$ is a single bond bonded to *c), a 2-fluoranthenyl group ($R^{22}$ or $R^{25}$ is a single bond bonded to *c), a 3-fluoranthenyl group ($R^{23}$ or $R^{24}$ is a single bond bonded to *c), a 7-fluoranthenyl group ($R^{27}$ or $R^{30}$ is a single bond bonded to *c), and a 8-fluoranthenyl group ($R^{28}$ or $R^{29}$ is a single bond bonded to *c), and preferably a 1-fluoranthenyl group, a 3-fluoranthenyl group, a 7-fluoranthenyl group, or a 8-fluoranthenyl group. In view of improving the performance of EL devices, for example, prolonging the lifetime, a 3-fluoranthenyl group and a 8-fluoranthenyl group are preferred.

In formulae (1) to (5) and (1a), $L^1$ and $L^2$ satisfy any one of the following (a) to (d), preferably (a) or (b):

(a) $L^1$ is a single bond, and $L^2$ is a substituted or unsubstituted arylene group having 6 to 18 ring carbon atoms or a substituted or unsubstituted heteroarylene group having 5 to 18 ring atoms, preferably a substituted or unsubstituted arylene group having 6 to 18 ring carbon atoms, and more preferably an unsubstituted arylene group having 6 to 18 ring carbon atoms, each mentioned above;

(b) $L^2$ is a single bond, and $L^1$ is a substituted or unsubstituted arylene group having 6 to 18 ring carbon atoms or a substituted or unsubstituted heteroarylene group having 5 to 18 ring atoms, preferably a substituted or unsubstituted arylene group having 6 to 18 ring carbon atoms, and more preferably an unsubstituted arylene group having 6 to 18 ring carbon atoms, each mentioned above;

(c) each of $L^1$ and $L^2$ is independently a substituted or unsubstituted arylene group having 6 to 18 ring carbon atoms or a substituted or unsubstituted heteroarylene group having 5 to 18 ring atoms, preferably a substituted or unsubstituted arylene group having 6 to 18 ring carbon atoms, and more preferably an unsubstituted arylene group having 6 to 18 ring carbon atoms, each mentioned above; and (d) $L^1$ and $L^2$ are both single bonds.

In formulae (1) to (5) and (1a), $Ar^1$ and $Ar^2$ satisfy any one of the following (e) to (g), preferably (e) or (f):

(e) $Ar^1$ is a substituted or unsubstituted aryl group having 6 to 18 ring carbon atoms and $Ar^2$ is a substituted or unsubstituted fluoranthenyl group, each mentioned above;

(f) $Ar^2$ is a substituted or unsubstituted aryl group having 6 to 18 ring carbon atoms and $Ar^1$ is a substituted or unsubstituted fluoranthenyl group, each mentioned above; and (g) each of $Ar^1$ and $Ar^2$ is independently a substituted or unsubstituted fluoranthenyl group mentioned above.

In the substituted or unsubstituted aryl group having 6 to 18 ring carbon atoms of formula (e) or (f), the aryl group having 6 to 18 ring carbon atoms is preferably selected from the group consisting of a phenyl group, a naphthyl group, a biphenylyl group, a phenanthryl group, and a triphenylenyl group, more preferably selected from the group consisting of a phenyl group, a 1-naphthyl group, a 2-naphthyl group, a 2-biphenylyl group, a 3-biphenylyl group, and a 4-biphenylyl group, and still more preferably a phenyl group.

Each of (a) to (d) may be combined with any of (e) to (g). The above substituted or unsubstituted fluoranthenyl group is as described above with respect to formula (8).

One of ordinary skill in the art could easily produce the compound (1) by selecting a starting compound corresponding to an aimed compound and reacting the selected starting compound with reference to the synthesis examples described below.

Examples of the compound (1) of the invention are shown below, although not limited thereto.

15 16
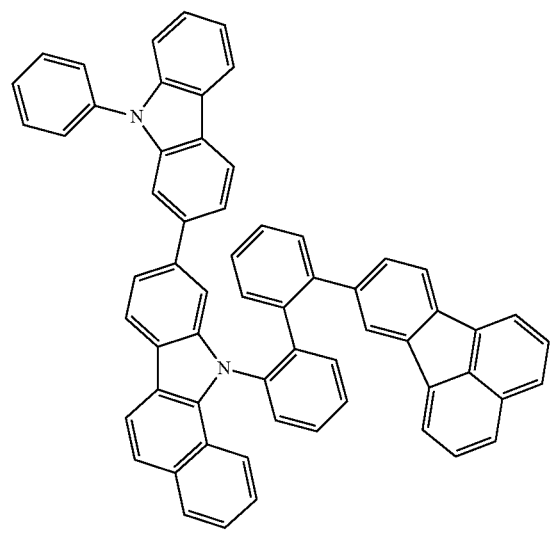
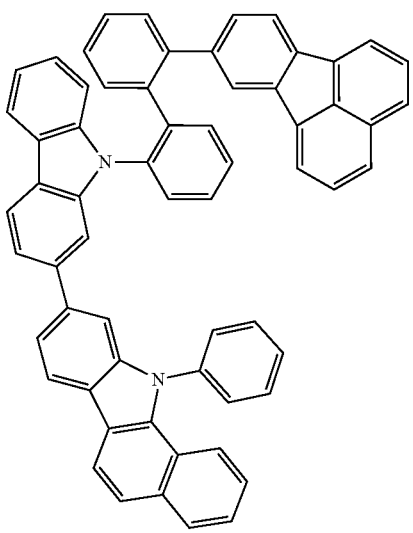
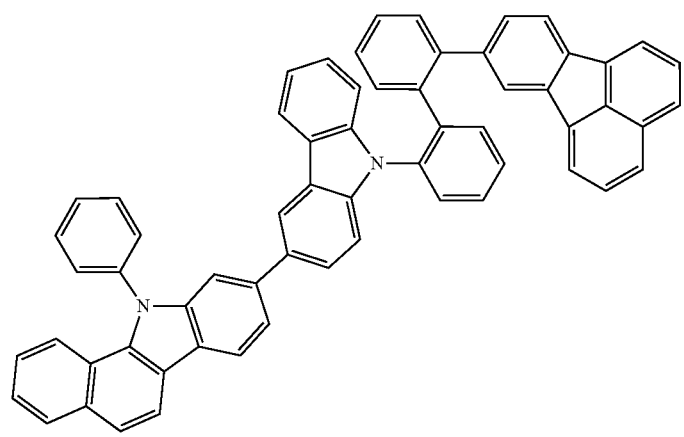
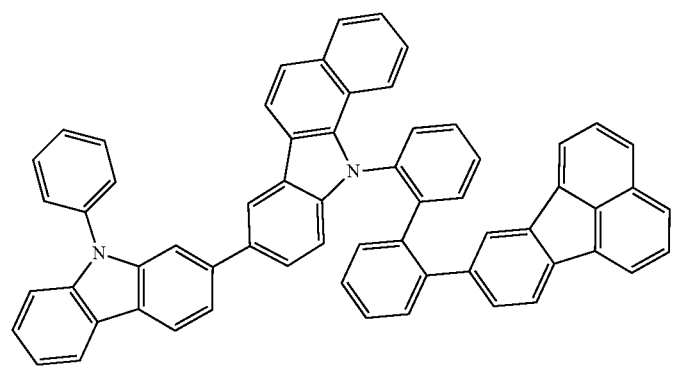

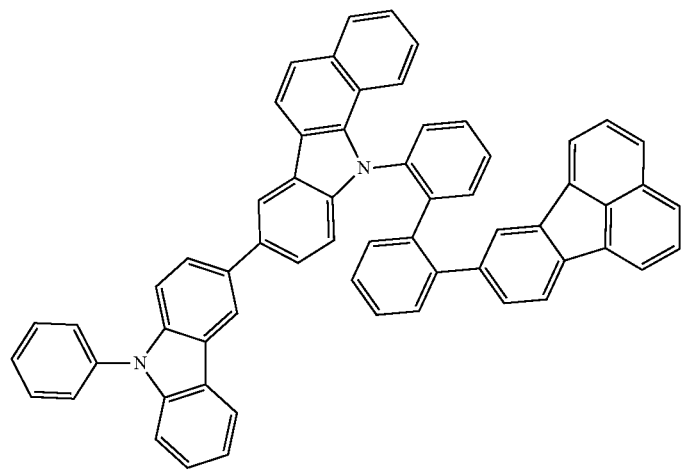
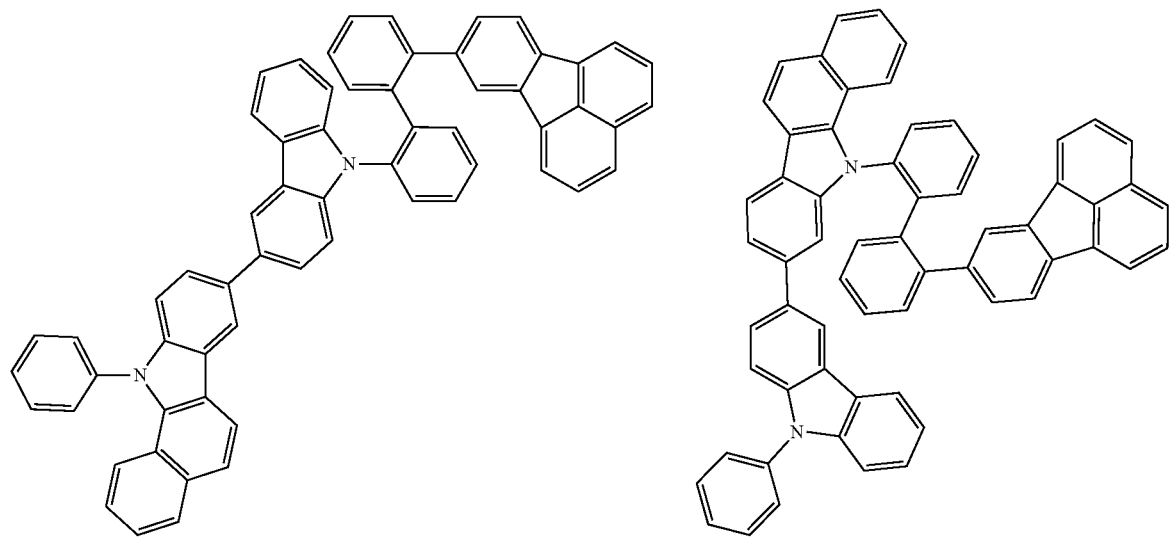
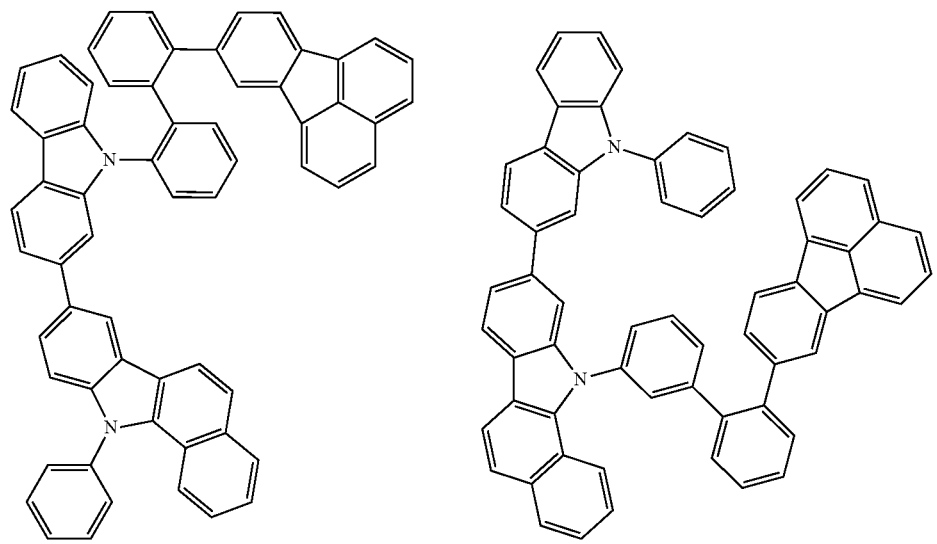

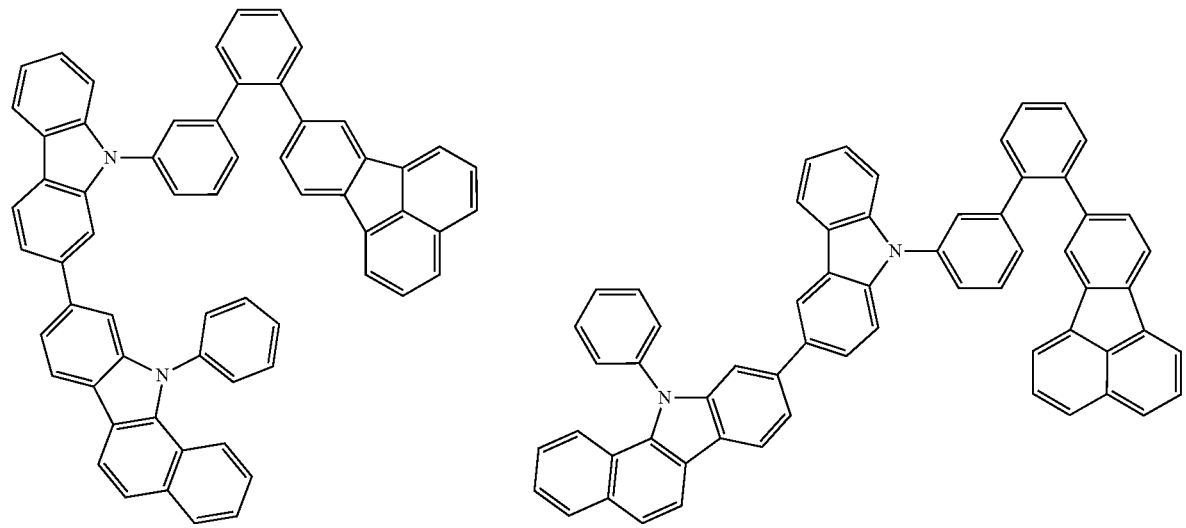
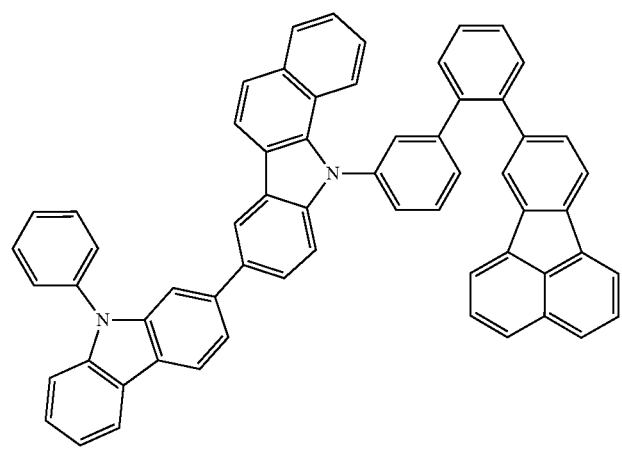
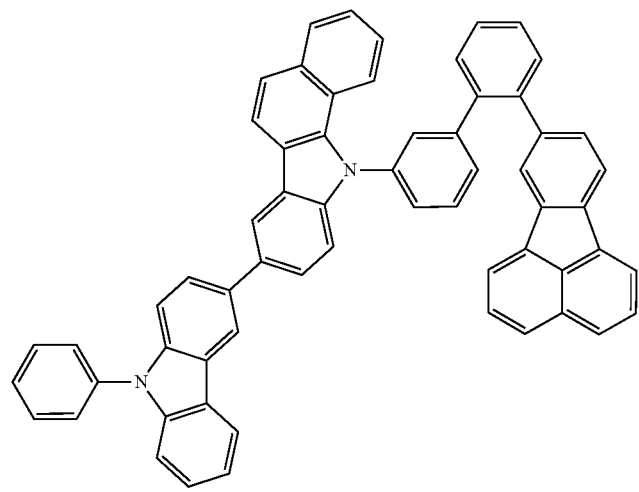

-continued
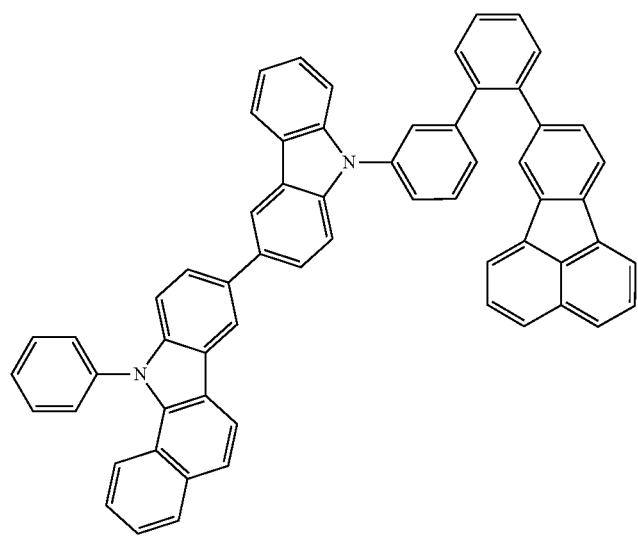
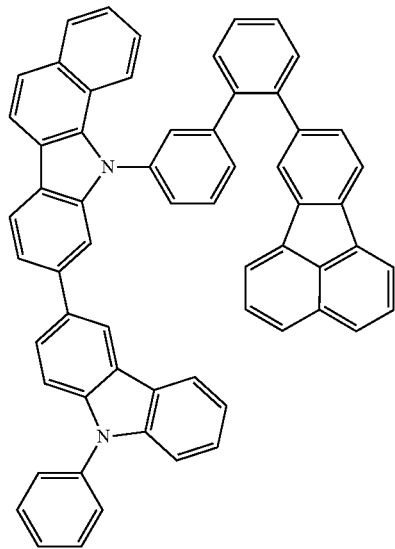
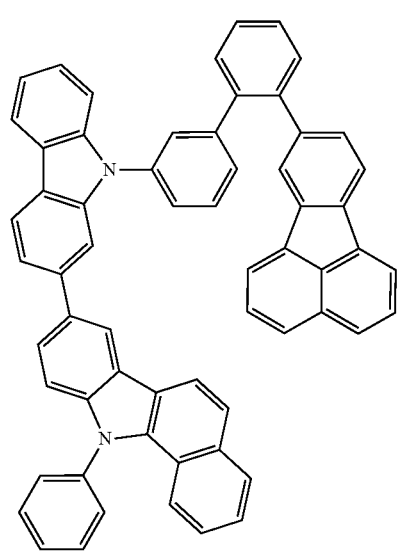
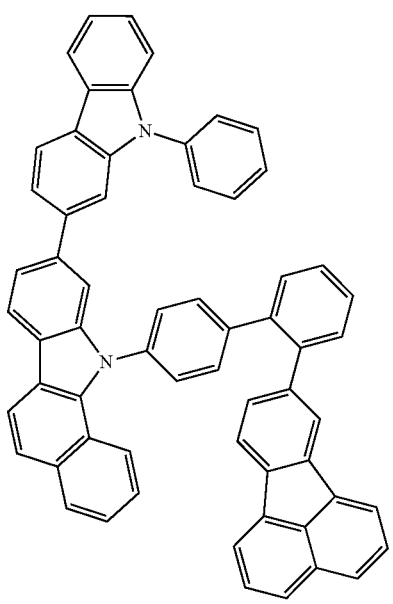

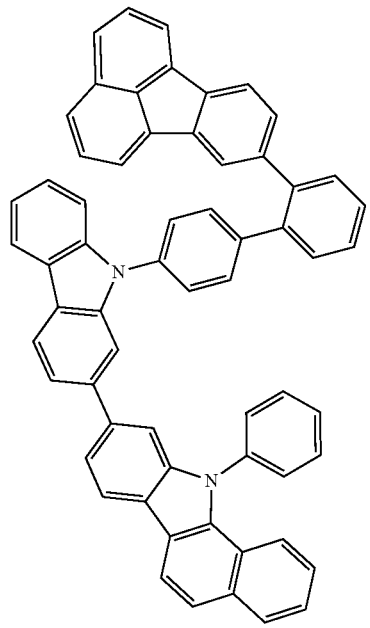
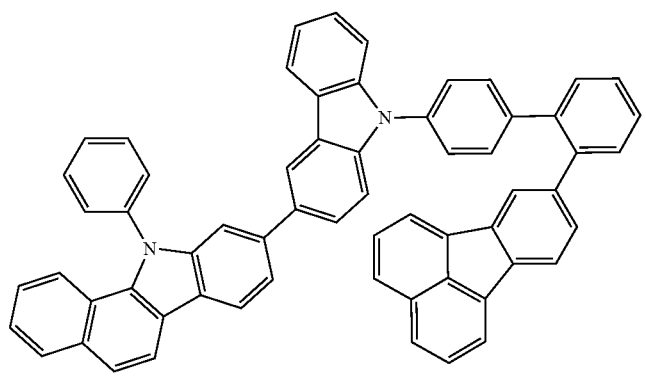
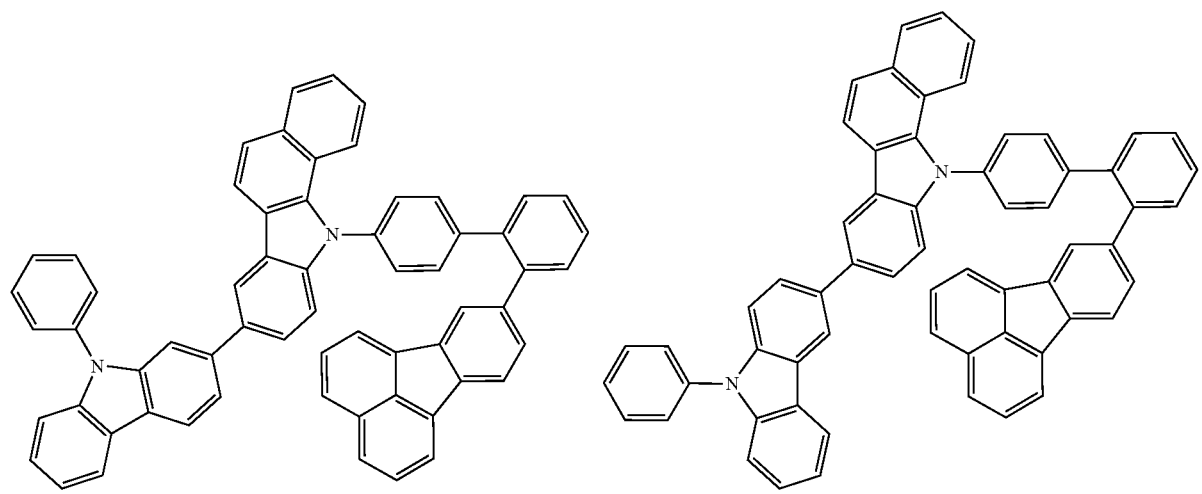

-continued
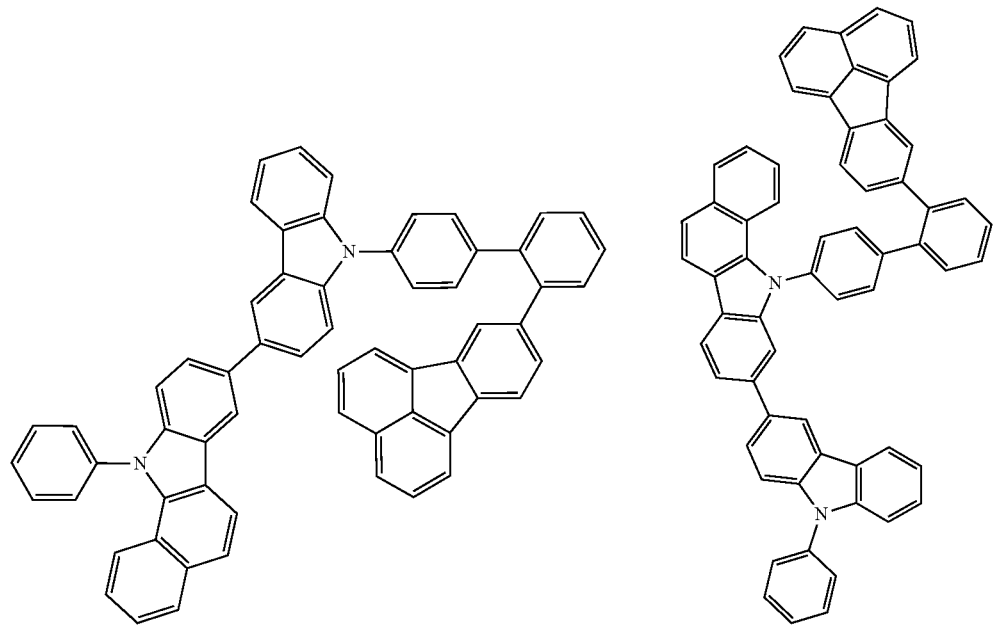
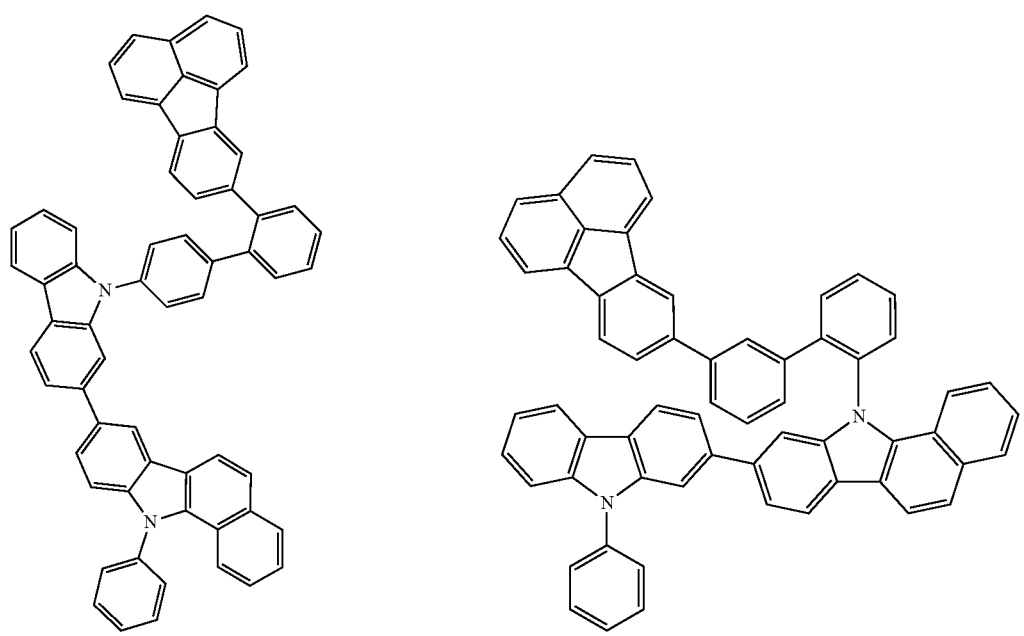

-continued
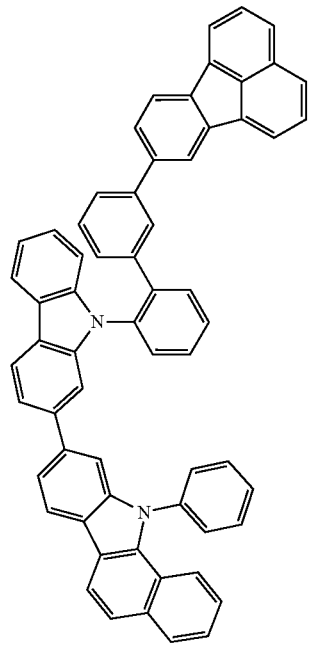
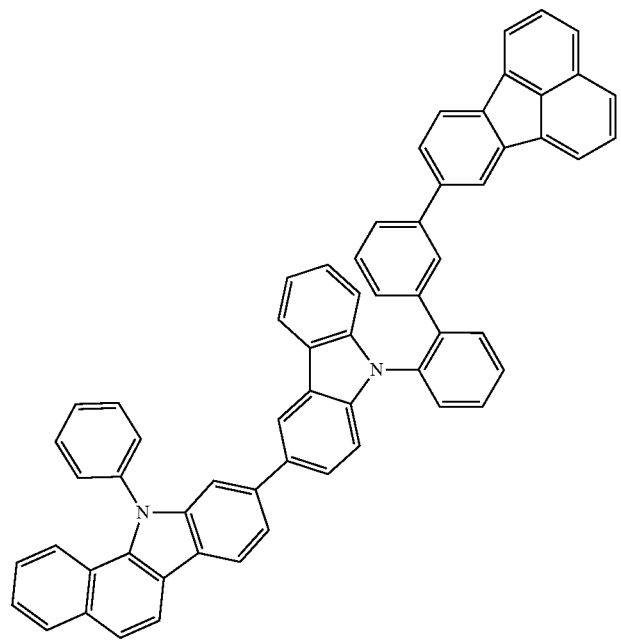
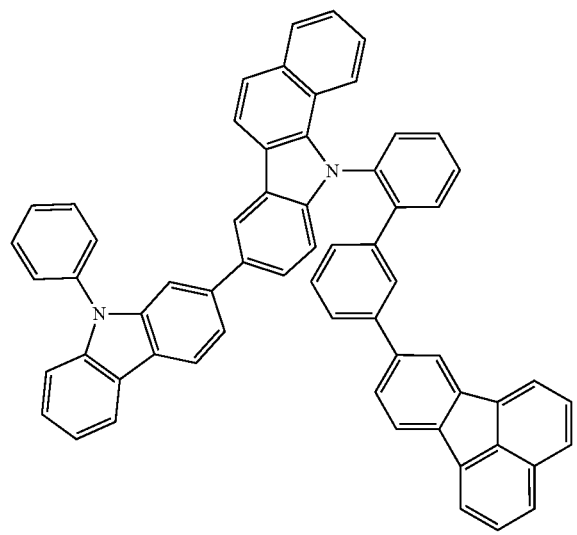
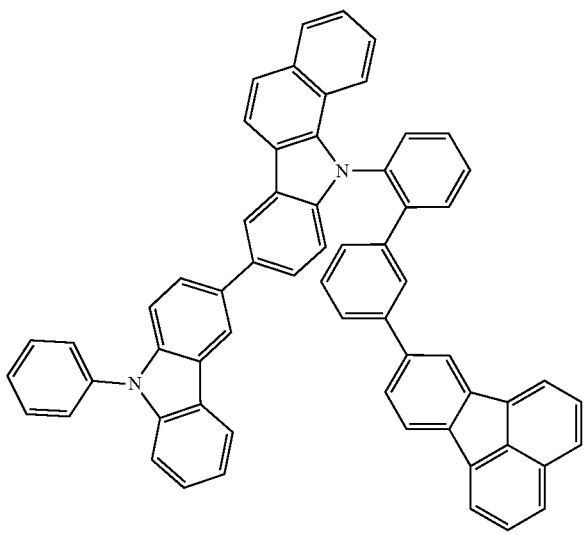

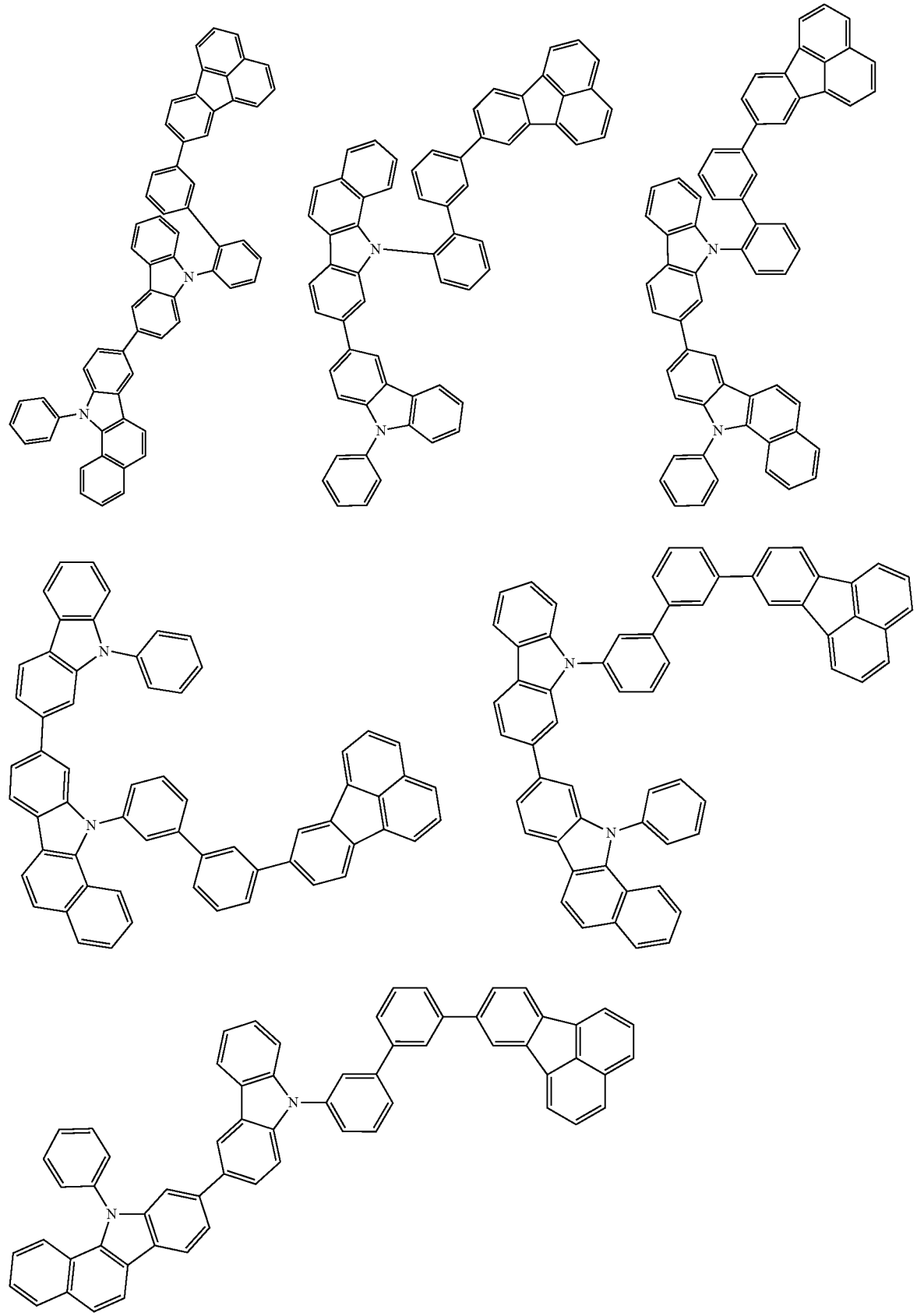

-continued
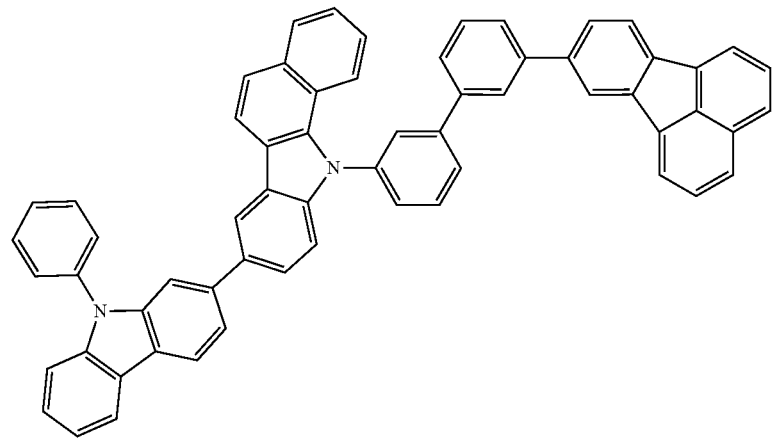
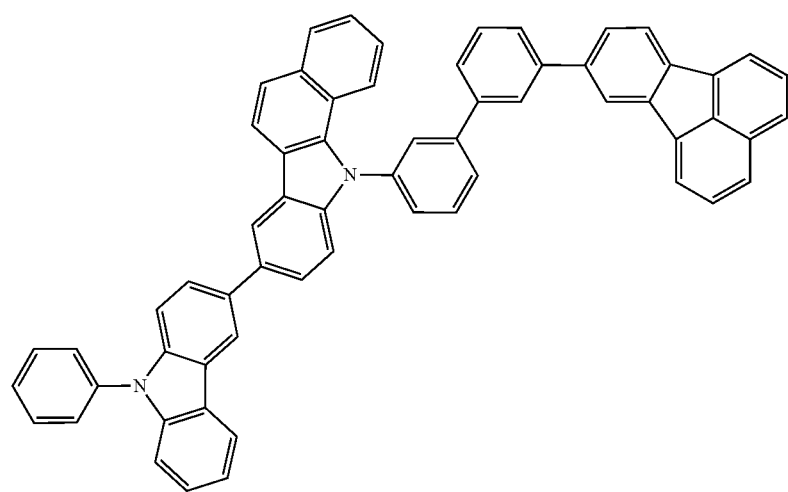
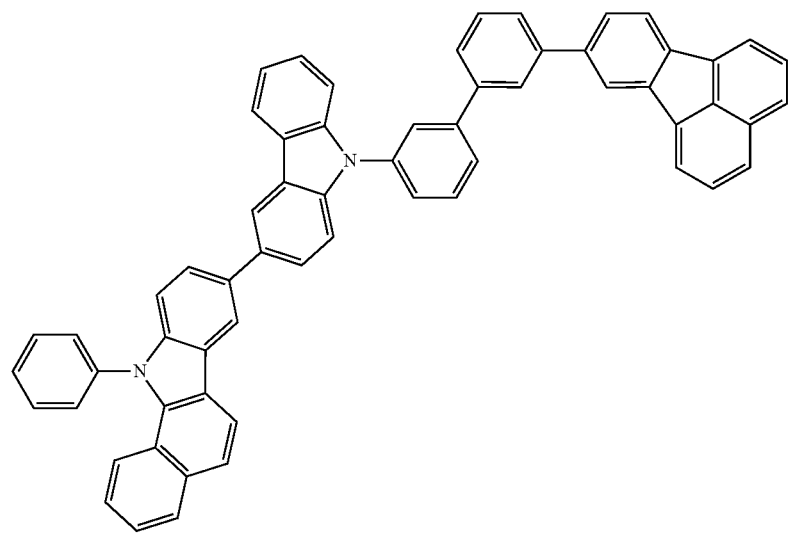

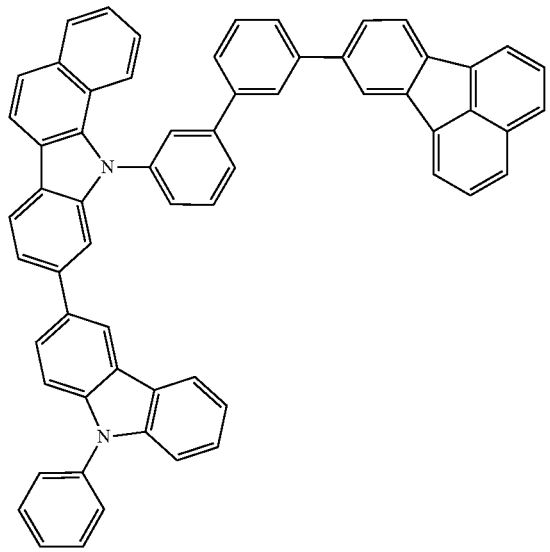
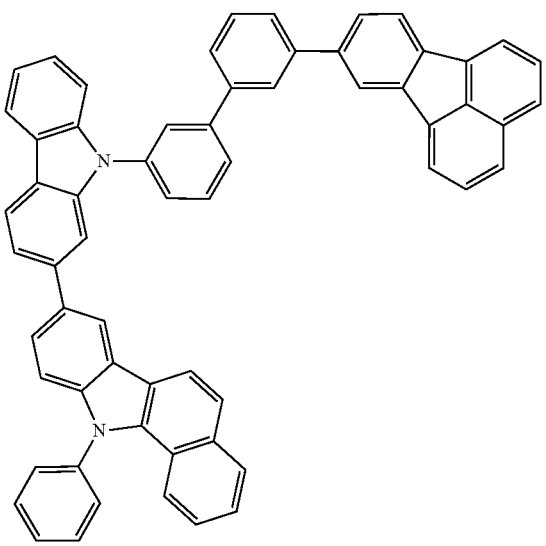
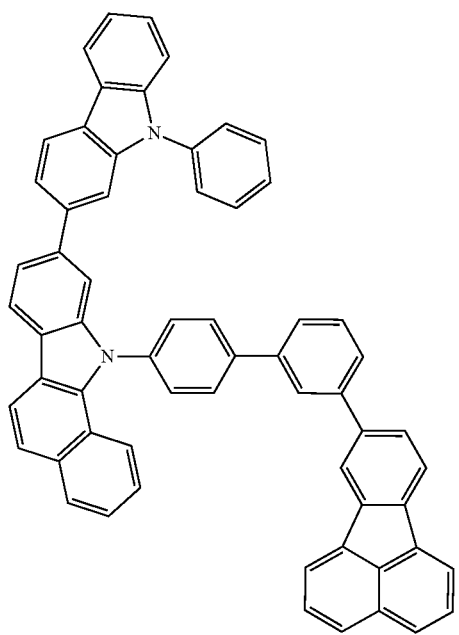
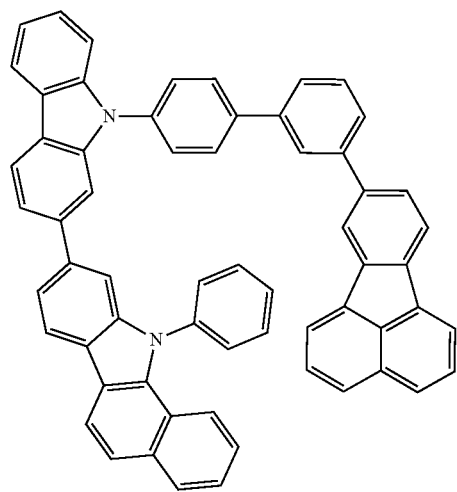
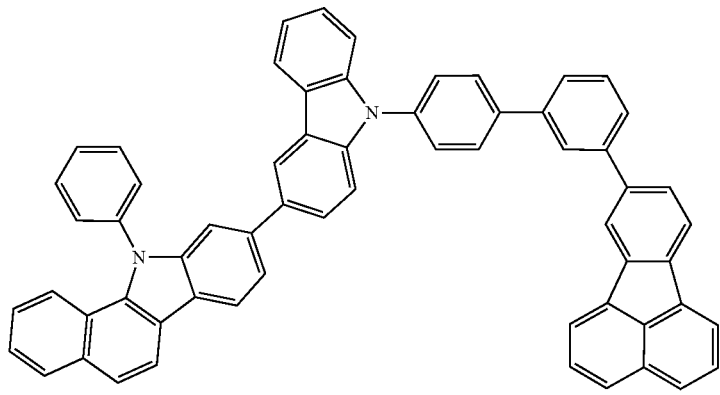

-continued
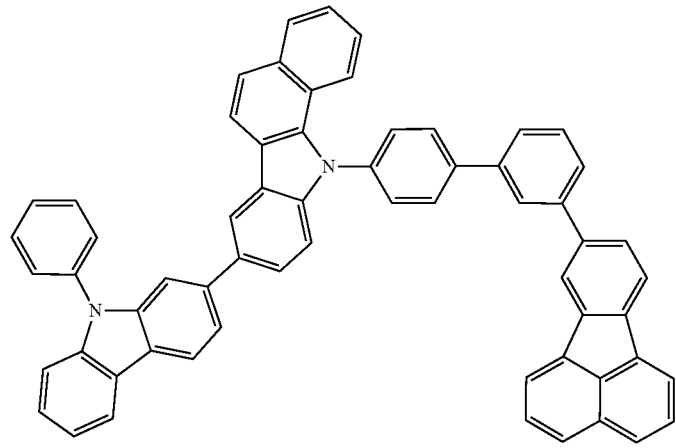
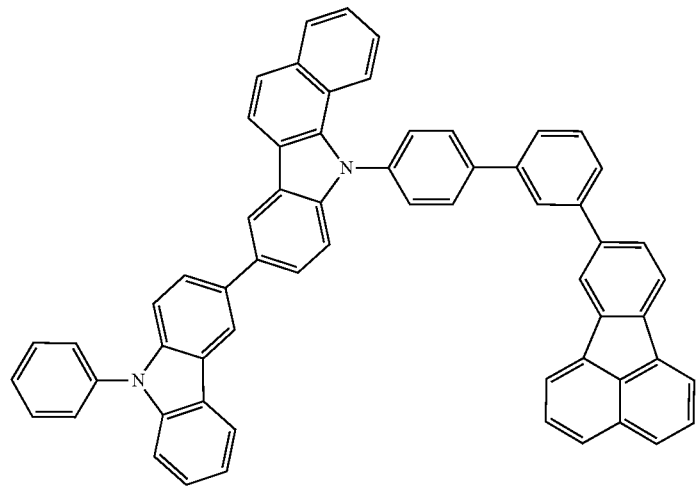
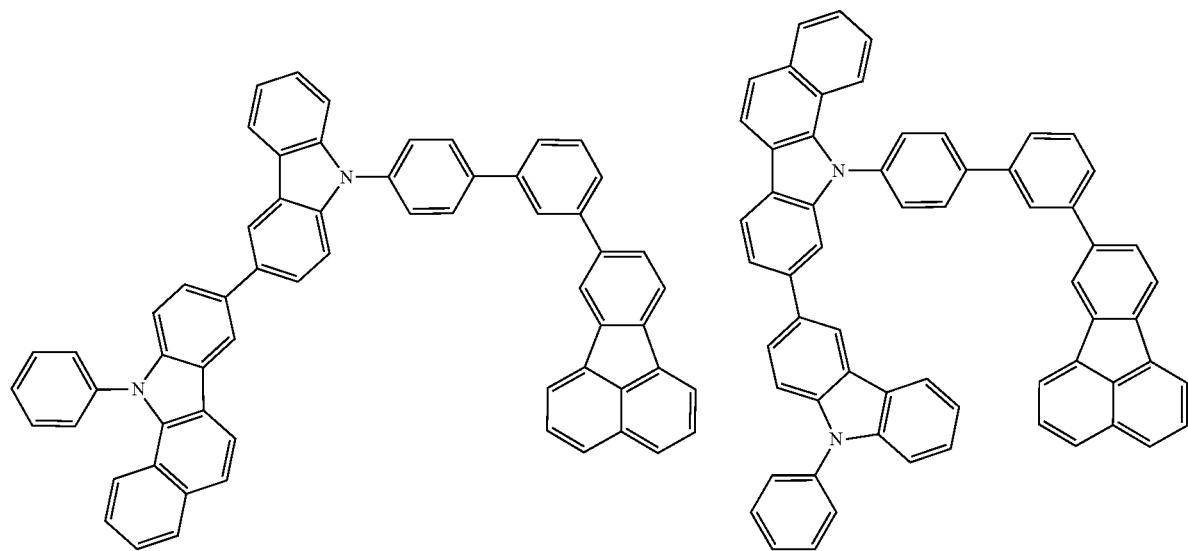

-continued
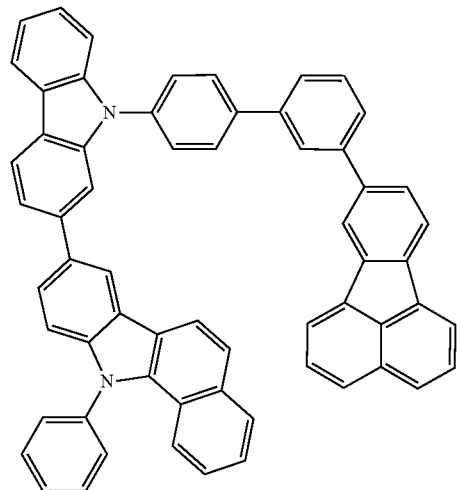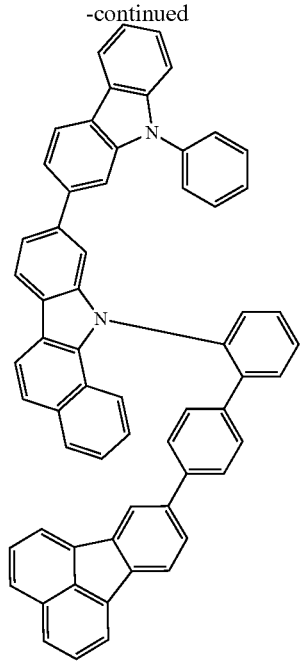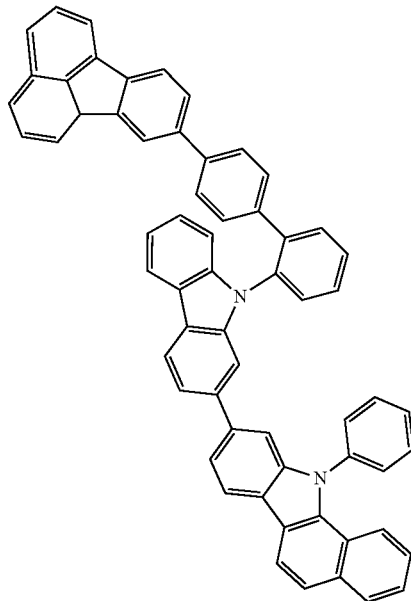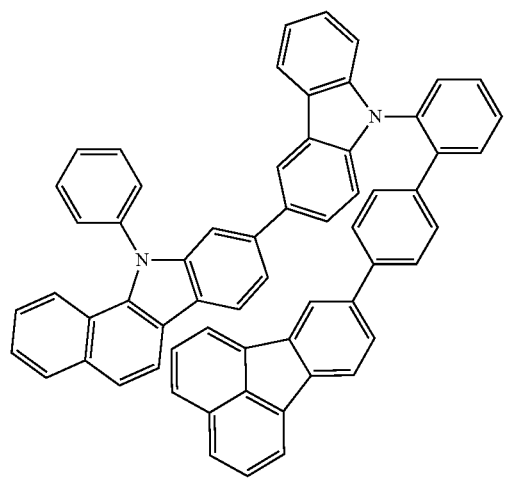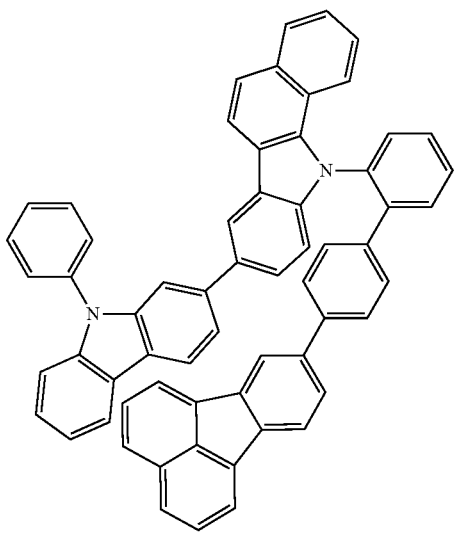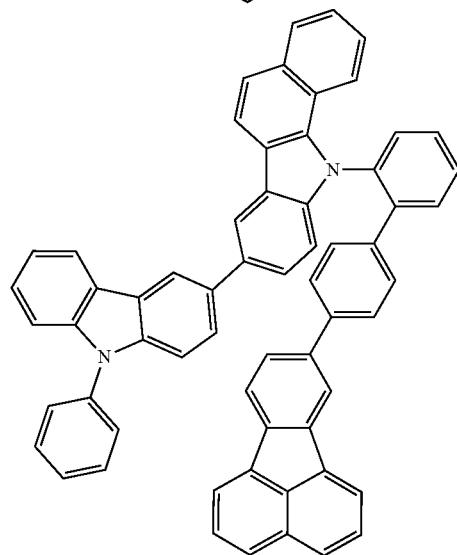

-continued
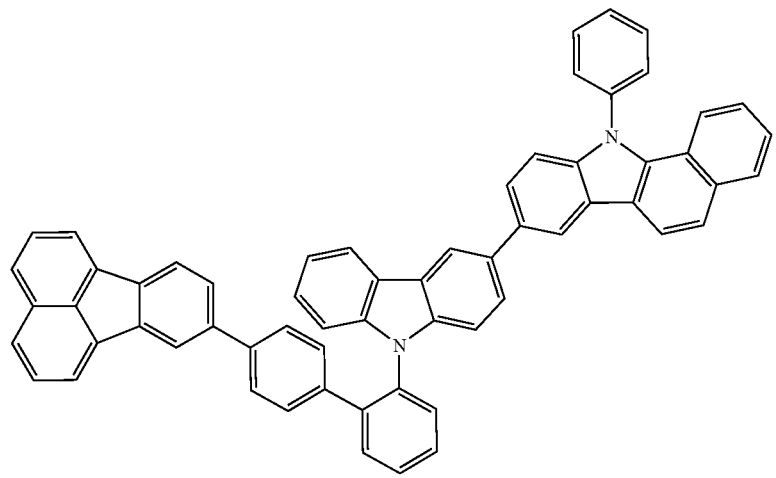
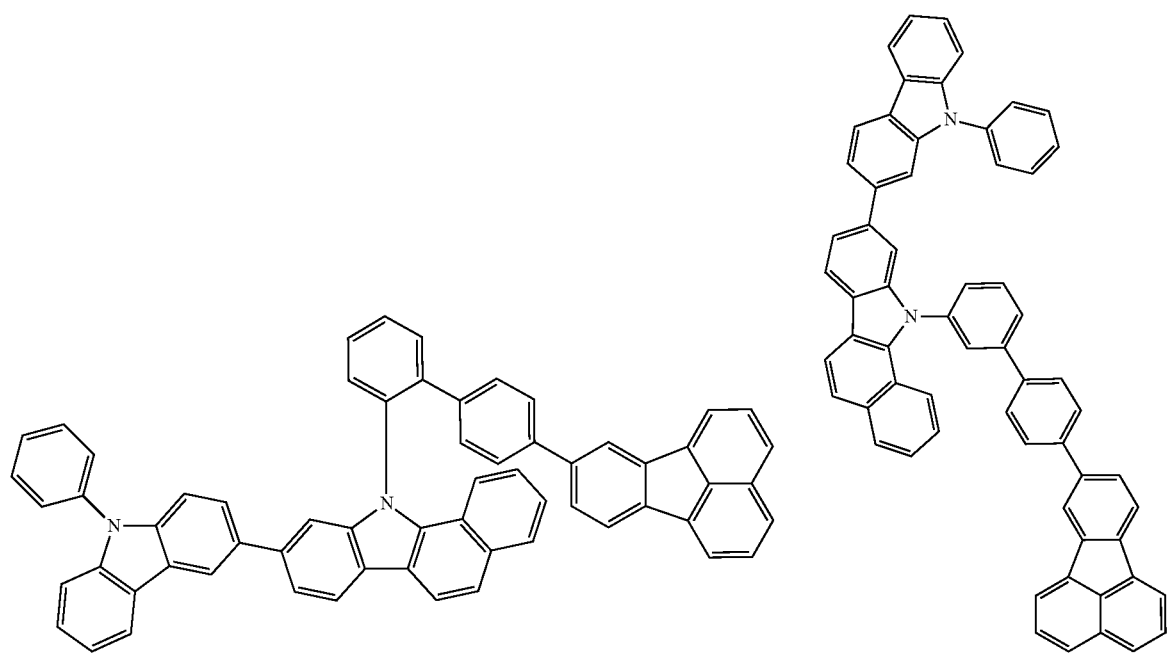

-continued
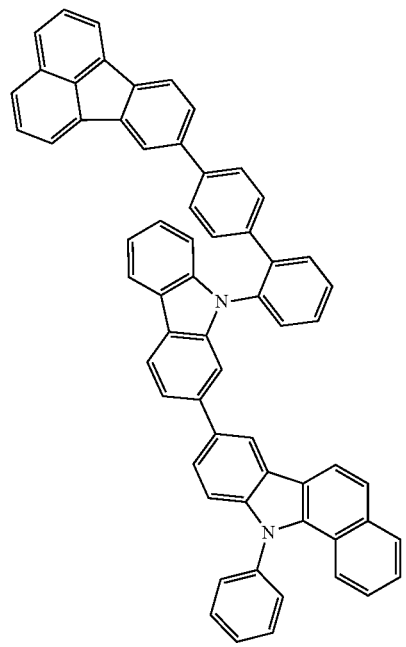
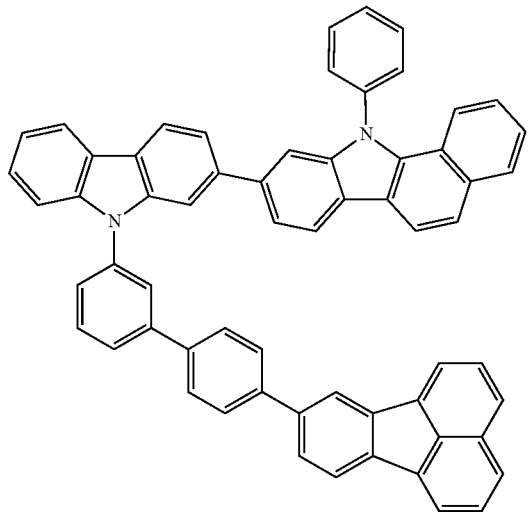
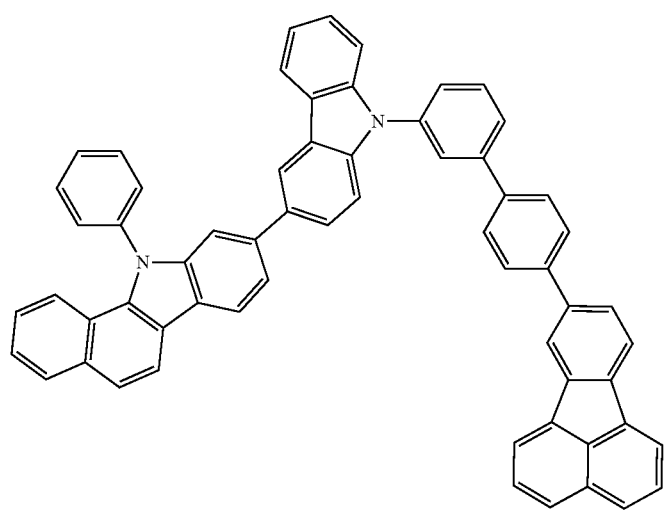
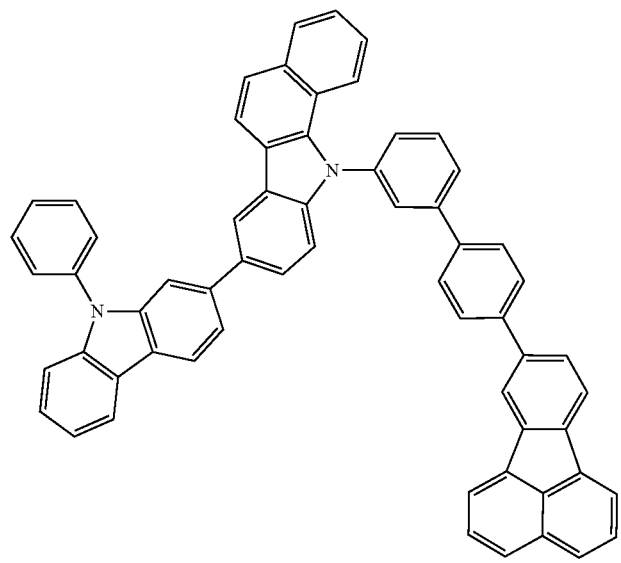

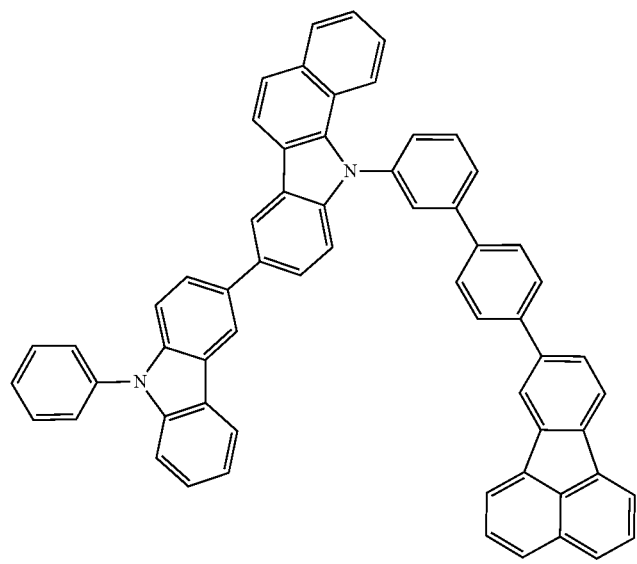
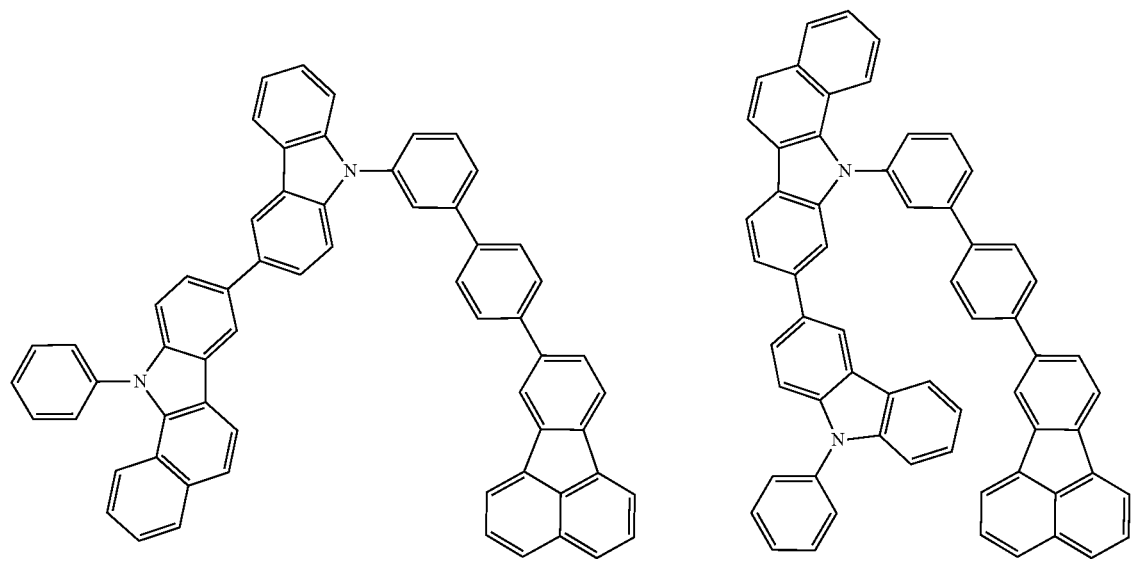
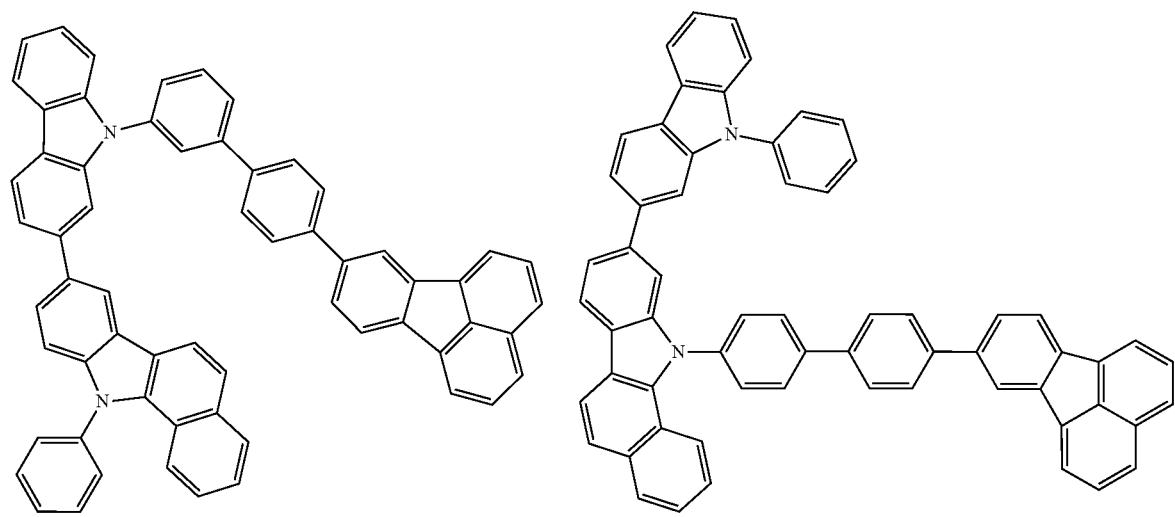

-continued
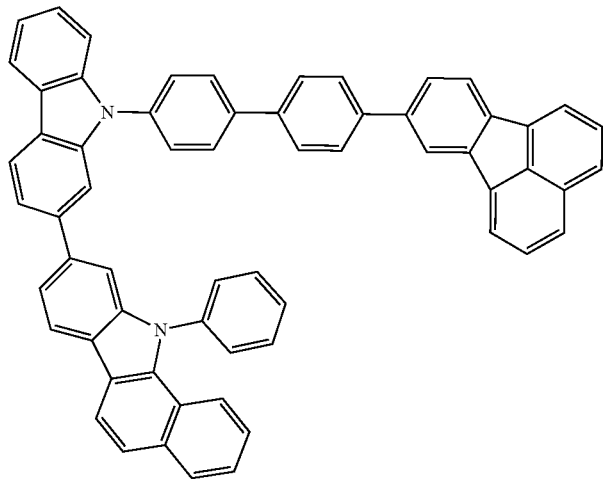
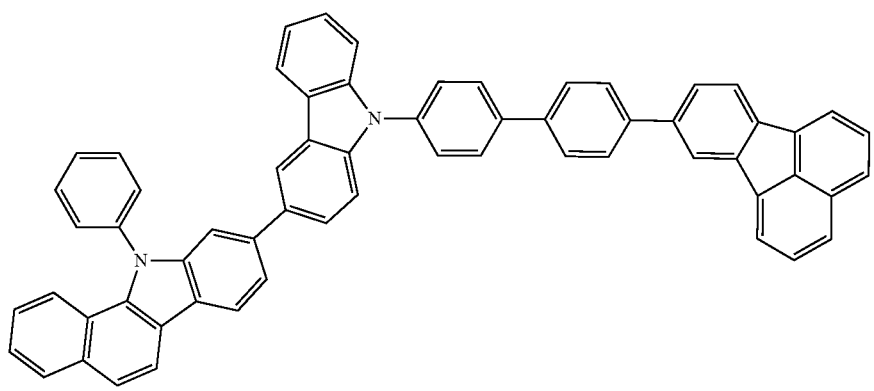
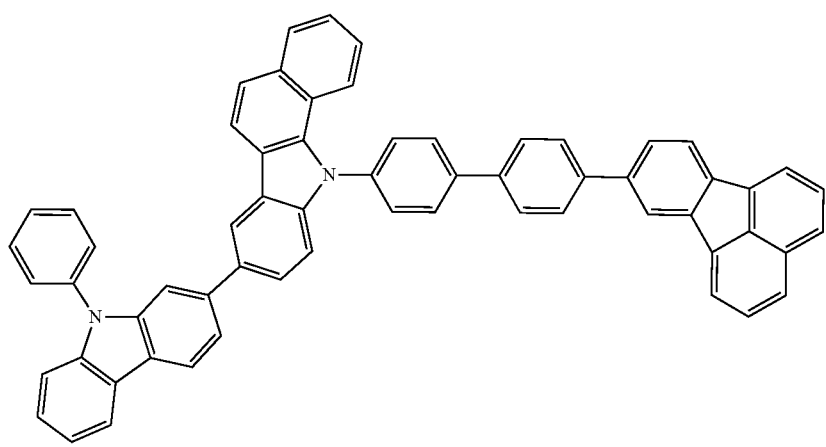

-continued
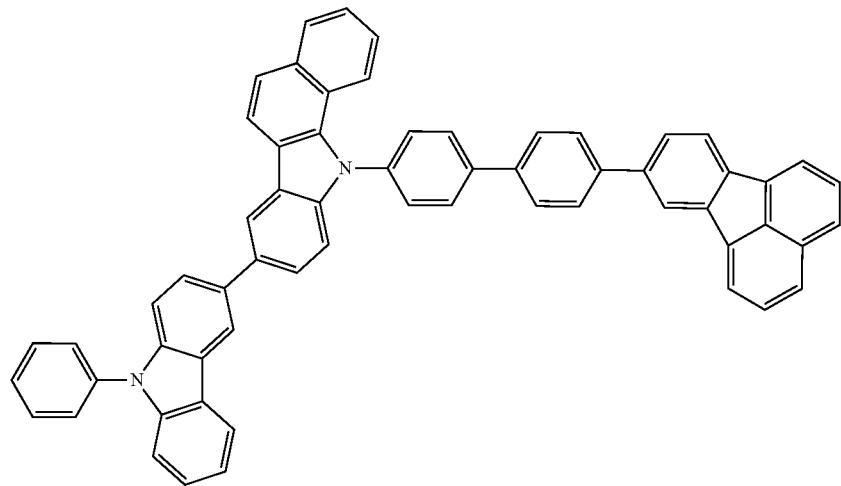
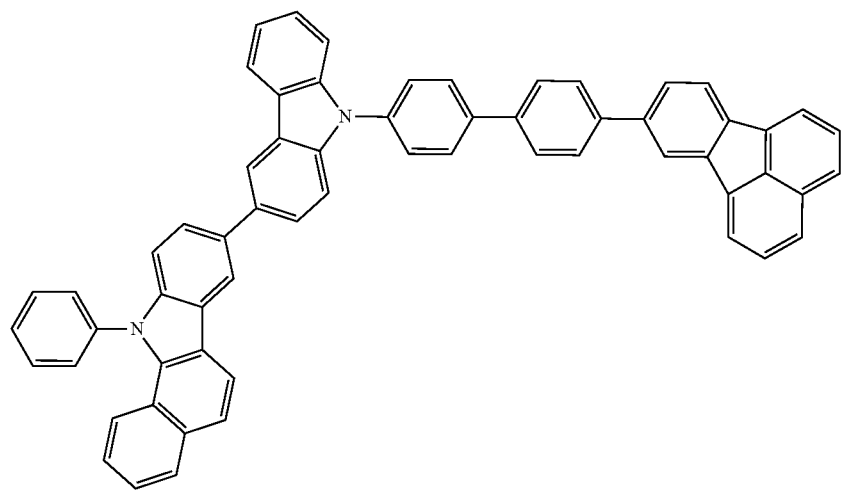
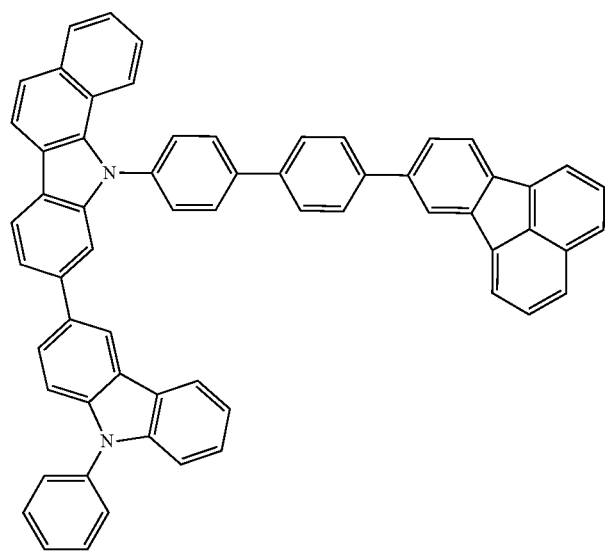

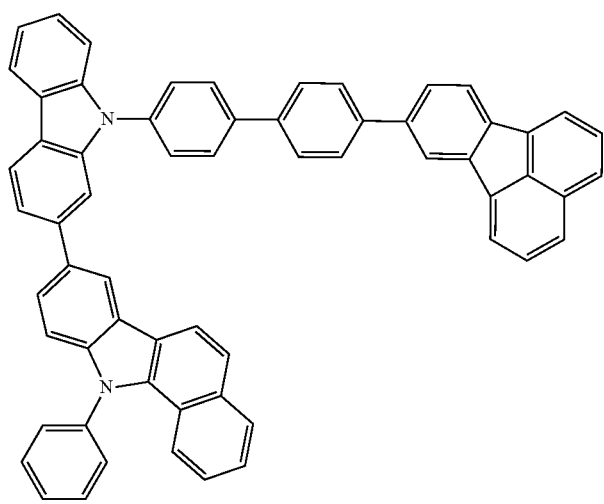

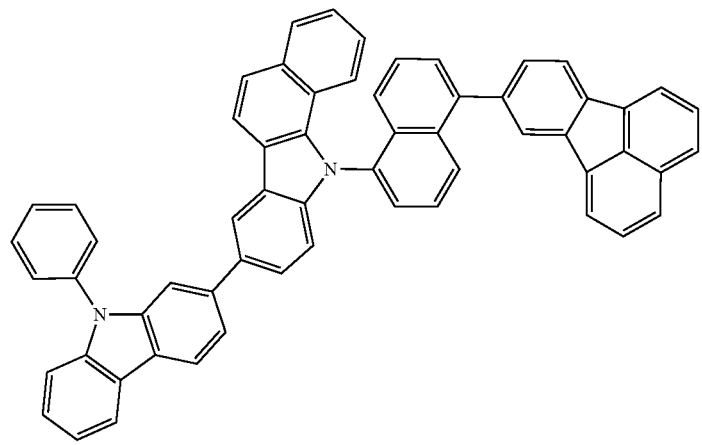
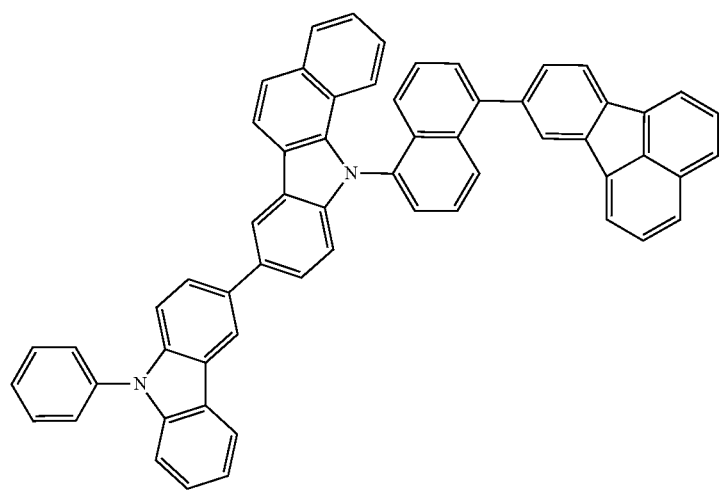
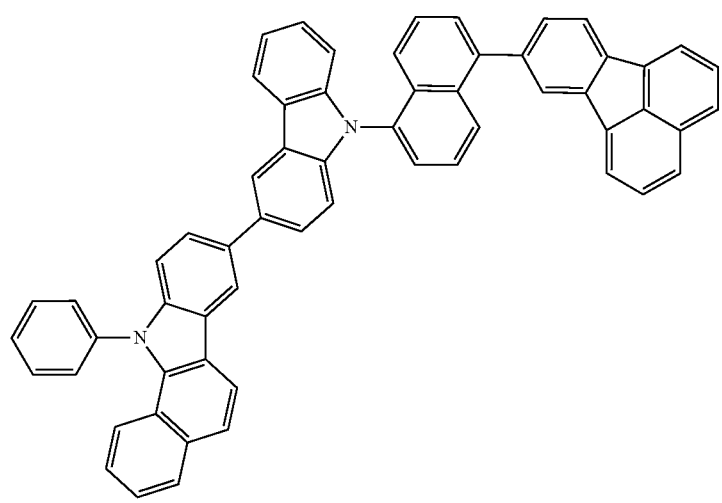

-continued
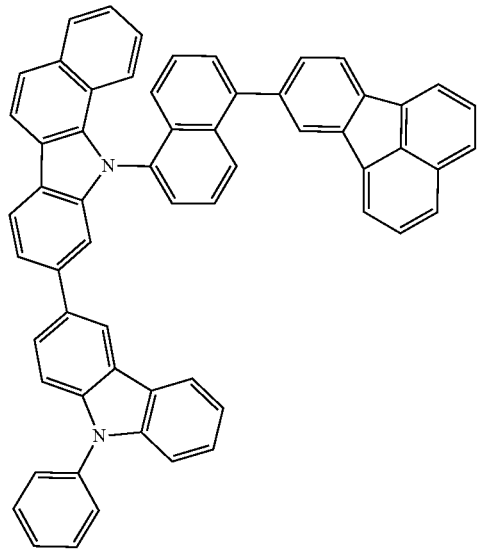
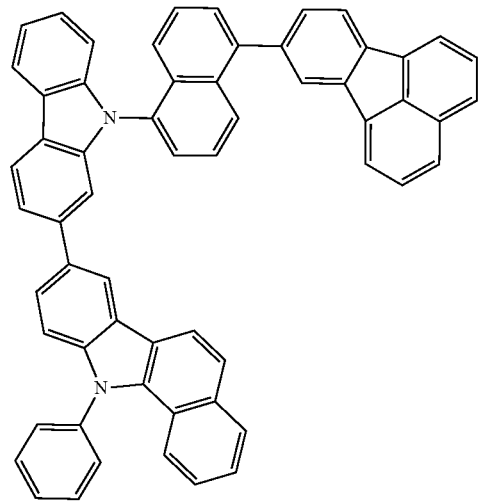
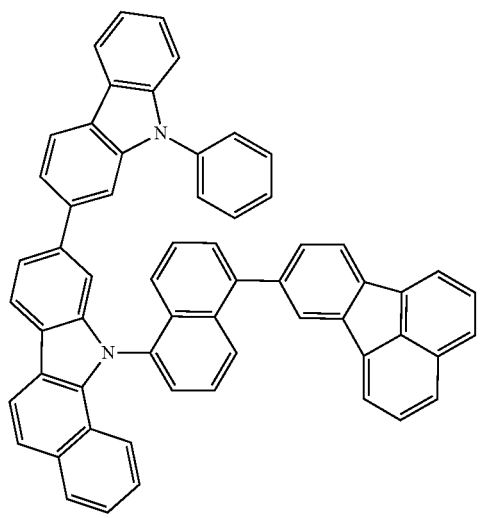
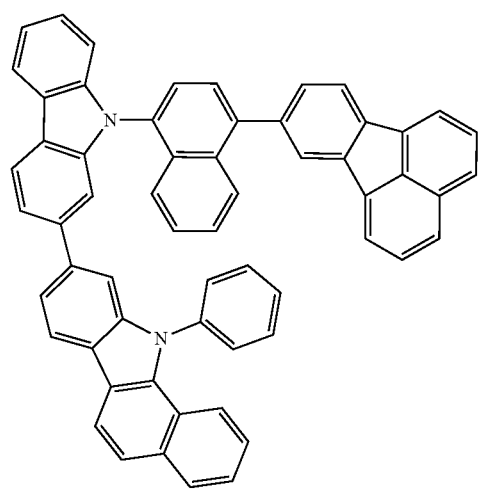
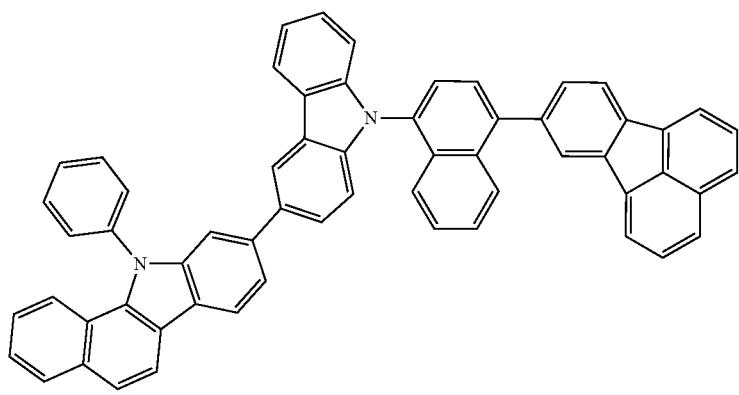

-continued
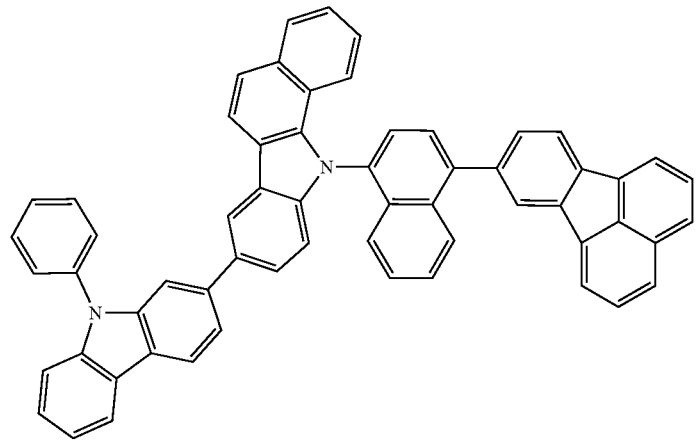
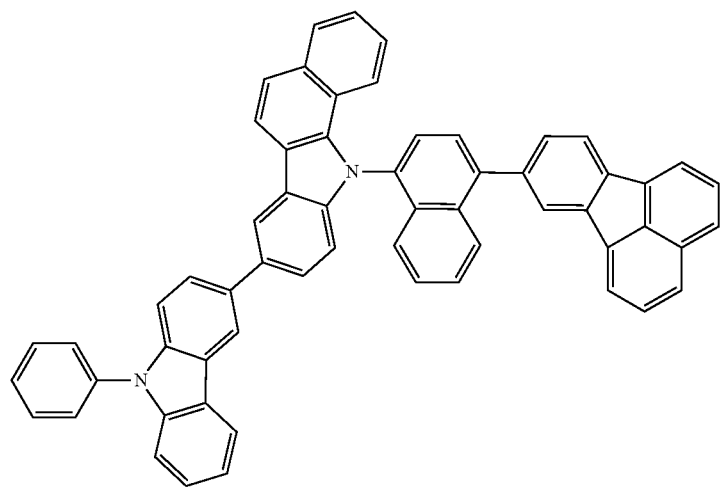
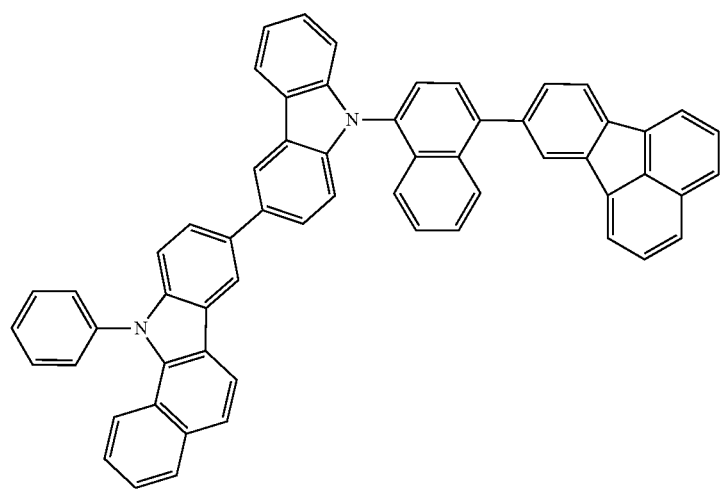

-continued
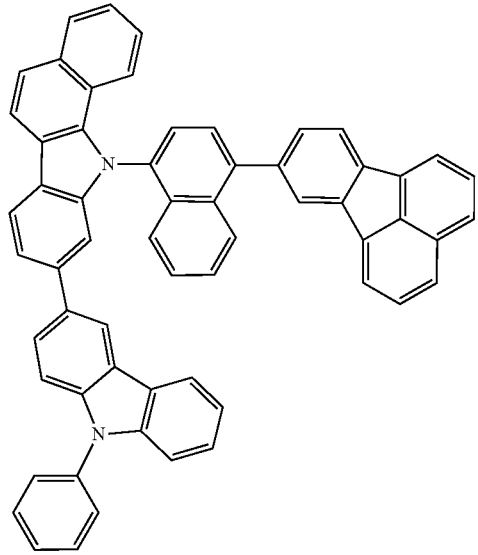
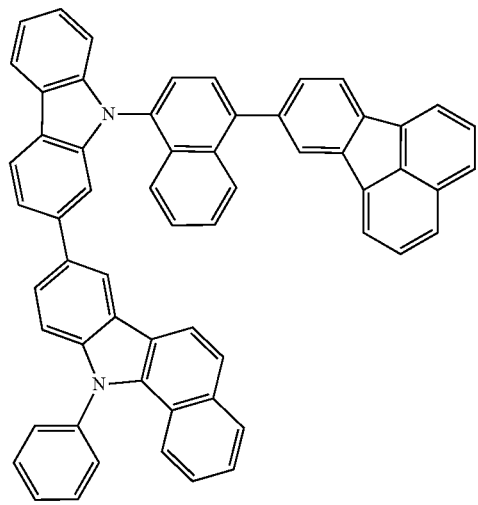
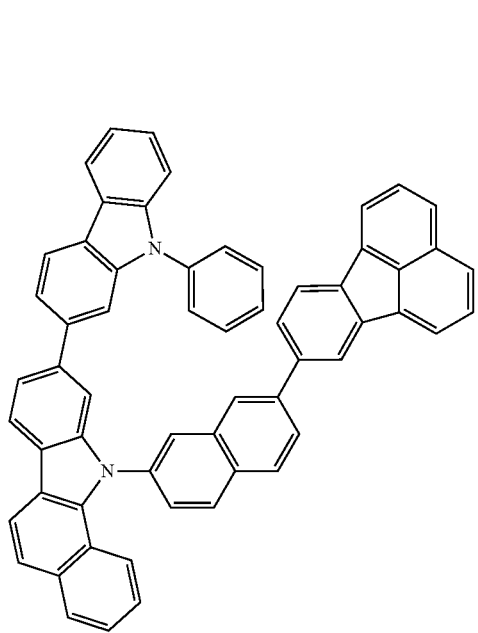
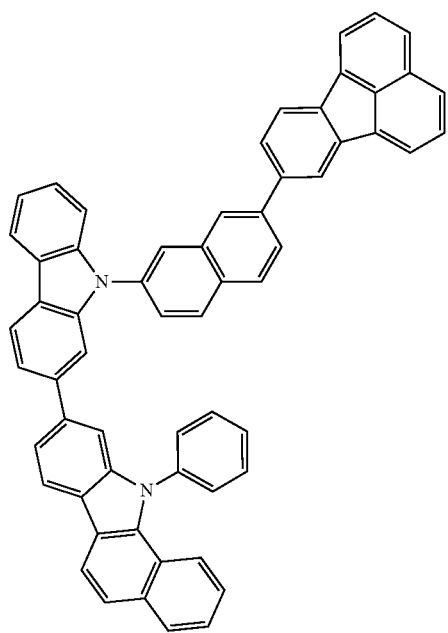

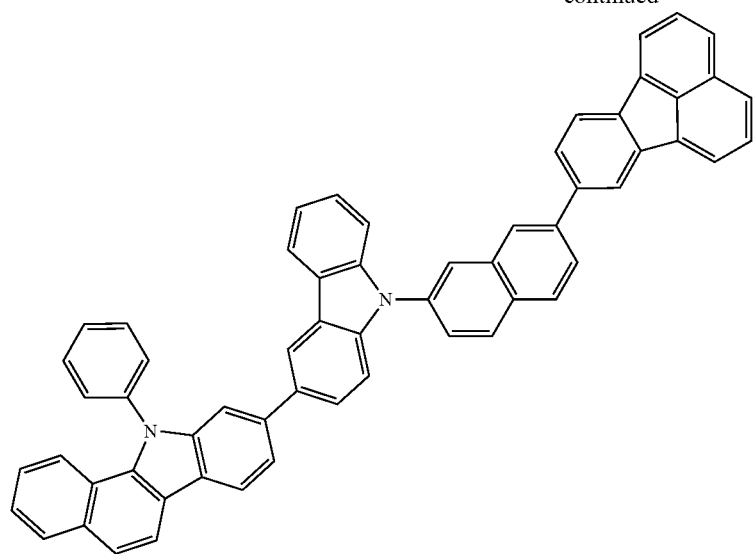
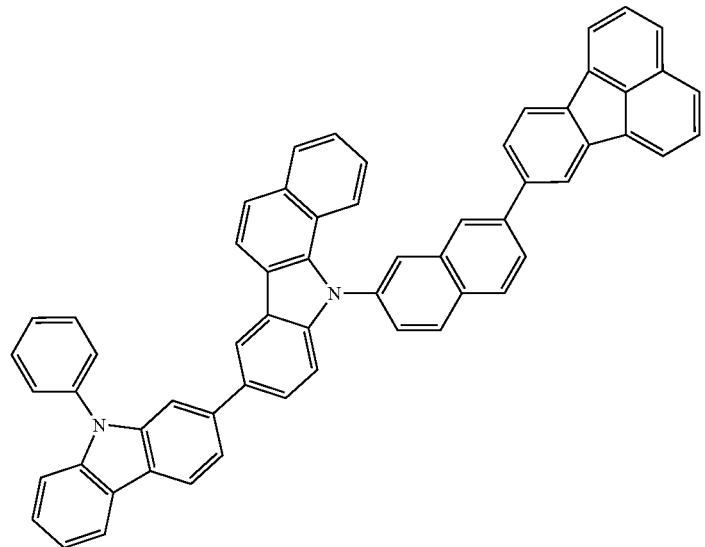
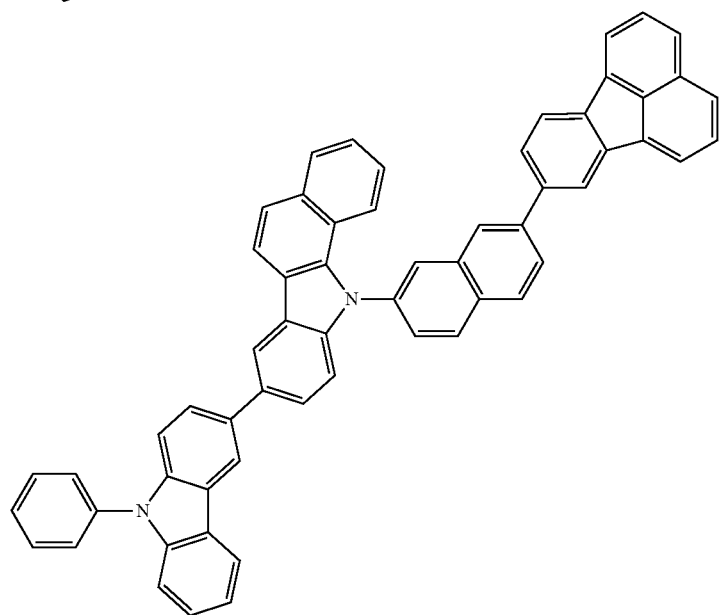

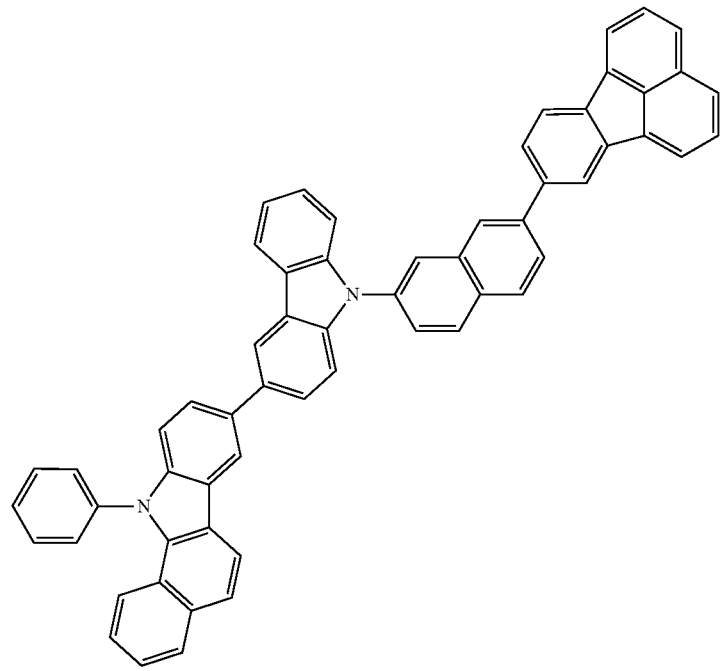
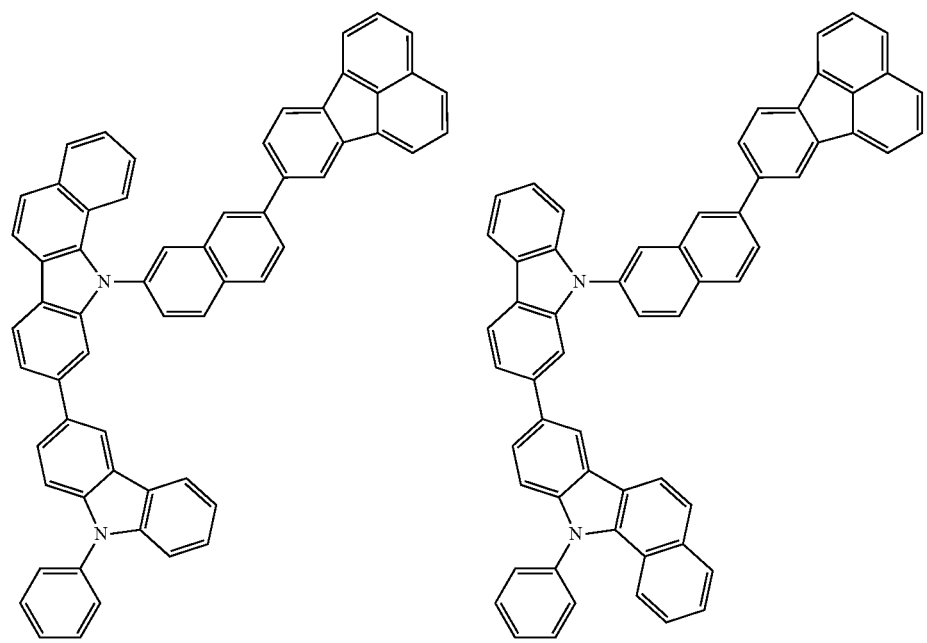

-continued
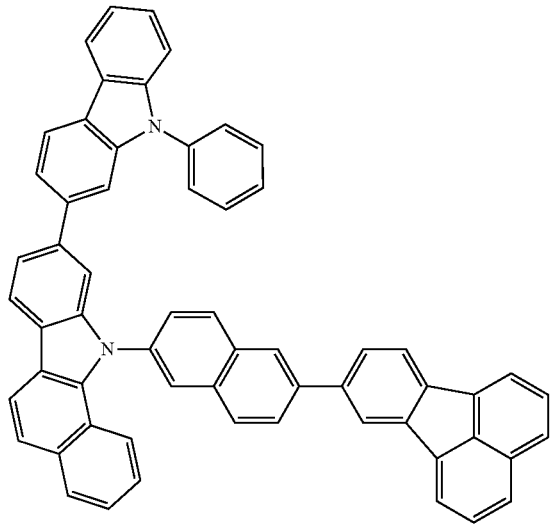
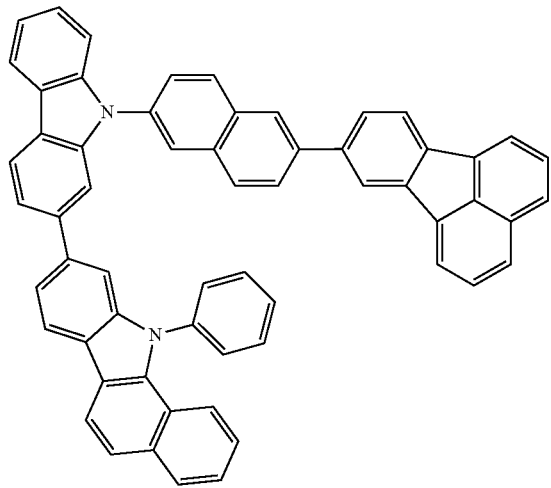
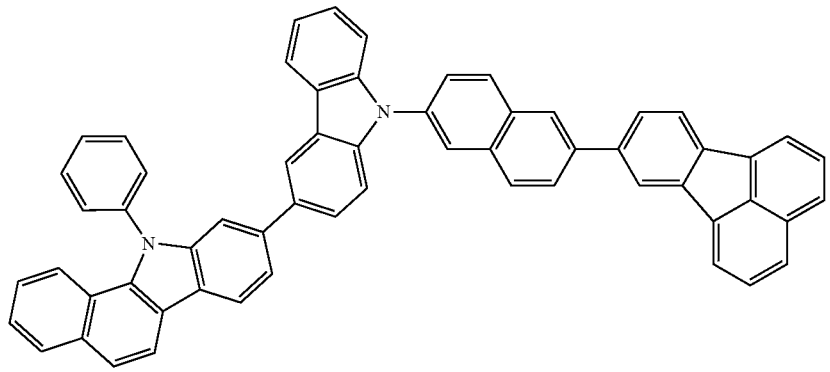
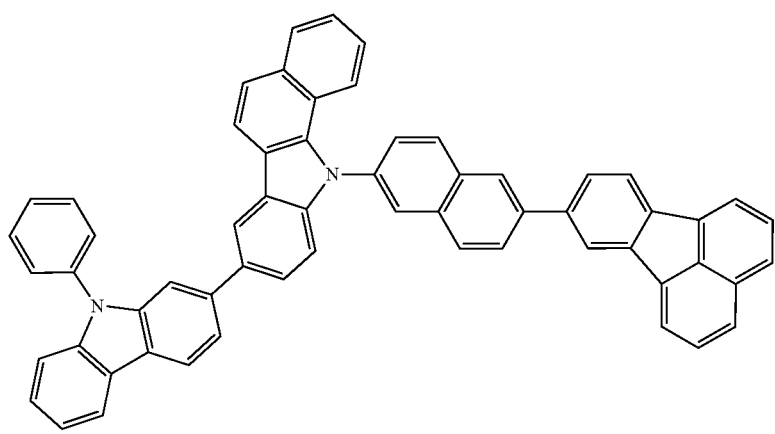

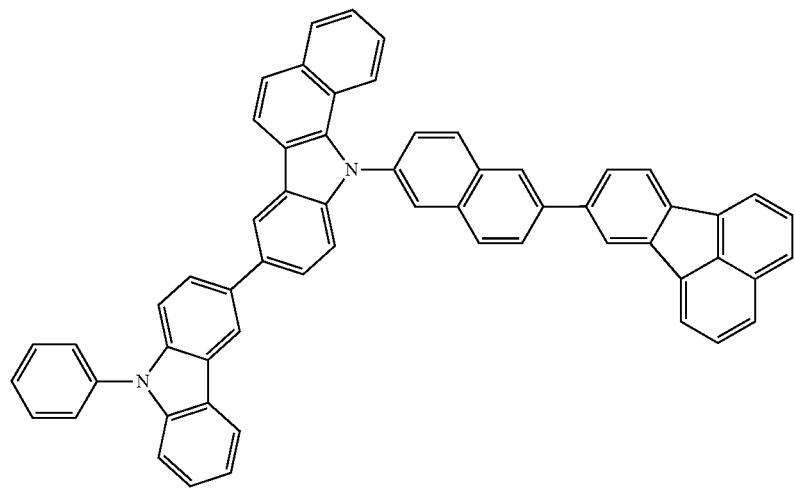
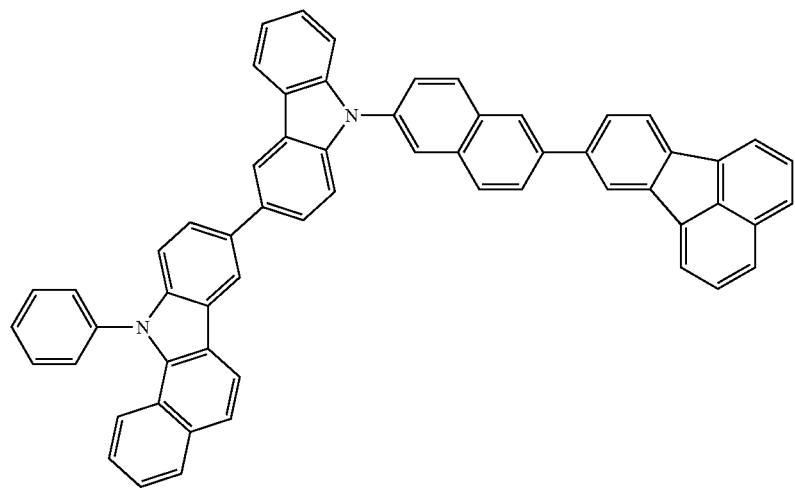
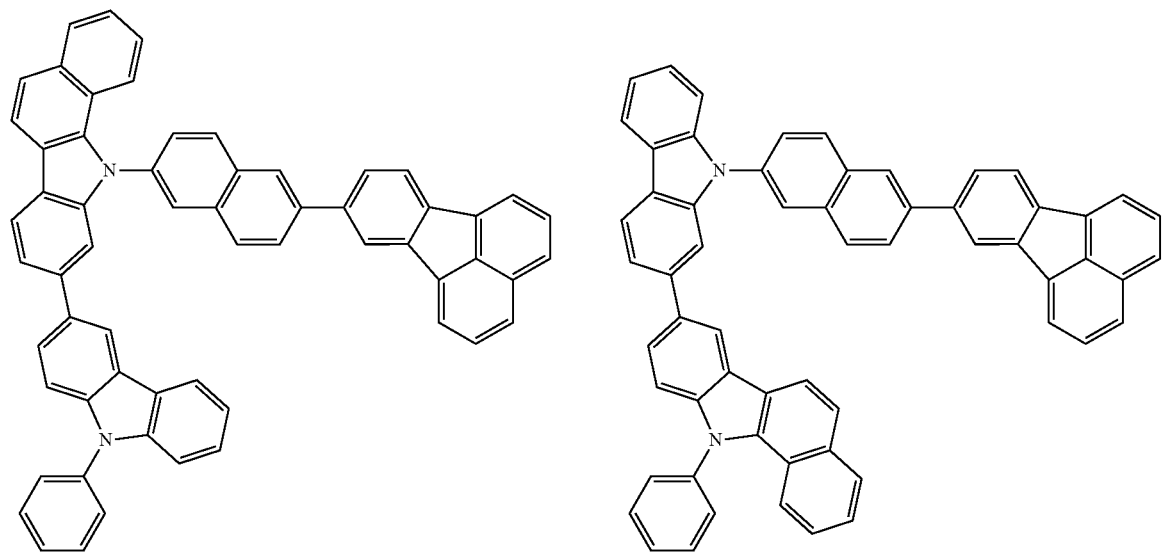

-continued
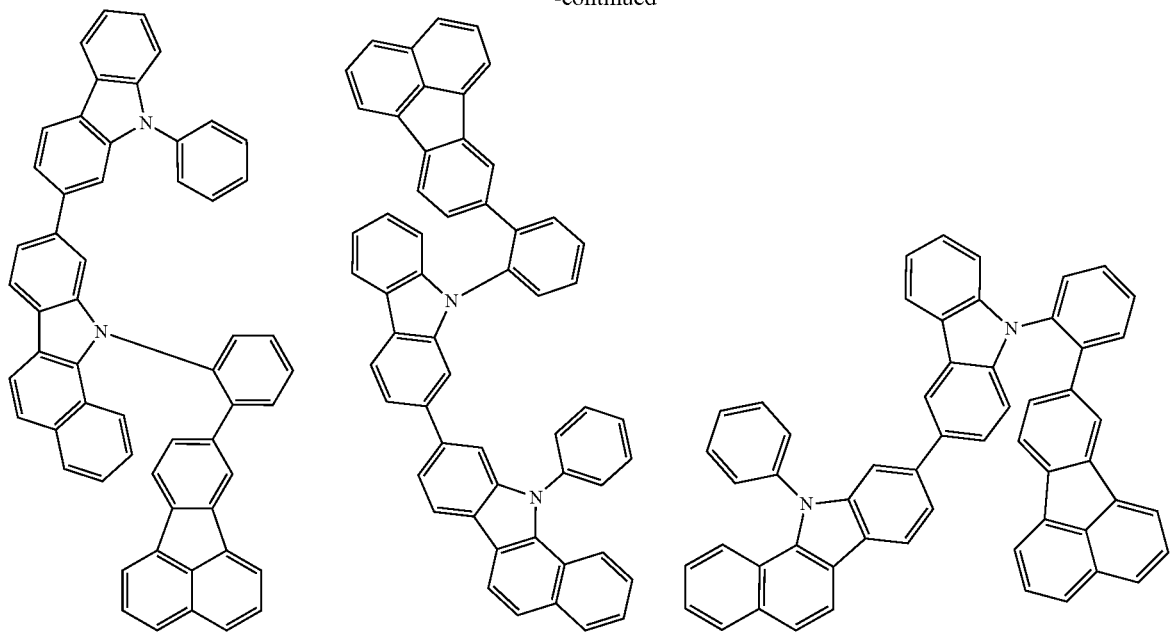
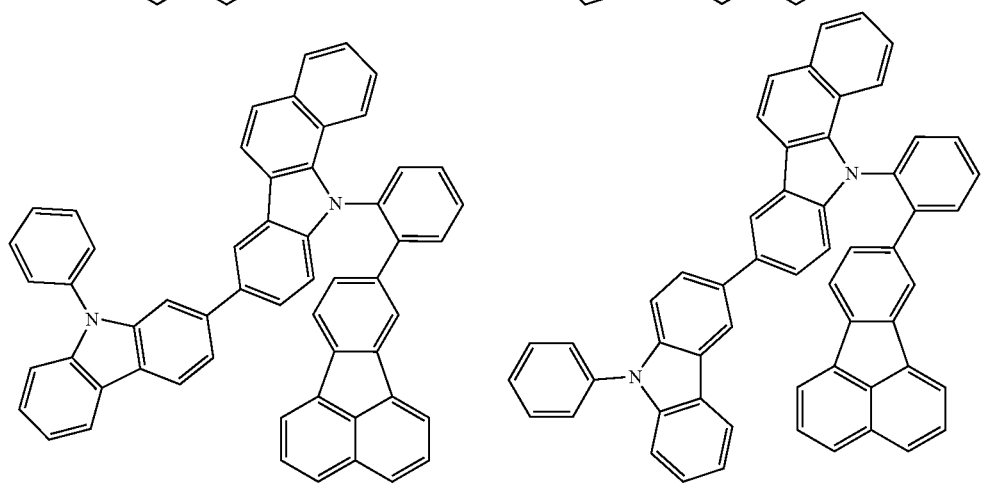
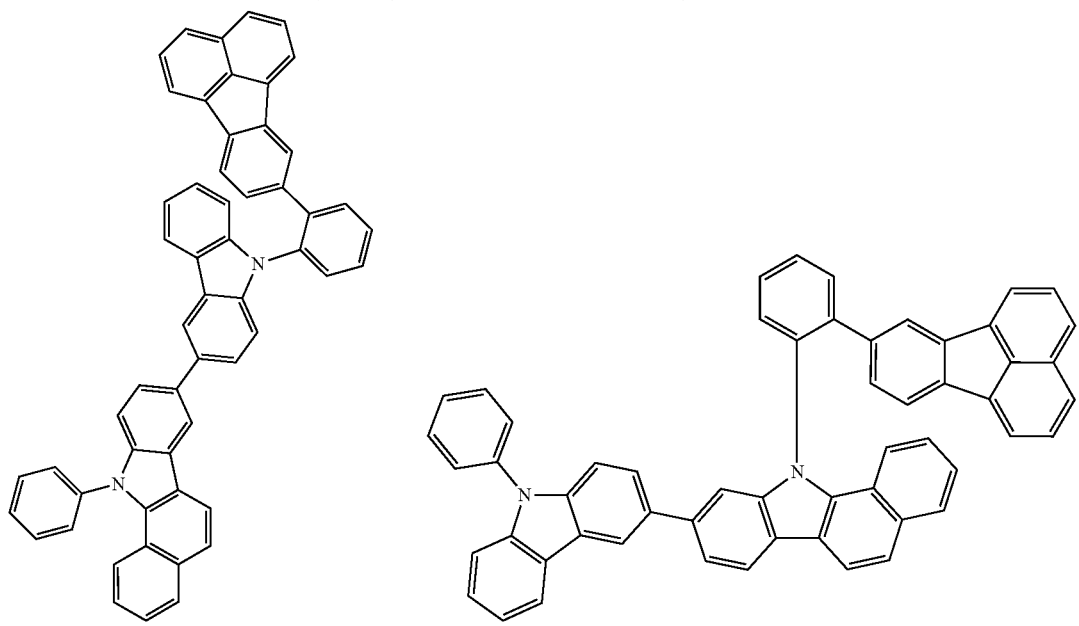

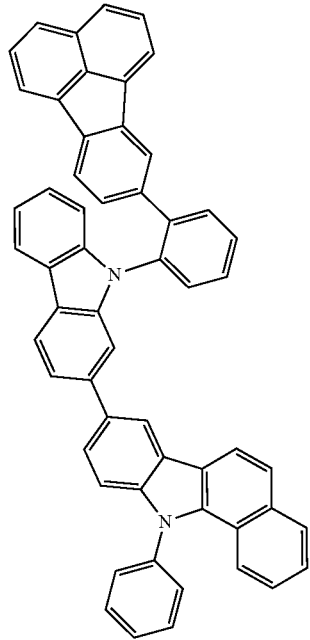
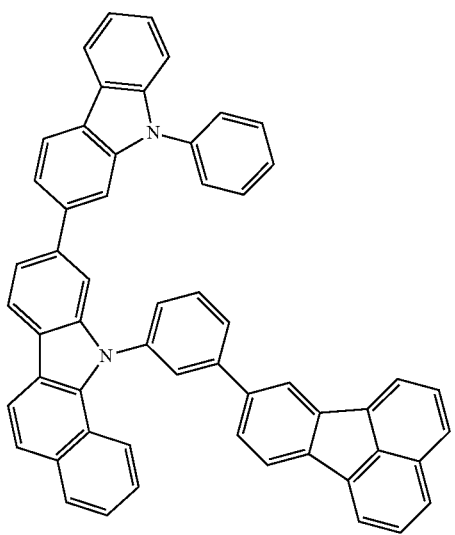
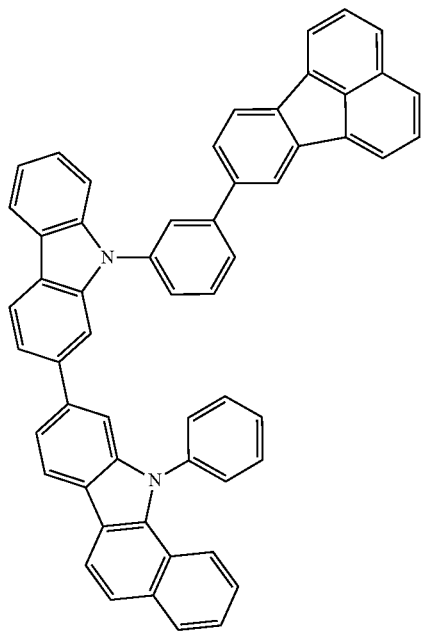
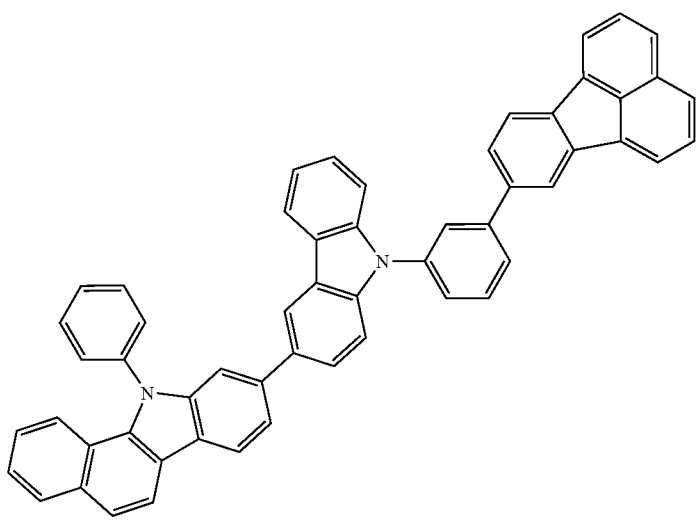

-continued
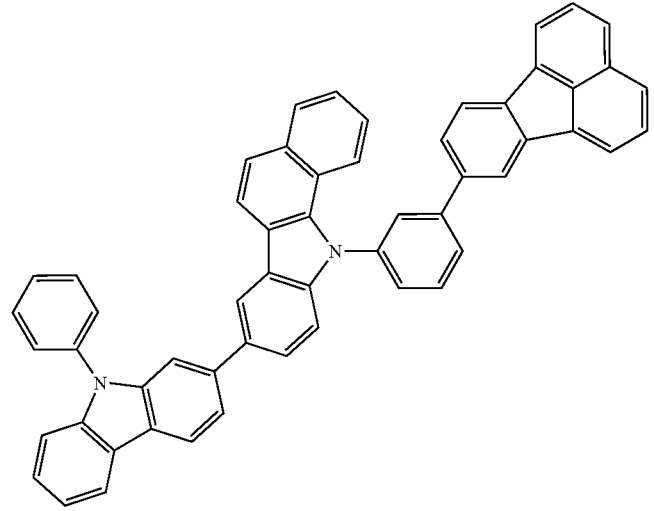
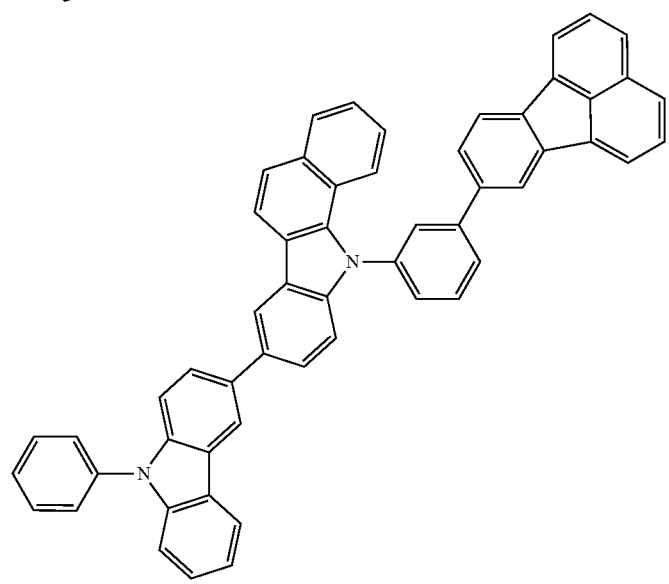
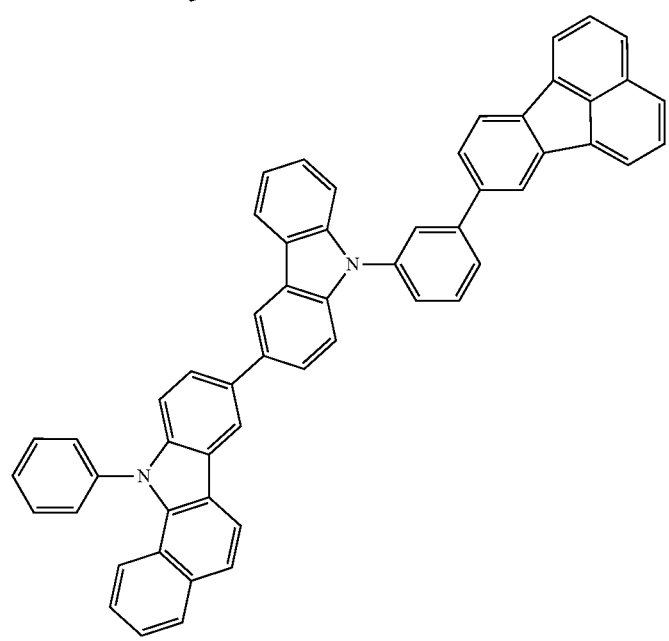

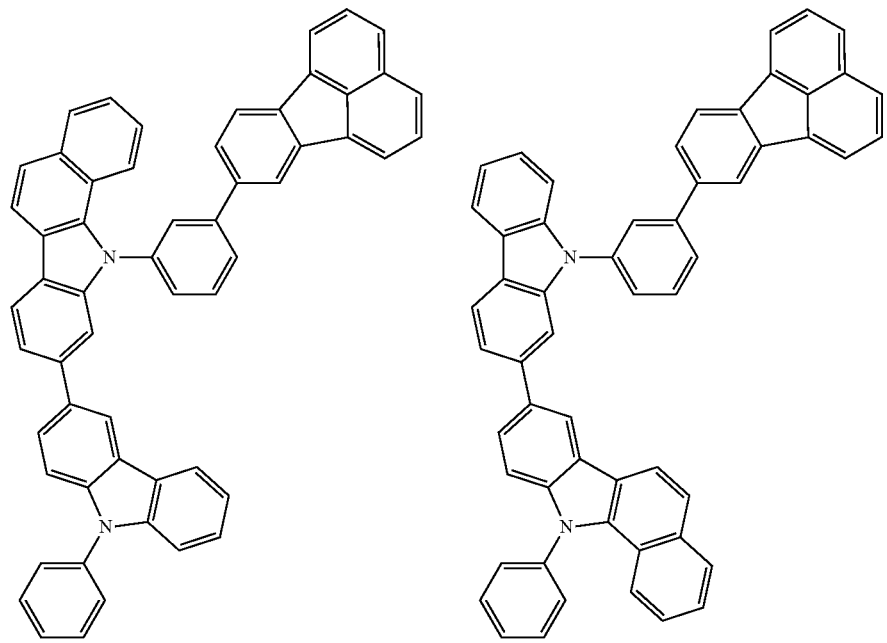
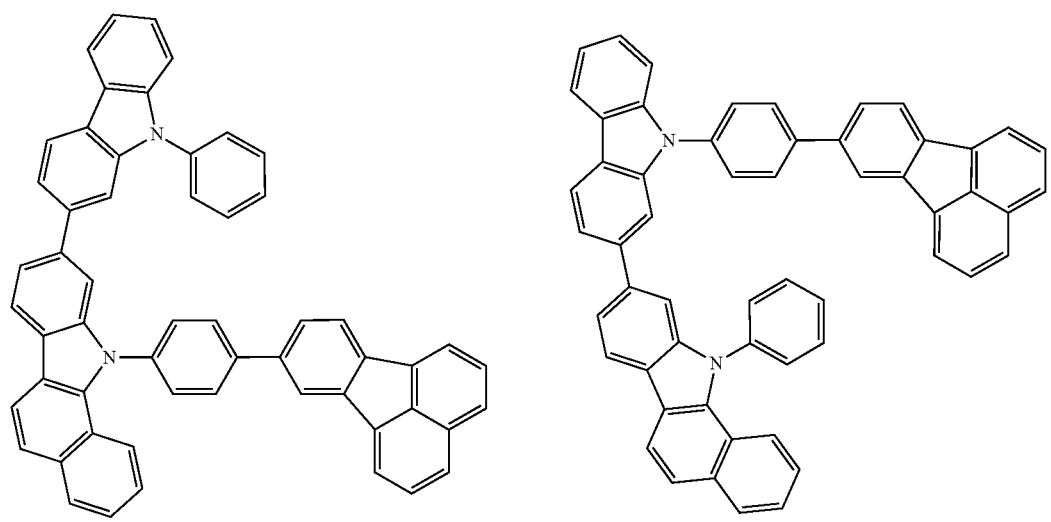
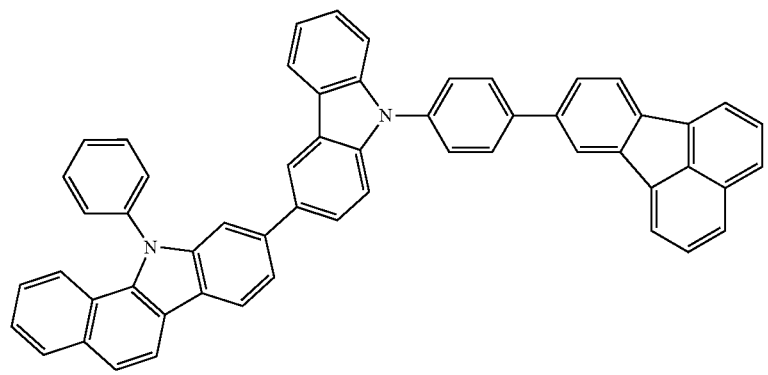

-continued
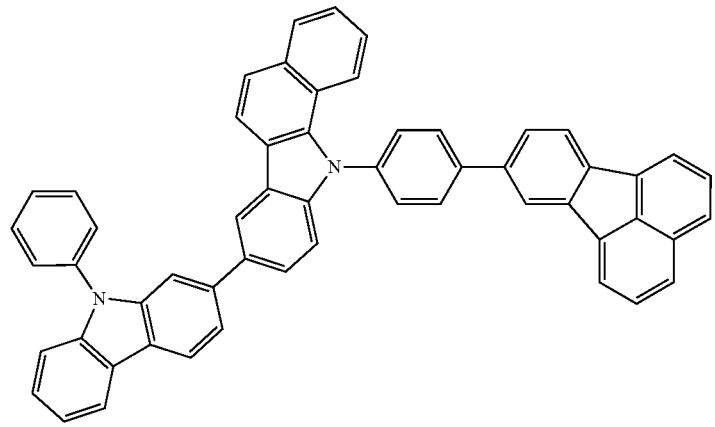
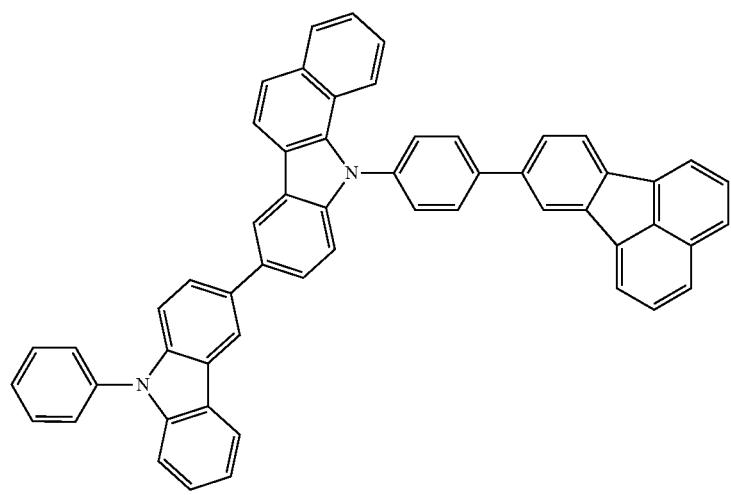
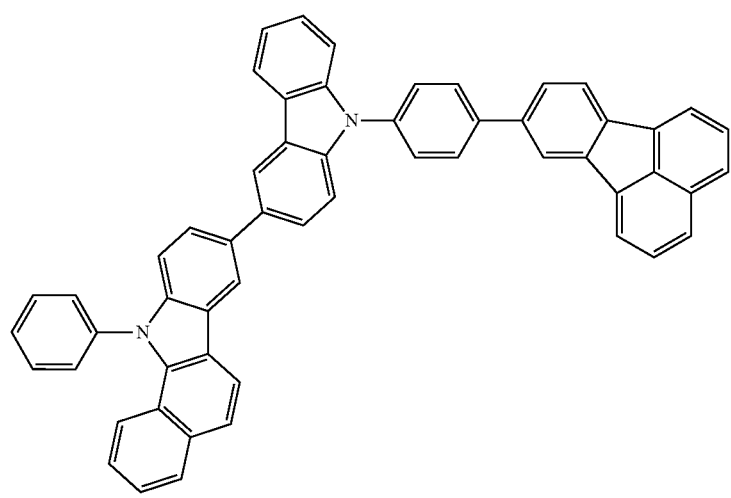

-continued
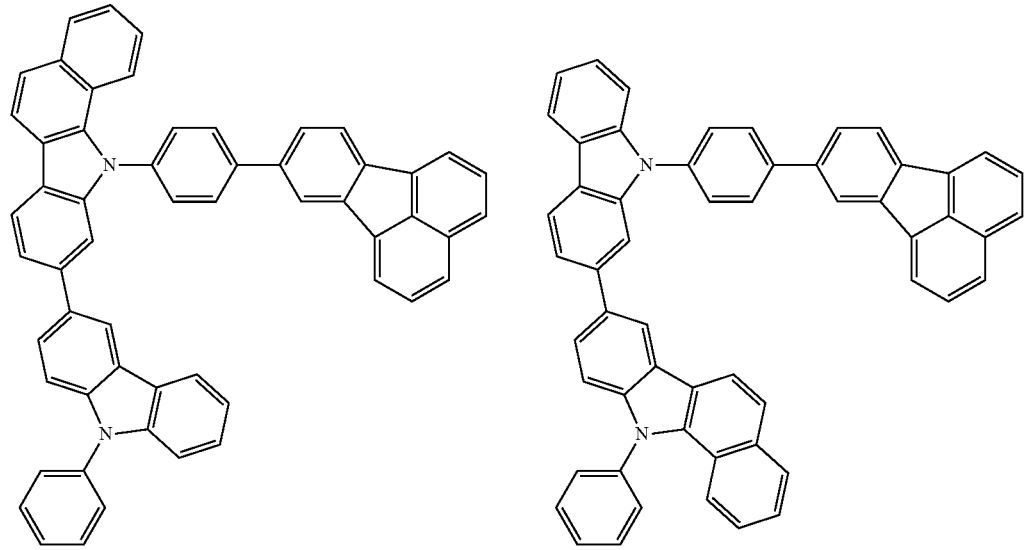
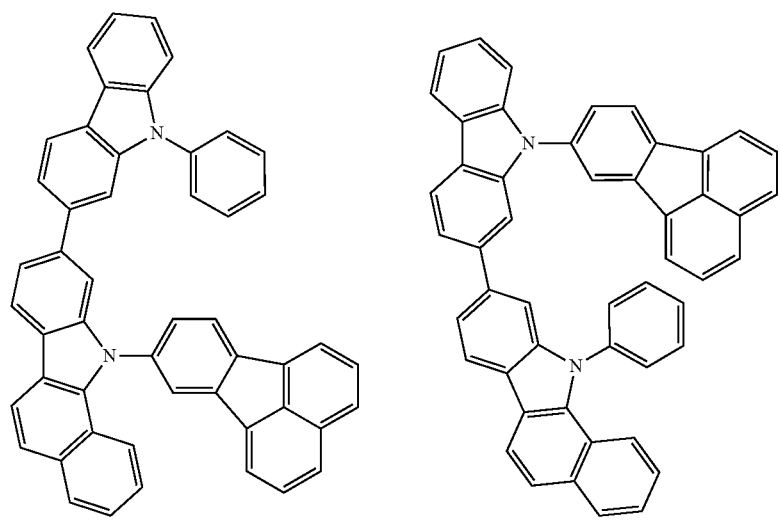
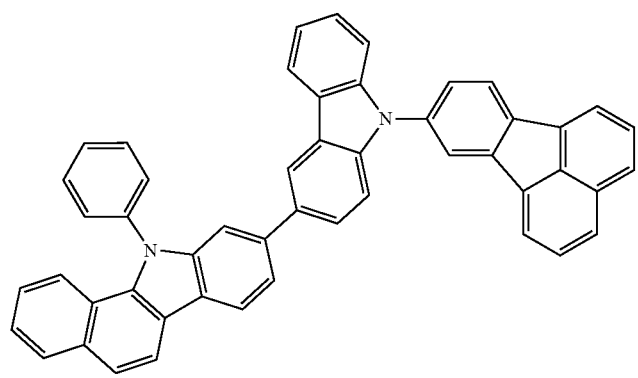

-continued
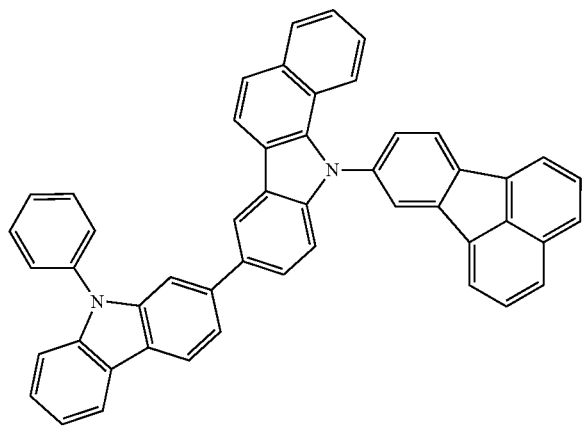
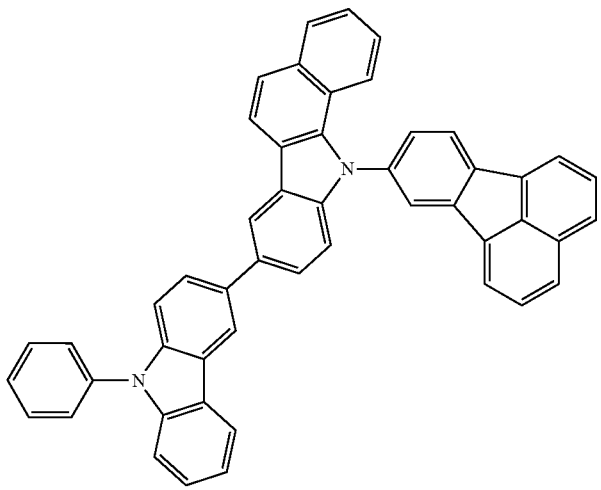
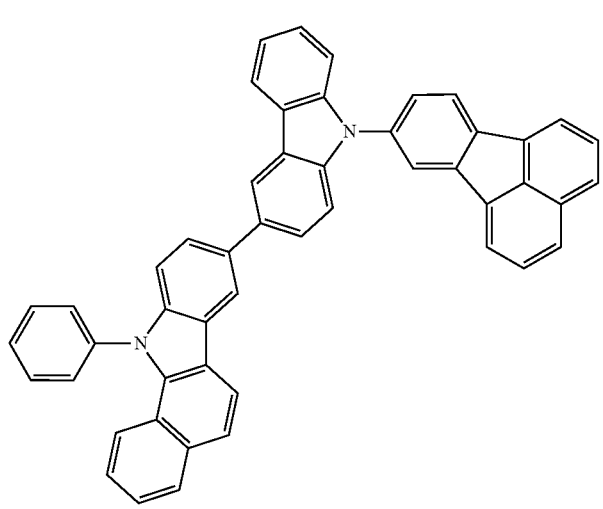
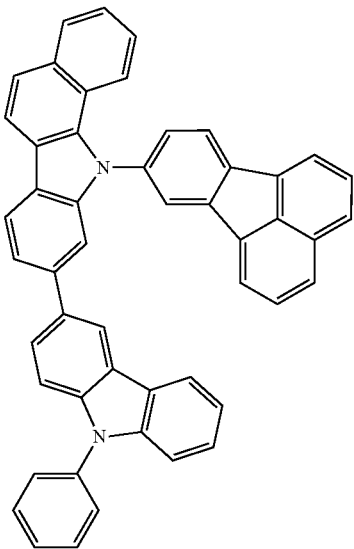
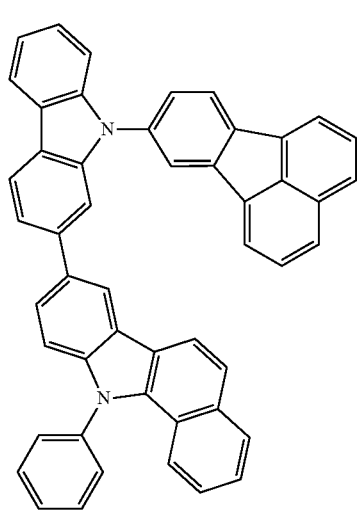
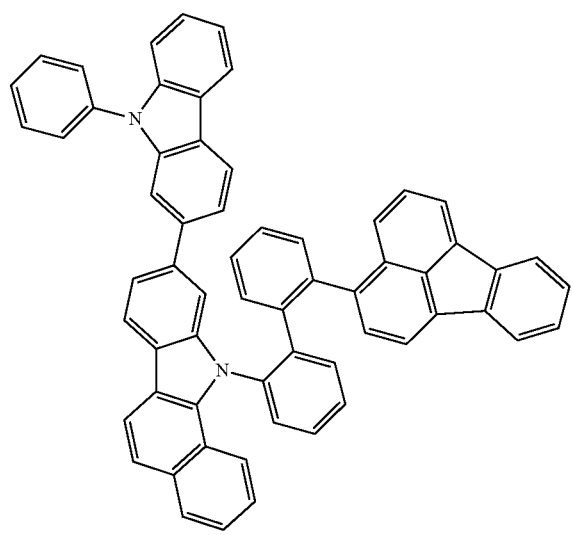

-continued
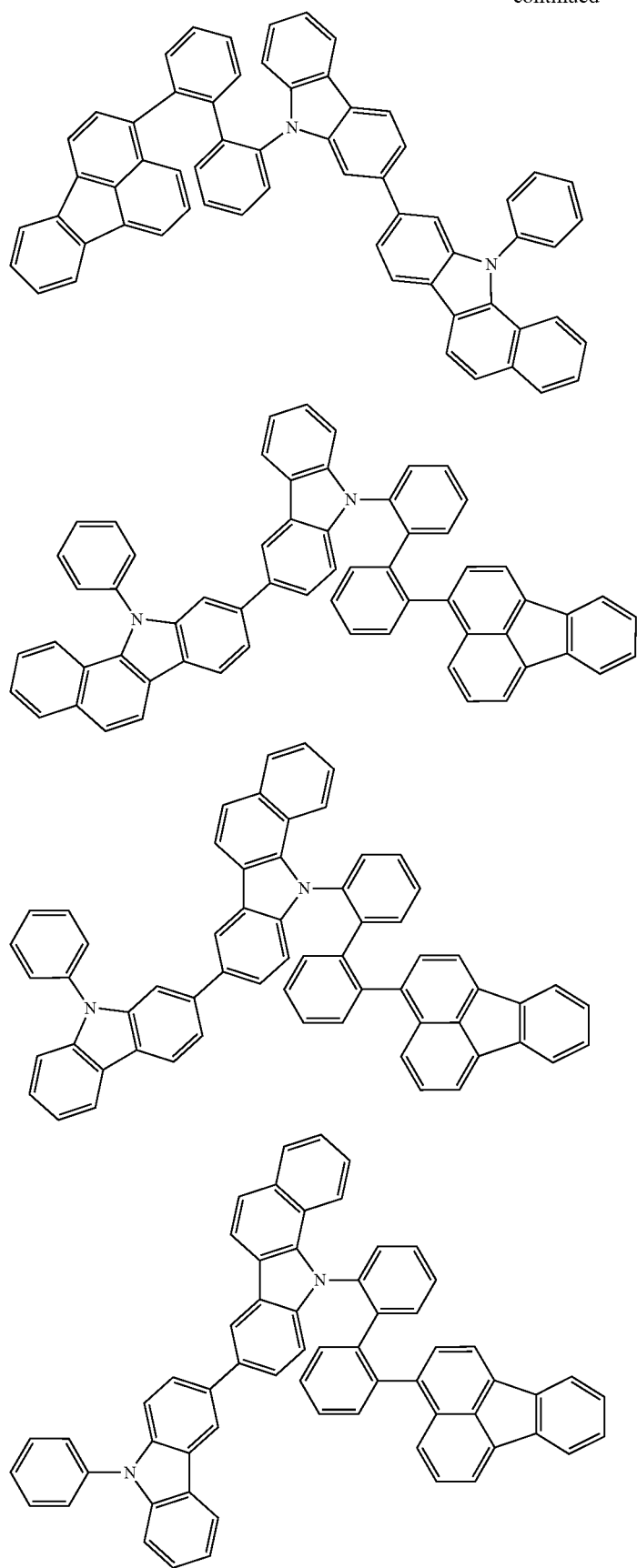

-continued
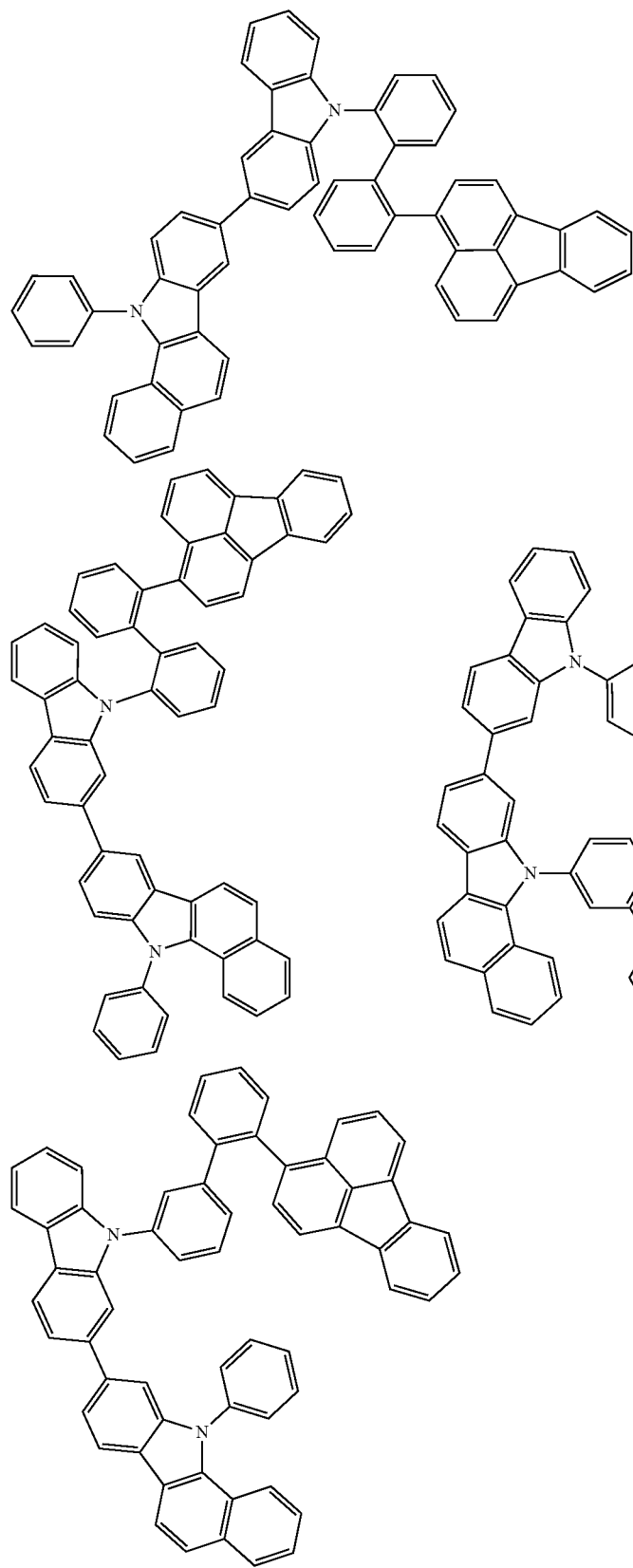
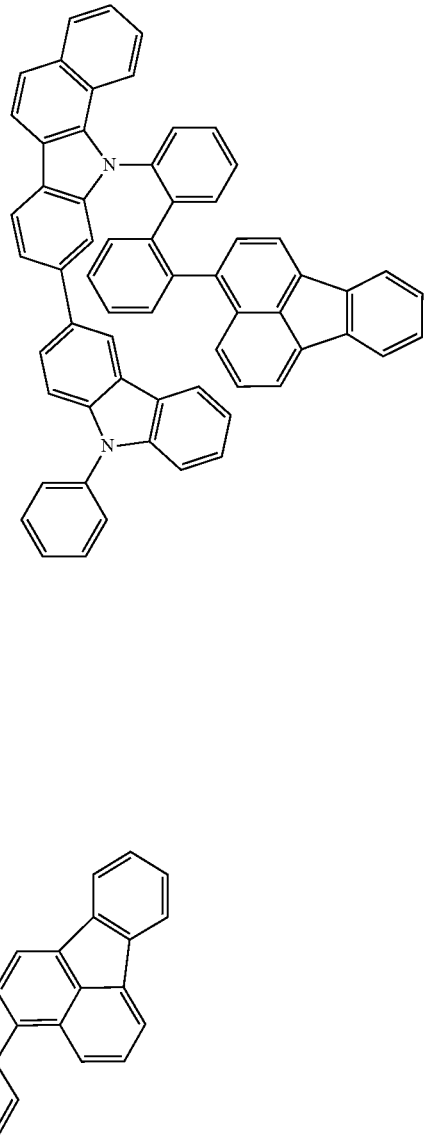

-continued
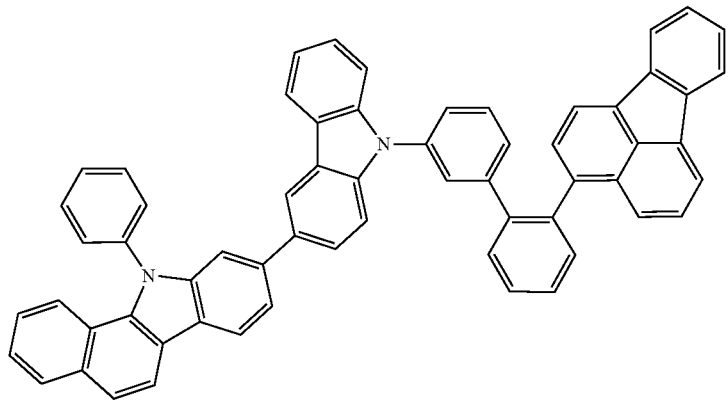
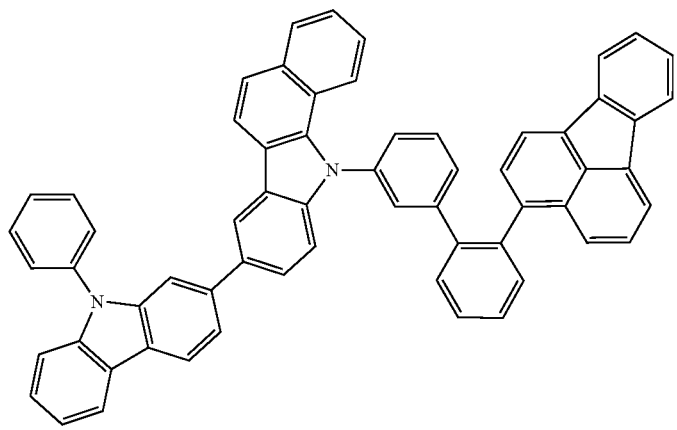
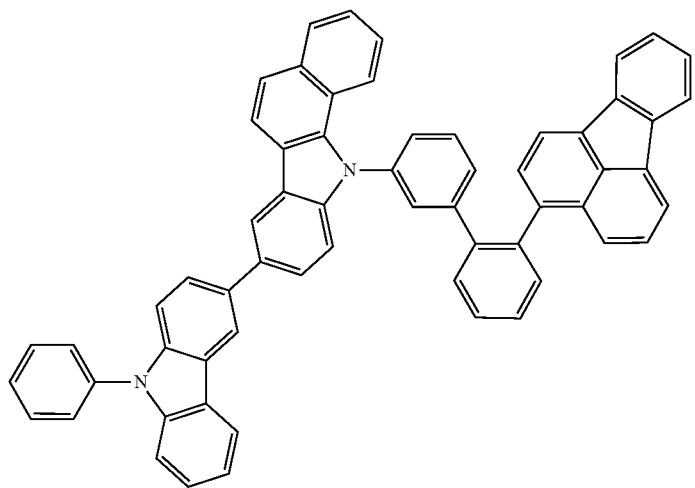

-continued
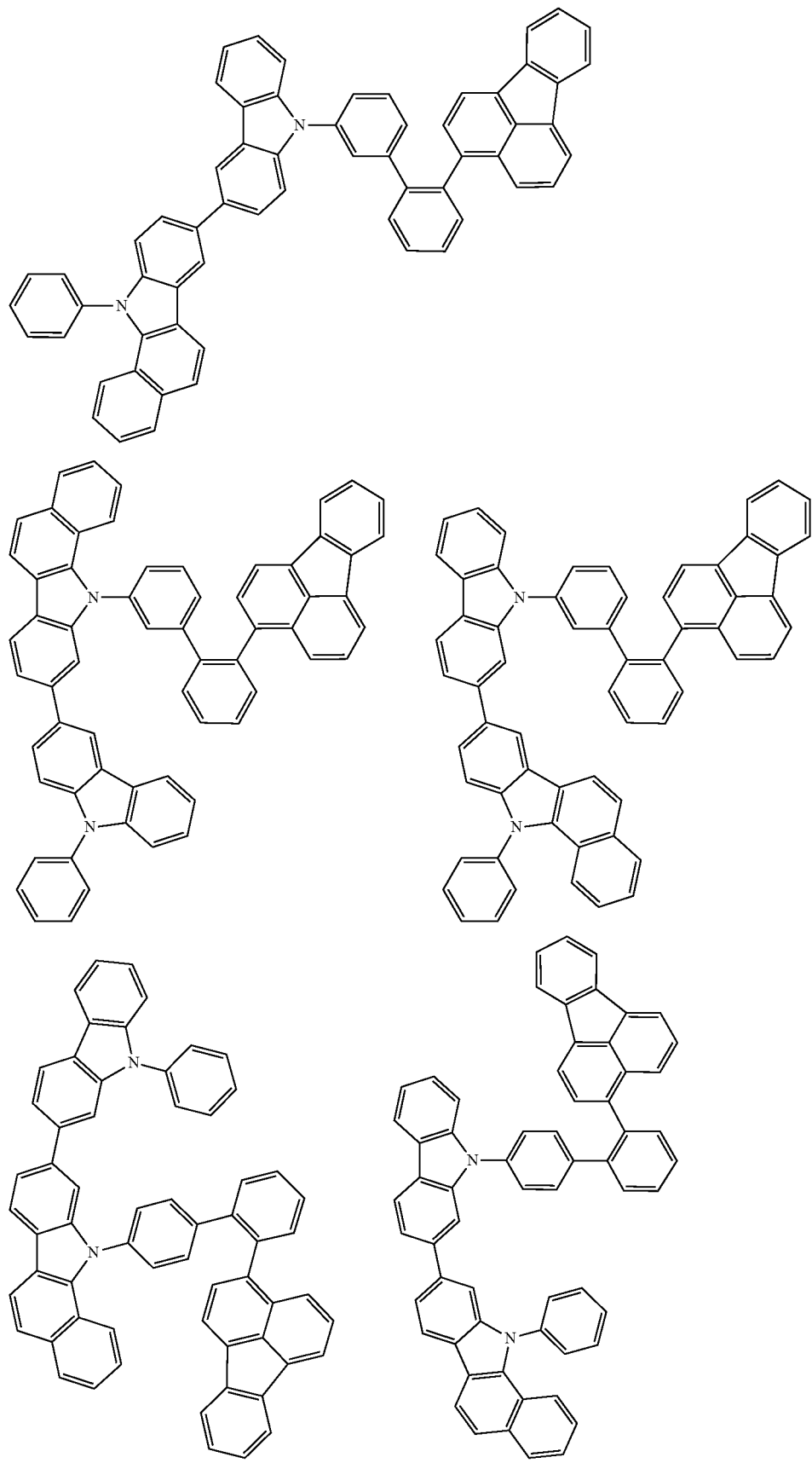

-continued
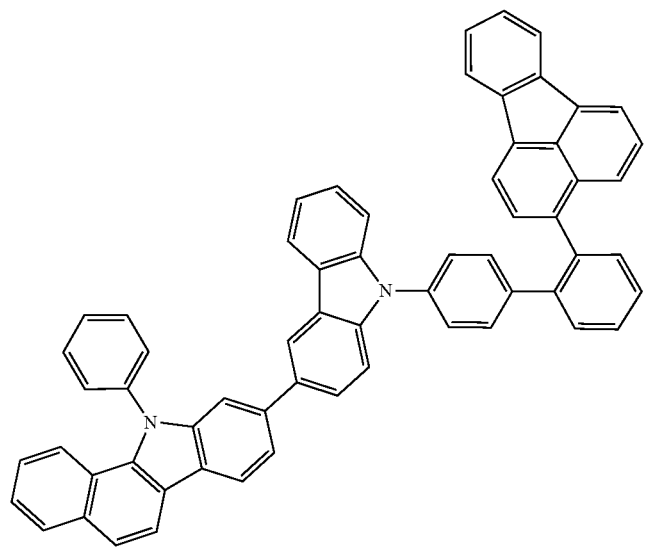
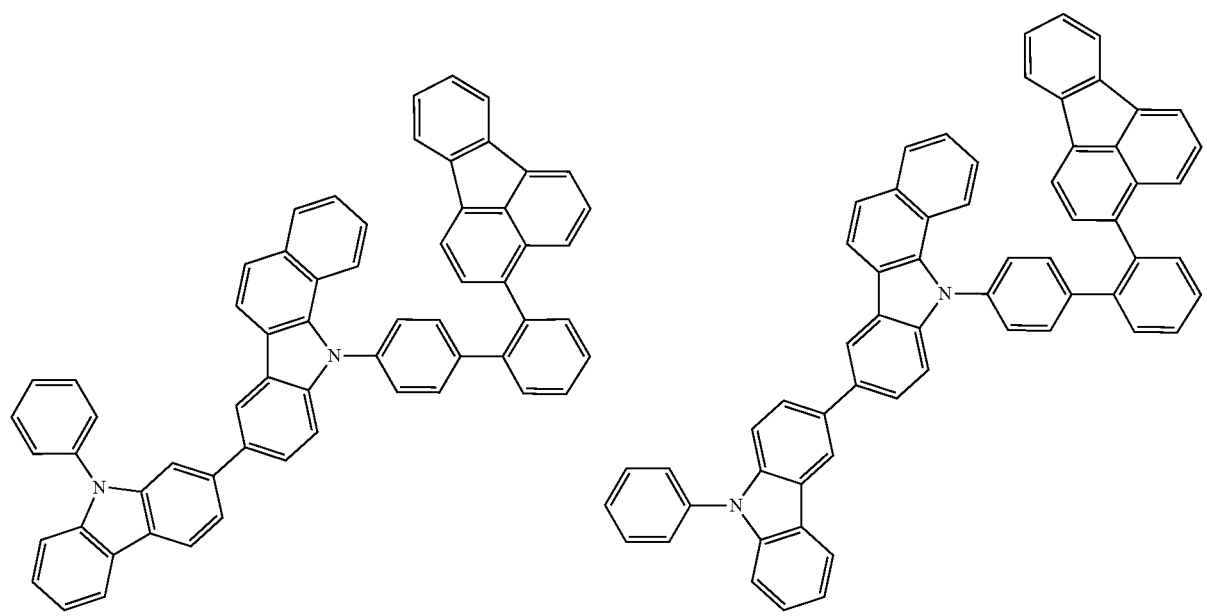

-continued
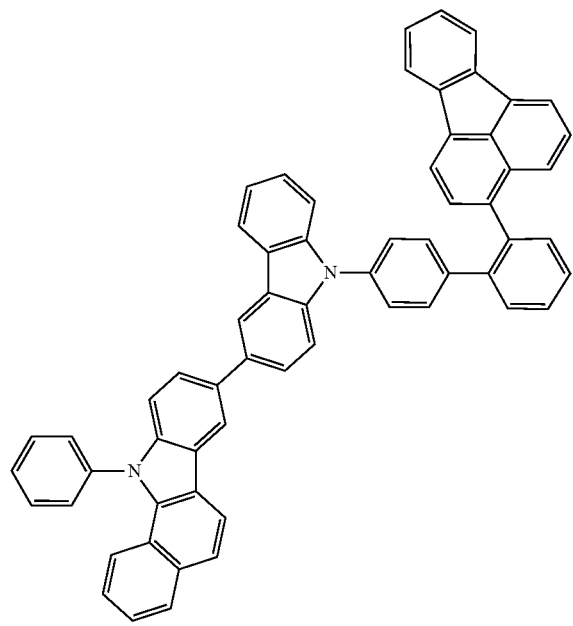
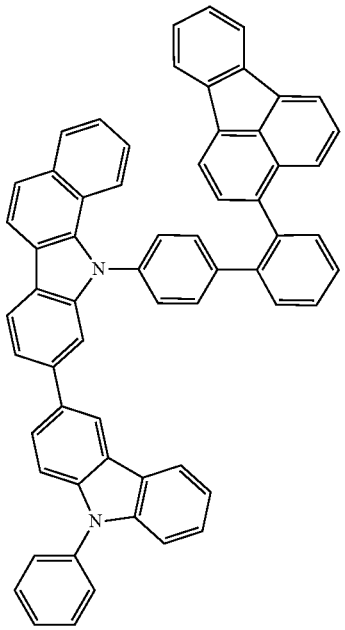
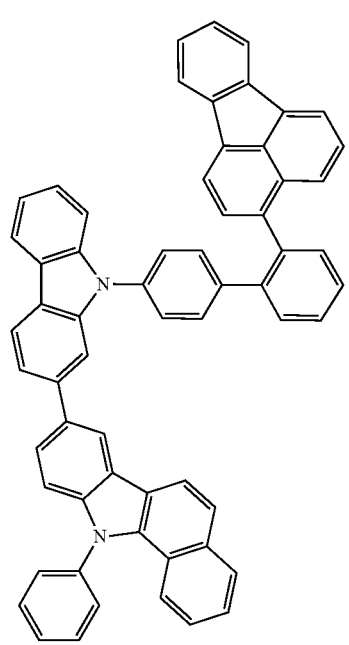
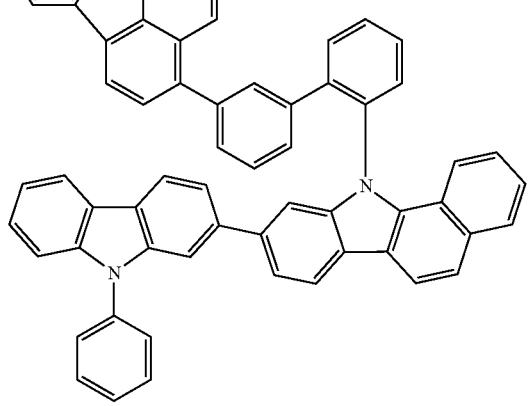
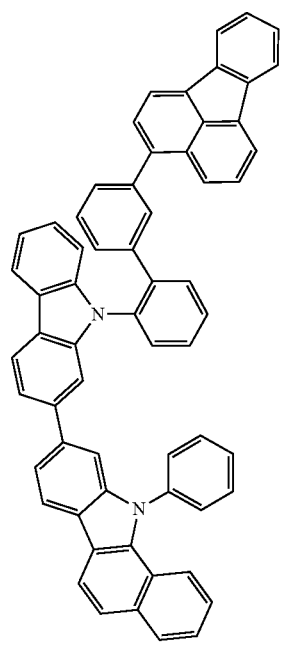

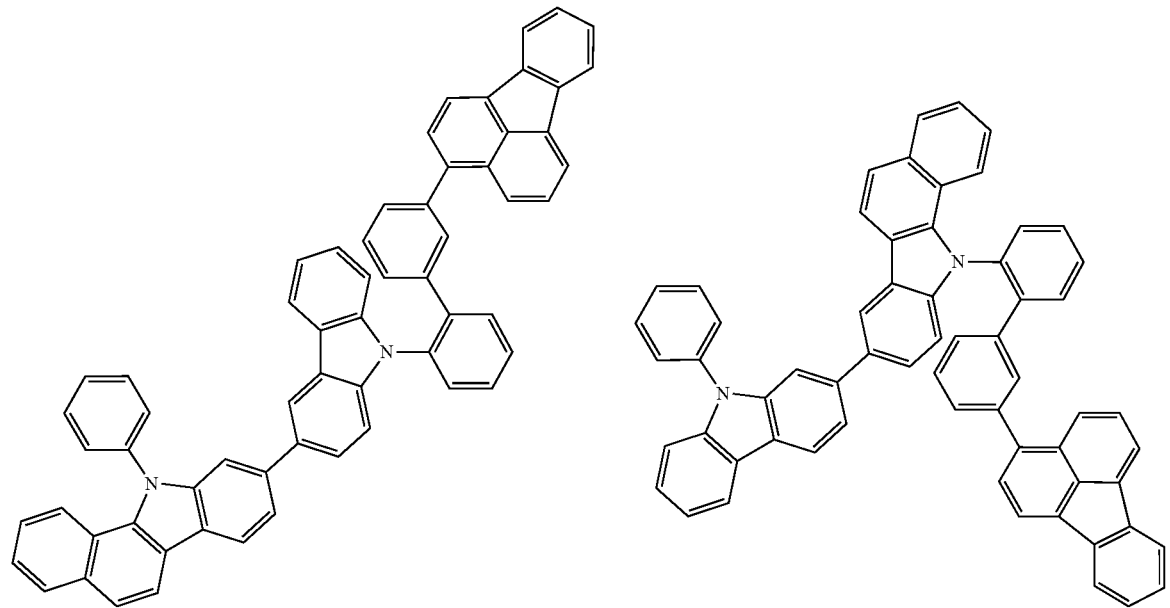
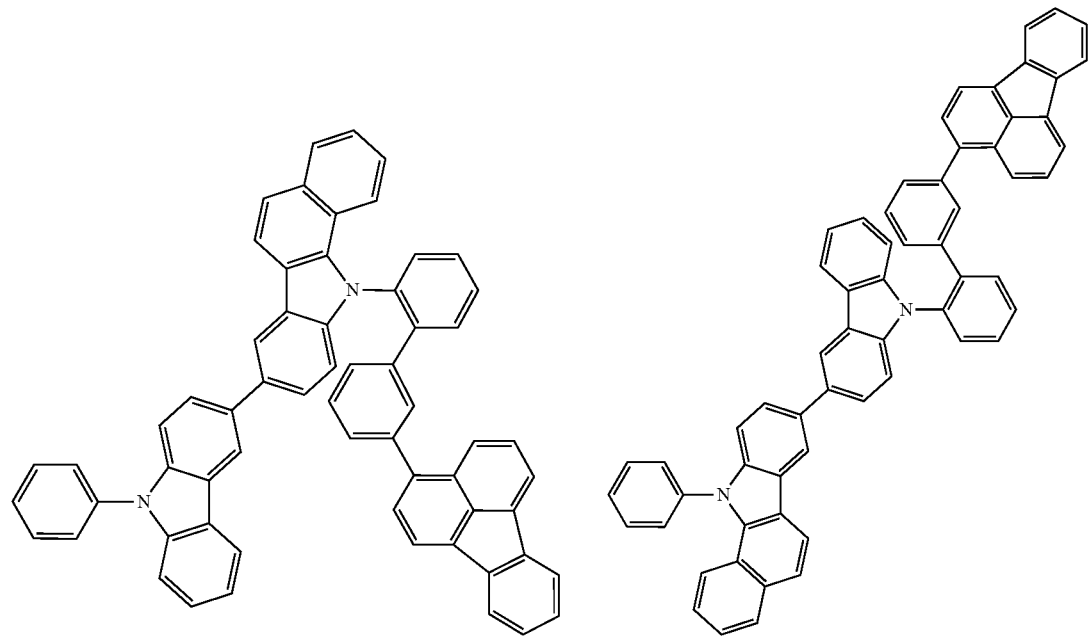

-continued
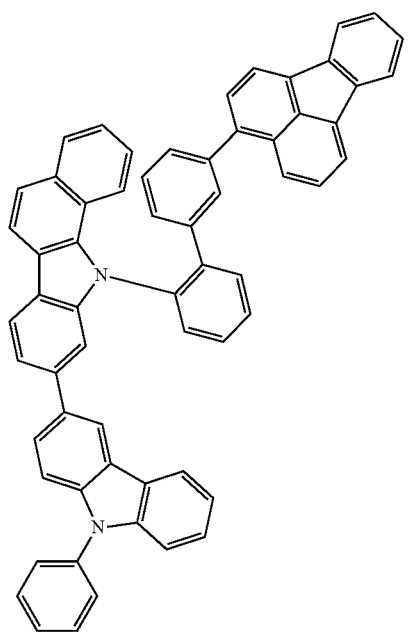
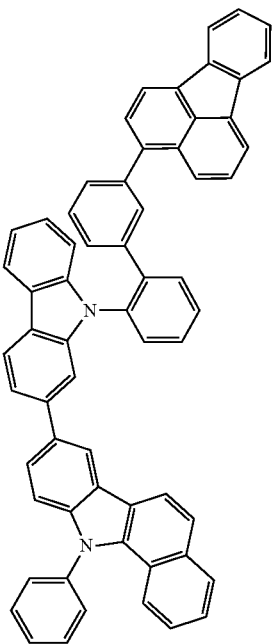
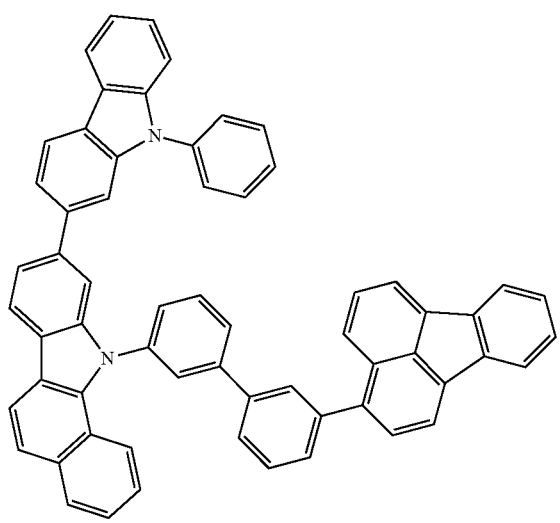
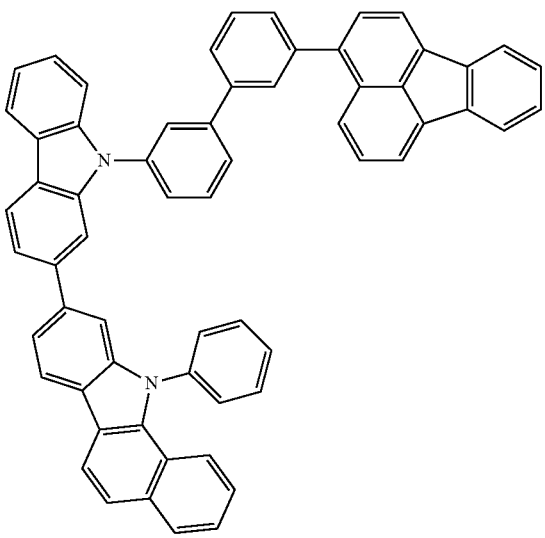
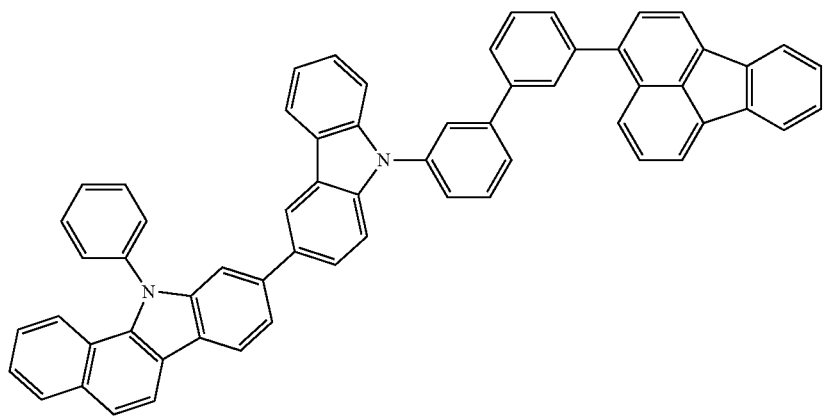

-continued
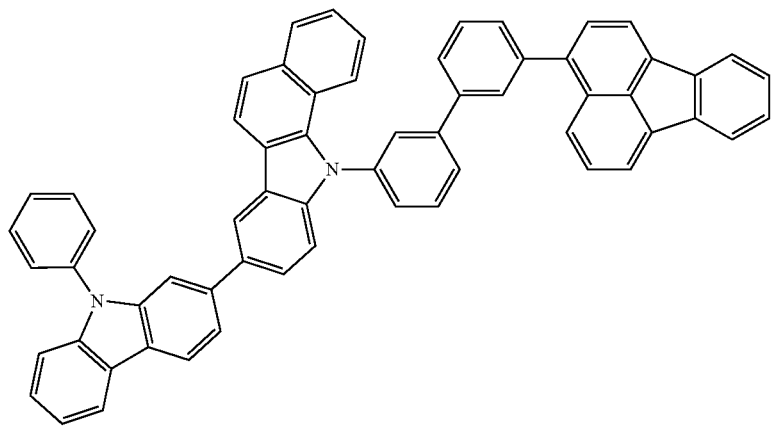
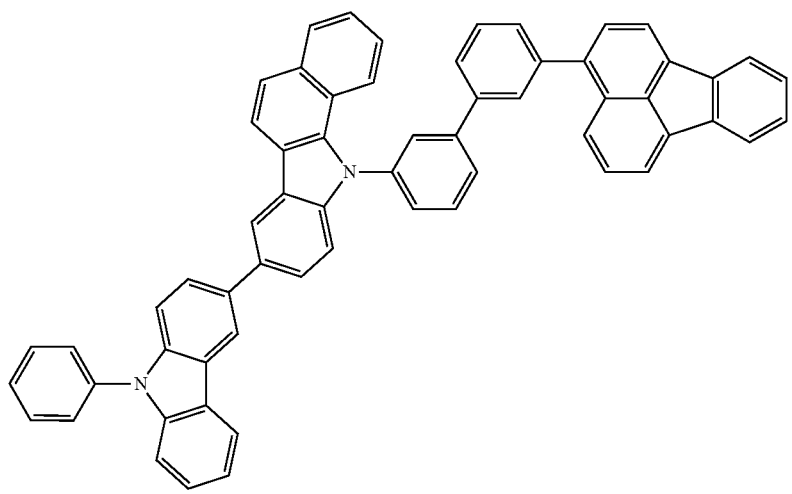
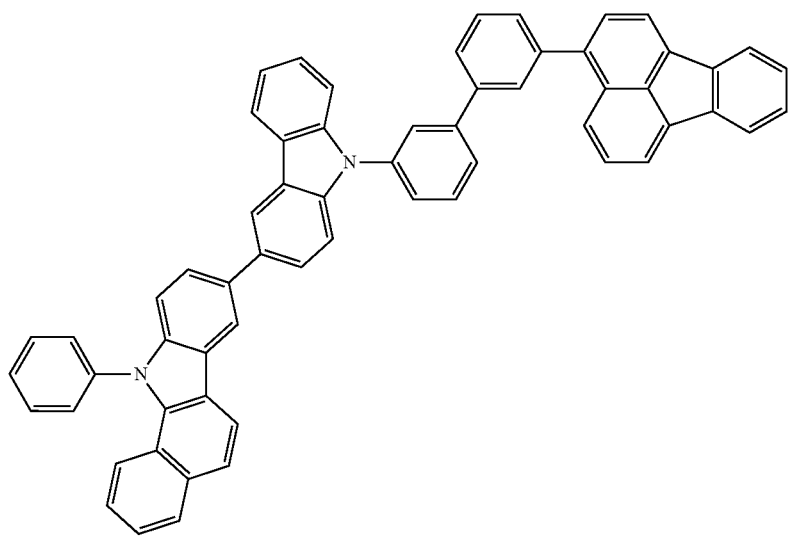

-continued
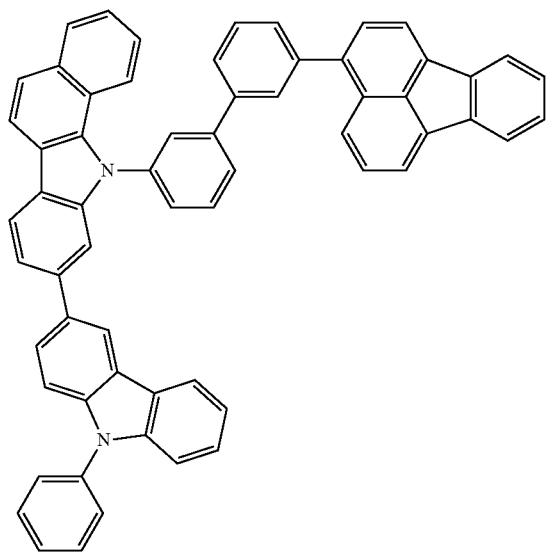
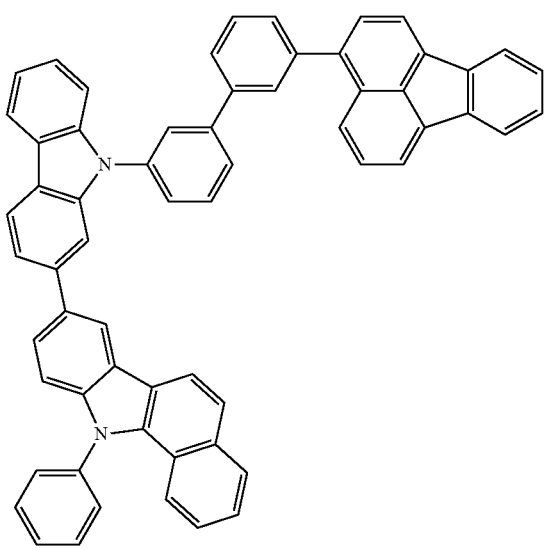
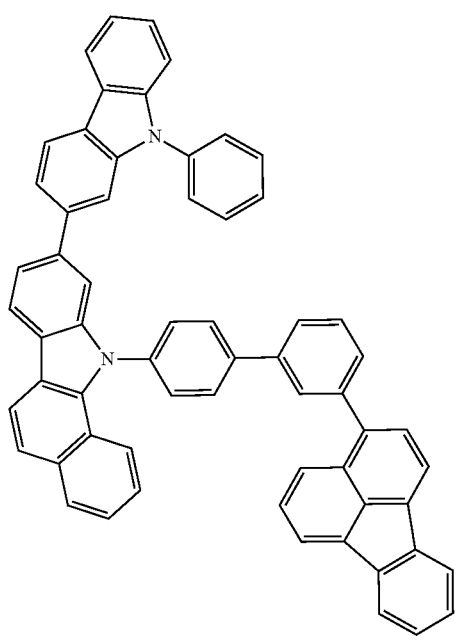
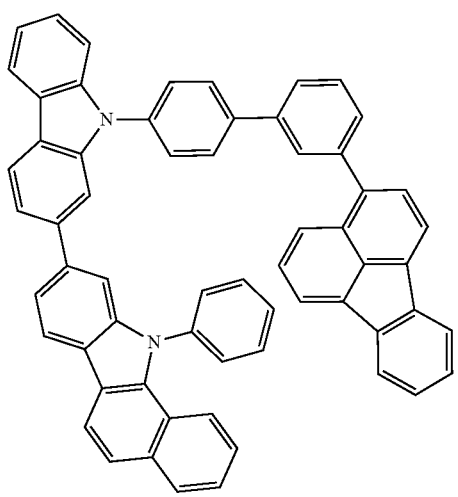
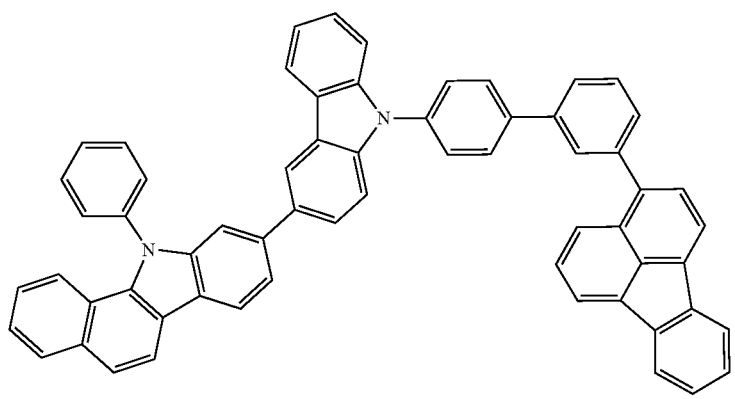

-continued
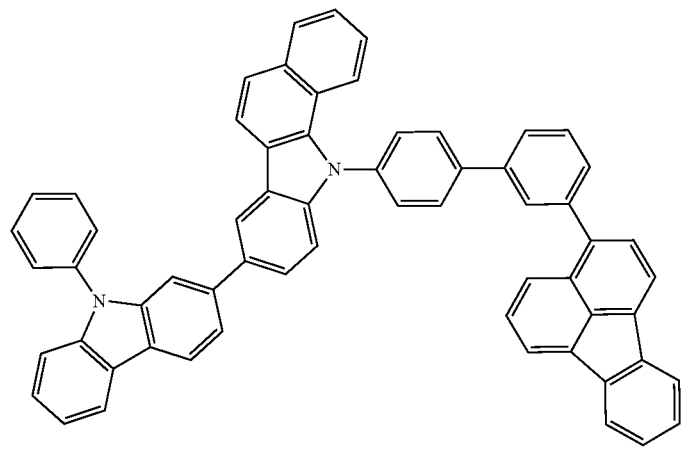
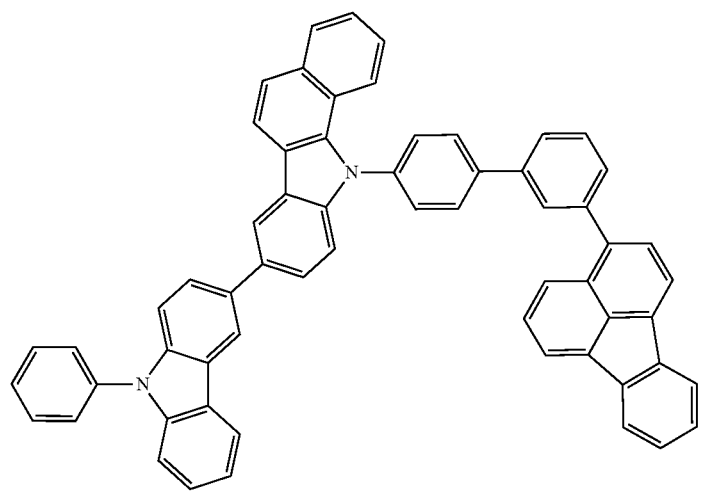
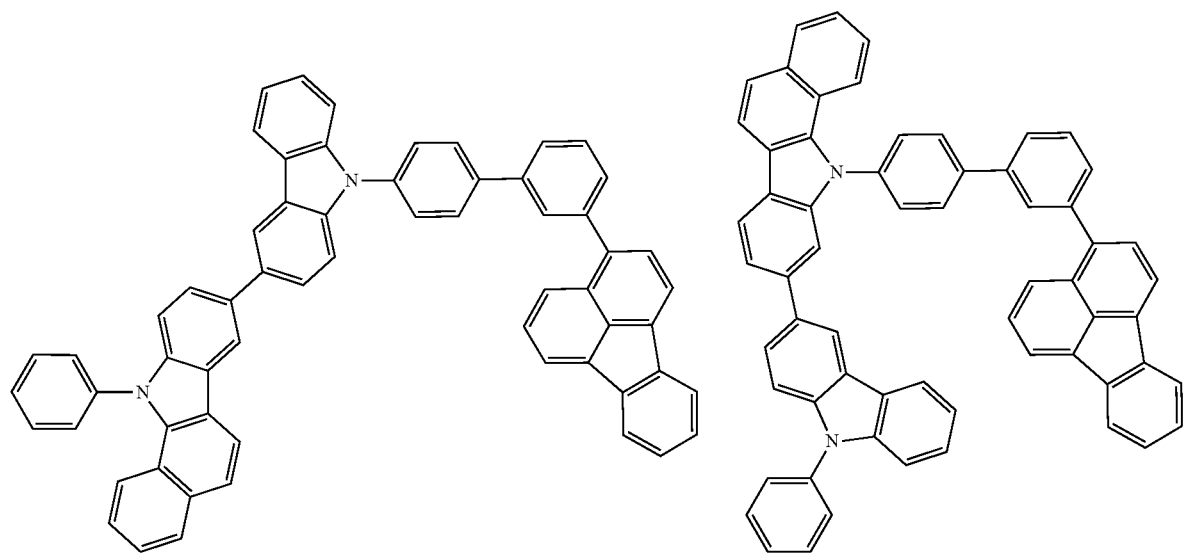

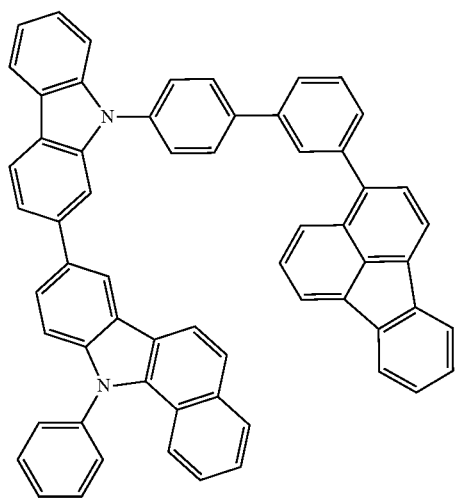
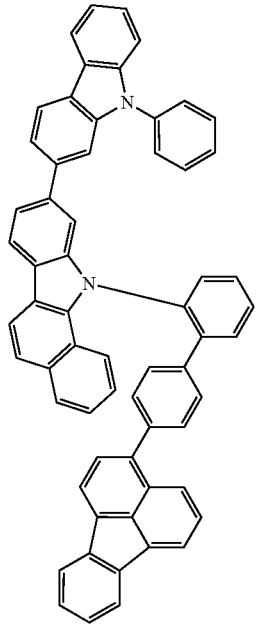
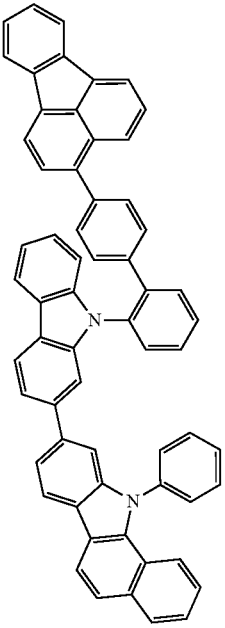
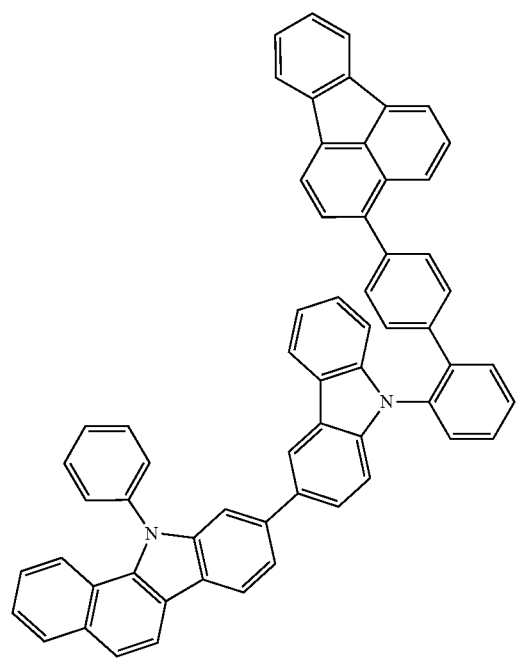
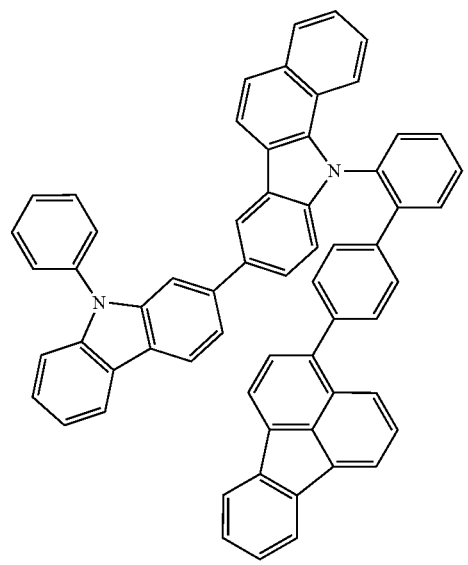

-continued
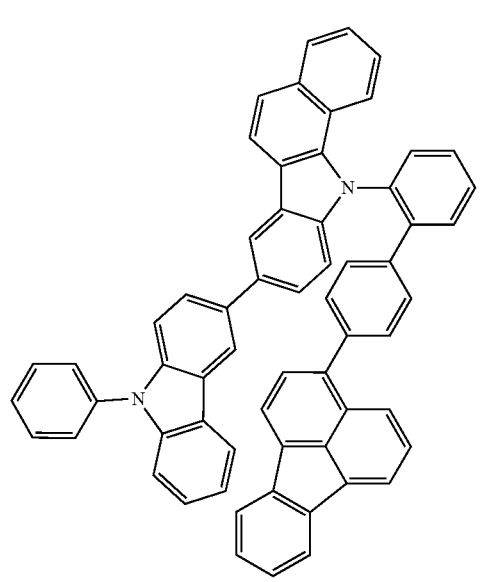
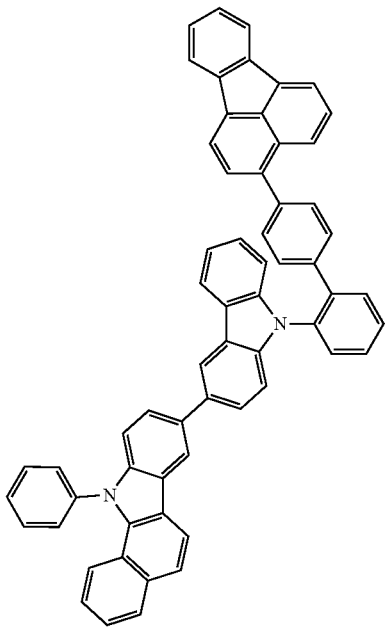
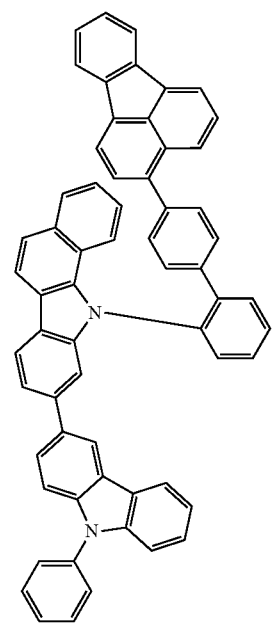
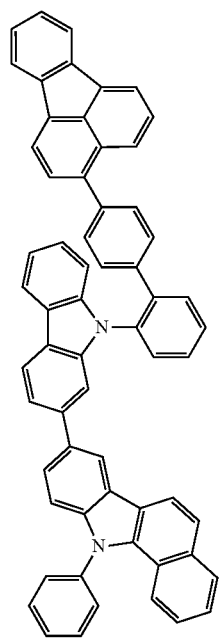
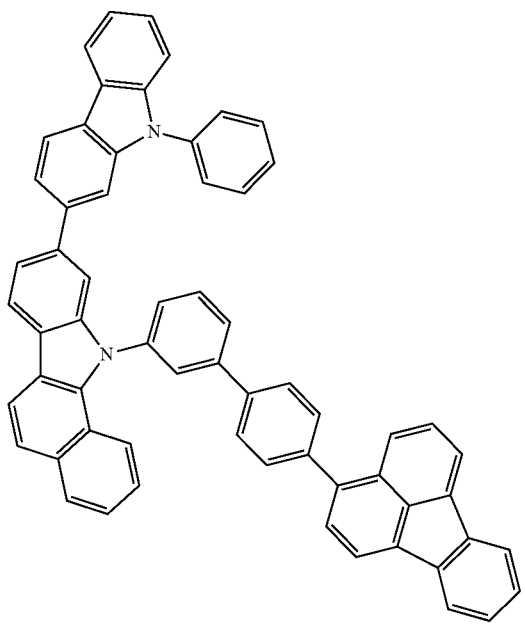

-continued
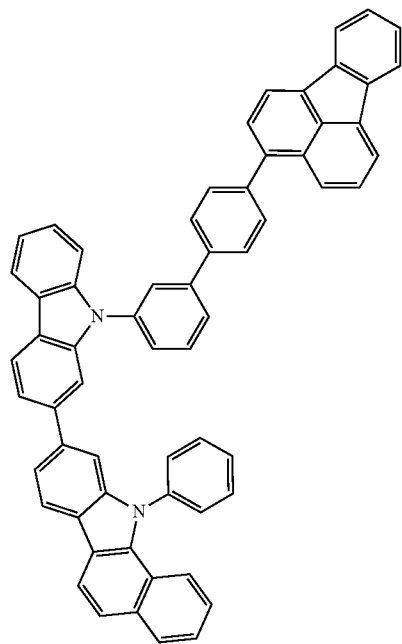
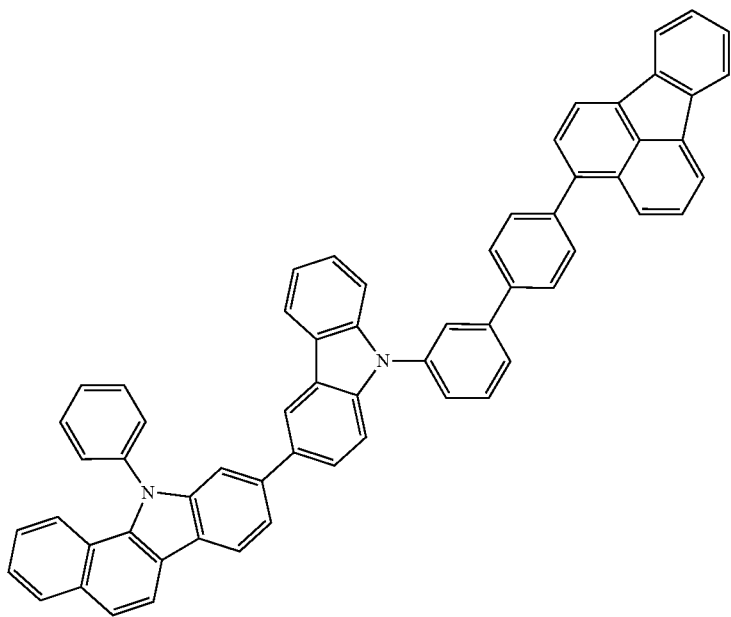
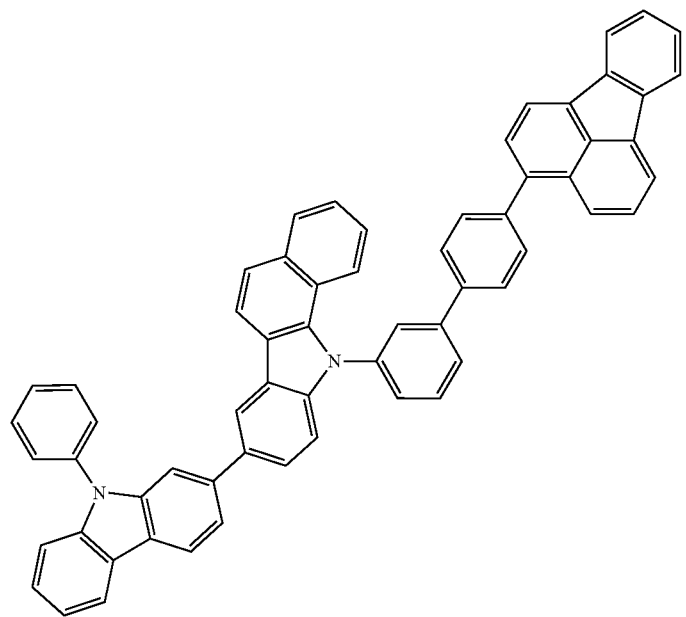

-continued
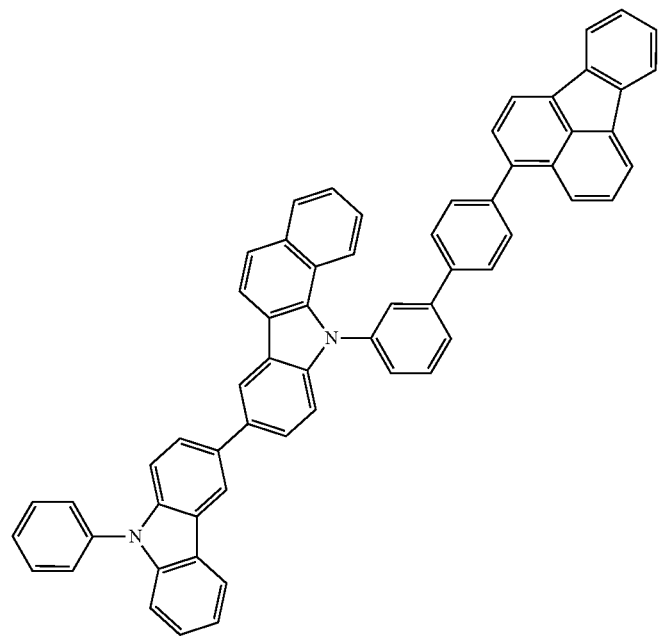
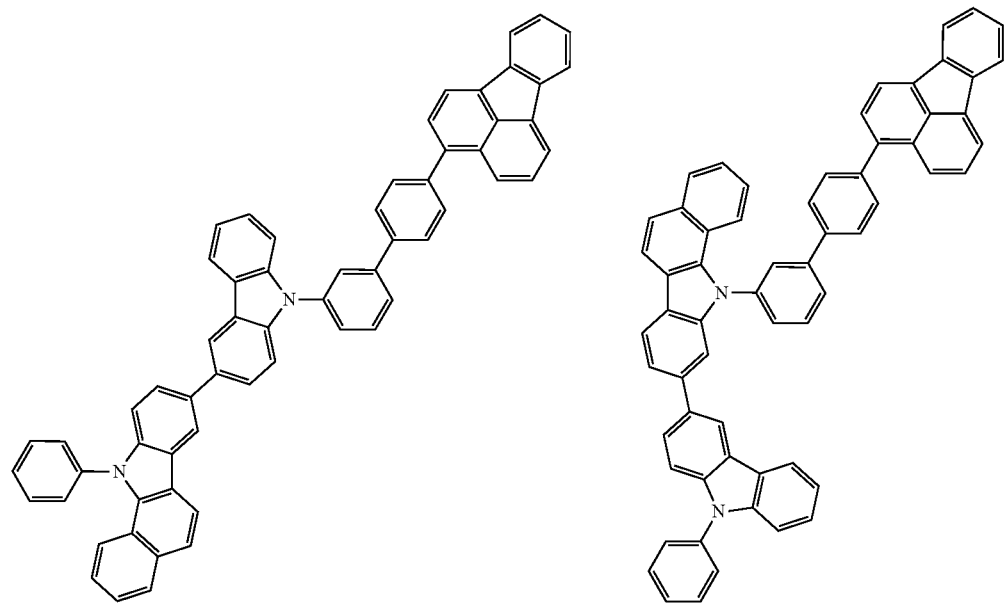

-continued
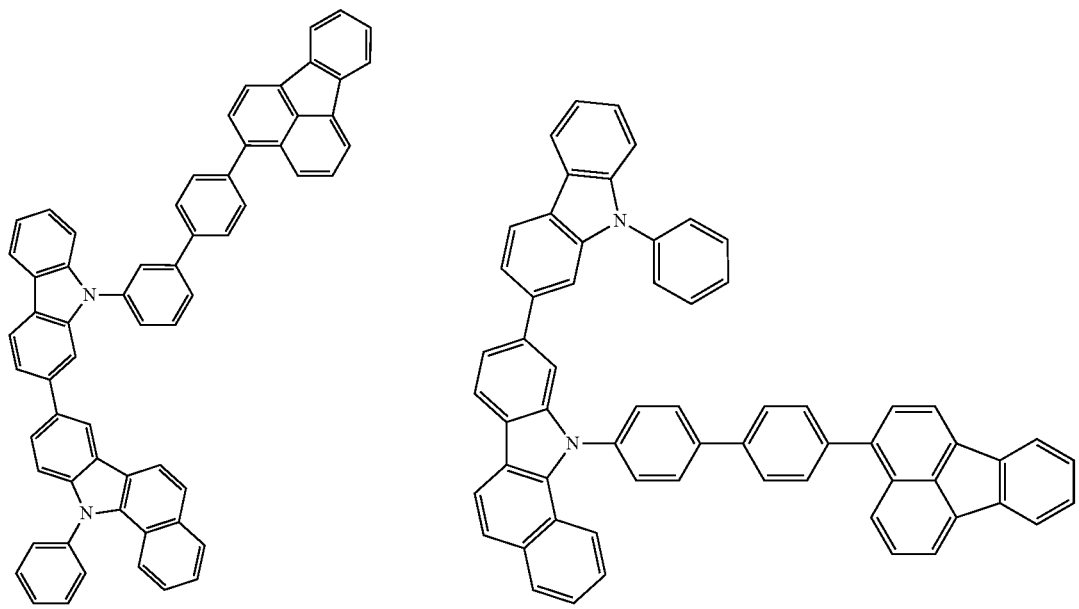
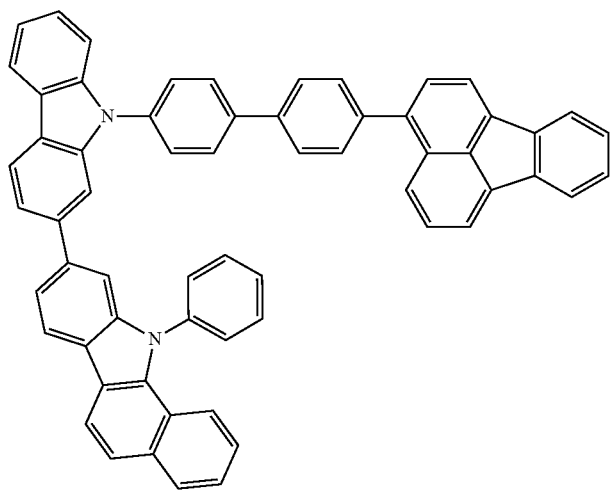
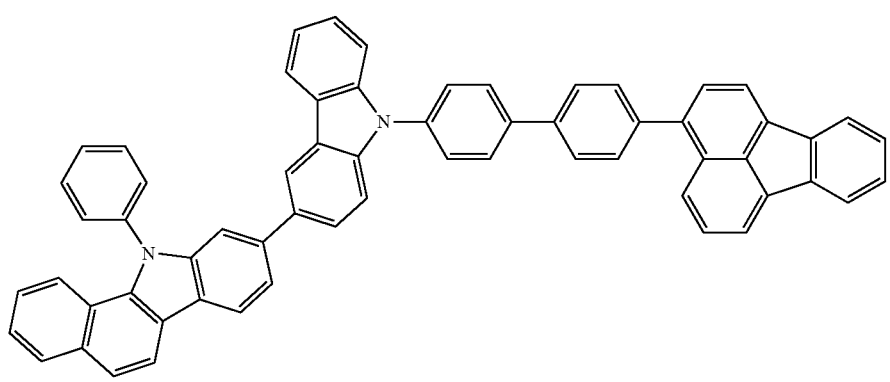

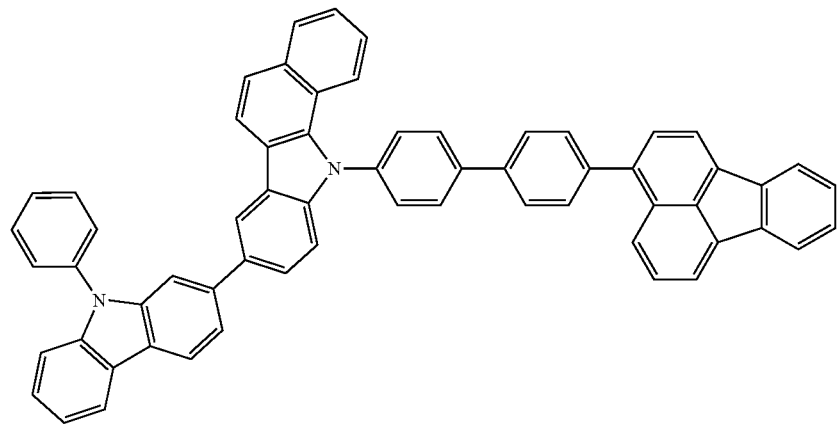
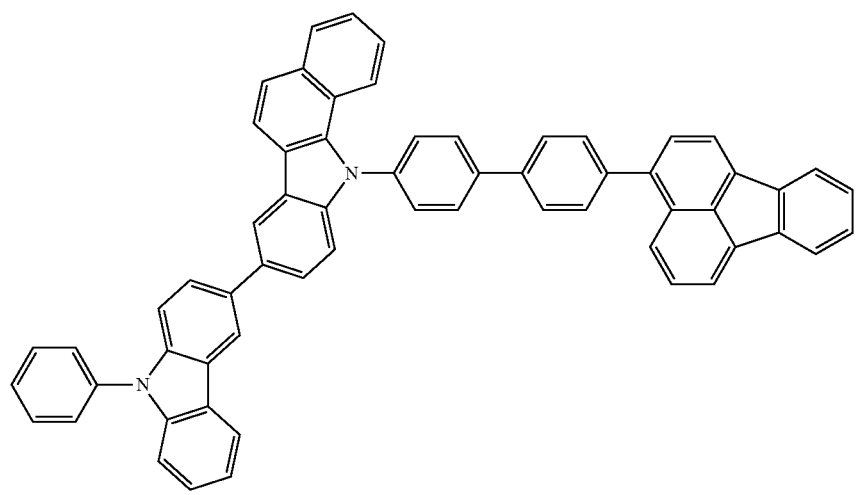
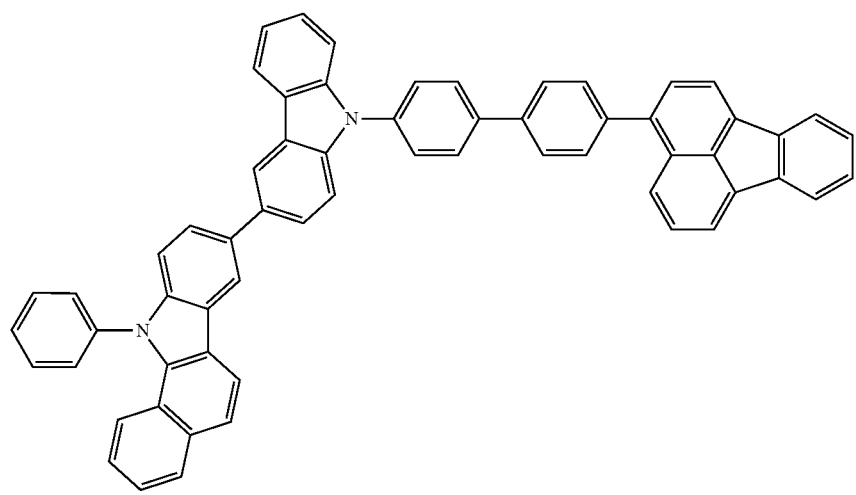

-continued
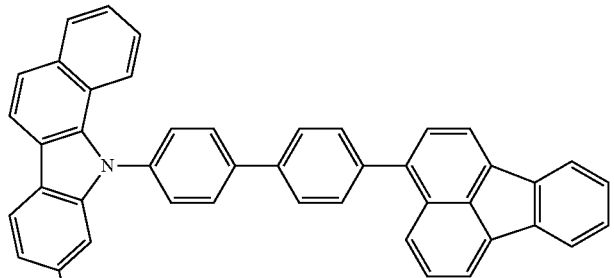
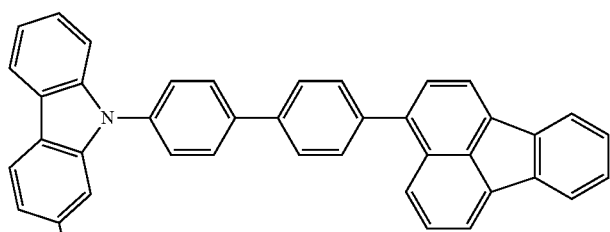
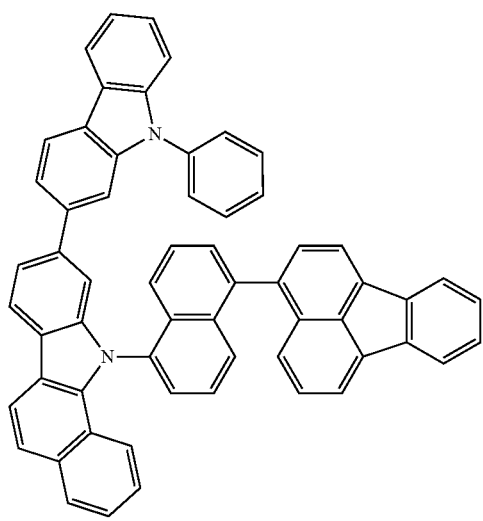
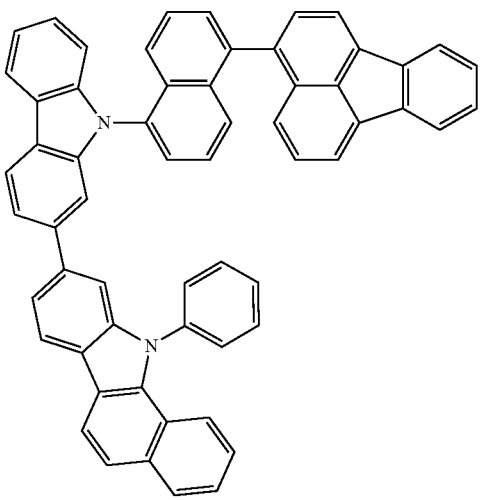

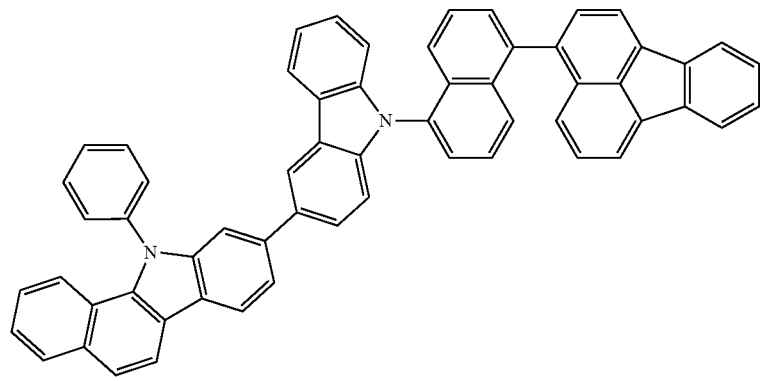
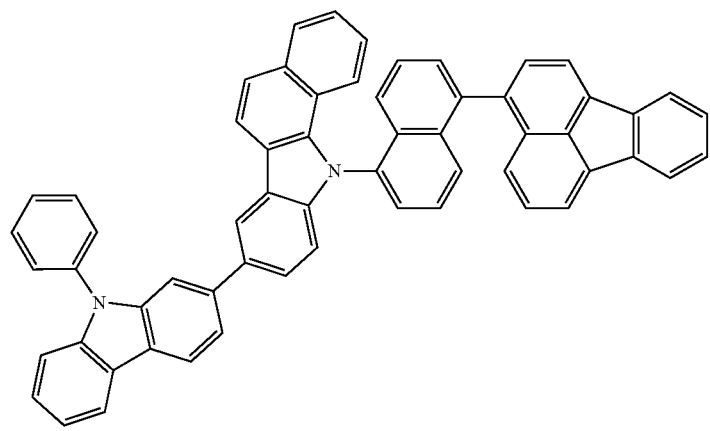
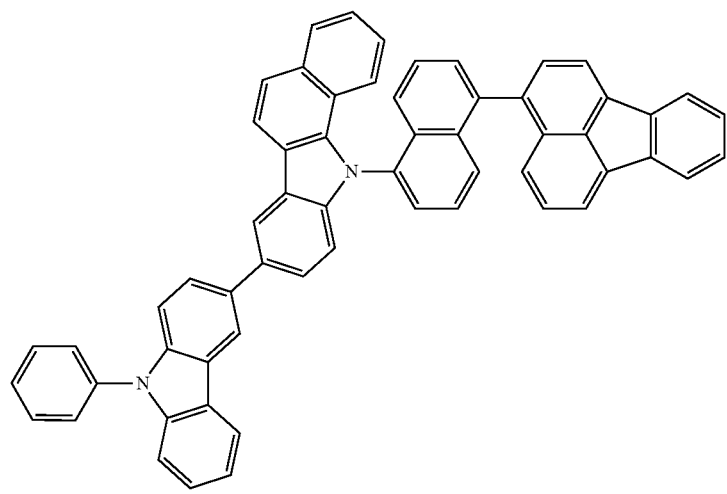

-continued
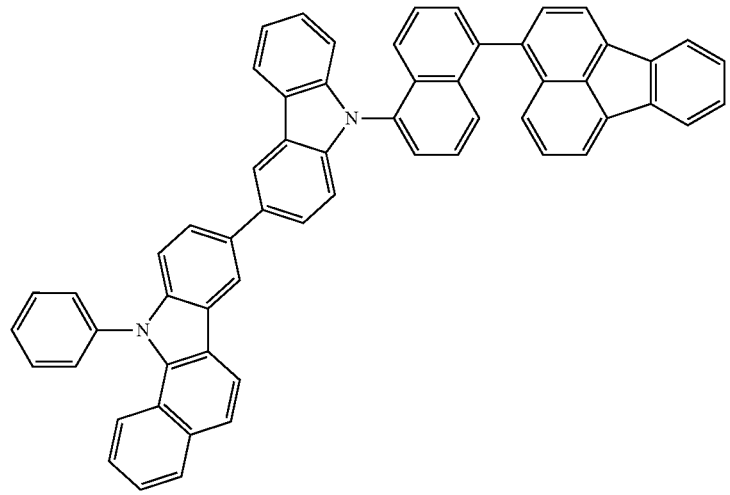
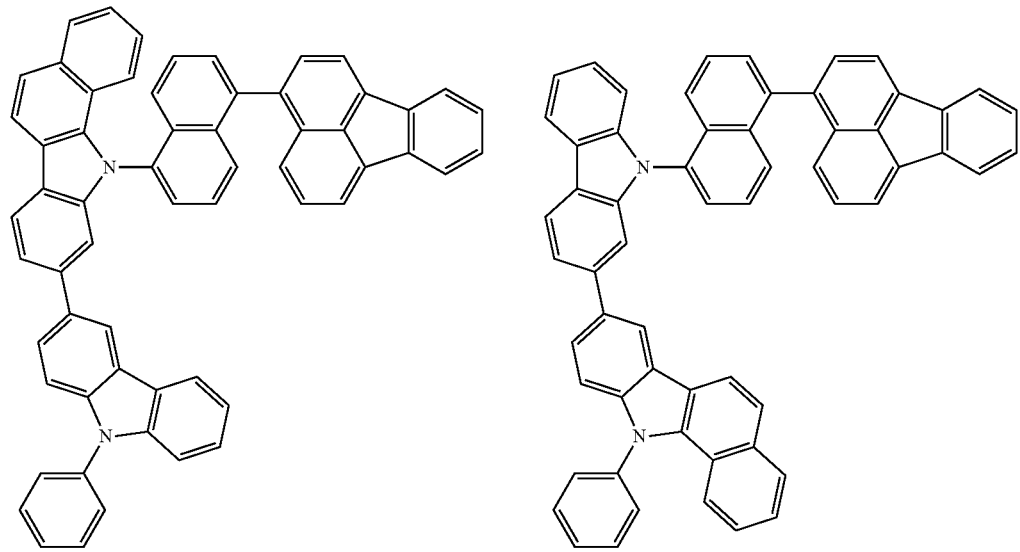
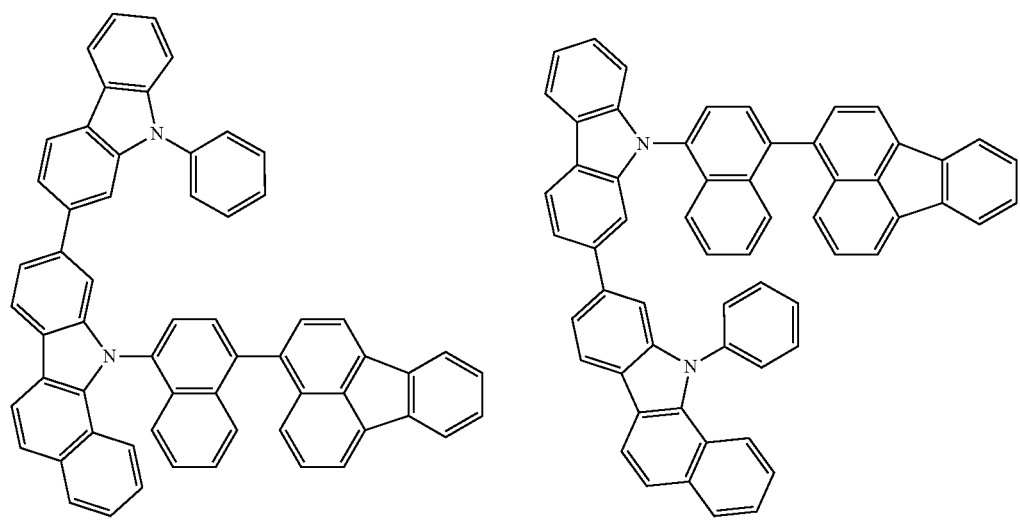

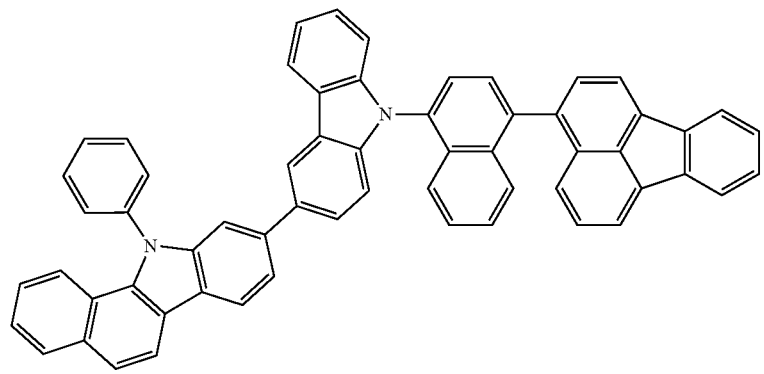
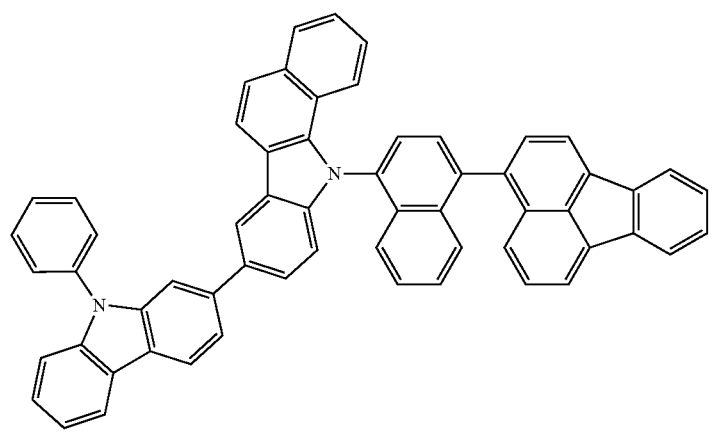
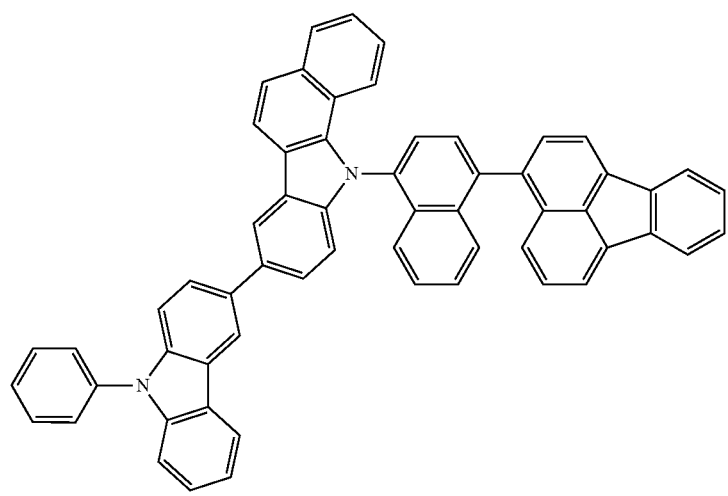

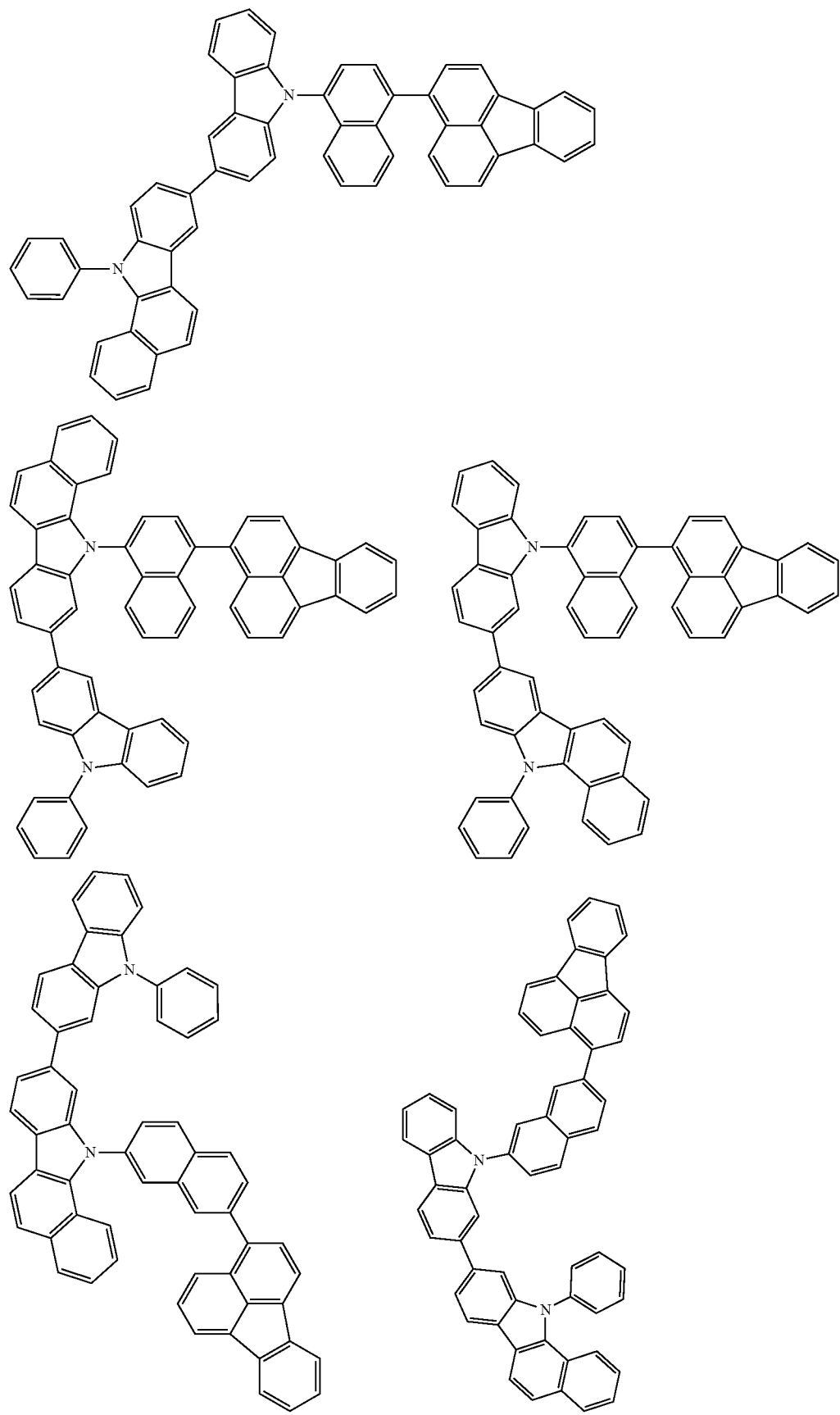

-continued
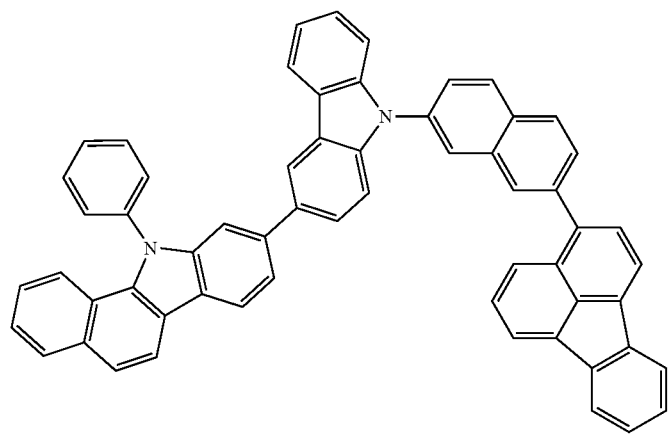

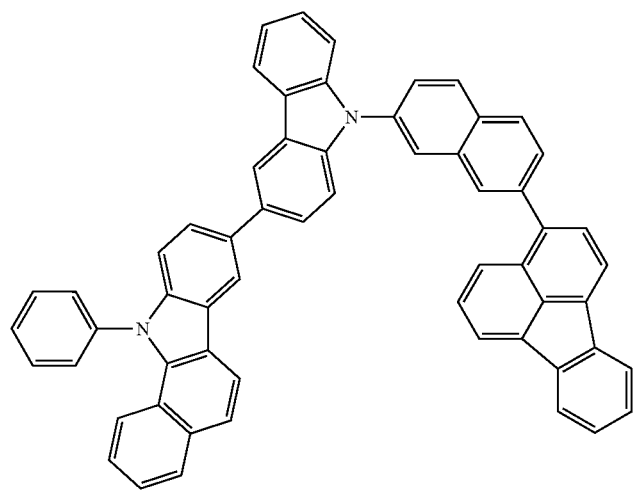
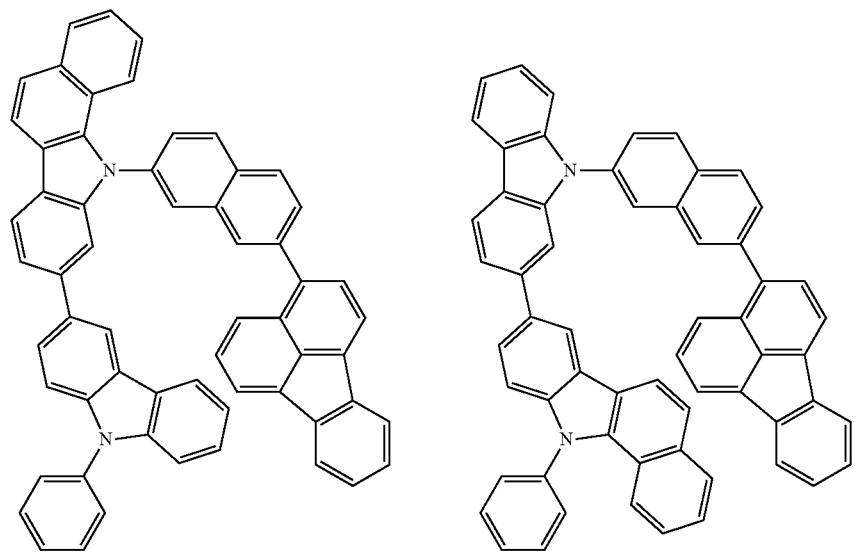
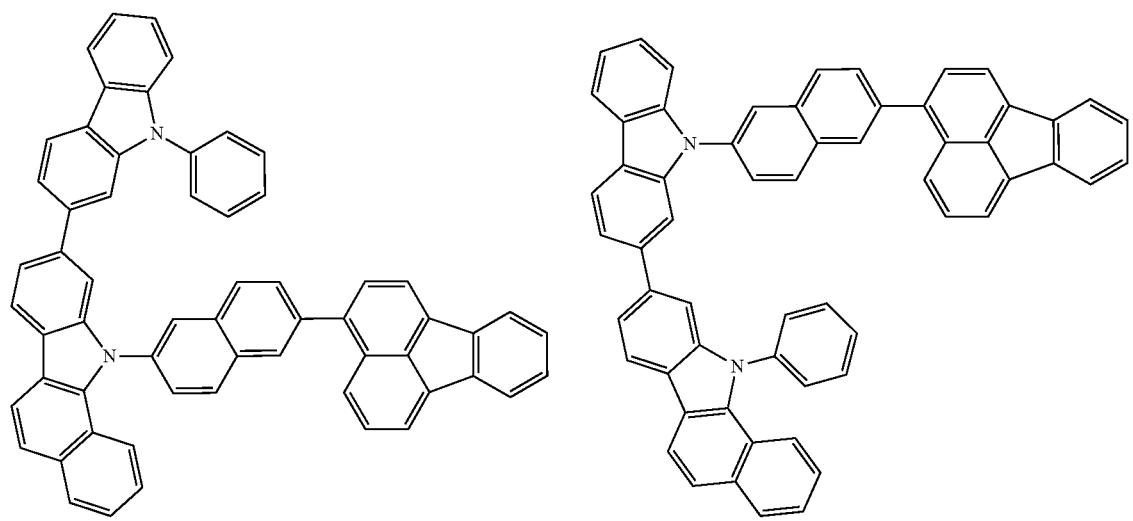

-continued
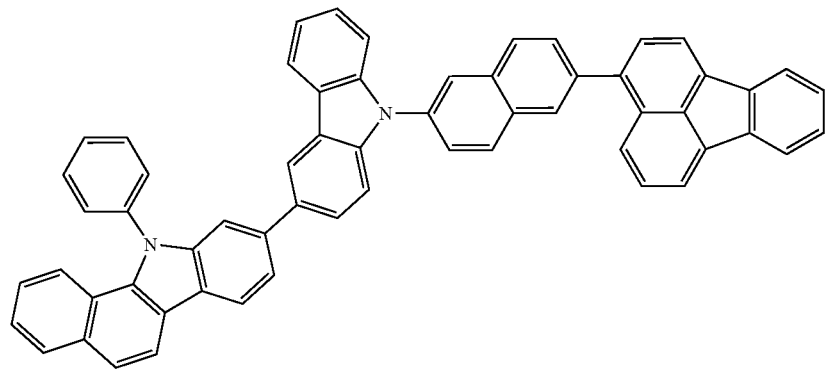
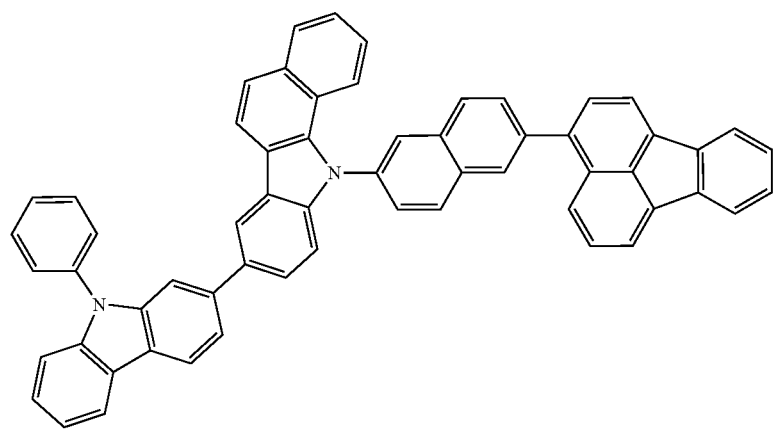
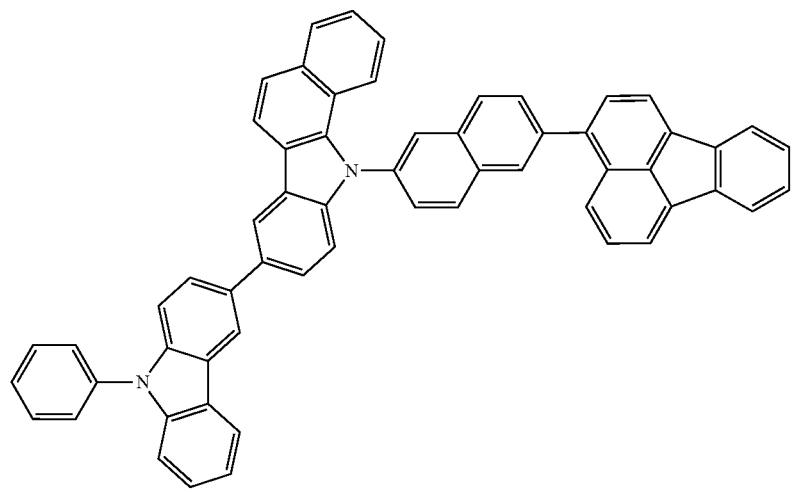

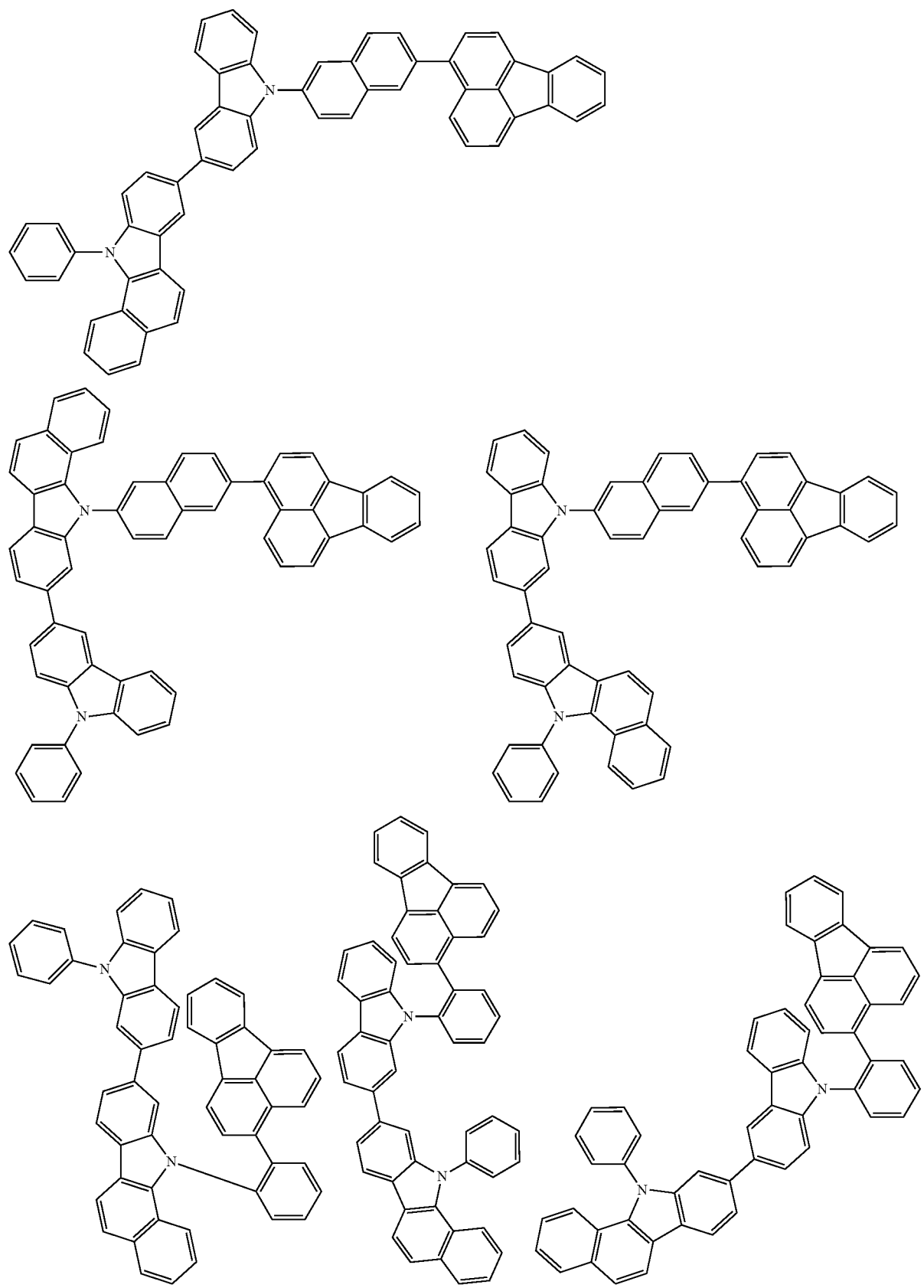

-continued
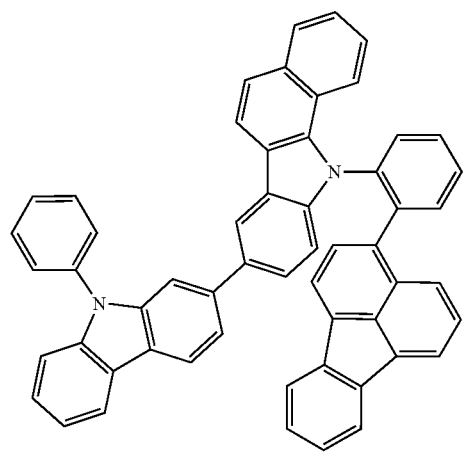
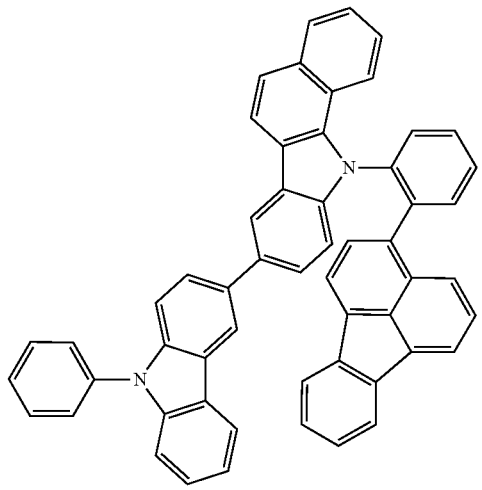
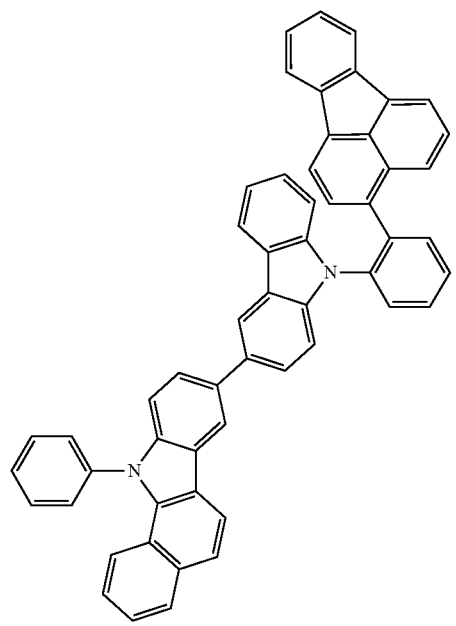
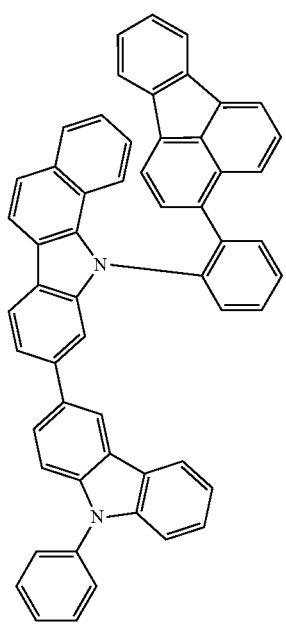
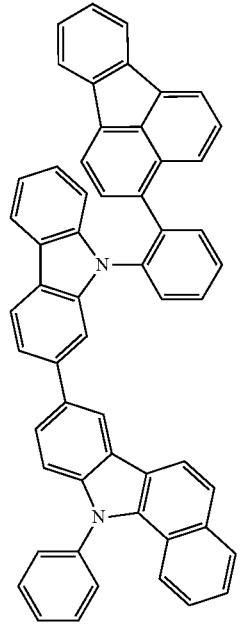

-continued
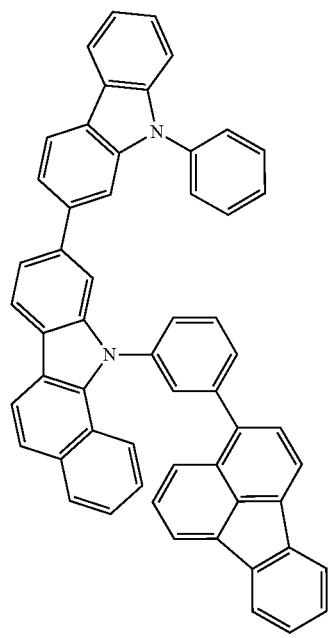
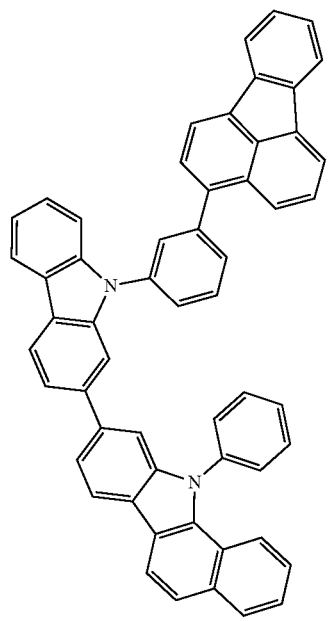
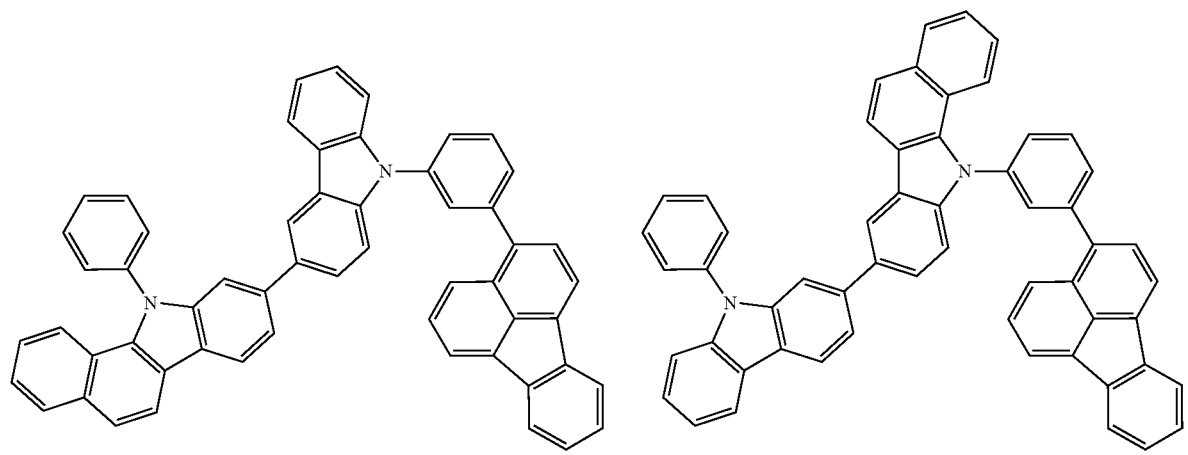
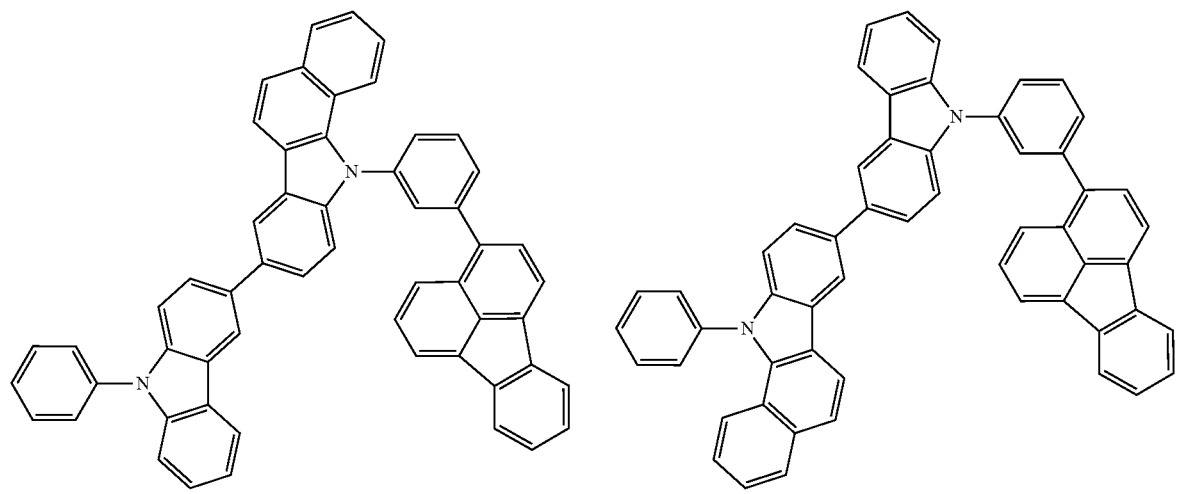

-continued
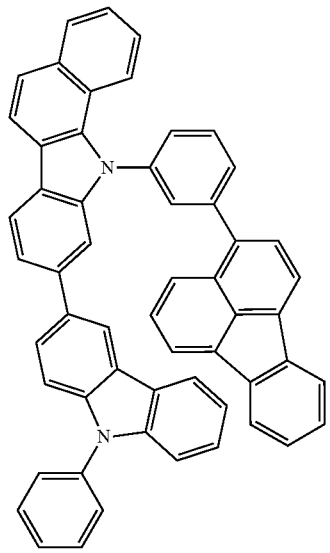 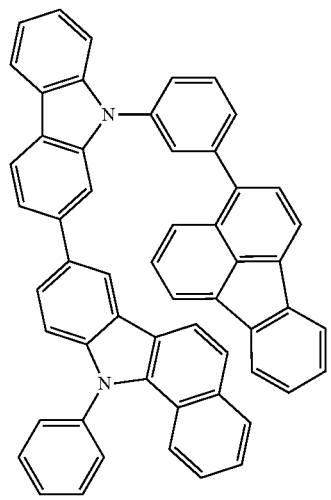 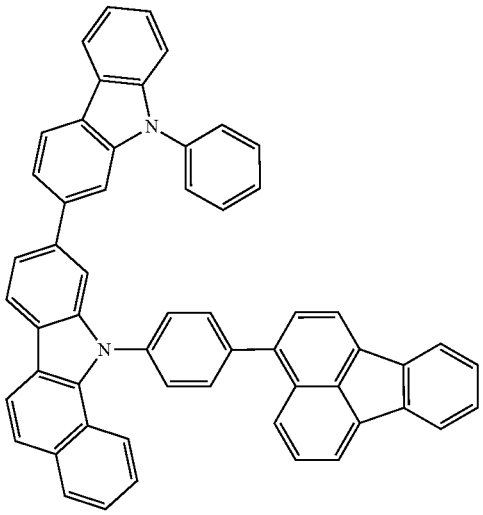
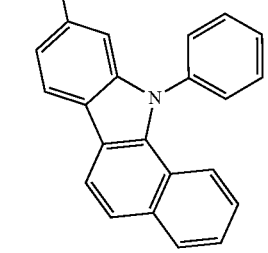
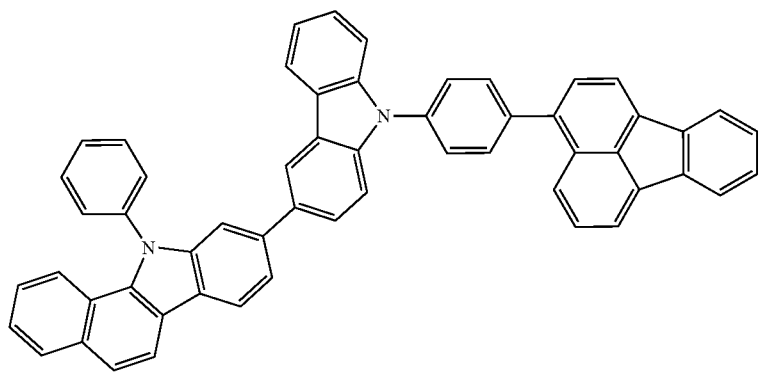

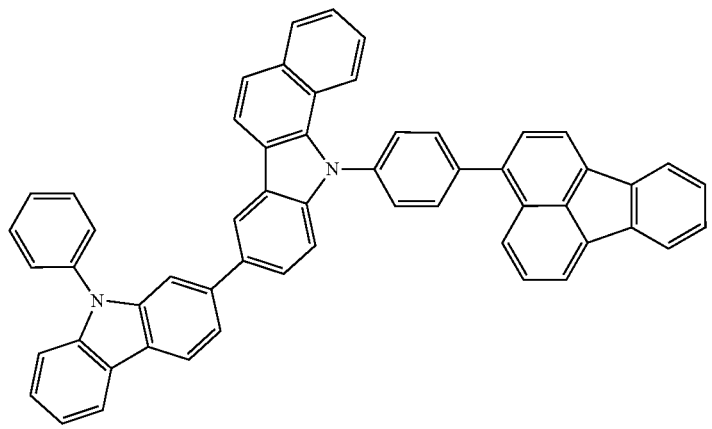
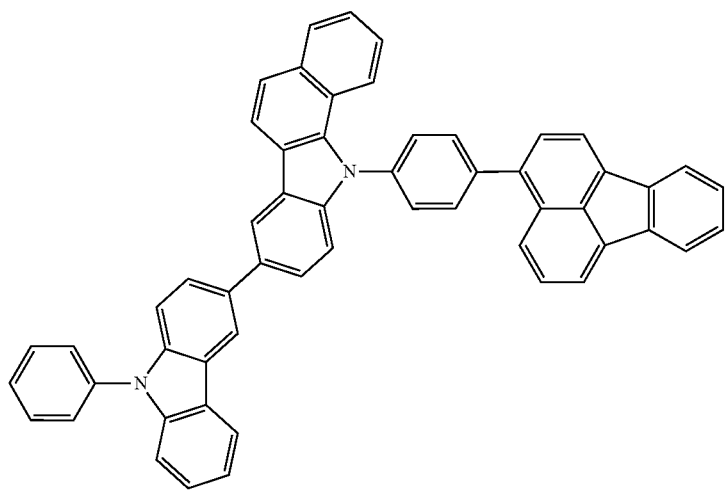
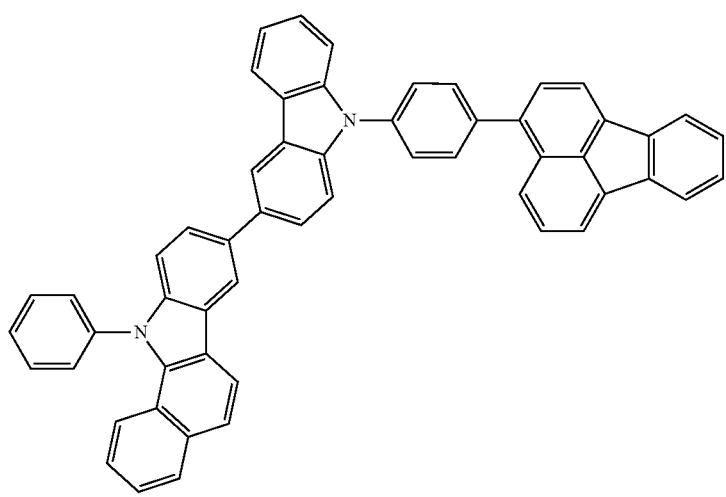

-continued
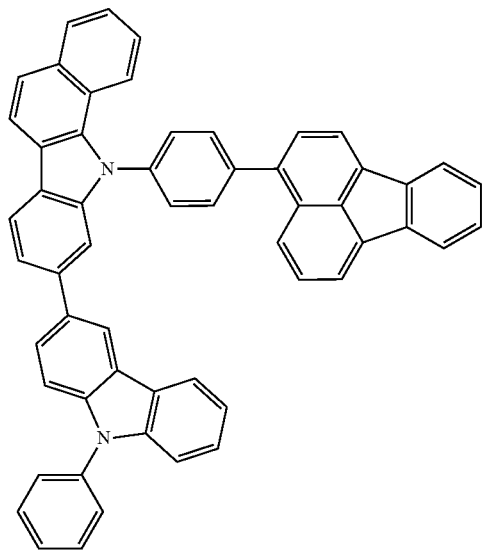
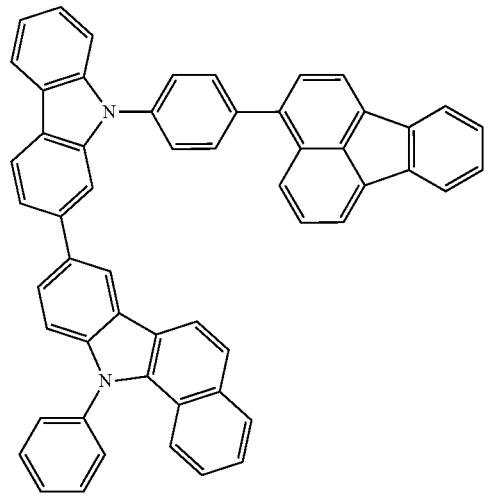
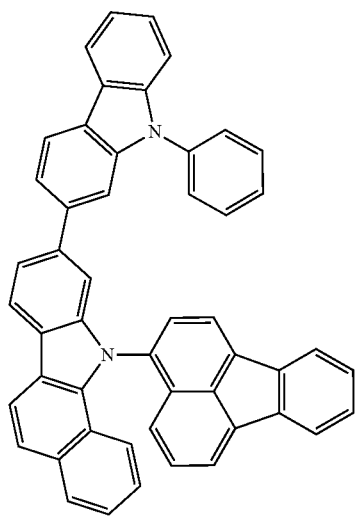
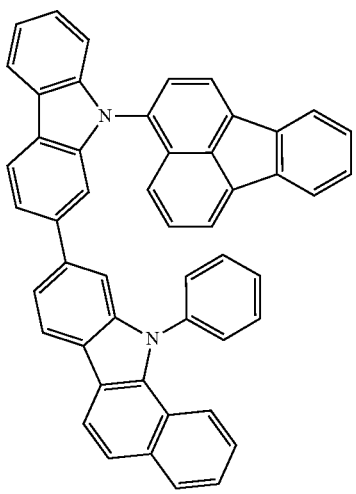
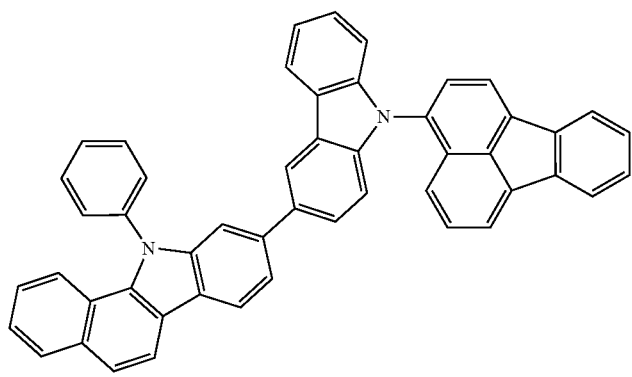

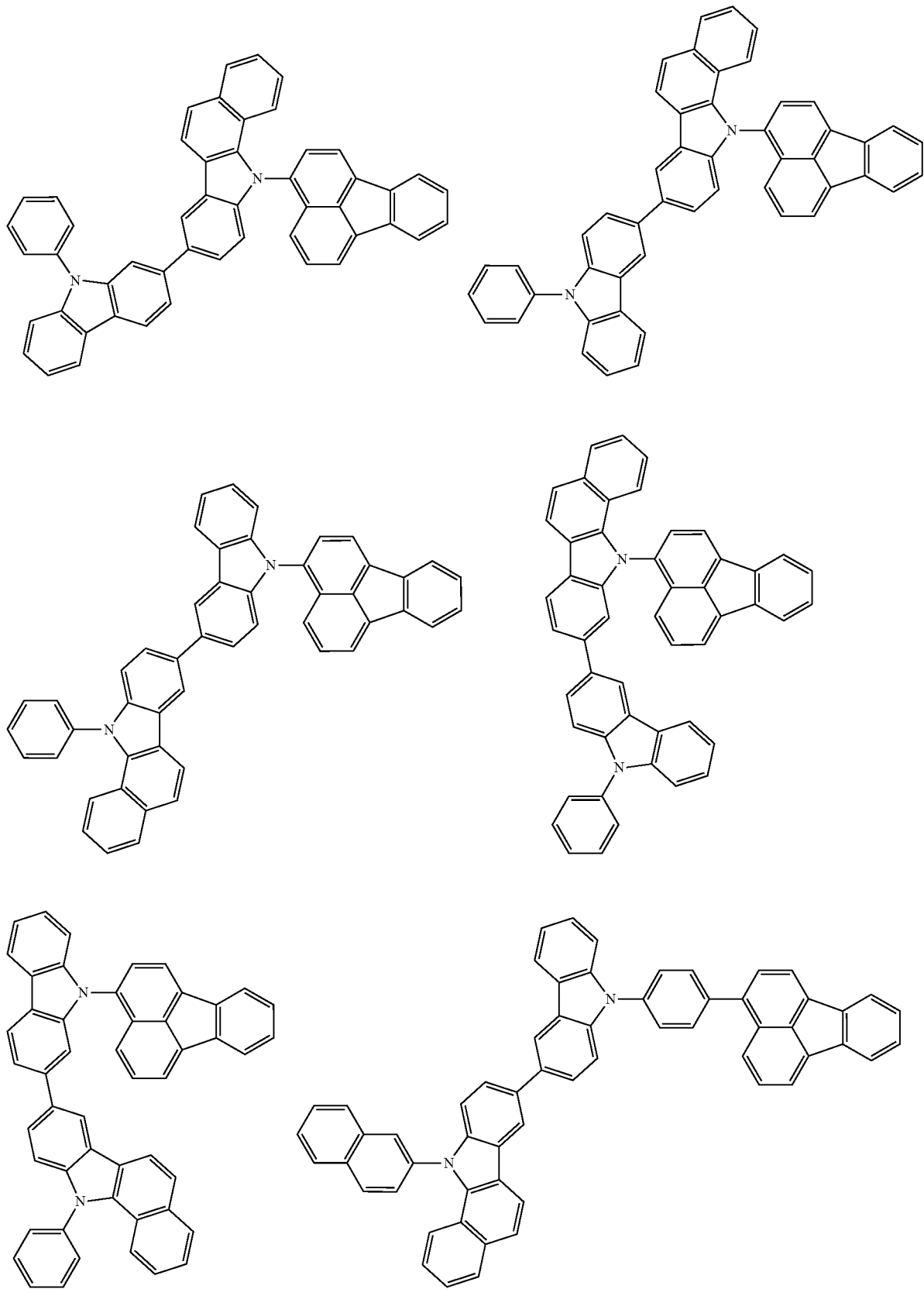

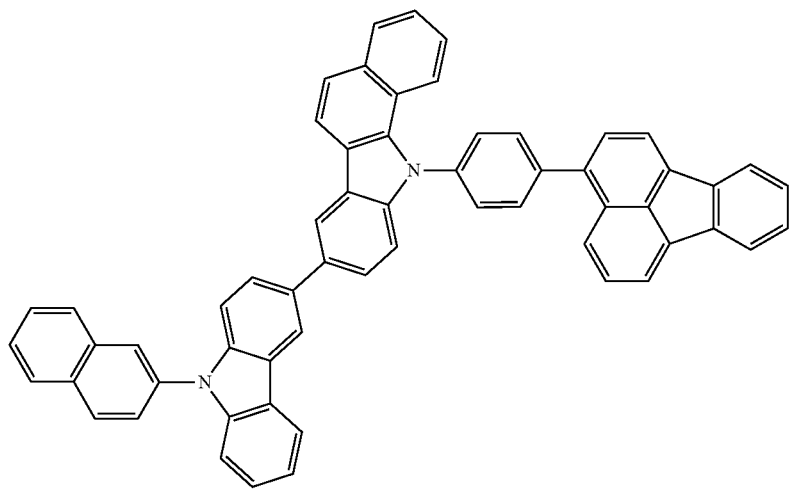
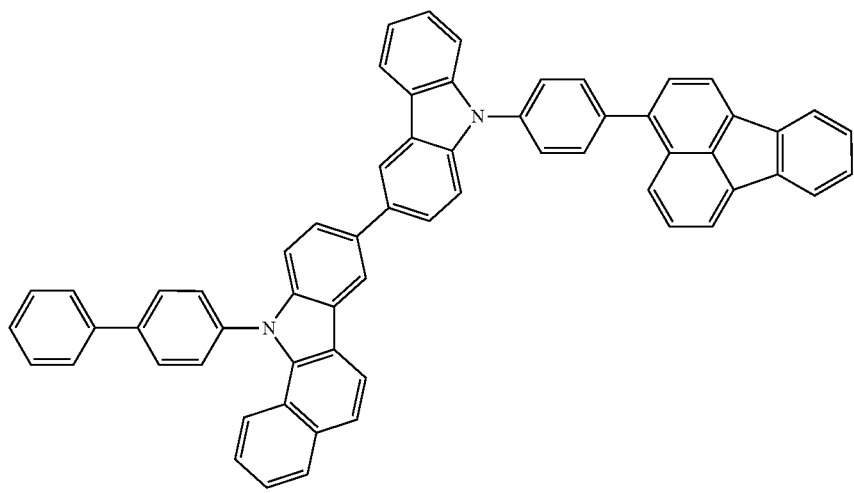
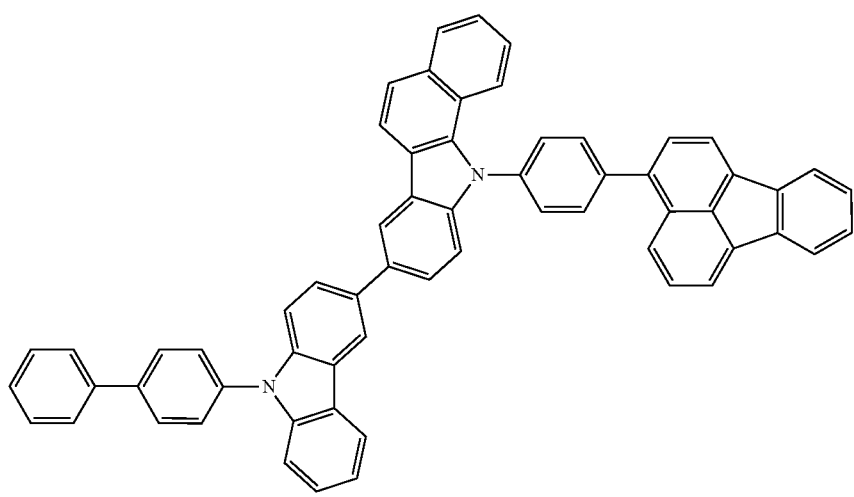

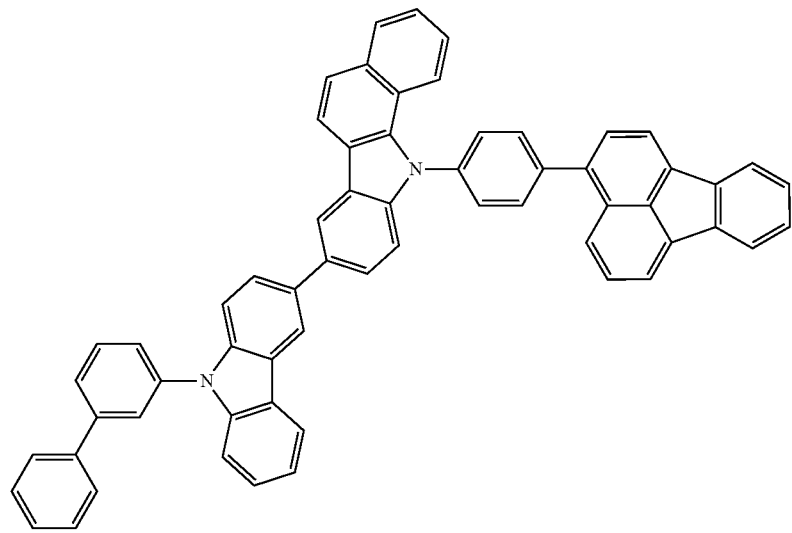
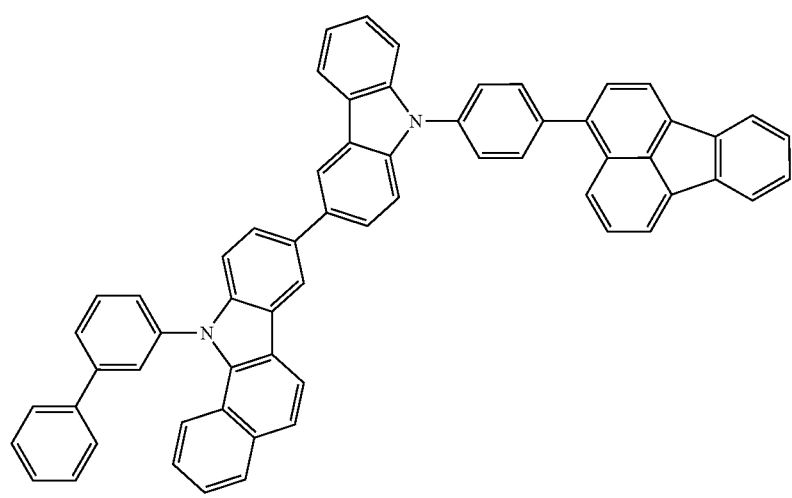
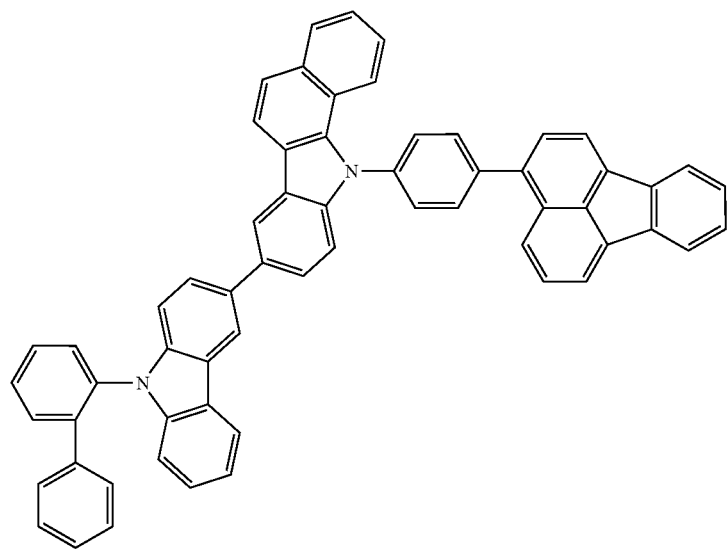

-continued
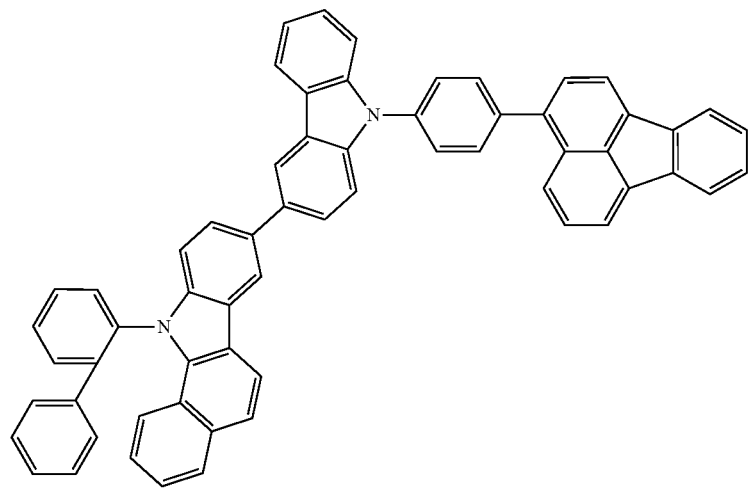
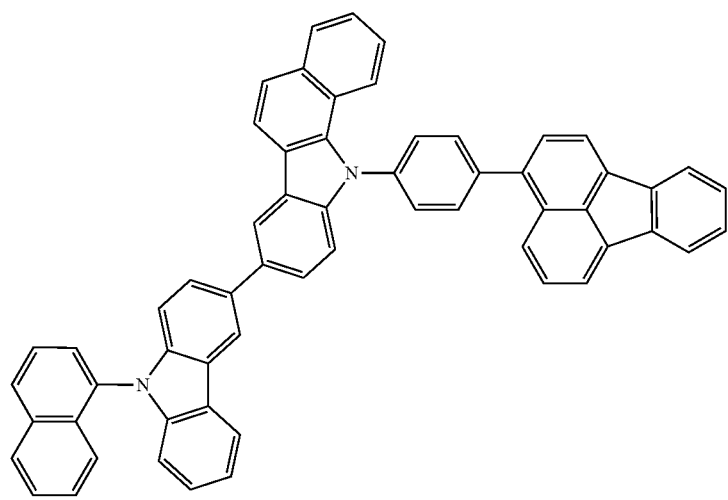
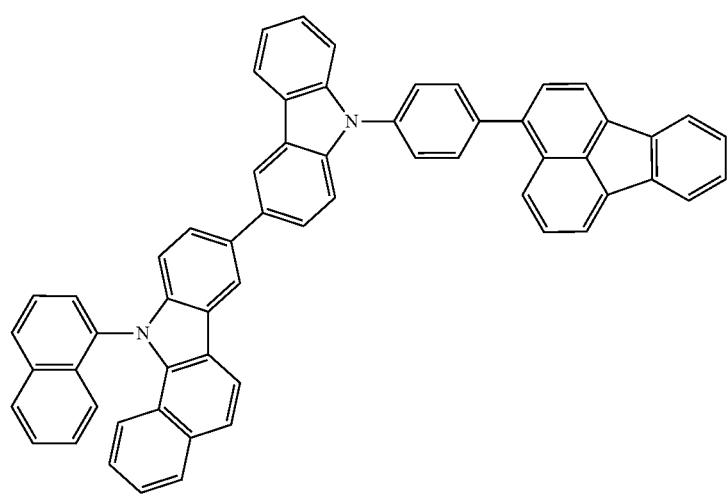

-continued
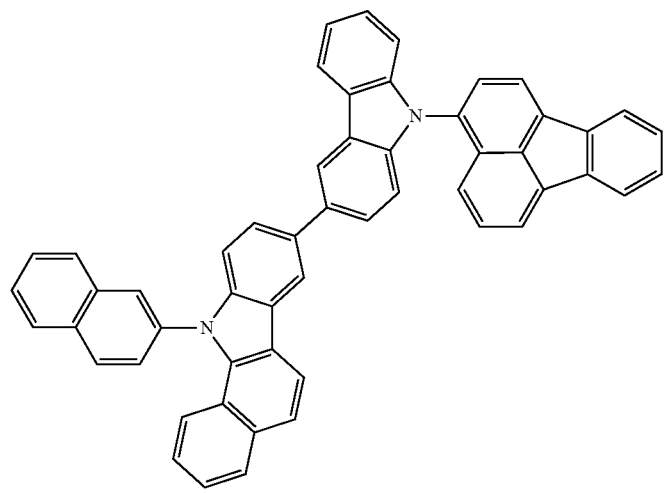
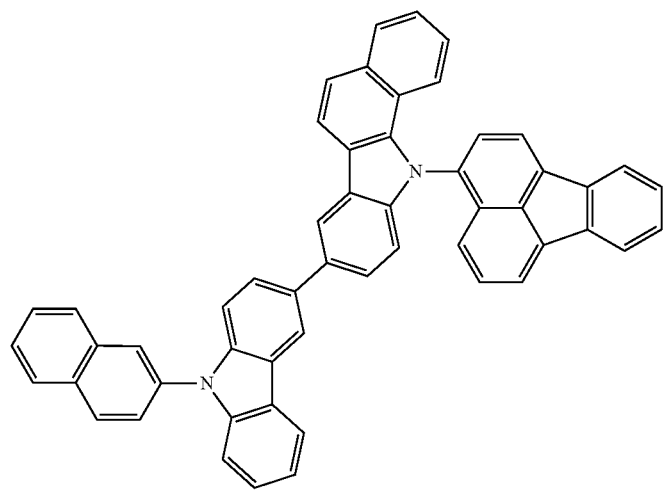
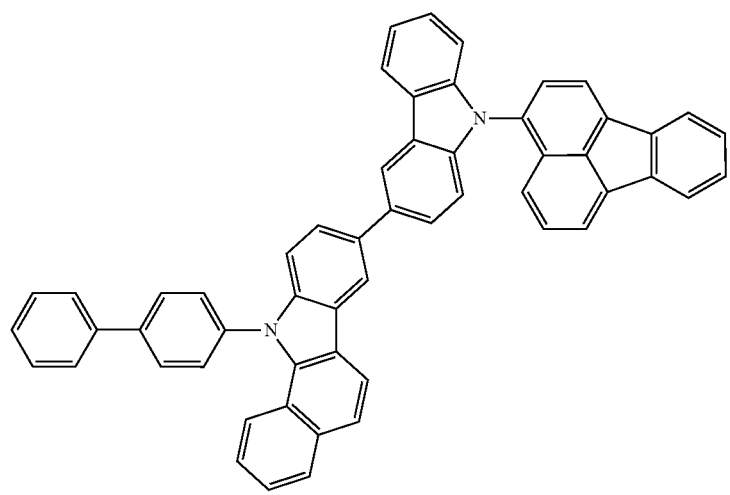

-continued
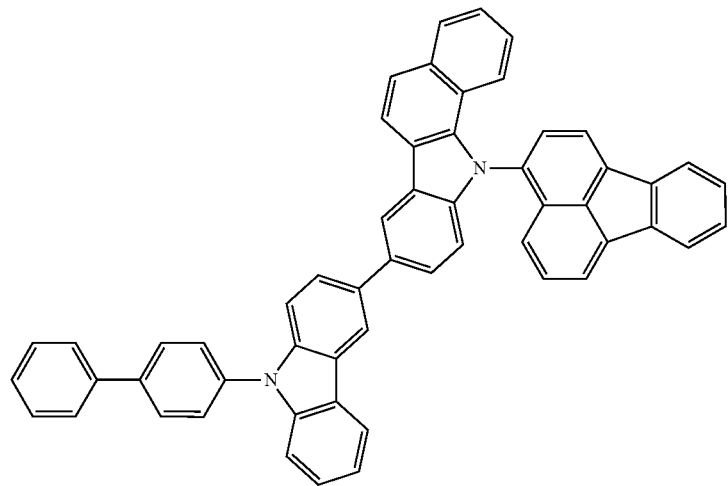
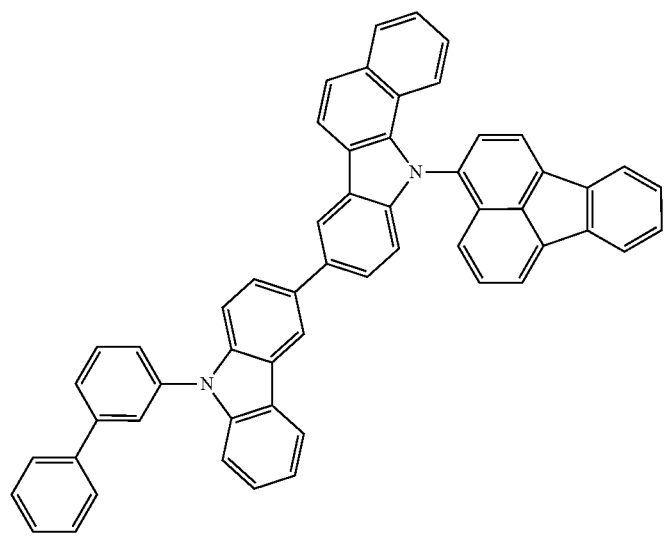
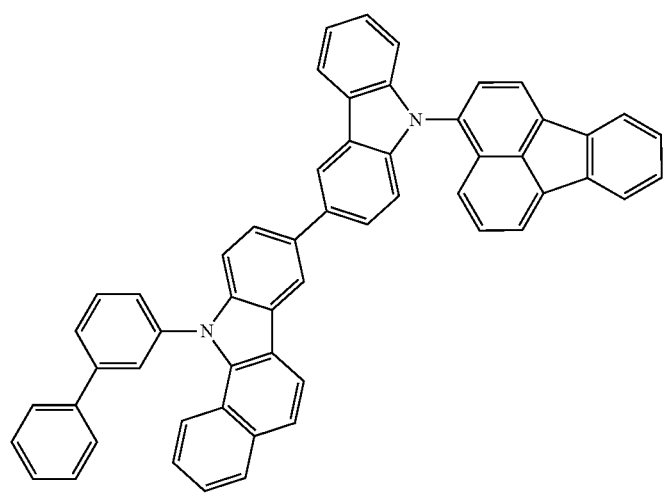

-continued
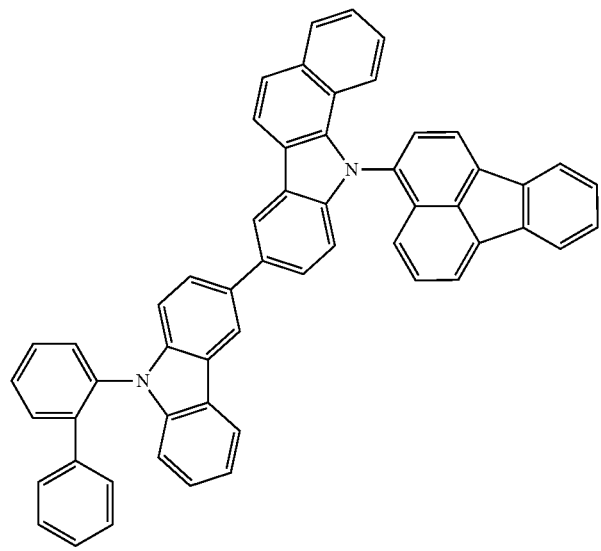
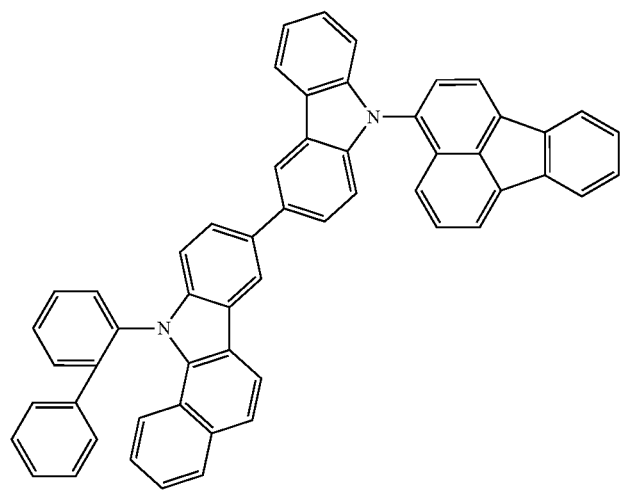
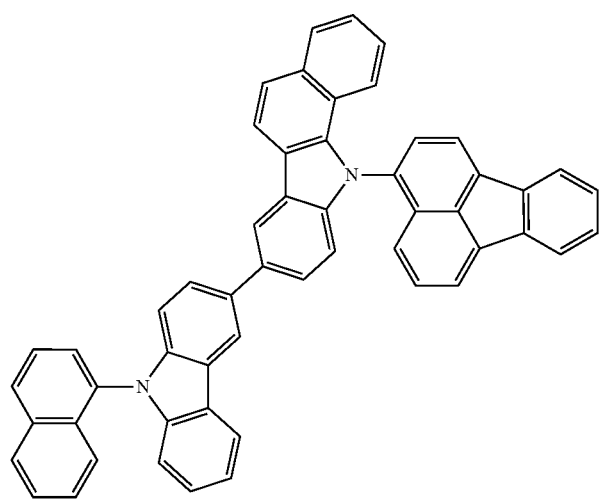

-continued
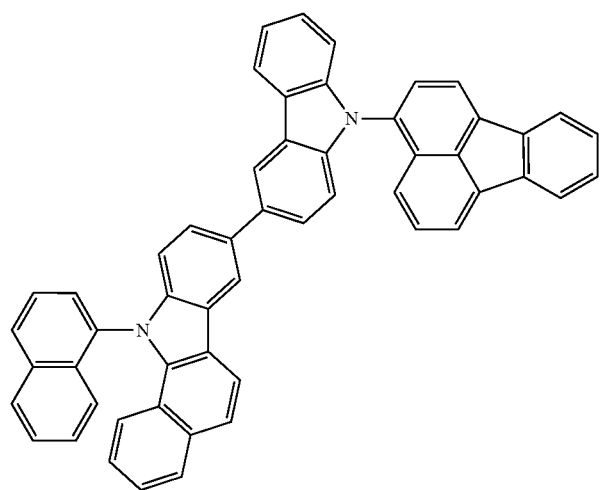
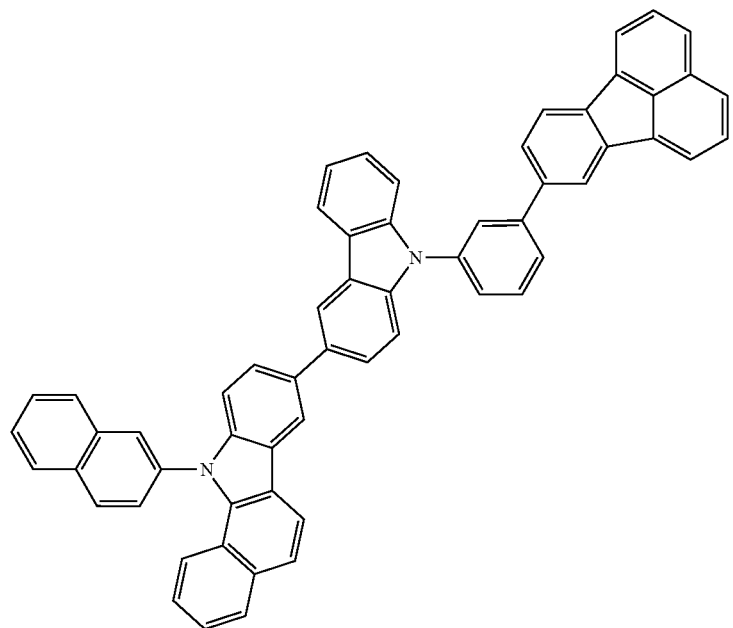
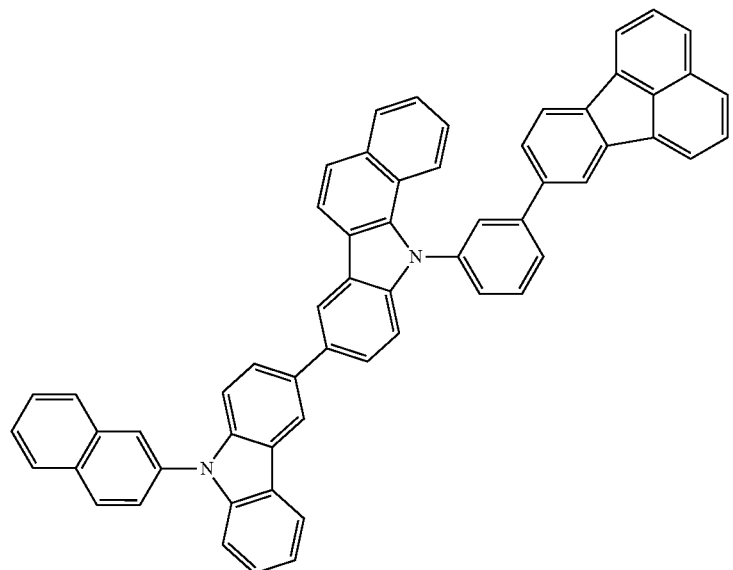

-continued
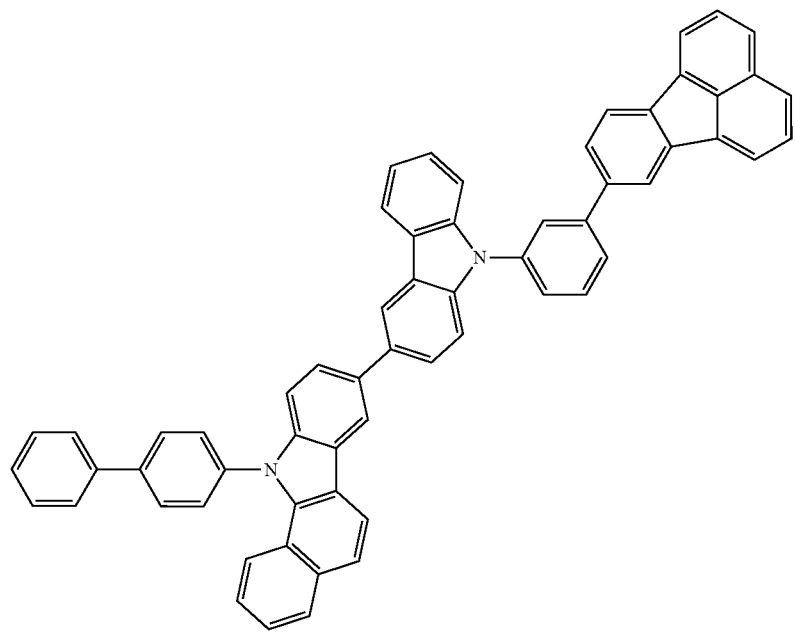
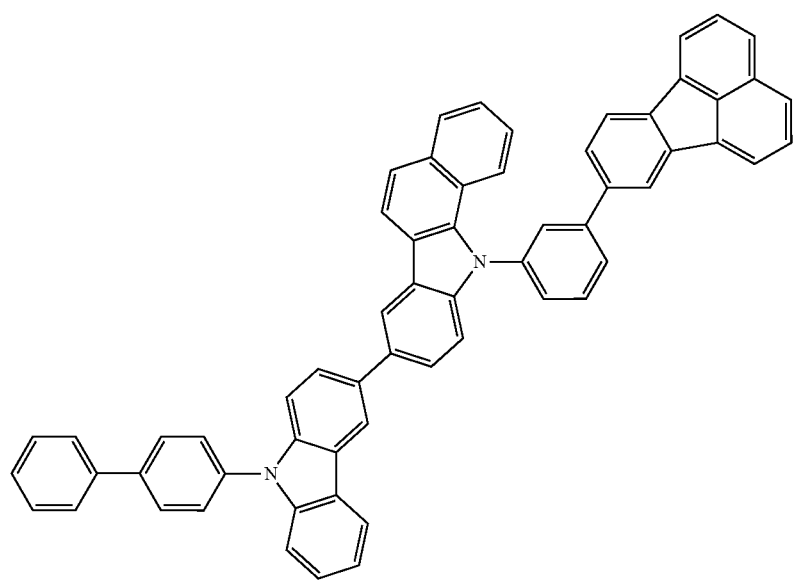

-continued
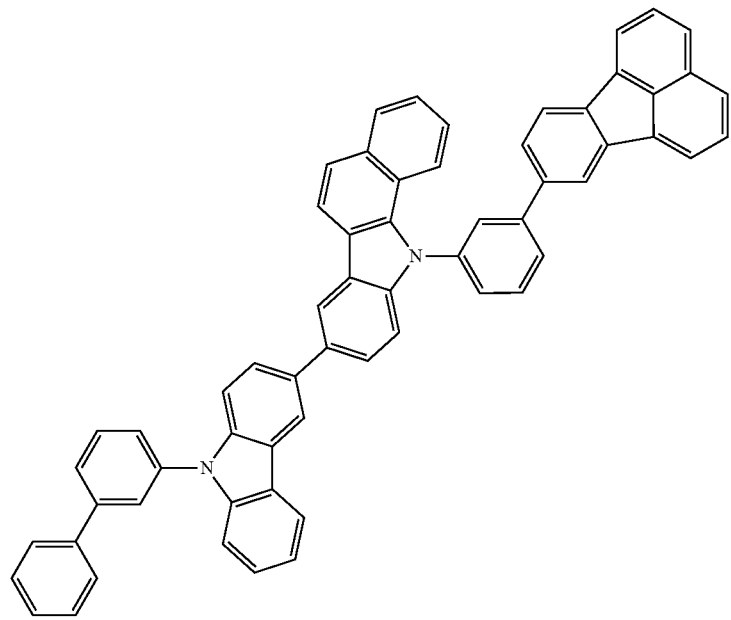
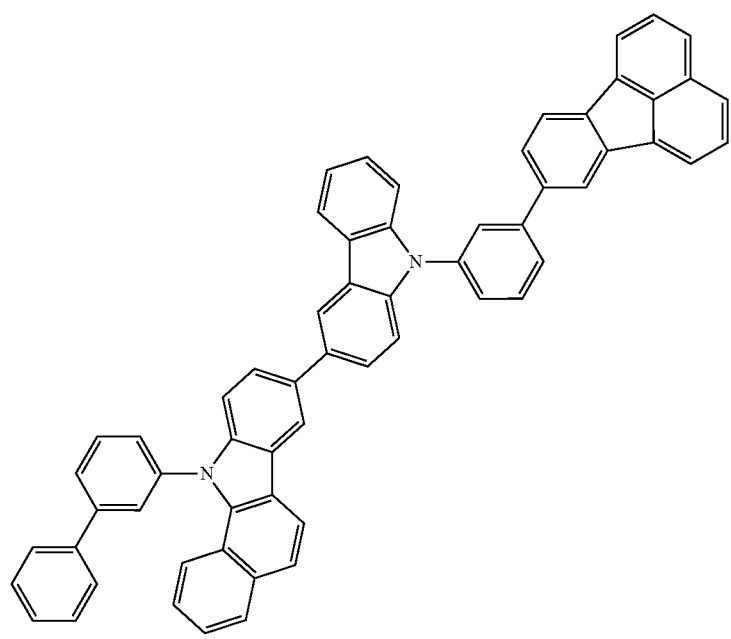

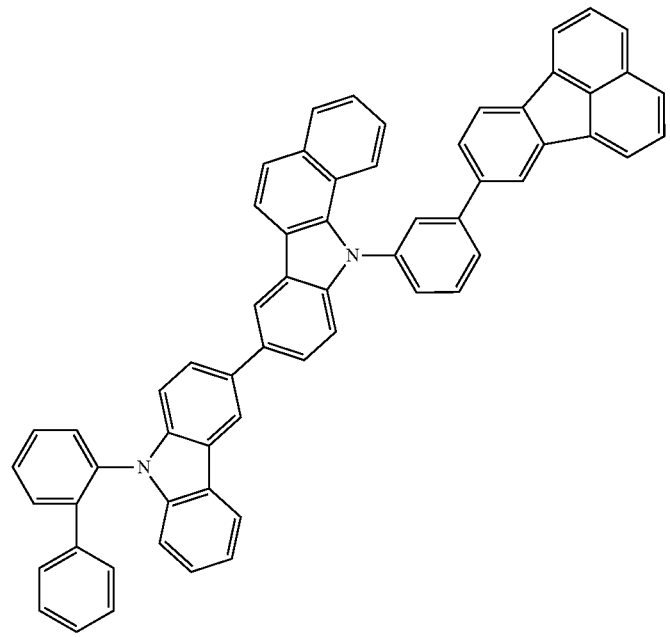
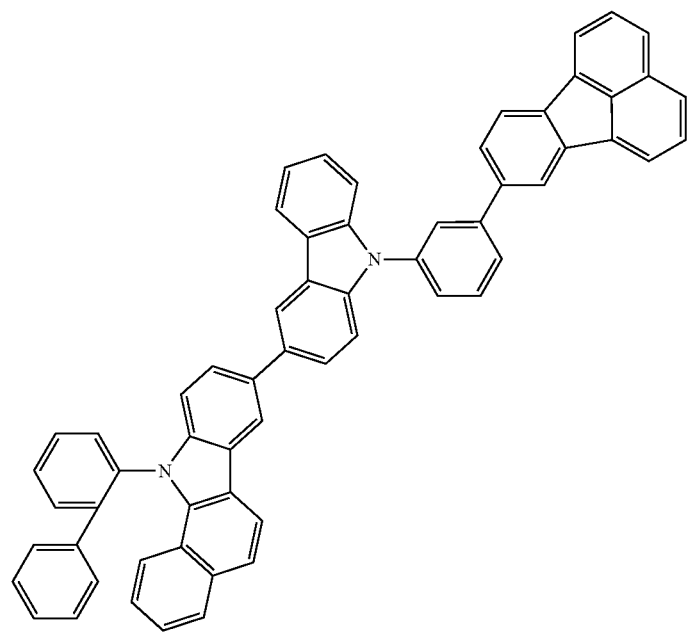

-continued
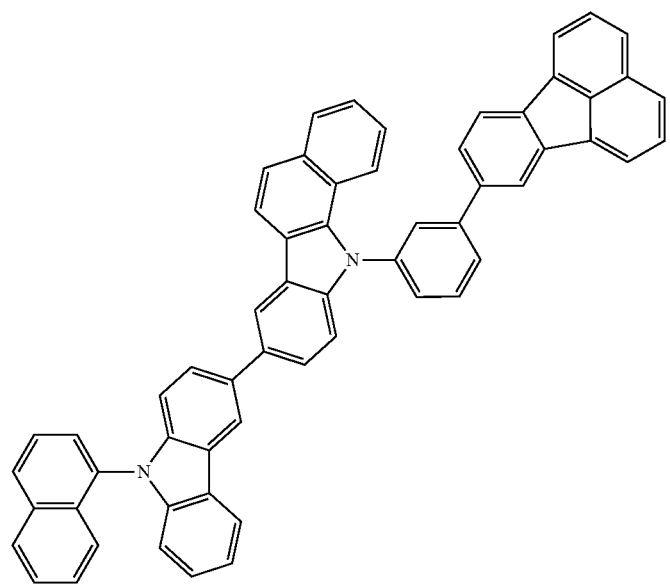
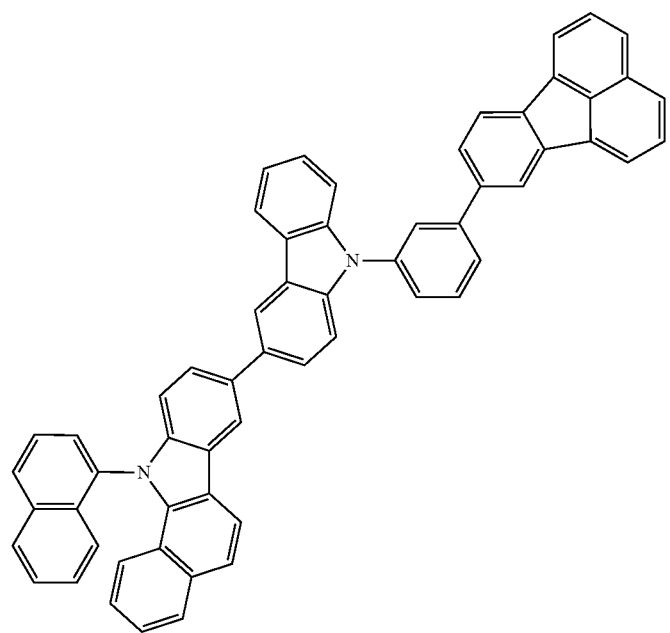 [SMILES: c1ccc(-n2c3ccc(-c4ccc5c(c4)c4ccccc4n5-c4cccc(-c5ccc6c(c5)-c5cccc7cccc-6c57)c4)cc3c3ccc4ccccc4c32)cc1]
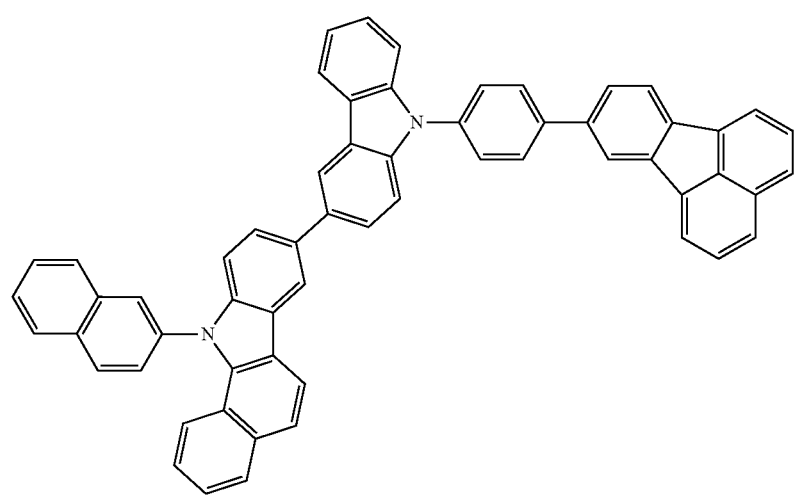

-continued
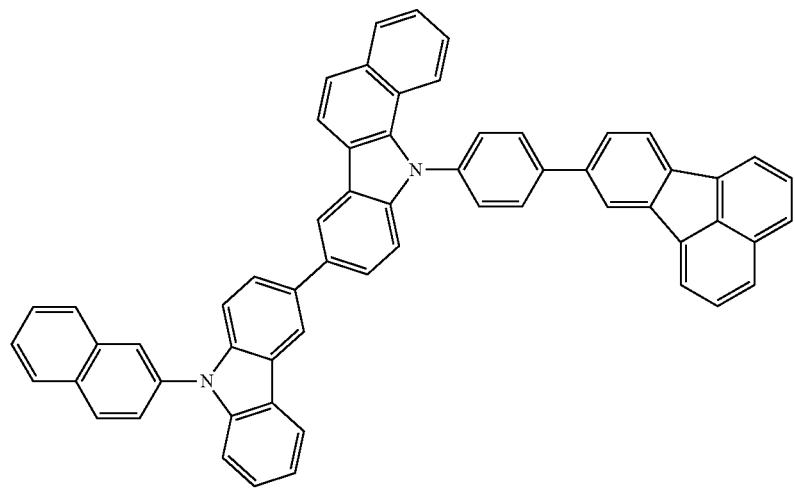
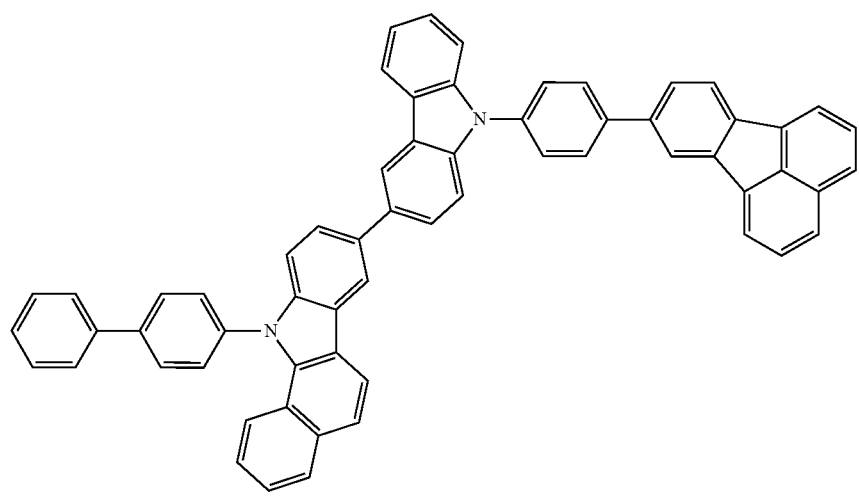
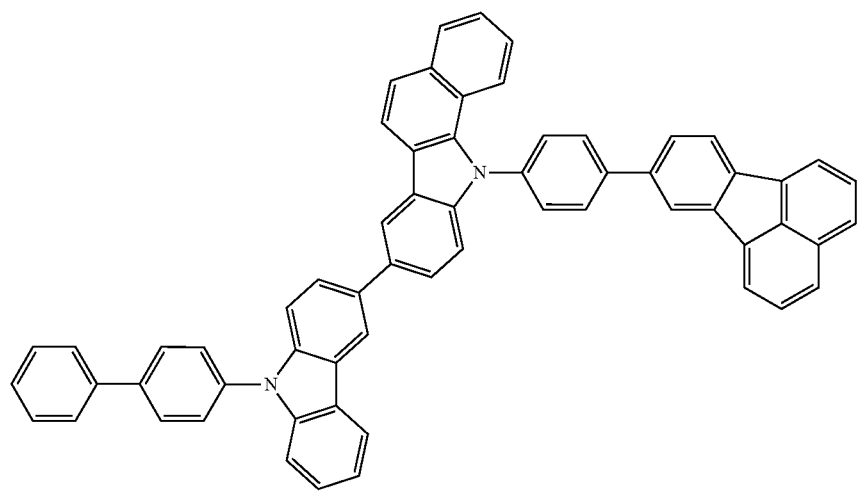

-continued
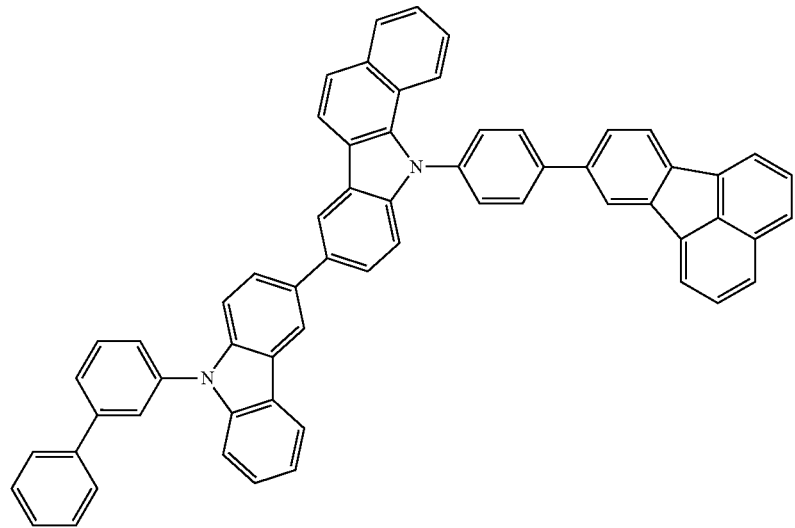
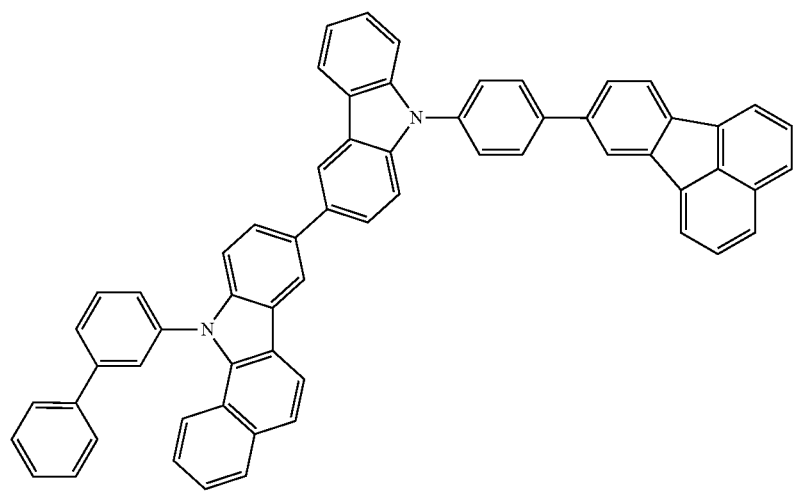
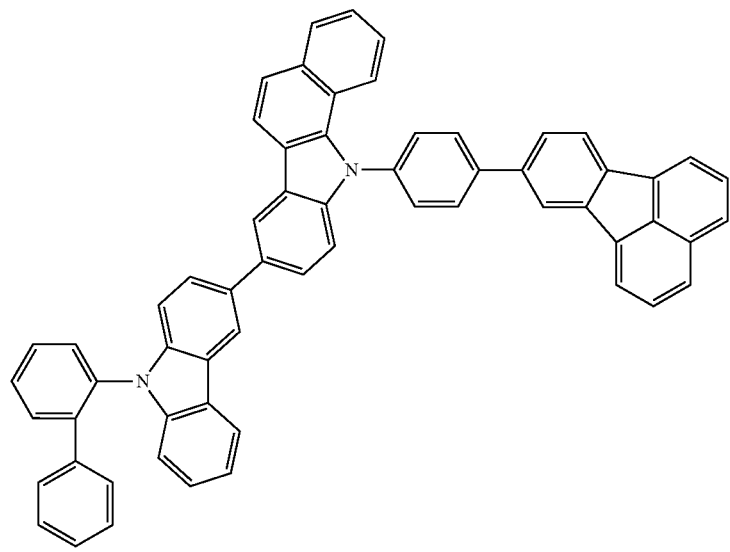

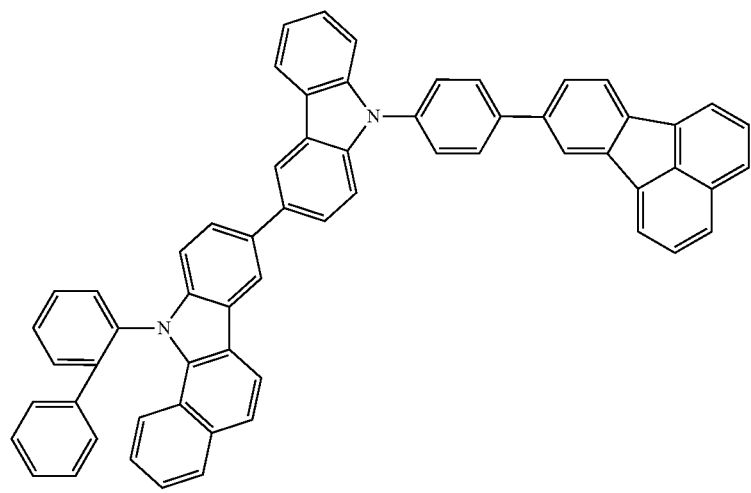
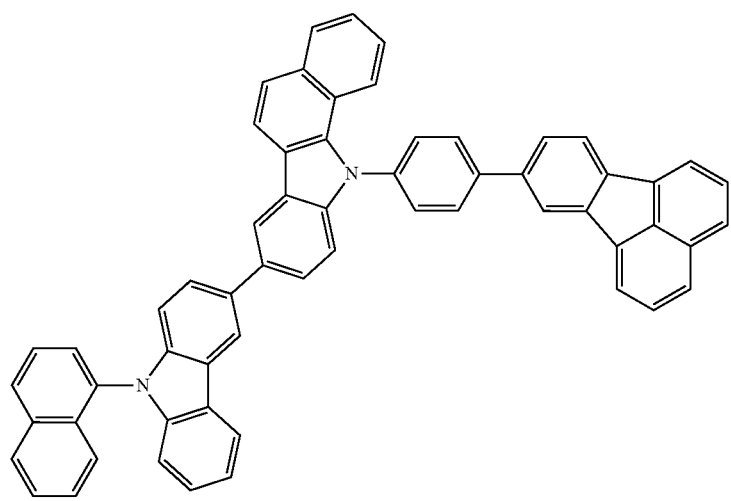
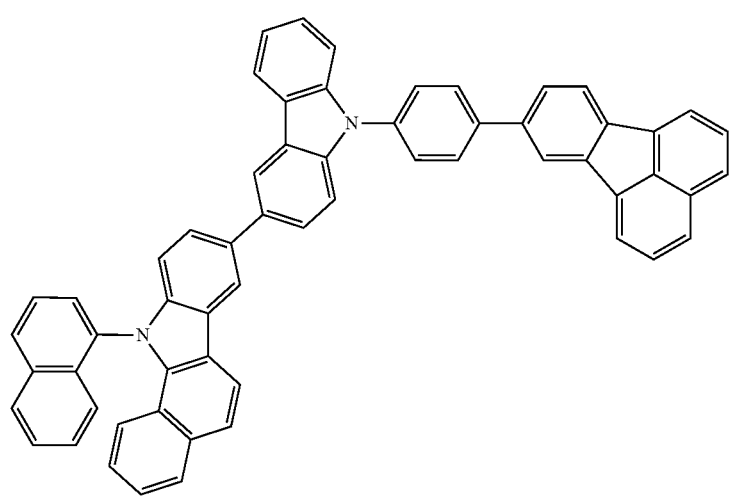

-continued
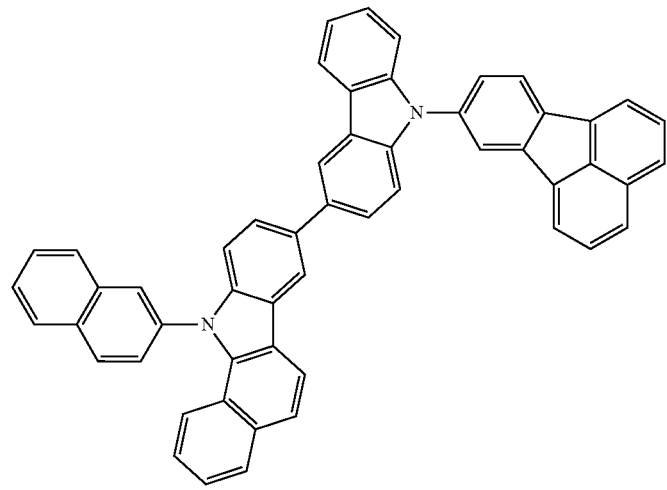
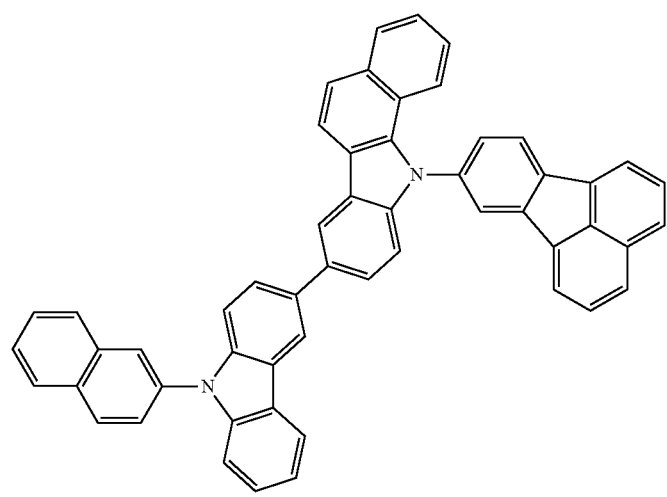
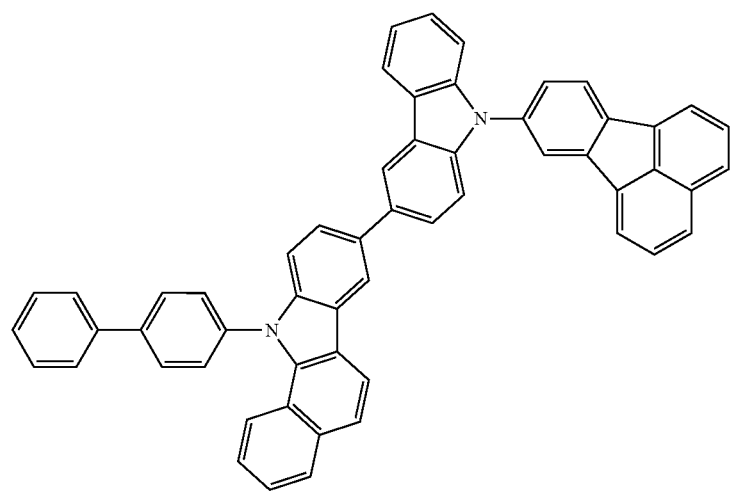

-continued
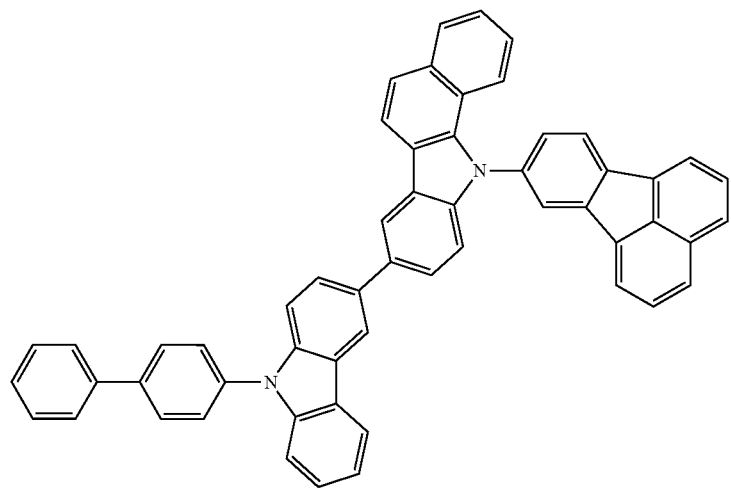
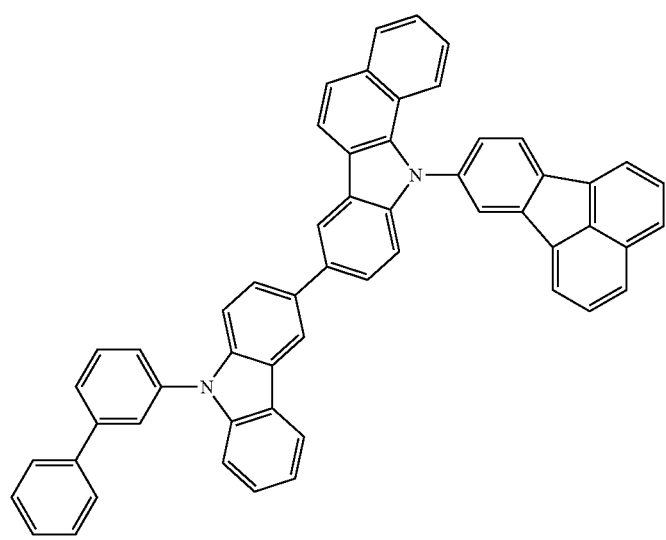
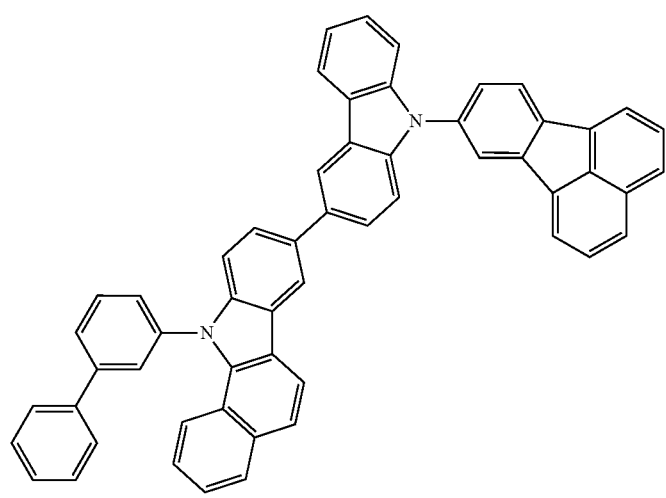

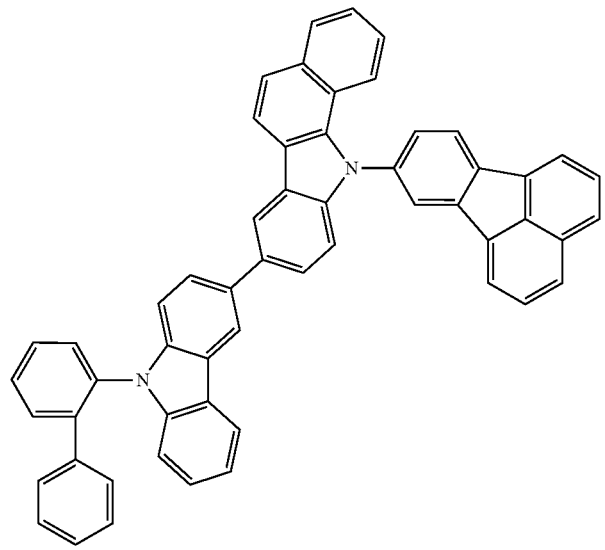
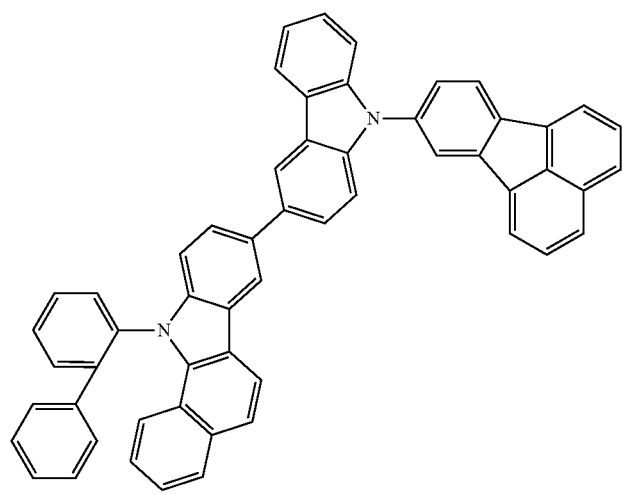
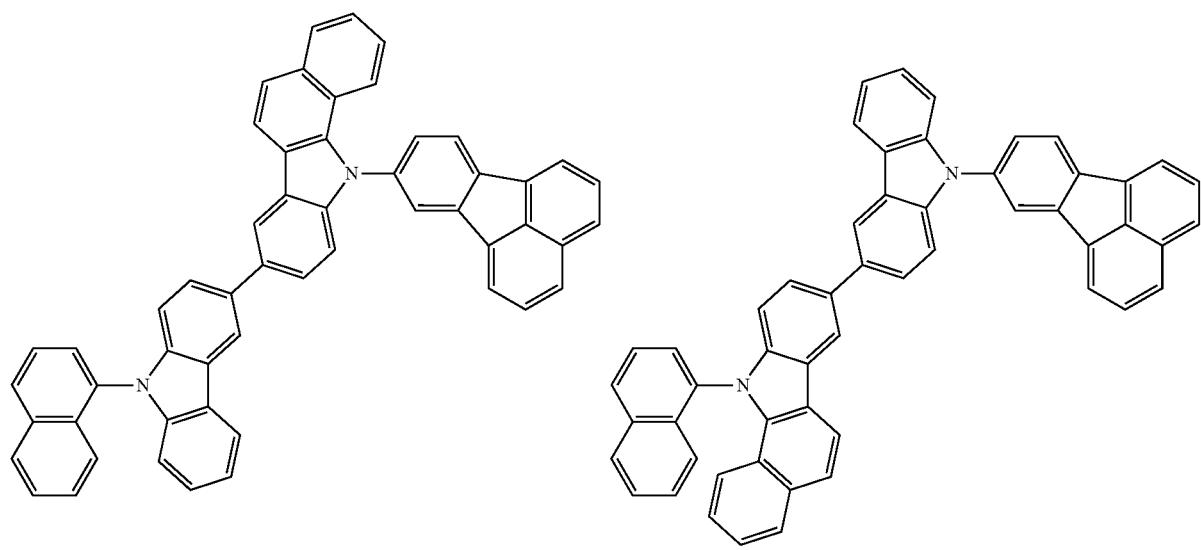

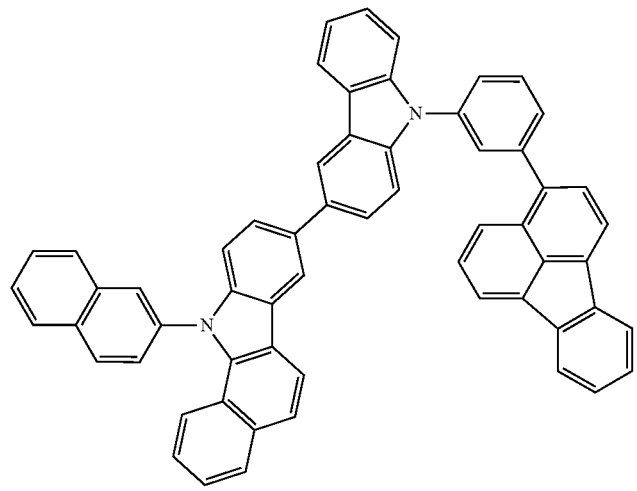
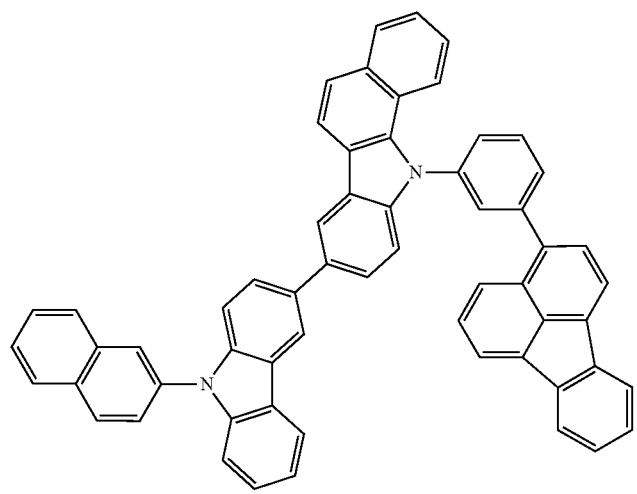
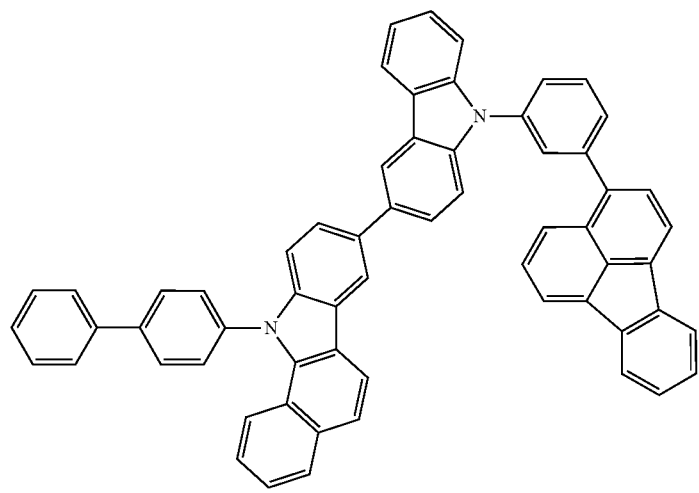

-continued
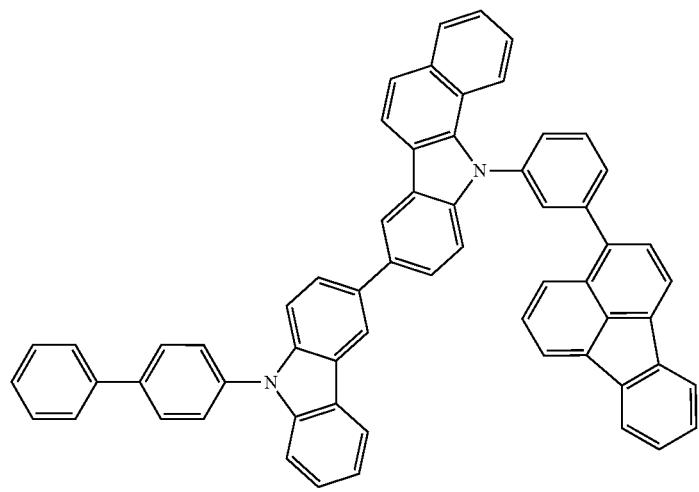
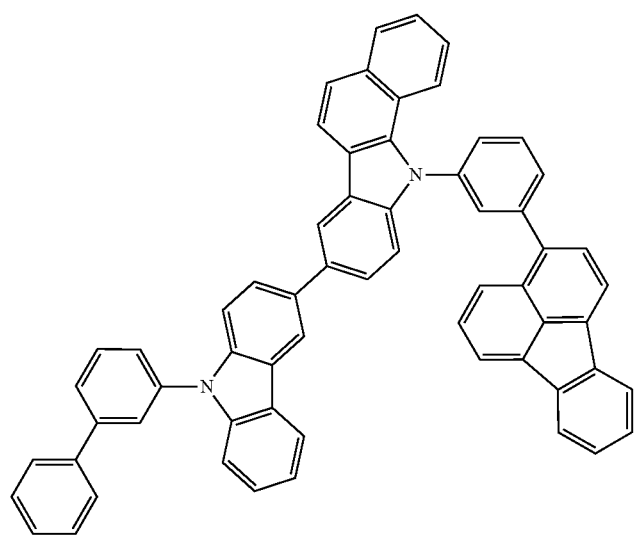
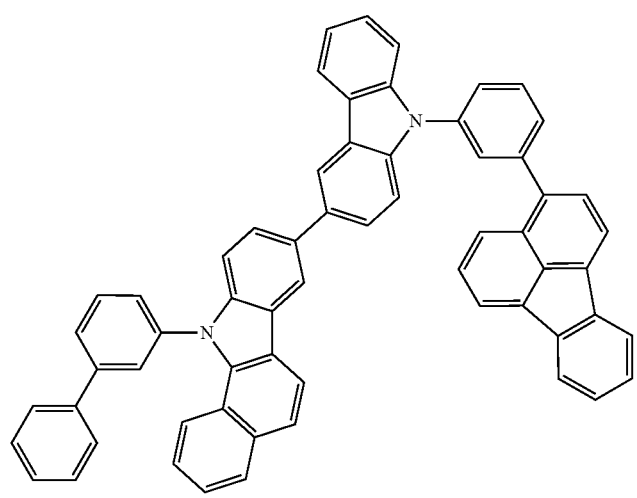

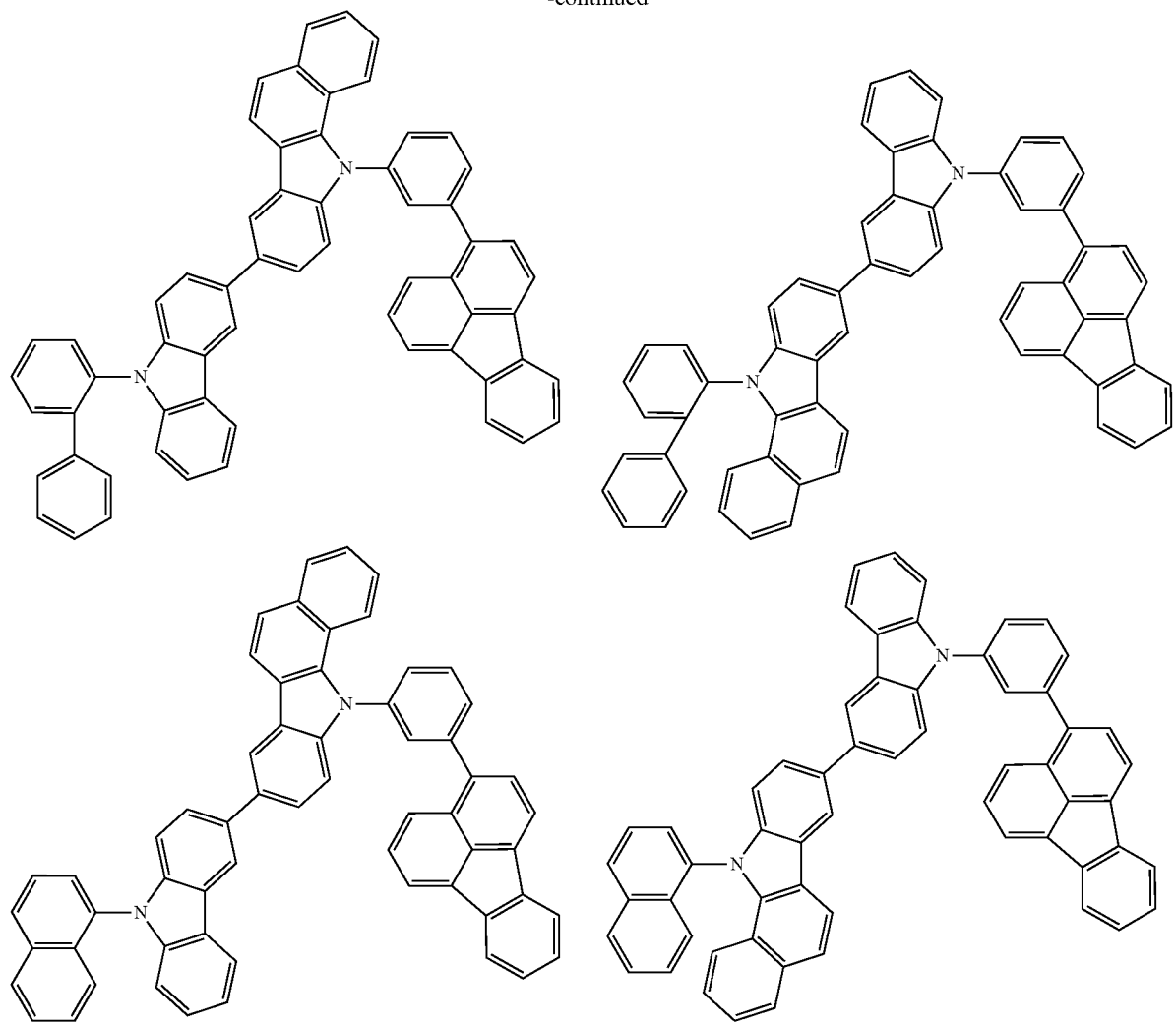

Material for Organic Electroluminescence Devices

The material for organic electroluminescence devices in an aspect of the invention comprises the compound represented by formula (1) (compound (1)). The content of the compound (1) in the material for organic electroluminescence devices is, but not particularly limited, 1% by mass or more (inclusive of 100%), preferably 10% by mass or more (inclusive of 100%), more preferably 50% by mass or more (inclusive of 100%), still more preferably 80% by mass or more (inclusive of 100%), and particularly preferably 90% by mass or more (inclusive of 100%).

The material for organic EL devices of the invention is useful as a material for producing an organic EL device and may be used, for example, in a light emitting layer of a phosphorescent emitting unit as a host material.

Organic Electroluminescence Device

The organic EL device in an aspect of the invention will be described below.

The organic EL device comprises an organic thin film layer between a cathode and an anode. The organic thin film layer comprises one or more layers and a light emitting layer, and at least one layer of the organic thin film layer comprises the compound (1).

Examples of the organic thin film layer which comprises the compound (1) include a light emitting layer, although not limited thereto. For example, the compound (1) is preferably used in a phosphorescent emission unit as a host material in a light emitting layer.

The organic EL device in an aspect of the invention may be any of a fluorescent or phosphorescent single color emitting device, a white-emitting device of fluorescent-phosphorescent hybrid type, a simple-type emitting device having a single emission unit, and a tandem emitting device having two or more emission units, with a fluorescent device being preferred. The "emission unit" referred to herein is the smallest unit for emitting light by the recombination of injected holes and injected electrons, which comprises an organic thin film layer comprising one or more layers, wherein at least one layer is a light emitting layer.

Representative device structures of the simple-type organic EL device are shown below:

(1) Anode/Emission Unit/Cathode

The emission unit may be a laminated unit comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the simple-type emission unit are shown below:

(a) (hole injecting layer/) hole transporting layer/fluorescent emitting layer (/electron transporting layer);
(b) (hole injecting layer/) hole transporting layer/first fluorescent emitting layer/second fluorescent emitting layer (/electron transporting layer);
(c) (hole injecting layer/) hole transporting layer/phosphorescent emitting layer/space layer/fluorescent emitting layer (/electron transporting layer);
(d) (hole injecting layer/) hole transporting layer/first phosphorescent emitting layer/second phosphorescent emitting layer/space layer/fluorescent emitting layer (/electron transporting layer);
(e) (hole injecting layer/) hole transporting layer/first phosphorescent emitting layer/space layer/second phosphorescent emitting layer/space layer/fluorescent emitting layer (/electron transporting layer);
(f) (hole injecting layer/) hole transporting layer/phosphorescent emitting layer/space layer/first fluorescent emitting layer/second fluorescent emitting layer (/electron transporting layer);
(g) (hole injecting layer/) hole transporting layer/electron blocking layer/fluorescent emitting layer (/electron transporting layer);
(h) (hole injecting layer/) hole transporting layer/electron blocking layer/phosphorescent emitting layer (/electron transporting layer);
(i) (hole injecting layer/) hole transporting layer/exciton blocking layer/fluorescent emitting layer (/electron transporting layer);
(j) (hole injecting layer/) hole transporting layer/exciton blocking layer/phosphorescent emitting layer (/electron transporting layer);
(k) (hole injecting layer/) first hole transporting layer/second hole transporting layer/fluorescent emitting layer (/electron transporting layer);
(l) (hole injecting layer/) first hole transporting layer/second hole transporting layer/phosphorescent emitting layer (/electron transporting layer);
(m) (hole injecting layer/) hole transporting layer/fluorescent emitting layer/hole blocking layer (/electron transporting layer); and
(n) (hole injecting layer/) hole transporting layer/fluorescent emitting layer/triplet blocking layer (/electron transporting layer).

The emission color of the fluorescent emitting layer and that of the phosphorescent emitting layer may be different. For example, the layered structure of the laminated emission unit (d) may be (hole injecting layer/) hole transporting layer/first phosphorescent emitting layer (red emission)/second phosphorescent emitting layer (green emission)/space layer/fluorescent emitting layer (blue emission)/electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such an electron blocking layer or a hole blocking layer, electrons and holes are confined in the light emitting layer to increase the charge recombination in the light emitting layer, thereby improving the emission efficiency.

Representative device structure of the tandem-type organic EL device is shown below:
(2) anode/first emission unit/intermediate layer/second emission unit/cathode.

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials which can supply electrons to the first emission unit and holes to the second emission unit.

A schematic structure of an example of the organic EL device is shown in the FIGURE, wherein the organic EL device 1 comprises a substrate 2, an anode 3, a cathode 4, and an emission unit 10 disposed between the anode 3 and the cathode 4. The emission unit 10 comprises a light emitting layer 5. A hole injecting layer or a hole transporting layer 6 (anode-side organic thin film layer) may be disposed between the light emitting layer 5 and the anode 3, and an electron injecting layer or a electron transporting layer 7 (cathode-side organic thin film layer) may be disposed between the light emitting layer 5 and the cathode 4. An electron blocking layer (not shown) may be disposed on the side of anode 3 of the light emitting layer 5, and a hole blocking layer (not shown) may be disposed on the side of cathode 4 of the light emitting layer 5. With these blocking layers, electrons and holes are confined in the light emitting layer 5 to increase the exciton generation in the light emitting layer 5.

In the present specification, a host is referred to as a fluorescent host when combinedly used with a fluorescent dopant (fluorescent emitting material) and as a phosphorescent host when combinedly used with a phosphorescent dopant. Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be utilized as a material for a fluorescent emitting layer. The same applies to the fluorescent host.

Substrate

The substrate is a support for the emitting device and made of, for example, glass, quartz, and plastics. The substrate may be a flexible substrate, for example, a plastic substrate made of polycarbonate, polyarylate, polyether sulfone, polypropylene, polyester, polyvinyl fluoride, and polyvinyl chloride. An inorganic deposition film is also usable.

Anode

The anode is formed on the substrate preferably from a metal, an alloy, an electrically conductive compound, and a mixture thereof, each having a large work function, for example, 4.5 eV or more. Examples of the material for the anode include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold (Au), platinum (Pt), nickel (Ni), tungsten (W), chromium (Cr), molybdenum (Mo), iron (Fe), cobalt (Co), copper (Cu), palladium (Pd), titanium (Ti), and a nitride of the above metal (for example, titanium nitride) are also usable.

These materials are made into a film generally by a sputtering method. For example, a film of indium oxide-zinc oxide is formed by sputtering an indium oxide target doped with 1 to 10 wt % of zinc oxide, and a film of indium oxide doped with tungsten oxide and zinc oxide is formed by sputtering an indium oxide target doped with 0.5 to 5 wt % of tungsten oxide and 0.1 to 1 wt % of zinc oxide. In addition, a vacuum vapor deposition method, a coating method, an inkjet method, and a spin coating method are usable.

A hole injecting layer to be optionally formed in contact with the anode is formed from a material which is capable of easily injecting holes independently of the work function of the anode. Therefore, the anode can be formed by a material generally known as an electrode material, for example, a metal, an alloy, an electroconductive compound, a mixture thereof, and a group 1 element and a group 2 element of the periodic table.

A material having a small work function, for example, the group 1 element and the group 2 element of the periodic table, i.e., an alkali metal, such as lithium (Li) and cesium (Cs), an alkaline earth metal, such as magnesium (Mg), calcium (Ca), and strontium (Sr), and an alloy thereof, such as MgAg and AlLi, are also usable. In addition, a rare earth metal, such as europium (Eu) and ytterbium (Yb), and an alloy thereof are also usable. The alkali metal, the alkaline earth metal, and the alloy thereof can be made into the anode by a vacuum vapor deposition or a sputtering method. When a silver paste, etc. is used, a coating method and an inkjet method are usable.

Hole Injecting Layer

The hole injecting layer comprises a highly hole injecting material (hole injecting material).

Examples of the hole injecting material include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

The following low molecular aromatic amine compound is also usable as the hole injecting material:
4,4',4"-tris(N,N-diphenylamino)triphenylamine (TDATA), 4,4',4"-tris[N-(3-methylphenyl)-N-phenylamino]triphenylamine (MTDATA), 4,4'-bis[N-(4-diphenylaminophenyl)-N-phenylamino]biphenyl (DPAB), 4,4'-bis(N-{4-[N'-(3-methylphenyl)-N'-phenylamino]phenyl}-N-phenylamino)biphenyl (DNTPD), 1,3,5-tris[N-(4-diphenylaminophenyl)-N-phenylamino]benzene (DPA3B), 3-[N-(9-phenylcarbazole-3-yl)-N-phenylamino]-9-phenylcarbazole (PCzPCA1), 3,6-bis[N-(9-phenylcarbazole-3-yl)-N-phenylamino]-9-phenylcarbazole (PCzPCA2), and 3-[N-(1-naphthyl)-N-(9-phenylcarbazole-3-yl)amino]-9-phenylcarbazole (PCzPCN1).

A macromolecular compound, such as an oligomer, a dendrimer, a polymer, is also usable. Examples thereof include poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide] (PTPDMA), and poly[N,N'-bis(4-butylphenyl)-N,N'-bis(phenyl)benzidine] (Poly-TPD). An acid-added macromolecular compound, such as poly(3,4-ethylenedioxythiophene)/poly(styrenesulfonic acid) (PEDOT/PSS) and polyaniline/poly(styrenesulfonic acid) (PAni/PSS), is also usable.

In addition, an acceptor material, such as a hexaazatriphenylene (HAT) compound represented by formula (K), is preferably used in combination with the compound (1):

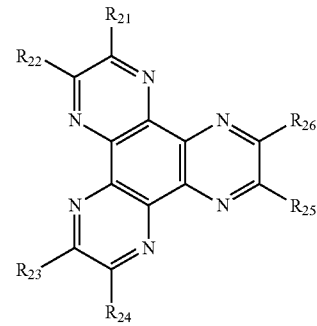

(K)

wherein $R_{21}$ to $R_{26}$ may be the same or different and each of $R_{21}$ to $R_{26}$ is independently a cyano group, —$CONH_2$, a carboxyl group, or —$COOR_{27}$ wherein $R_{27}$ is an alkyl group having 1 to 20 carbon atoms or a cycloalkyl group having 3 to 20 carbon atoms, or $R_{21}$ and $R_{22}$, $R_{23}$ and $R_{24}$, or $R_{25}$ and $R_{26}$ may be bonded to each other to form a group represented by —CO—O—CO—.

Examples of $R_{27}$ include a methyl group, an ethyl group, a n-propyl group, an isopropyl group, a n-butyl group, an isobutyl group, a t-butyl group, a cyclopentyl group, and a cyclohexyl group.

Hole Transporting Layer

The hole transporting layer comprises a highly hole transporting material (hole transporting material).

Examples of the hole transporting material include an aromatic amine compound, a carbazole derivative, and an anthracene derivative. Examples of the aromatic amine compound are 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4-phenyl-4'-(9-phenylfluoren-9-yl)triphenylamine (BAFLP), 4,4'-bis[N-(9,9-dimethylfluoren-2-yl)-N-phenylamino]biphenyl (DFLDPBi), 4,4',4"-tris(N,N-diphenylamino)triphenylamine (TDATA), 4,4',4"-tris[N-(3-methylphenyl)-N-phenylamino]triphenylamine (MTDATA), and 4,4'-bis[N-(spiro-9,9'-bifluoren-2-yl)-N-phenylamino]biphenyl (BSPB). The above compounds have a hole mobility of mainly $10^{-6}$ cm$^2$/Vs or more.

The hole transporting layer may comprise a carbazole derivative, such as 4,4'-di(9-carbazolyl)biphenyl (CBP), 9-[4-(9-carbazolyl)phenyl]-10-phenylanthracene (CzPA), and 9-phenyl-3-[4-(10-phenyl-9-anthryl)phenyl]-9H-carbazole (PCzPA); an anthracene derivative, such as 2-t-butyl-9,10-di(2-naphthyl)anthracene (t-BuDNA), 9,10-di(2-naphthyl)anthracene (DNA), and 9,10-diphenylanthracene (DPAnth); and a macromolecular compound, such as poly(N-vinylcarbazole) (PVK) and poly(4-vinyltriphenylamine) (PVTPA).

Compounds other than those mentioned above are also usable if their hole transporting ability is higher than their electron transporting ability. The layer comprising a highly hole-transporting material may be a single layer or a laminate of two or more layers each comprising the compound mentioned above. For example, the hole transporting layer may be a two-layered structure of a first hole transporting layer (anode side) and a second hole transporting layer (cathode side). In this case, the compound (1) may be used in either of the first hole transporting layer and the second hole transporting layer. In an embodiment of the invention, the compound (1) is preferably used in the first hole transporting layer. In another embodiment of the invention, the compound (1) is preferably used in the second hole transporting layer.

Dopant Material of Light Emitting Layer

The light emitting layer comprises a highly light-emitting material (dopant material) and may be formed from a various kind of materials. For example, a fluorescent emitting material and a phosphorescent emitting material are usable as the dopant material. The fluorescent emitting material is a compound capable of emitting light from a singlet excited state, and the phosphorescent emitting material is a compound capable of emitting light from a triplet excited state.

Examples of blue fluorescent emitting material for use in the light emitting layer include a pyrene derivative, a styrylamine derivative, a chrysene derivative, a fluoranthene derivative, a fluorene derivative, a diamine derivative, and a triarylamine derivative, such as N,N'-bis[4-(9H-carbazole-9-yl)phenyl]-N,N'-diphenylstilbene-4,4'-diamine (YGA2S), 4-(9H-carbazole-9-yl)-4'-(10-phenyl-9-anthryl)triphenylamine (YGAPA), and 4-(10-phenyl-9-anthryl)-4'-(9-phenyl-9H-carbazole-3-yl)triphenylamine (PCBAPA).

Examples of green fluorescent emitting material for use in the light emitting layer include an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PCABPhA), N-(9,10-diphenyl-2-anthryl)-N,N',N'-triphenyl-1,4-phenylenediamine (2DPAPA), N-[9,10-bis(1,1'-biphenyl-2-yl)-2-anthryl]-N,N',N'-triphenyl-1,4-phenylenediamine (2DPABPhA), N-[9,10-bis(1,1'-biphenyl-2-yl)]-N-[4-(9H-carbazole-9-yl)phenyl]-N-phenylanthracene-2-amine (2YGABPhA), and N,N,9-triphenylanthracene-9-amine (DPhAPhA).

Examples of red fluorescent emitting material for use in the light emitting layer include a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material for use in the light emitting layer include a metal complex, such as an iridium complex, an osmium complex, and a platinum complex. Examples thereof include bis[2-(4',6'-difluorophenyl)pyridinato-N,C2']iridium(III) tetrakis(1-pyrazolyl)borato (FIr$_6$), bis[2-(4',6'-difluorophenyl)pyridinato-N,C2'] iridium(III) picolinato (FIrpic), bis[2-(3',5'-bistrifluoromethylphenyl)pyridinato-N,C2']iridium(III) picolinato (Ir(CF$_3$ppy)$_2$(pic)), and bis[2-(4',6'-difluorophenyl)pyridinato-N,C2']iridium(III) acetylacetonato (FIracac).

Examples of green phosphorescent emitting material for use in the light emitting layer include an iridium complex, such as tris(2-phenylpyridinato-N,C2')iridium(III) (Ir(ppy)$_3$), bis(2-phenylpyridinato-N,C2')iridium(III) acetylacetonato (Ir(ppy)$_2$(acac)), bis(1,2-diphenyl-1H-benzimidazolato)iridium(III) acetylacetonato (Ir(pbi)$_2$(acac)), and bis(benzo[h]quinolinato)iridium(III) acetylacetonato (Ir(bzq)$_2$ (acac)).

Examples of red phosphorescent emitting material for use in the light emitting layer include a metal complex, such as an iridium complex, a platinum complex, a terbium complex, and a europium complex. Examples thereof include an organometallic complex, such as bis[2-(2'-benzo[4,5-α]thienyl)pyridinato-N,C3']iridium(III) acetylacetonato (Ir(btp)$_2$ (acac)), bis(1-phenylisoquinolinato-N,C2')iridium(III) acetylacetonato (Ir(piq)$_2$(acac)), (acetylacetonato)bis[2,3-bis(4-fluorophenyl)quinoxalinato]iridium(III) (Ir(Fdpq)$_2$ (acac)), and 2,3,7,8,12,13,17,18-octaethyl-21H,23H-porphyrin platinum(II) (PtOEP).

Examples of red phosphorescent emitting material for use in the light emitting layer include a metal complex, such as an iridium complex, a platinum complex, a terbium complex, and a europium complex. Examples thereof include an organometallic complex, such as bis[2-(2'-benzo[4,5-α]thienyl)pyridinato-N,C3']iridium(III) acetylacetonato (Ir(btp)$_2$ (acac)), bis(1-phenylisoquinolinato-N,C2')iridium(III) acetylacetonato (Ir(piq)$_2$(acac)), (acetylacetonato)bis[2,3-bis(4-fluorophenyl)quinoxalinato]iridium(III) (Ir(Fdpq)$_2$ (acac)), and 2,3,7,8,12,13,17,18-octaethyl-21H,23H-porphyrin platinum(II) (PtOEP).

A rare earth metal complex, such as tris(acetylacetonato)(monophenanthroline)terbium(III) (Tb(acac)$_3$(Phen)), tris(1,3-diphenyl-1,3-propanedionato)(monophenanthroline)europium(III) (Eu(DBM)$_3$(Phen)), and tris[1-(2-thenoyl)-3,3,3-trifluoroacetonato](monophenanthroline)europium(III) (Eu (TTA)$_3$(Phen)), emits light from the rare earth metal ion (electron transition between different multiple states), and therefore, usable as a phosphorescent emitting compound.

Host Material for Light Emitting Layer

The light emitting layer may be formed by dispersing the dopant material mentioned above in another material (host material). The host material is preferably the compound (1) of the invention which can be used in combination with another material. The host material preferably has a lowest unoccupied molecular orbital level (LUMO level) higher than that of the dopant material and a highest occupied molecular orbital level (HOMO level) lower than that of the dopant material.

The host material other than the compound (1) may include, for example, (1) a metal complex, such as an aluminum complex, a beryllium complex, and a zinc complex;

(2) a heterocyclic compound, such as an oxadiazole derivative, a benzimidazole derivative, and a phenanthroline derivative;

(3) a fused aromatic compound, such as a carbazole derivative, an anthracene derivative, a phenanthrene derivative, a pyrene derivative, and a chrysene derivative; and (4) an aromatic amine compound, such as a triarylamine derivative and a fused aromatic polycyclic amine derivative.

Examples thereof include:

a metal complex, such as tris(8-quinolinolato)aluminum (III) (Alq), tris(4-methyl-8-quinolinolato)aluminum(III) (Almq$_3$), bis(10-hydroxybenzo[h]quinolinato)beryllium(H) (BeBq$_2$), bis(2-methyl-8-quinolinolato)(4-phenylphenolato) aluminum(III) (BAlq), bis(8-quinolinolato)zinc(II) (Znq), bis[2-(2-benzoxazolyl)phenolato]zinc(II) (ZnPBO), and bis [2-(2-benzothiazolyl)phenolato]zinc(II) (ZnBTZ);

a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-biphenylyl)-4-phenyl-5-(4-tert-butylphenyl)-1,2,4-triazole (TAZ), 2,2',2"-(1,3,5-benzenetriyl)tris(1-phenyl-1H-benzimidazole) (TPBI), bathophenanthroline (BPhen), and bathocuproin (BCP);

a fused aromatic compound, such as 9-[4-(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilbene-3,3'-diyl)diphenanthrene (DPNS), 9,9'-(stilbene-4,4'-diyl)diphenanthrene (DPNS2), 3,3',3"-(benzene-1,3,5- triyl)tripyrene (TPB3), 9,10-diphenylanthracene (DPAnth), and 6,12-dimethoxy-5,11-diphenylchrysene; and an aromatic amine compound, such as N,N-diphenyl-9-[4-(10-phenyl-9-anthryl)phenyl]-9H-carbazole-3-amine (CzA1PA), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl]phenyl}-9H-carbazole-3-amine (PCAPBA), N-(9,10-diphenyl-2-anthryl)-N,9-diphenyl-9H-carbazole-3-amine (2PCAPA), 4,4'-bis[N-(1-anthryl)-N-phenylamino]biphenyl (NPB or α-NPD), N,N'-bis(3-methylphenyl)-N,N'-diphenyl-[1,1'-biphenyl]-4,4'-diamine (TPD), 4,4'-bis[N-(9,9-dimethylfluorene-2-yl)-N-phenylamino]biphenyl (DFLDPBi), and 4,4'-bis[N-(spiro-9,9'-bifluorene-2-yl)-N-phenylamino]biphenyl (BSPB). The host material may be used alone or in combination of two or more.

Electron Transporting Layer

The electron transporting layer comprises a highly electron-transporting material (electron transporting material). Examples thereof are:

(1) a metal complex, such as an aluminum complex, a beryllium complex, and a zinc complex;

(2) a heteroaromatic compound, such as an imidazole derivative, a benzimidazole derivative, an azine derivative, a carbazole derivative, and a phenanthroline derivative; and (3) a macromolecular compound.

Examples of the metal complex include tris(8-quinolinolato)aluminum (III) (Alq), tris(4-methyl-8-quinolinolato)aluminum (Almq$_3$), bis(10-hydroxybenzo[h]quinolinato)beryllium (BeBq$_2$), bis(2-methyl-8-quinolinolato)(4-phenylphenolato)aluminum (III)(BAlq), bis(8-quinolinato)zinc(II) (Znq), bis[2-(2-benzoxazolyl)phenolato]zinc(II) (ZnPBO), and bis[2-(2-benzothiazolyl)phenolato]zinc(II) (ZnBTZ).

Examples of the heteroaromatic compound include 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), and 4,4'-bis(5-methylbenzoxazole-2-yl)stilbene (BzOs).

Examples of the macromolecular compound include poly[(9,9-dihexylfluorene-2,7-diyl)-co-(pyridine-3,5-diyl)] (PF-Py), and poly[(9,9-dioctylfluorene-2,7-diyl)-co-(2,2'-bipyridine-6,6'-diyl)] (PF-BPy).

The above compounds have an electron mobility of mainly $10^{-6}$ cm$^2$/Vs or more. Materials other than those mentioned above are also usable in the electron transporting layer if their electron transporting ability is higher than their hole transporting ability. The electron transporting layer may be a single layer or a laminate of two or more layers each comprising the material mentioned above.

Electron Injecting Layer

The electron injecting layer comprises a highly electron-injecting material, for example, an alkali metal, an alkaline earth metal, and a compound of these metals, such as lithium (Li), cesium (Cs), calcium (Ca), lithium fluoride (LiF), cesium fluoride (CsF), calcium fluoride (CaF2), and lithium oxide (LiOx). In addition, an electron transporting material which is doped with an alkali metal, an alkaline earth metal or a compound thereof, for example, Alq doped with magnesium (Mg), is also usable. By using such a material, electrons are efficiently injected from the cathode.

A composite material obtained by mixing an organic compound and an electron donor is also usable in the electron injecting layer. Such a composite material is excellent in the electron injecting ability and the electron transporting ability, because the organic compound receives electrons from the electron donor. The organic compound is preferably a material excellent in transporting the received electrons. Examples thereof are the materials for the electron transporting layer mentioned above, such as the metal complex and the aromatic heterocyclic compound. Any material capable of giving its electron to another organic compound is usable as the electron donor. Preferred examples thereof are an alkali metal, an alkaline earth metal, and a rare earth metal, such as lithium, cesium, magnesium, calcium, erbium, and ytterbium; an alkali metal oxide and an alkaline earth metal oxide, such as, lithium oxide, calcium oxide, and barium oxide; a Lewis base, such as magnesium oxide; and an organic compound, such as tetrathiafulvalene (TTF).

Cathode

The cathode is formed preferably from a metal, an alloy, an electrically conductive compound, or a mixture thereof, each having a small work function, for example, a work function of 3.8 eV or less. Examples of the material for the cathode include a metal of the group 1 or 2 of the periodic table, for example, an alkali metal, such as lithium (Li) and cesium (Cs), an alkaline earth metal, such as magnesium (Mg), an alloy containing these metals (for example, MgAg and AlLi), a rare earth metal, such as europium (Eu) and ytterbium (Yb), and an alloy containing a rare earth metal.

The alkali metal, the alkaline earth metal, and the alloy thereof can be made into the cathode by a vacuum vapor deposition or a sputtering method. When a silver paste, etc. is used, a coating method and an inkjet method are usable.

When the electron injecting layer is formed, the material for the cathode can be selected independently from the work function and various electroconductive materials, such as Al, Ag, ITO, graphene, and indium oxide-tin oxide doped with silicon or silicon oxide, are usable. These electroconductive materials are made into films by a sputtering method, an inkjet method, and a spin coating method.

Insulating Layer

Since electric field is applied to the ultra-thin films of organic EL devices, the pixel defects due to leak and short circuit tends to occur. To prevent the defects, an insulating thin film layer is preferably interposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. These materials may be used in combination or may be made into laminated layers.

Space Layer

For example, in an organic EL device wherein a fluorescent emitting layer and a phosphorescent emitting layer are laminated, a space layer is disposed between the fluorescent emitting layer and the phosphorescent emitting layer to prevent the diffusion of excitons generated in the phosphorescent emitting layer to the fluorescent emitting layer or to control the carrier balance. The space layer may be disposed between two or more phosphorescent emitting layers.

Since the space layer is disposed between the light emitting layers, a material combining the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described with respect to the hole transporting layer are usable as the material for the space layer.

Blocking Layer

In the organic EL device, a blocking layer, such as an electron blocking layer, a hole blocking layer, and a triplet blocking layer, may be provided in the portion adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The triplet blocking layer prevents the diffusion of excitons generated in the light emitting layer to adjacent layers and has a function of confining the excitons in the light emitting layer. The compound (1) of the invention is also suitable as the material for the electron blocking layer and the triplet blocking layer.

Each layer of the organic EL device can be formed by a known method, such as a vapor deposition method and a coating method. For example, each layer can be formed by a known vapor deposition method, such as a vacuum vapor deposition method and a molecular beam evaporation method (MBE method), and a known coating method using a solution of the compound for forming the layer, such as a dipping method, a spin coating method, a casting method, a bar coating method, and a roll coating method.

The thickness of each layer is not particularly limited and preferably 5 nm to 10 μm, more preferably 10 nm to 0.2 μm, because an excessively small thickness may cause defects such as pin holes and an excessively large thickness may require a high driving voltage.

The organic EL device can be used in an electronic device, for example, as display parts, such as organic EL panel module, display devices of television sets, mobile phones, personal computer, etc., and light emitting sources of lighting equipment and vehicle lighting equipment.

EXAMPLES

The invention will be described in more detail with reference to the examples and comparative examples. It should be noted that the scope of the invention is not limited to the following examples.

Intermediate Synthesis 1: Synthesis of Intermediate (A)

(1) Synthesis of 8-bromo-11-phenylbenzo[a]carbazole

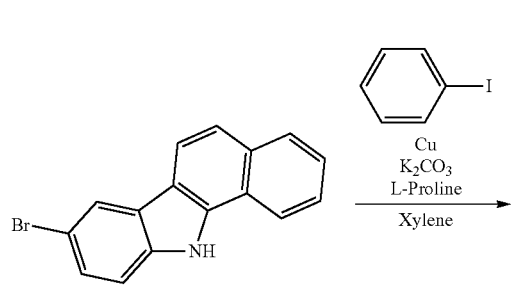

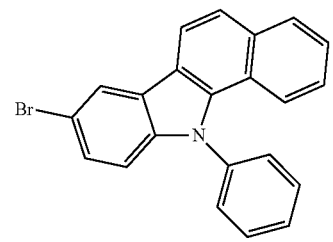
-continued

Under argon atmosphere, 29.6 g of 8-bromo-11H-benzo[a]carbazole, 12.7 g of copper, 41.5 g of potassium carbonate, 40.8 g of iodobenzene, and 80 mL of xylene were charged in a flask, and the contents were stirred at 135° C. for 65 h under heating. After adding 21.0 g of L-proline, the contents were stirred at the same temperature for 67 h under heating.

After cooling to room temperature, the reaction solution was filtered and then extracted with toluene. The filtrate was washed with water and the obtained organic layer was concentrated. The residue was purified by a column chromatography and further by a recrystallization to obtain 22.2 g of 8-bromo-11-phenylbenzo[a]carbazole. The result of mass spectrographic analysis was m/e=371 to the molecular weight of 371 of 8-bromo-11-phenylbenzo[a]carbazole.

(2) Synthesis of Intermediate (A)

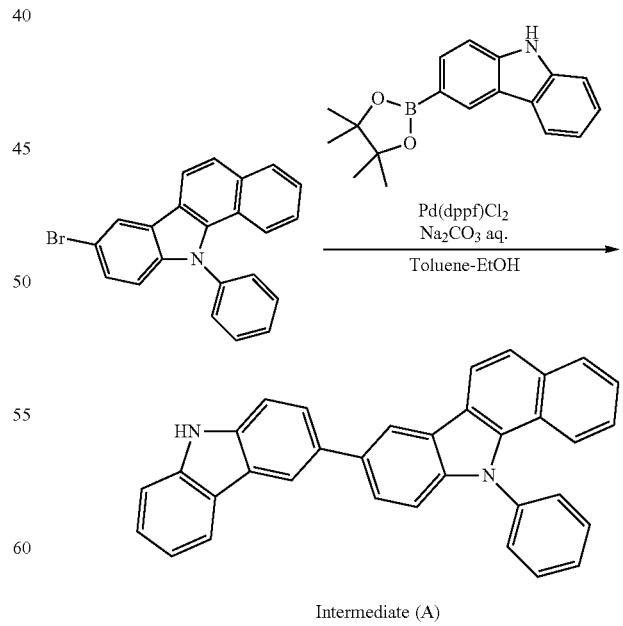

Intermediate (A)

Under argon atmosphere, 26.7 g of 8-bromo-11-phenylbenzo[a]carbazole, 2.34 g of [1,1'-bis(diphenylphosphino)ferrocene]palladium(II) dichloride dichloromethane adduct, 270 mL of toluene, 90 mL of ethanol, and 107 mL of a 2 M aqueous solution of sodium carbonate were charged in a flask, and the contents were stirred at 70° C. under heating. After adding 21.0 g of 3-(4,4,5,5-tetramethyl-1,3,2-dioxaborolan-2-yl)carbazole, the contents were stirred at the same temperature for 56 h under heating.

After cooling to room temperature, the reaction solution was filtered and then extracted with toluene. The filtrate was washed with water and the obtained organic layer was concentrated. The residue was purified by a column chromatography and further by a recrystallization to obtain 16.5 g of the intermediate (A). The result of mass spectrographic analysis was m/e=458 to the molecular weight of 458 of the intermediate (A).

Intermediate Synthesis 2: Synthesis of Intermediate (F)

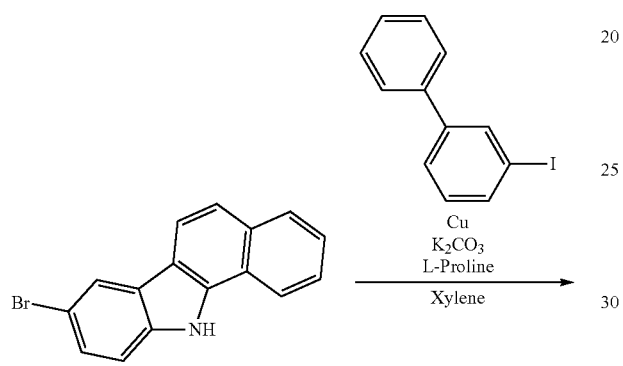

-continued

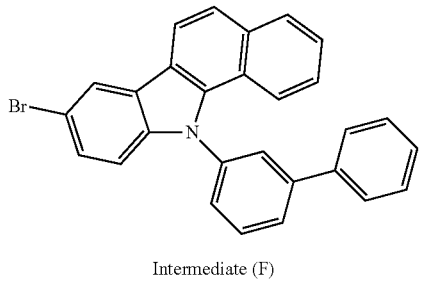

Intermediate (F)

The intermediate (F) was synthesized in the same manner as in the synthesis of 8-bromo-11-phenylbenzo[a]carbazole of Intermediate Synthesis 1 except for using 3-iodobiphenyl in place of iodobenzene. The result of mass spectrographic analysis was m/e=447 to the molecular weight of 447 of the intermediate (F).

Intermediate Synthesis 3: Synthesis of Intermediate (G)

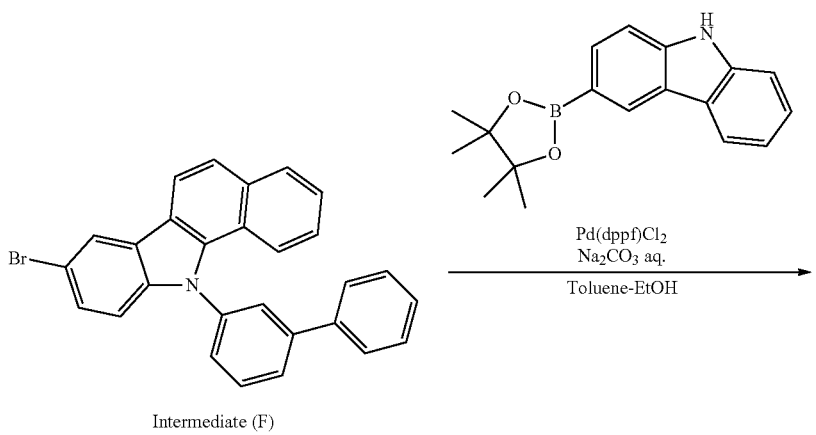

Intermediate (F)

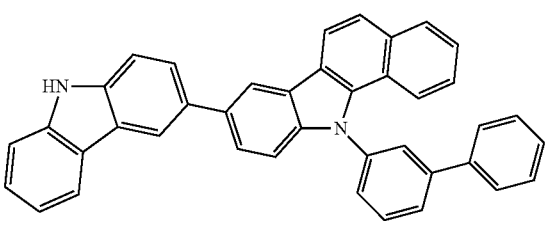

Intermediate (G)

The intermediate (G) was synthesized in the same manner as in the synthesis of the intermediate (A) of Intermediate Synthesis 1 except for using the intermediate (F) in place of 8-bromo-11-phenylbenzo[a]carbazole. The result of mass spectrographic analysis was m/e=534 to the molecular weight of 534 of the intermediate (G).

Intermediate Synthesis 4: Synthesis of Intermediate (H)

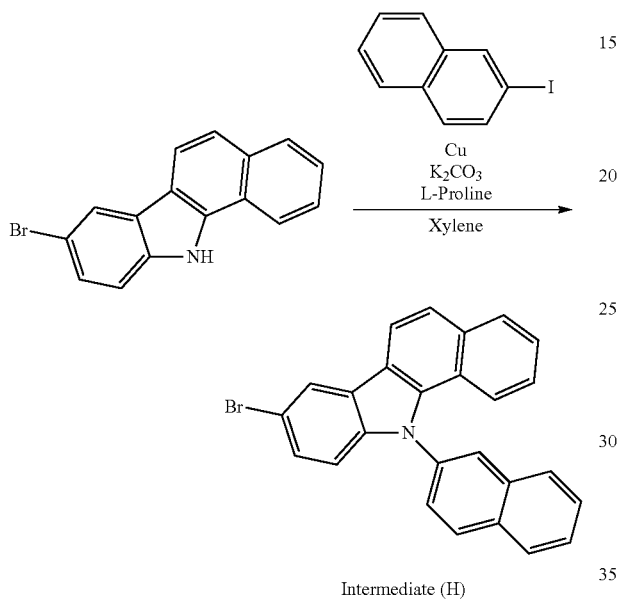

Intermediate (H)

The intermediate (H) was synthesized in the same manner as in the synthesis of 8-bromo-11-phenylbenzo[a]carbazole of Intermediate Synthesis 1 except for using 2-iodonaphthalene in place of iodobenzene. The result of mass spectrographic analysis was m/e=421 to the molecular weight of 421 of the intermediate (H).

Intermediate Synthesis 4: Synthesis of Intermediate (I)

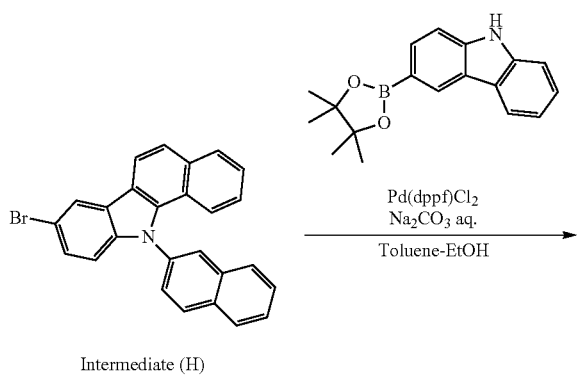

Intermediate (H)

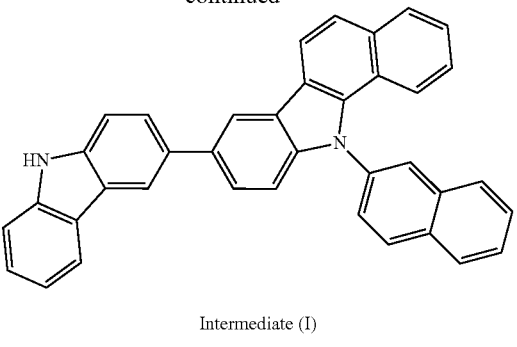

Intermediate (I)

The intermediate (I) was synthesized in the same manner as in the synthesis of the intermediate (A) of Intermediate Synthesis 1 except for using the intermediate (H) in place of 8-bromo-11-phenylbenzo[a]carbazole. The result of mass spectrographic analysis was m/e=508 to the molecular weight of 508 of the intermediate (I).

Intermediate Synthesis 5: Synthesis of Intermediate (J)

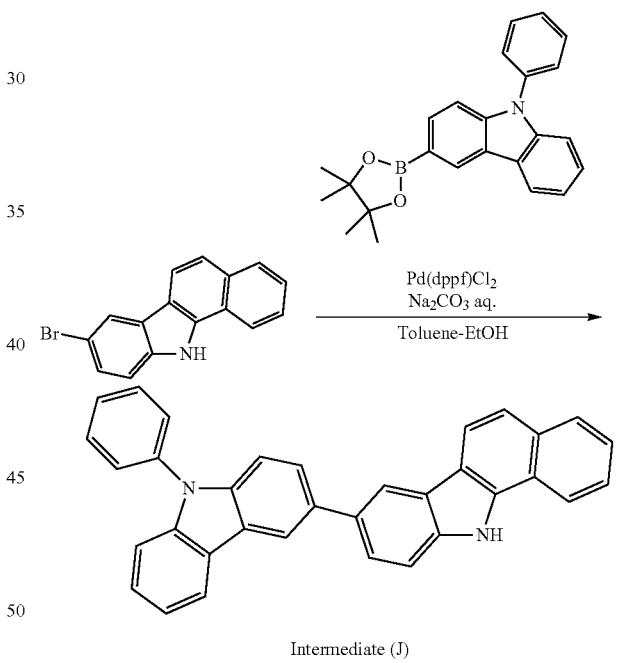

Intermediate (J)

Under argon atmosphere, 12.7 g of 8-bromo-11H-benzo[a]carbazole, 1.4 g of [1,1'-bis(diphenylphosphino)ferrocene]palladium(II)dichloride dichloromethane adduct, 110 mL of toluene, 55 mL of ethanol, and 64 mL of a 2 M aqueous solution of sodium carbonate were charged in a flask, and the contents were stirred at 70° C. After adding 15.8 g of 9-phenyl-3-(4,4,5,5-tetramethyl-1,3,2-dioxaborolan-2-yl)carbazole, the contents were stirred at the same temperature for 64 h under heating.

After cooling to room temperature, the reaction solution was filtered and then extracted with toluene. The filtrate was washed with water and then the obtained organic layer was concentrated. The residue was purified by a column chromatography and further by a recrystallization to obtain 10.5 g of the intermediate (J). The result of mass spectrographic analysis was m/e=458 to the molecular weight of 458 of the intermediate (J).

Intermediate Synthesis 6: Synthesis of Intermediate (K)

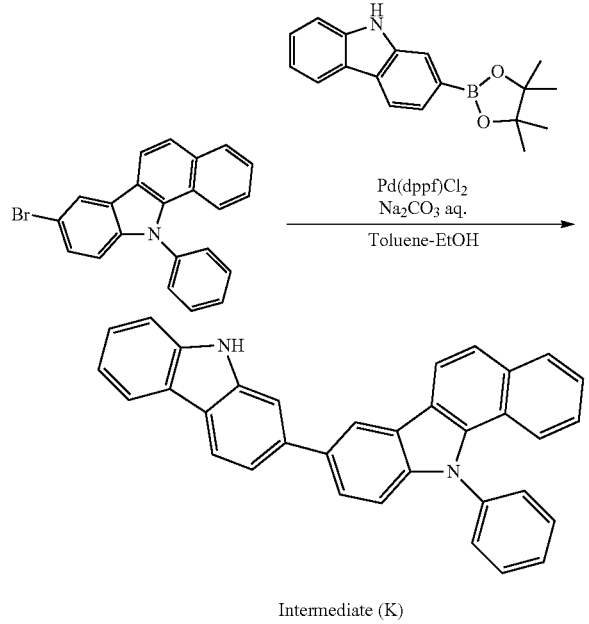

Intermediate (K)

The intermediate (K) was synthesized in the same manner as in the synthesis of the intermediate (A) of Intermediate Synthesis 1 except for using 2-(4,4,5,5-tetramethyl-1,3,2-dioxaborolan-2-yl)carbazole synthesized by a known method in place of 3-(4,4,5,5-tetramethyl-1,3,2-dioxaborolan-2-yl)carbazole. The result of mass spectrographic analysis was m/e=458 to the molecular weight of 458 of the intermediate (K).

Synthesis Example 1: Synthesis of Compound H1

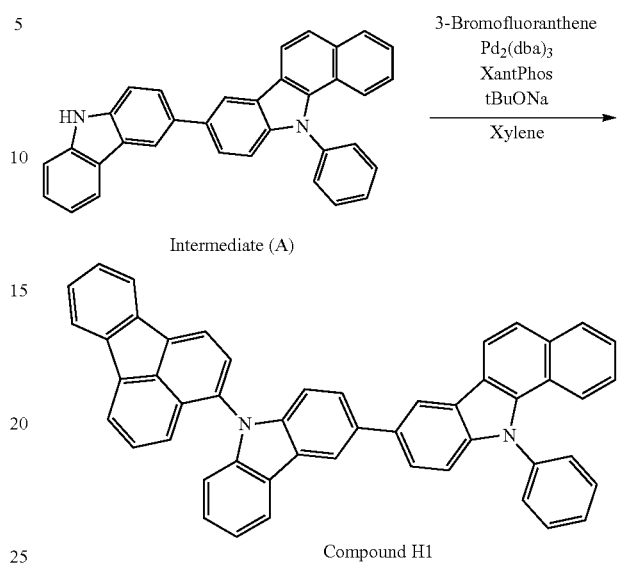

Compound H1

Under argon atmosphere, 11.3 g of the intermediate (A), 7.0 g of 3-bromofluoranthene, 460 mg of tris(dibenzylideneacetone)dipalladium(0), 1.1 g of 4,5-bis(diphenylphosphino)-9,9-dimethylxanthene, 7.15 g of sodium t-butoxide, and 250 mL of xylene were charged in a flask, and the contents were refluxed for 10 h under heating. After cooling to room temperature, the reaction solution was extracted with toluene, and the organic layer was dried and concentrated. The obtained residue was purified by a column chromatography to obtain the compound H1 (8.0 g, 49%). The result of mass spectrographic analysis was m/e=658 to the molecular weight of 658 of the compound H1.

Synthesis Example 2: Synthesis of Compound H2

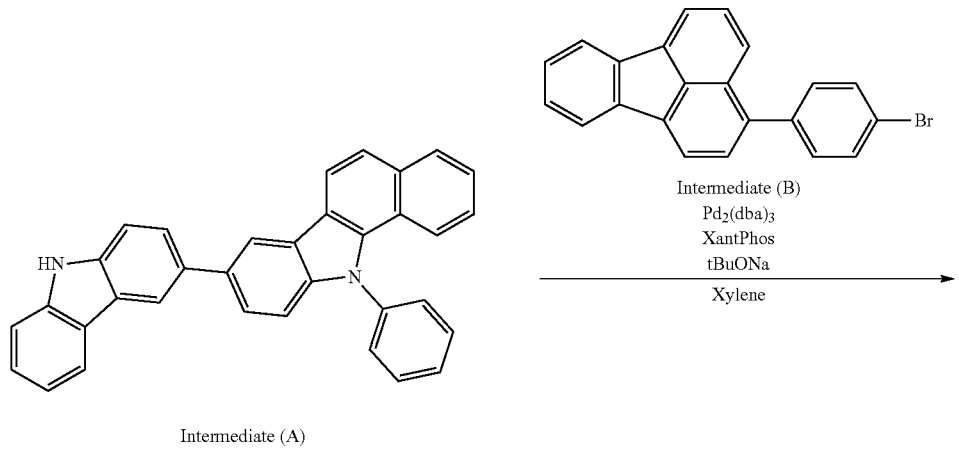

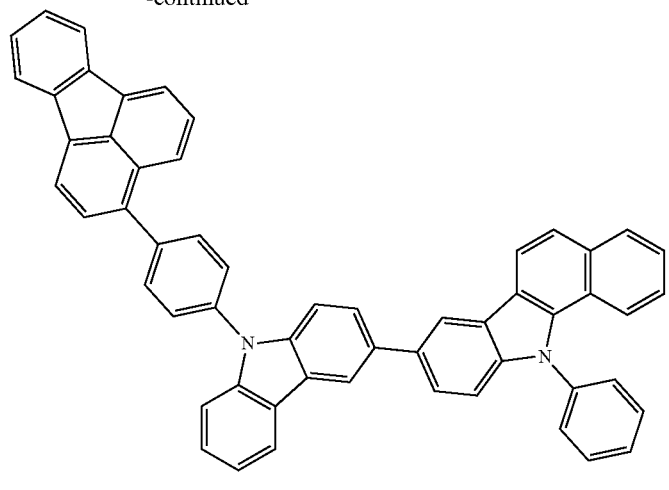
Compound H2
The compound H2 was synthesized in the same manner as in Synthesis Example 1 except for using the intermediate (B) synthesized by a known method in place of 3-bromofluoranthene. The result of mass spectrographic analysis was m/e=734 to the molecular weight of 734 of the compound H2.
Synthesis Example 3: Synthesis of Compound H3
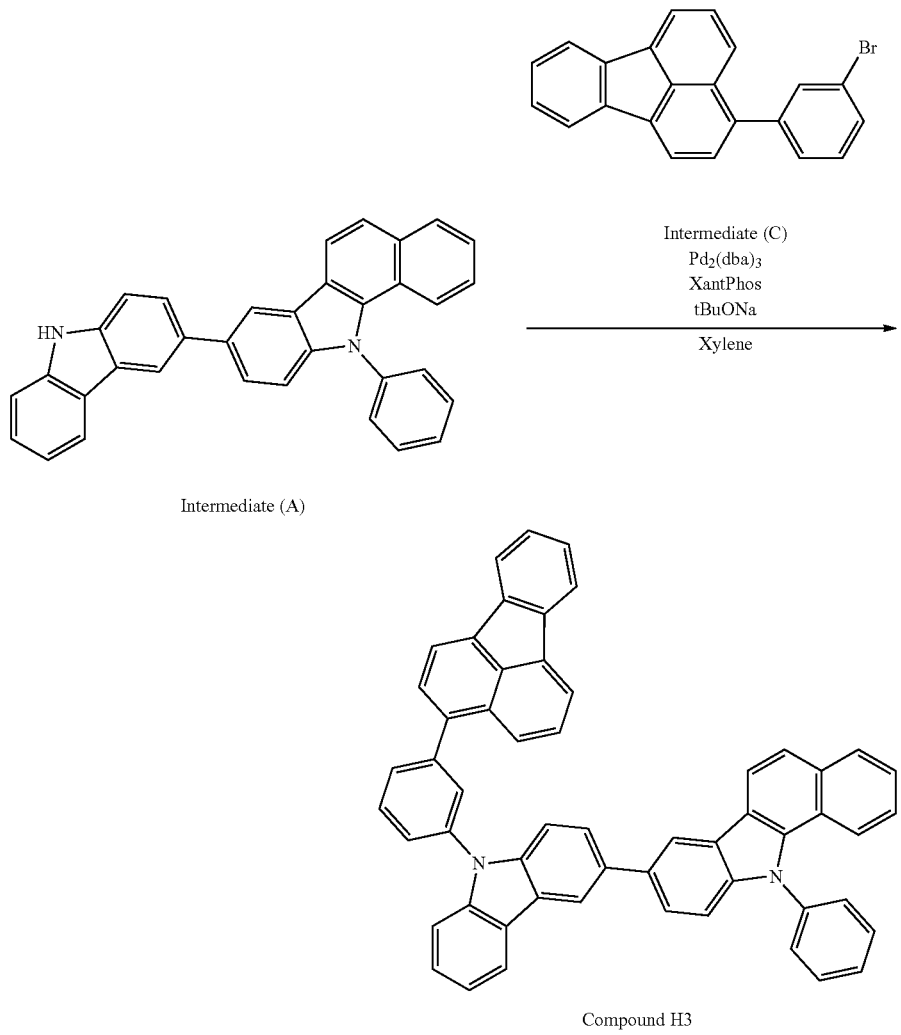
Compound H3

The compound H3 was synthesized in the same manner as in Synthesis Example 1 except for using the intermediate (C) in place of 3-bromofluoranthene. The result of mass spectrographic analysis was m/e=685 to the molecular weight of 685 of the compound H3.

Synthesis Example 4: Synthesis of Compound H4

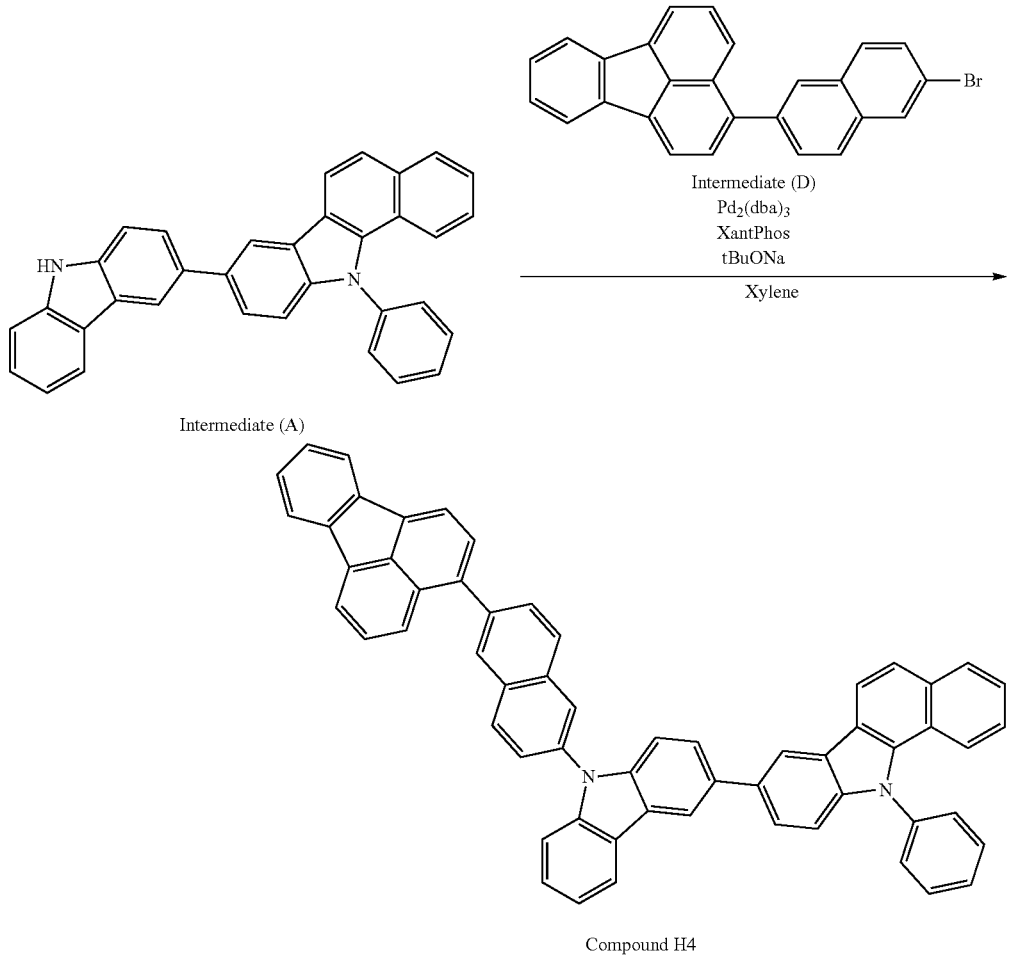

The compound H4 was synthesized in the same manner as in Synthesis Example 1 except for using the intermediate (D) in place of 3-bromofluoranthene. The result of mass spectrographic analysis was m/e=784 to the molecular weight of 784 of the compound H4.

Synthesis Example 5: Synthesis of Compound H5

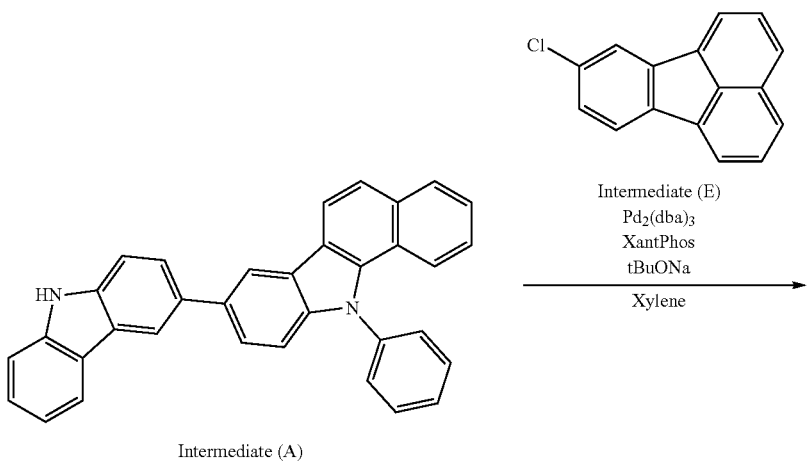

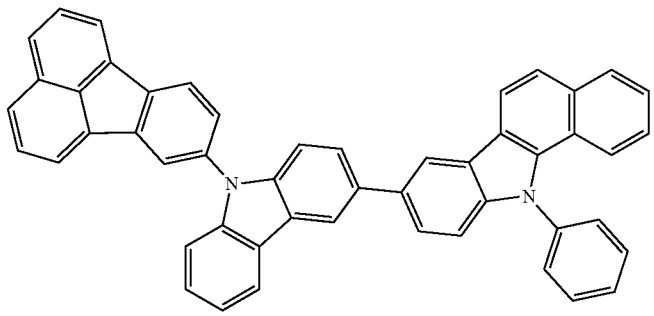
Compound H5
The compound H5 was synthesized in the same manner as in Synthesis Example 1 except for using the intermediate (E) in place of 3-bromofluoranthene. The result of mass spectrographic analysis was m/e=658 to the molecular weight of 658 of the compound H5.
Synthesis Example 6: Synthesis of Compound H6
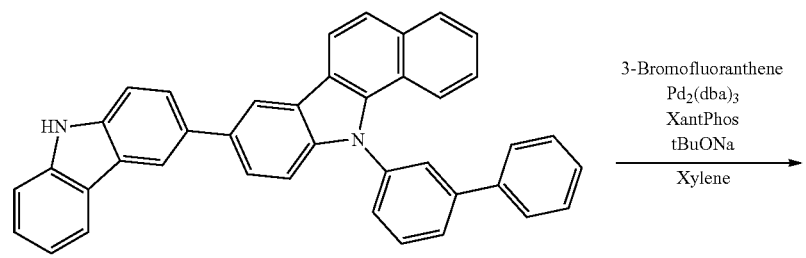
Intermediate (G)
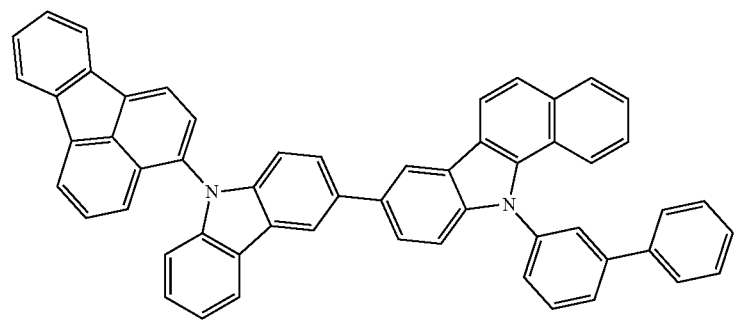
Compound H6

The compound H6 was synthesized in the same manner as in Synthesis Example 1 except for using the intermediate (G) in place of the intermediate (A). The result of mass spectrographic analysis was m/e=734 to the molecular weight of 734 of the compound H6.

Synthesis Example 7: Synthesis of Compound H7

Intermediate (E)

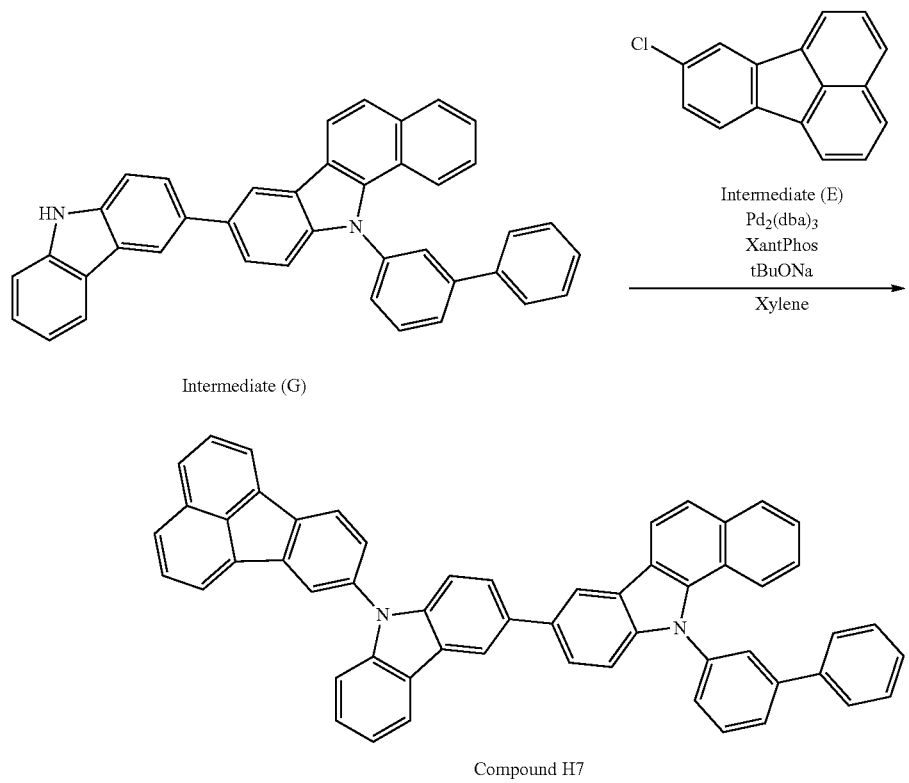

The compound H7 was synthesized in the same manner as in Synthesis Example 5 except for using the intermediate (G) in place of the intermediate (A). The result of mass spectrographic analysis was m/e=734 to the molecular weight of 734 of the compound H7.

Synthesis Example 8: Synthesis of Compound H8

The compound H8 was synthesized in the same manner as in Synthesis Example 1 except for using the intermediate (I) in place of the intermediate (A). The result of mass spectrographic analysis was m/e=708 to the molecular weight of 708 of the compound H8.

Synthesis Example 9: Synthesis of Compound H9

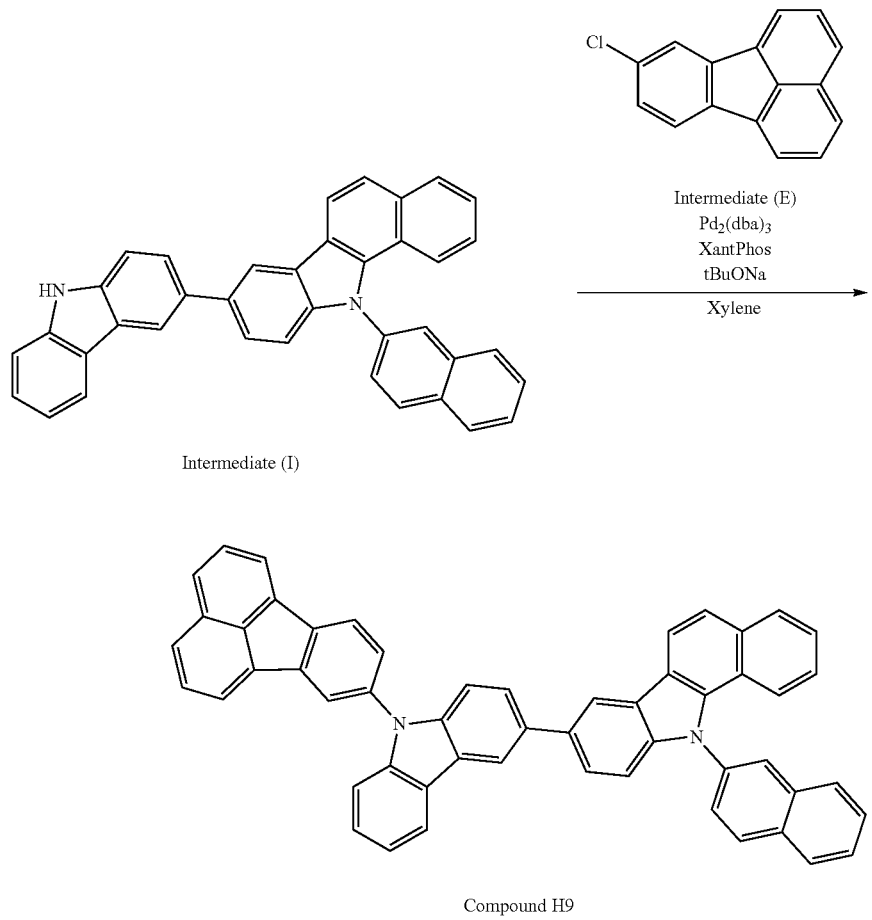

The compound H9 was synthesized in the same manner as in Synthesis Example 5 except for using the intermediate (I) in place of the intermediate (A). The result of mass spectrographic analysis was m/e=708 to the molecular weight of 708 of the compound H9.

Synthesis Example 10: Synthesis of Compound H10

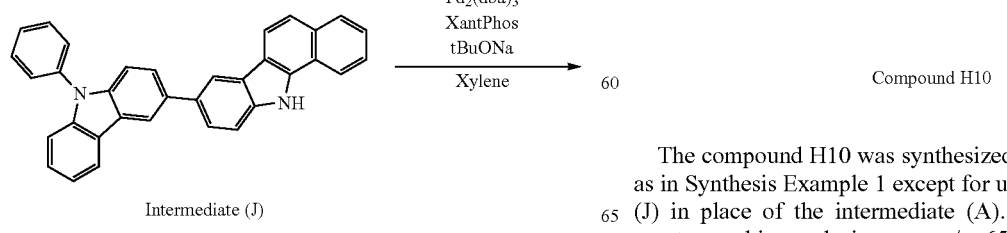

The compound H10 was synthesized in the same manner as in Synthesis Example 1 except for using the intermediate (J) in place of the intermediate (A). The result of mass spectrographic analysis was m/e=658 to the molecular weight of 658 of the compound H10.

Synthesis Example 11: Synthesis of Compound H11
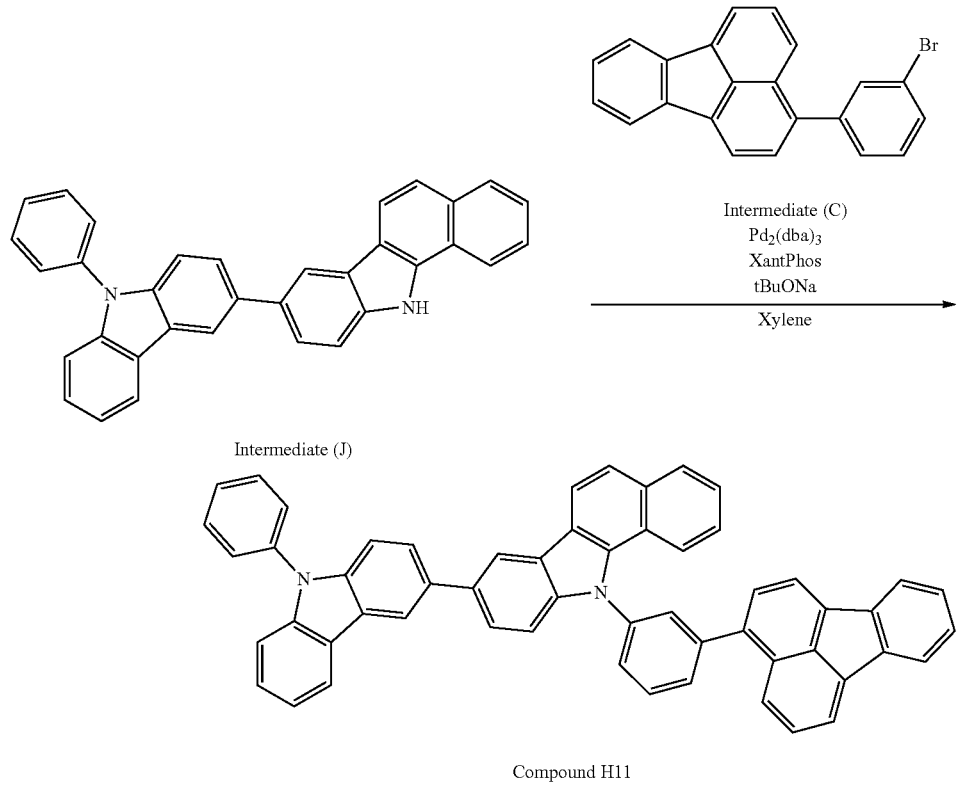
The compound H11 was synthesized in the same manner as in Synthesis Example 3 except for using the intermediate (J) in place of the intermediate (A). The result of mass spectrographic analysis was m/e=734 to the molecular weight of 734 of the compound H11.
Synthesis Example 12: Synthesis of Compound H12
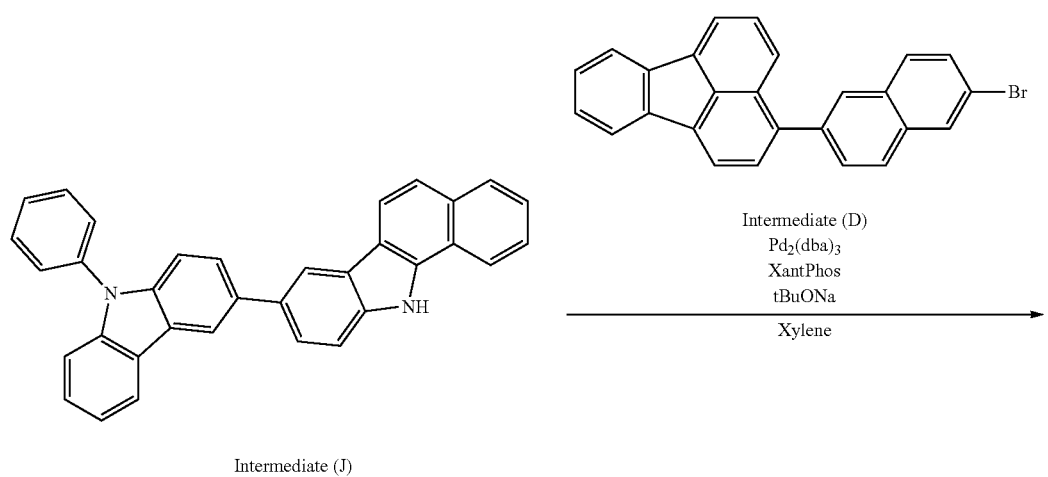

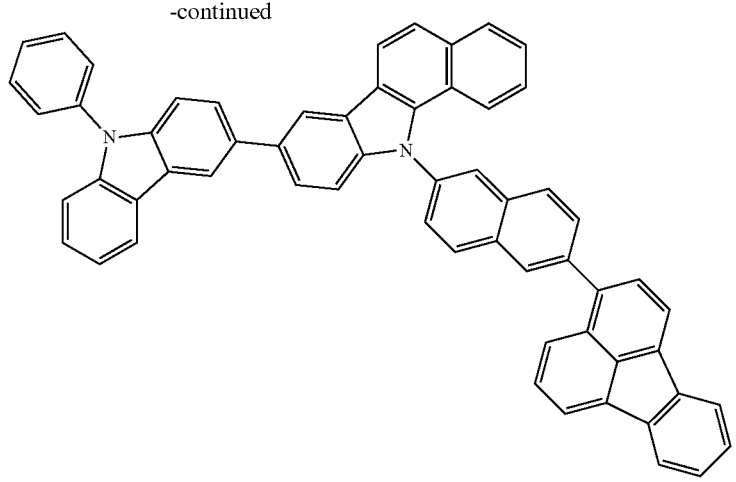
Compound H12
The compound H12 was synthesized in the same manner as in Synthesis Example 4 except for using the intermediate (J) in place of the intermediate (A). The result of mass spectrographic analysis was m/e=784 to the molecular weight of 784 of the compound H12.
Synthesis Example 13: Synthesis of Compound H13
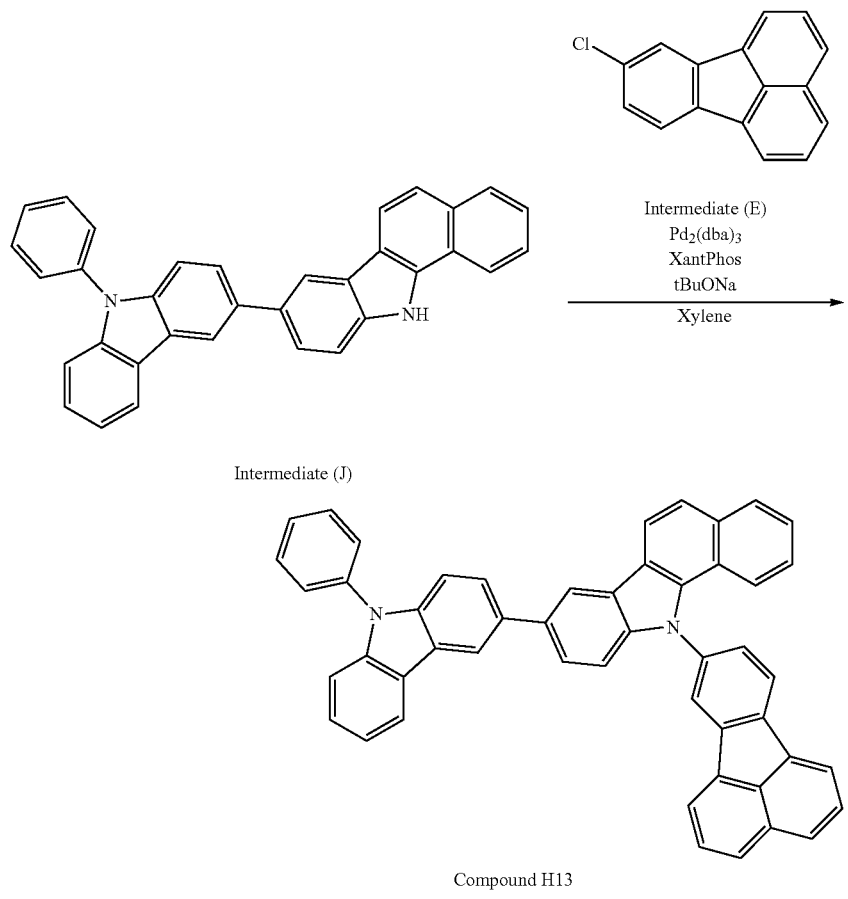
Compound H13

The compound H13 was synthesized in the same manner as in Synthesis Example 5 except for using the intermediate (J) in place of the intermediate (A). The result of mass spectrographic analysis was m/e=658 to the molecular weight of 658 of the compound H13.

Synthesis Example 14: Synthesis of Compound H14

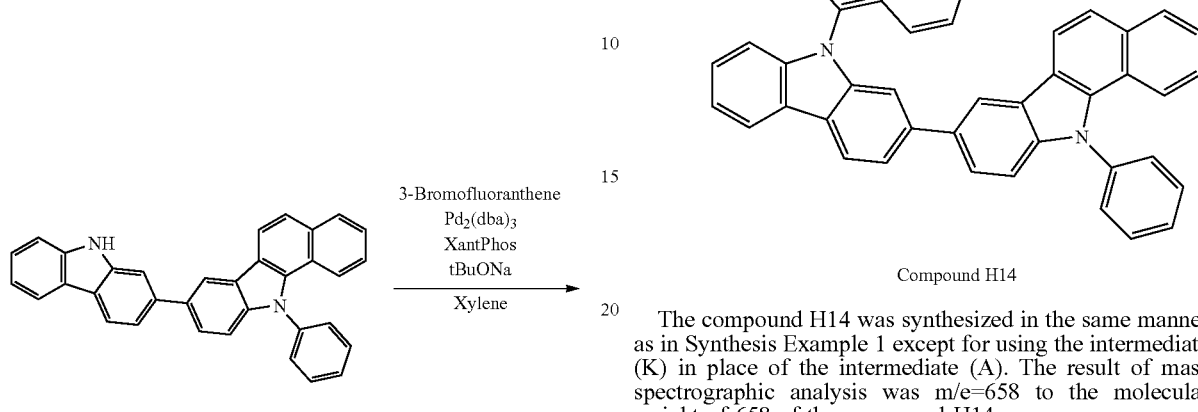

Compound H14

The compound H14 was synthesized in the same manner as in Synthesis Example 1 except for using the intermediate (K) in place of the intermediate (A). The result of mass spectrographic analysis was m/e=658 to the molecular weight of 658 of the compound H14.

Synthesis Example 15: Synthesis of Compound H15

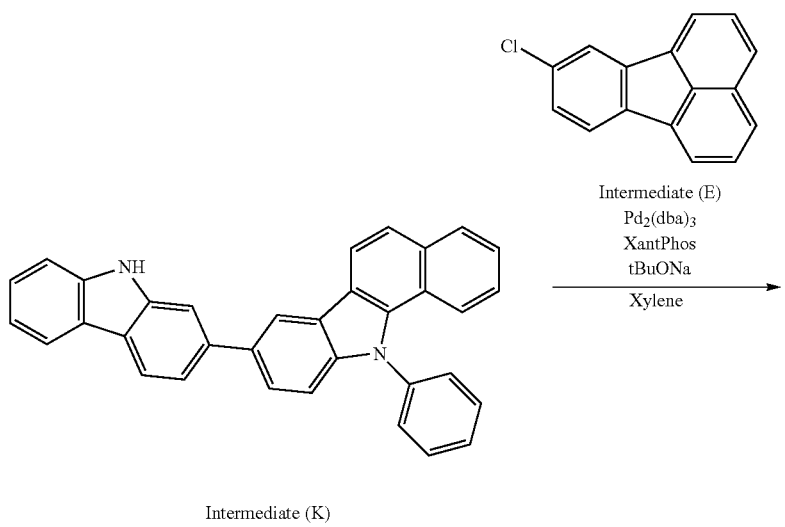

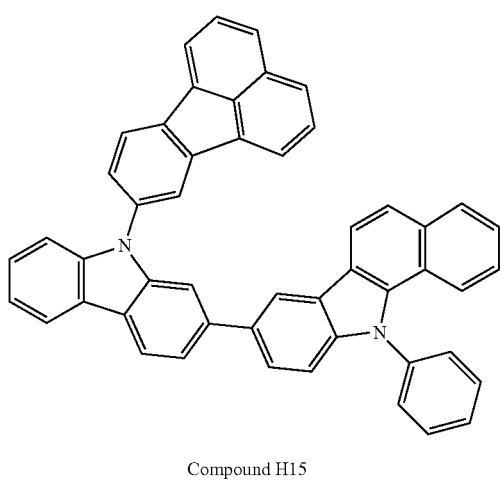

Compound H15

The compound H15 was synthesized in the same manner as in Synthesis Example 5 except for using the intermediate (K) in place of the intermediate (A). The result of mass spectrographic analysis was m/e=658 to the molecular weight of 658 the compound H15.

Example 1

Production of Organic EL Device

A glass substrate of 25 mm×75 mm×1.1 mm having an ITO transparent electrode (product of Geomatec Company) was cleaned by ultrasonic cleaning in isopropyl alcohol for 5 min and then UV/ozone cleaning for 30 min. The thickness of the ITO transparent electrode was 130 nm.

The cleaned glass substrate was mounted to a substrate holder of a vacuum vapor deposition apparatus. First, the following compound HAT was vapor-deposited so as to cover the transparent electrode line to form an acceptor layer with a thickness of 5 nm.

On the acceptor layer, the following compound HT1 was vapor-deposited to form a first hole transporting layer with a thickness of 100 nm. Successively, the following compound HT2 was vapor-deposited to form a second hole transporting layer with a thickness of 65 nm.

On the second hole transporting layer, the compound H1 obtained in Synthesis Example 1 (host material) and Ir(piq)$_3$ (dopant material) were vapor co-deposited to form a co-deposited film with a thickness of 40 nm. The concentration of Ir(piq)$_3$ was 2% by mass. The co-deposited film works as a light emitting layer.

On the light emitting layer, the following compound ET was vapor-deposited to form an electron transporting layer with a thickness of 30 nm.

Then, on the electron transporting layer, LiF was vapor-deposited in a film-forming speed of 0.1 Å/min to form an electron injecting cathode with a thickness of 1 nm.

Further, on the LiF film, metallic Al was deposited into a thickness of 80 nm to form a metallic Al cathode, thereby producing an organic EL device.

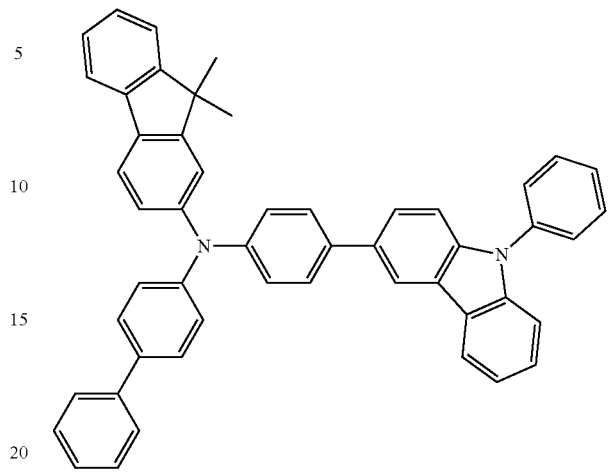
HT1

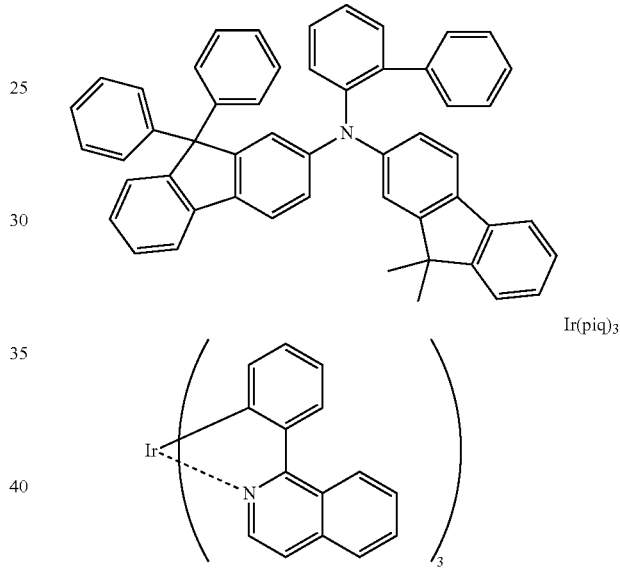
HT2

Ir(piq)$_3$

ET

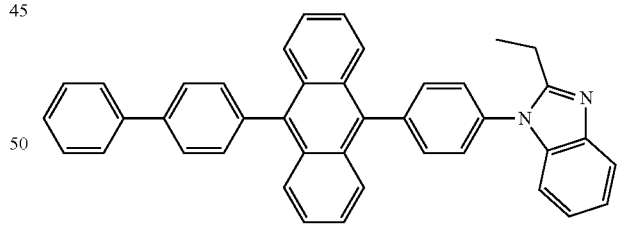

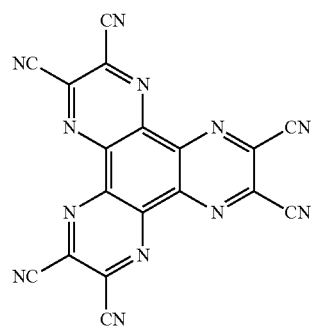
HAT

Evaluation of Organic EL Device

The organic EL device thus produced was driven at a constant direct current to measure the driving voltage at a current density of 10 mA/cm² by using a luminance meter. From the measured results, the external quantum efficiency EQE (%) was determined.

Separately, the organic EL device thus obtained was driven at a constant direct current at a current density of 10 mA/cm² to measure the time taken until the luminance was reduced to 97% of the initial luminance (LT97).

The results are shown in Table 1.

Comparative Example 1

An organic EL device was produced in the same manner as in Example 1 except for using the following comparative compound 1 as the host material. The obtained organic EL device was evaluated in the same manner as in Example 1. The results are shown in Table 1.

Compound H1

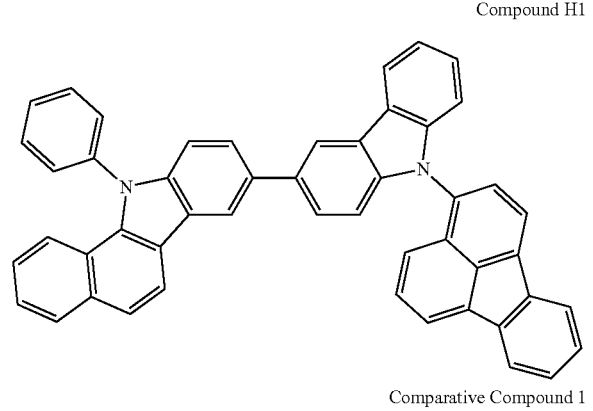

Comparative Compound 1

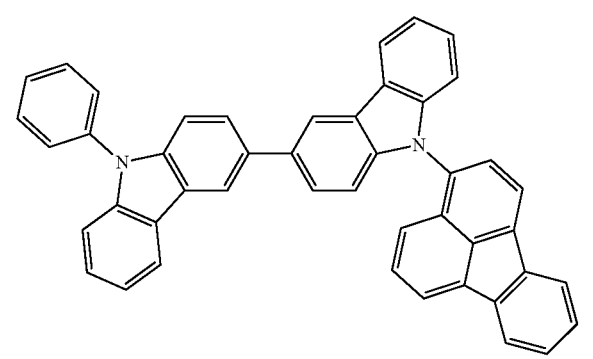

TABLE 1

| Host material | Driving voltage (V) | External quantum efficiency (%) | LT97 (h) |
|---|---|---|---|
| Example 1 | compound H1 | 3.70 | 15.2 | 1790 |
| Comparative Example 1 | comparative compound 1 | 3.68 | 14.8 | 1087 |

The compound H1 of the invention is structurally different from the comparative compound 1 in that one of the carbazole structures of the comparative compound 1 is changed to a 1,2-benzocarbazole (benzo[a]carbazole) structure. As seen from Table 1, as compared with the organic EL device comprising the comparative compound 1, the lifetime of the organic EL device comprising the compound H1 is improved without deteriorating other EL performances.

Example 1

Production of Organic EL Device

A glass substrate of 25 mm×75 mm×1.1 mm having an ITO transparent electrode (product of Geomatec Company) was cleaned by ultrasonic cleaning in isopropyl alcohol for 5 min and then UV/ozone cleaning for 30 min. The thickness of the ITO transparent electrode was 130 nm.

The cleaned glass substrate was mounted to a substrate holder of a vacuum vapor deposition apparatus. First, the following compound H1 was vapor-deposited so as to cover the transparent electrode line to form a hole injecting layer with a thickness of 5 nm. Successively, the following compound HT was vapor-deposited to form a hole transporting layer with a thickness of 210 nm.

On the hole transporting layer, the compound H1 obtained in Synthesis Example 1 (host material) and the following compound PRD-1 (dopant material) were vapor co-deposited to form a co-deposited film with a thickness of 40 nm. The concentration of PRD-1 was 2% by mass. The co-deposited film works as a light emitting layer.

On the light emitting layer, the following compound ET-1 and the following compound Liq were vapor co-deposited to form an electron transporting layer with a thickness of 30 nm. The concentration of Liq in the electron transporting layer was 50% by mass.

Then, on the electron transporting layer, the compound Liq (electron injecting material) was vapor-deposited in a film-forming speed of 0.1 Å/min to form an electron injecting layer with a thickness of 1 nm.

Further, on the electron injecting layer, metallic Al was deposited into a thickness of 80 nm to form a metallic Al cathode, thereby producing an organic EL device.

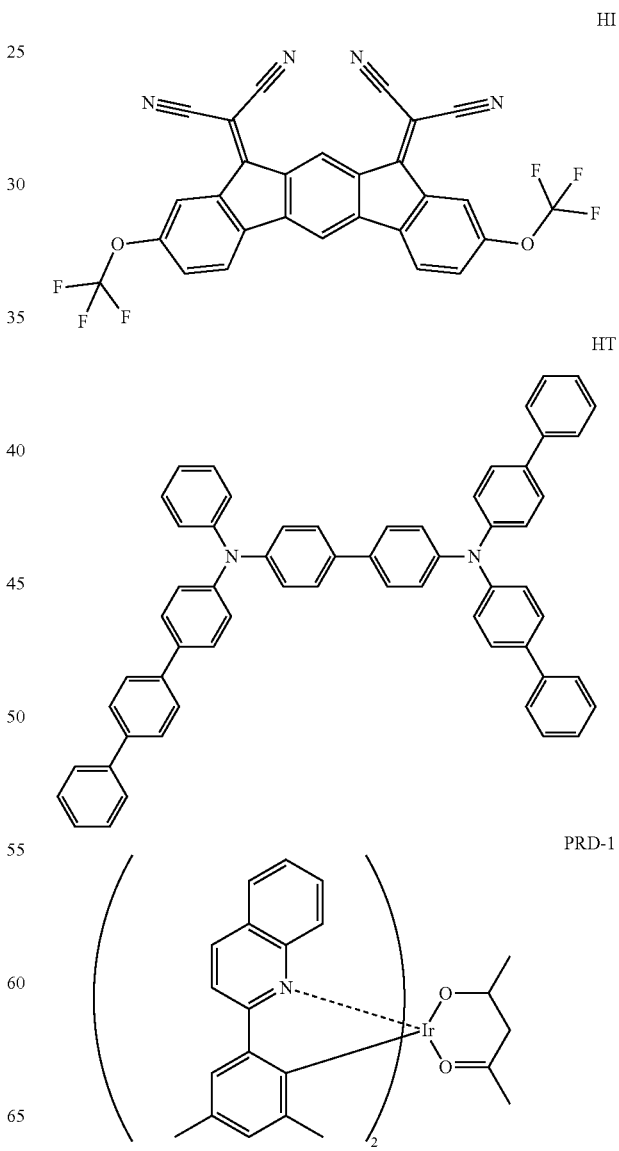

ET-1

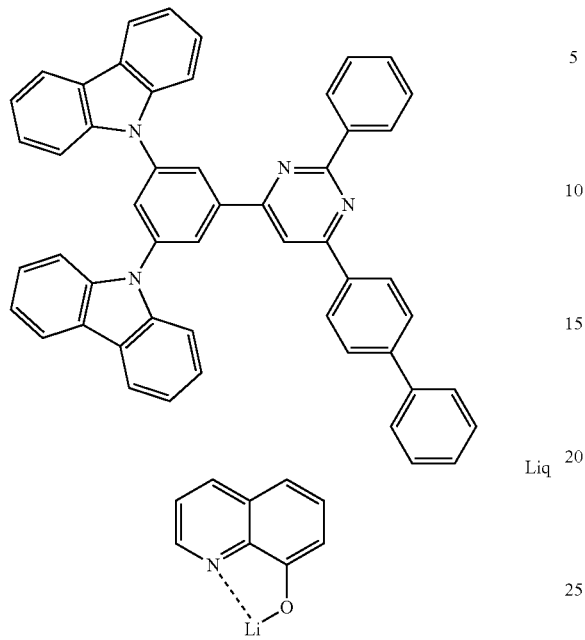

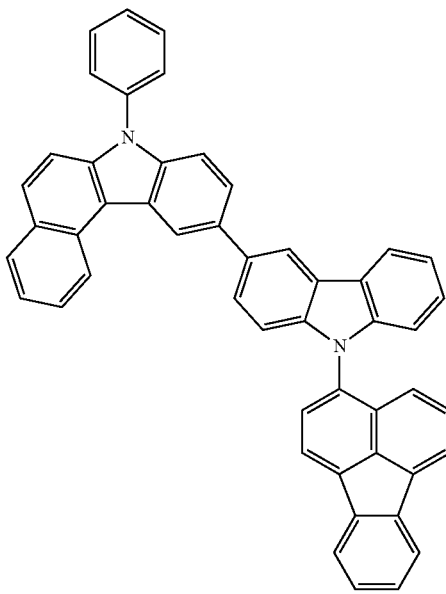

Comparative Compound 2

Liq

Evaluation of Organic EL Device

The organic EL device thus obtained was driven at a constant direct current at a current density of 10 mA/cm² to measure the time taken until the luminance was reduced to 80% of the initial luminance (LT80).

The results are shown in Table 2.

Comparative Example 2 to 5

Each organic EL device was produced in the same manner as in Example 2 except for using each of the following comparative compounds 2 to 5. The obtained organic EL devices were evaluated in the same manner as in Example 2. The results are shown in Table 2.

Compound H1

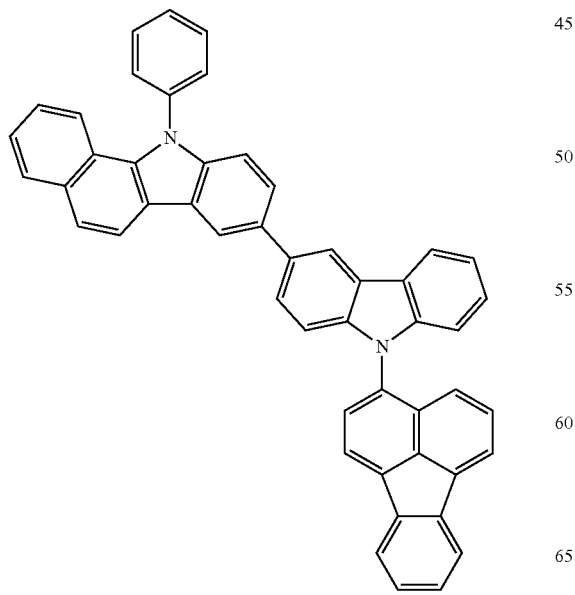

Comparative Compound 3

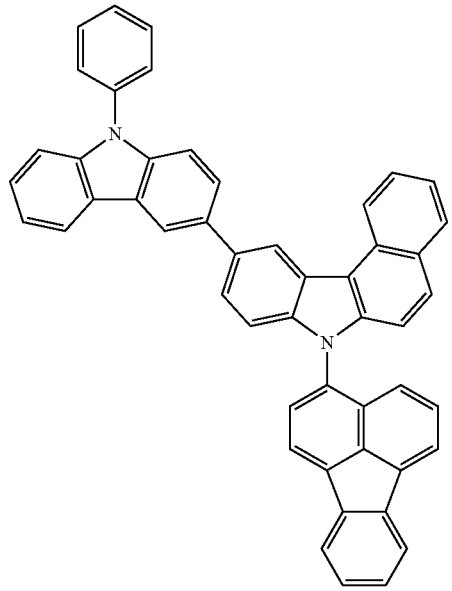

Comparative Compound 4

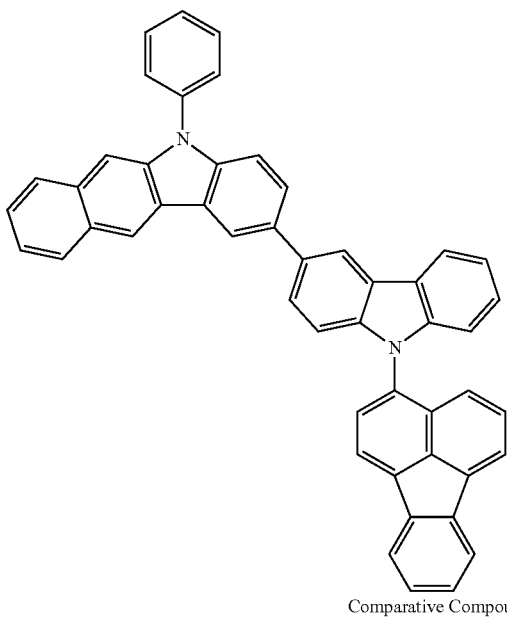

Comparative Compound 5

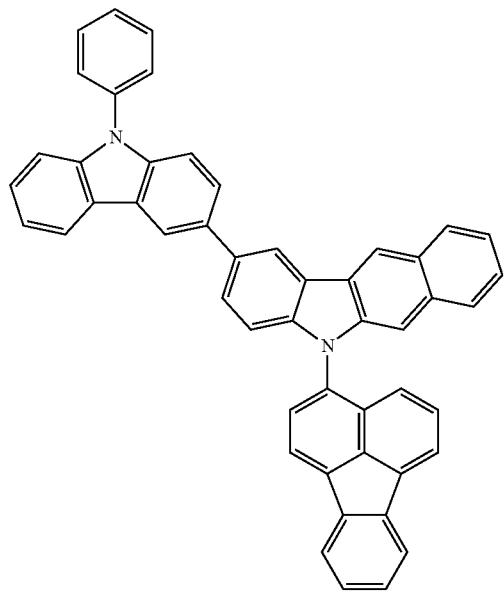

TABLE 2

| | Host material | LT80 (h) |
|---|---|---|
| Example 2 | compound H1 | 534 |
| Comparative Example 2 | comparative compound 2 | 411 |
| Comparative Example 3 | comparative compound 3 | 378 |
| Comparative Example 4 | comparative compound 4 | 360 |
| Comparative Example 5 | comparative compound 5 | 304 |

Table 2 shows the dependency of the lifetime of EL device on the fused position of the benzene ring on the carbazole structure. It can be seen that the lifetime is drastically improved by the benzo[a]carbazole structure of the compound H1 as compared with the benzo[b]carbazole structure (comparative compounds 4 and 5) and the benzo[c]carbazole structure (comparative compounds 2 and 3).

REFERENCE SIGNS LIST

1: Organic EL device
2: Substrate
3: Anode
4: Cathode
5: Light emitting layer
6: Anode-side organic thin film layer
7: Cathode-side organic thin film layer
10: Emission unit

The invention claimed is:
1. A compound represented by formula (1):

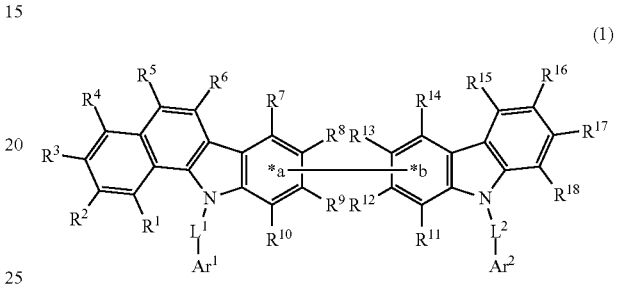

wherein:
each of $R^1$ to $R^6$ is independently a hydrogen atom, a substituted or unsubstituted alkyl group having 1 to 20 carbon atoms, a substituted or unsubstituted cycloalkyl group having 3 to 10 ring carbon atoms, a substituted or unsubstituted aryl group having 6 to 18 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 18 ring carbon atoms, a halogen atom, or a cyano group;
one of $R^7$ to $R^{10}$ is a single bond bonded to *a, and each of the others of $R^7$ to is independently a hydrogen atom, a substituted or unsubstituted alkyl group having 1 to 20 carbon atoms, a substituted or unsubstituted cycloalkyl group having 3 to 10 ring carbon atoms, a substituted or unsubstituted aryl group having 6 to 18 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 18 ring carbon atoms, a halogen atom, or a cyano group;
one of $R^{11}$ to $R^{14}$ is a single bond bonded to *b, and each of the others of $R^{11}$ to $R^{14}$ is independently a hydrogen atom, a substituted or unsubstituted alkyl group having 1 to 20 carbon atoms, a substituted or unsubstituted cycloalkyl group having 3 to 10 ring carbon atoms, a substituted or unsubstituted aryl group having 6 to 18 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 18 ring carbon atoms, a halogen atom, or a cyano group;
each of $R^{15}$ to $R^{18}$ is independently a hydrogen atom, a substituted or unsubstituted alkyl group having 1 to 20 carbon atoms, a substituted or unsubstituted cycloalkyl group having 3 to 10 ring carbon atoms, a substituted or unsubstituted aryl group having 6 to 18 ring carbon atoms, a substituted or unsubstituted haloalkyl group having 1 to 20 carbon atoms, a substituted or unsubstituted alkoxy group having 1 to 20 carbon atoms, a substituted or unsubstituted haloalkoxy group having 1 to 20 carbon atoms, a substituted or unsubstituted aryloxy group having 6 to 18 ring carbon atoms, a halogen atom, or a cyano group;

with the proviso that each of adjacent two groups selected from $R^1$ to $R^6$, adjacent two groups selected from $R^7$ to $R^{10}$, adjacent two groups selected from $R^{11}$ to $R^{14}$, and adjacent two groups selected from $R^{15}$ to $R^{18}$ may be respectively bonded to each other to form a substituted or unsubstituted ring;

each of $L^1$ and $L^2$ is independently a single bond, a substituted or unsubstituted arylene group having 6 to 18 ring carbon atoms, or a substituted or unsubstituted heteroarylene group having 5 to 18 ring atoms; and each of $Ar^1$ and $Ar^2$ is independently a substituted or unsubstituted aryl group having 6 to 18 ring carbon atoms;

provided that at least one selected from $Ar^1$ and $Ar^2$ is a substituted or unsubstituted fluoranthenyl group.

2. The compound according to claim 1, wherein the compound is represented by formula (2):

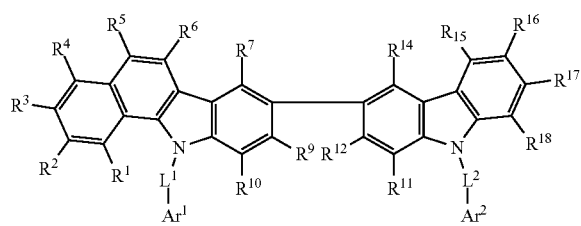

(2)

wherein $R^1$ to $R^7$, $R^9$ to $R^{12}$, $R^{14}$ to $R^{18}$, $L^1$, $L^2$, $Ar^1$ and $Ar^2$ are the same as defined above.

3. The compound according to claim 1, wherein the compound is represented by formula (3):

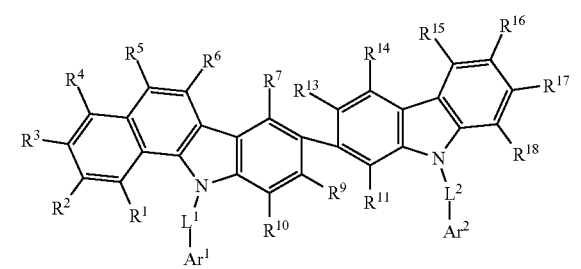

(3)

wherein $R^1$ to $R^7$, $R^9$ to $R^{11}$, $R^{13}$ to $R^{18}$, $L^1$, $L^2$, $Ar^1$, and $Ar^2$ are the same as defined above.

4. The compound according to claim 1, wherein the compound is represented by formula (4):

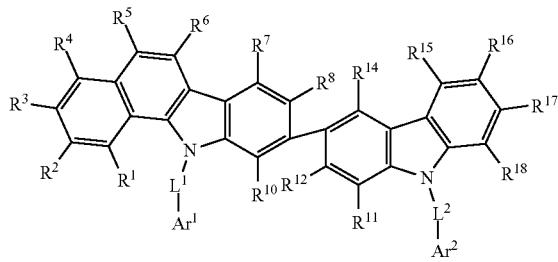

(4)

wherein $R^1$ to $R^8$, $R^{10}$ to $R^{12}$, $R^{14}$ to $R^{18}$, $L^1$, $L^2$, $Ar^1$, and $Ar^2$ are the same as defined above.

5. The compound according to claim 1, wherein the compound is represented by formula (5):

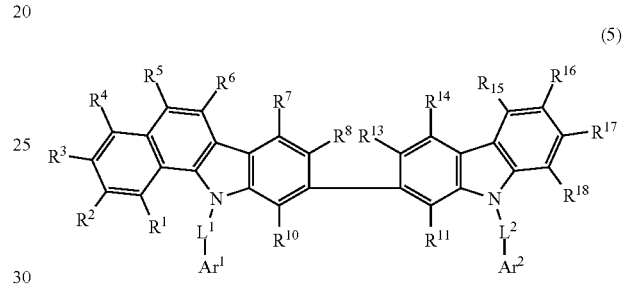

(5)

wherein $R^1$ to $R^8$, $R^{10}$, $R^{11}$, $R^{13}$ to $R^{18}$, $L^1$, $L^2$, $Ar^1$, and $Ar^2$ are the same as defined above.

6. The compound according to claim 1, wherein:
the an alkyl group having 1 to 20 carbon atoms in the substituted or unsubstituted alkyl group having 1 to 20 carbon atoms for $R^1$ to $R^{18}$ is selected from the group consisting of a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups);
the cycloalkyl group having 3 to 10 ring carbon atoms in the substituted or unsubstituted cycloalkyl group having 3 to 10 ring carbon atoms for $R^1$ to $R^{18}$ is selected from the group consisting of a cyclopropyl group, a cyclobutyl group, a cyclopentyl group, a cyclohexyl group, and a cycloheptyl group;
the aryl group having 6 to 18 ring carbon atoms in the substituted or unsubstituted aryl group having 6 to 18 ring carbon atoms for $R^1$ to $R^{18}$ is selected from the group consisting of a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a triphenylenyl group, a phenalenyl group, a fluorenyl group, a pyrenyl group, a chrysenyl group, a s-indanyl group, an as-indanyl group, and a fluoranthenyl group;
the haloalkyl group having 1 to 20 carbon atoms in the substituted or unsubstituted haloalkyl group having 1 to 20 carbon atoms for $R^1$ to $R^{18}$ is selected from the group consisting of a heptafluoropropyl group (inclusive of isomeric groups), a pentafluoroethyl group, a 2,2,2-trifluoroethyl group, and a trifluoromethyl group;

the alkoxy group having 1 to 20 carbon atoms in the substituted or unsubstituted alkoxy group having 1 to 20 carbon atoms for $R^1$ to $R^{18}$ is selected from the group consisting of a t-butoxy group, a propoxy group (inclusive of isomeric groups), an ethoxy group, and a methoxy group;

the haloalkoxy group having 1 to 20 carbon atoms in the substituted or unsubstituted haloalkoxy group having 1 to 20 carbon atoms for $R^1$ to $R^{18}$ is selected from the group consisting of a heptafluoropropoxy group (inclusive of isomeric groups), a pentafluoroethoxy group, a 2,2,2-trifluoroethoxy group, and a trifluoromethoxy group;

the aryloxy group having 6 to 18 ring carbon atoms in the substituted or unsubstituted aryloxy group having 6 to 18 ring carbon atoms for $R^1$ to $R^{18}$ comprises an aryl group selected from the group consisting of a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a triphenylenyl group, a phenalenyl group, a fluorenyl group, a pyrenyl group, a chrysenyl group, a s-indanyl group, an as-indanyl group, and a fluoranthenyl group;

the halogen atom for $R^1$ to $R^{18}$ is selected from the group consisting of a fluorine atom, a chlorine atom, a bromine atom, and an iodine atom;

the arylene group having 6 to 18 ring carbon atoms in the substituted or unsubstituted arylene group having 6 to 18 ring carbon atoms for $L^1$ and $L^2$ is a group obtained by removing one hydrogen atom from an aryl group selected from the group consisting of a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a triphenylenyl group, a phenalenyl group, a fluorenyl group, a pyrenyl group, a chrysenyl group, a s-indanyl group, an as-indanyl group, and a fluoranthenyl group;

the heteroarylene group having 5 to 18 ring atoms in the substituted or unsubstituted heteroarylene group having 5 to 18 ring atoms for $L^1$ and $L^2$ is a group obtained by removing one hydrogen atom from a heteroaryl group selected from the group consisting of a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazoly group, a benzisothiazolyl group, a dibenzofuranyl group, a naphthobenzofuranyl group, a dibenzotiophenyl group, a naphthobenzotiophenyl group, a carbazolyl group, a benzocarbazolyl group, a phenanthridinyl group, an acridinyl group, a phenanthrolinyl group, a phenazinyl group, a phenothiazinyl group, a phenoxazinyl group, and a xanthenyl group; and the aryl group having 6 to 18 ring carbon atoms in the substituted or unsubstituted aryl group having 6 to 18 ring carbon atoms for $Ar^1$ and $Ar^2$ is selected from the group consisting of a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a triphenylenyl group, a phenalenyl group, a fluorenyl group, a pyrenyl group, a chrysenyl group, a s-indanyl group, an as-indanyl group, and a fluoranthenyl group.

7. The compound according to claim 1, wherein adjacent two groups selected from $R^1$ to $R^6$, $R^7$ to $R^{10}$, $R^{11}$ to $R^{14}$, and $R^{15}$ to $R^{18}$ do not form a ring.

8. The compound according to claim 1, wherein $R^1$ to $R^6$, $R^7$ to $R^{10}$ which is not a single bond bonded to *a, $R^{11}$ to $R^{14}$ which is not a single bond bonded to *b, and $R^{15}$ to $R^{18}$ are all hydrogen atoms.

9. The compound according to claim 1, wherein $L^1$ is a single bond and $L^2$ is a substituted or unsubstituted arylene group having 6 to 18 ring carbon atoms or a substituted or unsubstituted heteroarylene group having 5 to 18 ring atoms.

10. The compound according to claim 1, wherein $L^2$ is a single bond and $L^1$ is a substituted or unsubstituted arylene group having 6 to 18 ring carbon atoms or a substituted or unsubstituted heteroarylene group having 5 to 18 ring atoms.

11. The compound according to claim 1, wherein each of $L^1$ and $L^2$ is independently a substituted or unsubstituted arylene group having 6 to 18 ring carbon atoms or a substituted or unsubstituted heteroarylene group having 5 to 18 ring atoms.

12. The compound according to claim 9, wherein the arylene group in the substituted or unsubstituted arylene group having 6 to 18 ring carbon atoms is selected from the group consisting of a phenylene group, a naphthylene group, and a biphenylylene group.

13. The compound according to claim 1, wherein each of $L^1$ and $L^2$ is a single bond.

14. The compound according to claim 1, wherein $Ar^1$ is a substituted or unsubstituted aryl group having 6 to 18 ring carbon atoms and $Ar^2$ is a substituted or unsubstituted fluoranthenyl group.

15. The compound according to claim 1, wherein $Ar^2$ is a substituted or unsubstituted aryl group having 6 to 18 ring carbon atoms and $Ar^1$ is a substituted or unsubstituted fluoranthenyl group.

16. The compound according to claim 14, wherein the aryl group having 6 to 18 ring carbon atoms in the substituted or unsubstituted aryl group having 6 to 18 ring carbon atoms is selected from the group consisting of a phenyl group, a naphthyl group, a biphenylyl group, a phenanthryl group, and a triphenylenyl group.

17. The compound according to claim 1, wherein the substituted or unsubstituted fluoranthenyl group is a substituted or unsubstituted 1-fluoranthenyl group, a substituted or unsubstituted 3-fluoranthenyl group, a substituted or unsubstituted 7-fluoranthenyl group, or a substituted or unsubstituted 8-fluoranthenyl group.

18. The compound according to claim 1, wherein when an optional substituent is present, the optional substituent referred to by "substituted or unsubstituted" is at least one group selected from the group consisting of an alkyl group having 1 to 20 carbon atoms, a cycloalkyl group having 3 to 10 ring carbon atoms, an aralkyl group having 7 to 30 carbon atoms comprising an aryl group having 6 to 18 ring carbon atoms, an aryl group having 6 to 18 ring carbon atoms, an alkoxy group having 1 to 20 carbon atoms, an aryloxy group having 6 to 18 ring carbon atoms, a mono-, di-, or tri-substituted silyl group, wherein the substituent is selected from an alkyl group having 1 to 20 carbon atoms and an aryl group having 6 to 18 ring carbon atoms, a haloalkyl group having 1 to 20 carbon atoms, a haloalkoxy group having 1 to 20 carbon atoms, a halogen atom, a cyano group, and a nitro group.

19. A material for organic electroluminescence devices comprising the compound according to claim 1.

20. An organic electroluminescence device comprising a cathode, an anode, and an organic thin film layer between the cathode and the anode, wherein the organic thin film layer comprises one or more layers, the organic thin film layer comprises a light emitting layer, and at least one layer of the organic thin film layer comprises the compound according to claim 1.

21. The organic electroluminescence device according to claim 20, wherein the light emitting layer comprises a host material and the host material is the compound.

22. The organic electroluminescence device according to claim 20, wherein the light emitting layer comprises a dopant material and the dopant material is a phosphorescent emitting material.

23. The organic electroluminescence device according to claim 22, wherein the phosphorescent emitting material is an ortho metallated complex of a metal atom selected from the group consisting of iridium, osmium, ruthenium, and platinum.

24. An electronic device comprising the organic electroluminescence device according to claim 20.

25. The compound according to claim 1, wherein the compound is any one selected from the following compounds:

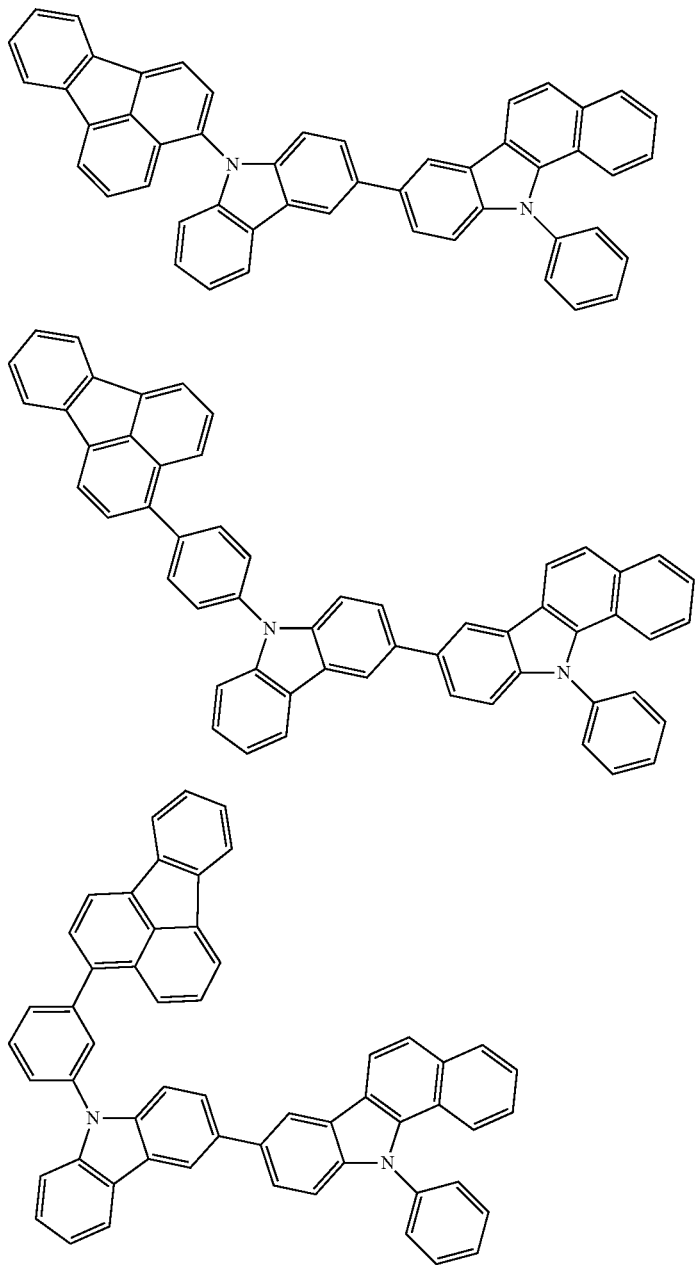

-continued
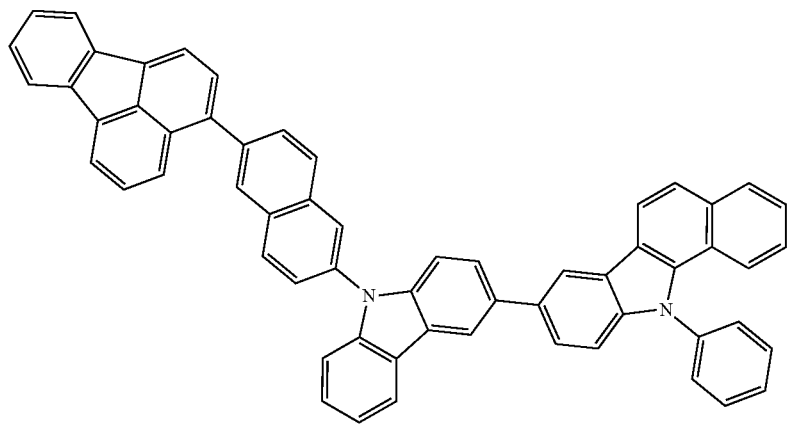
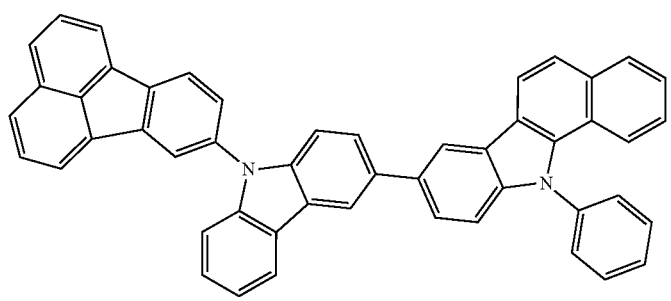
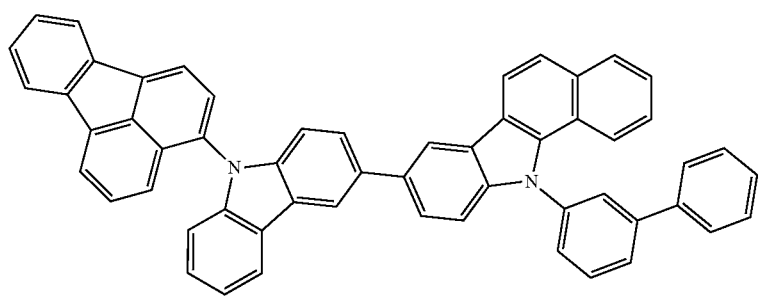
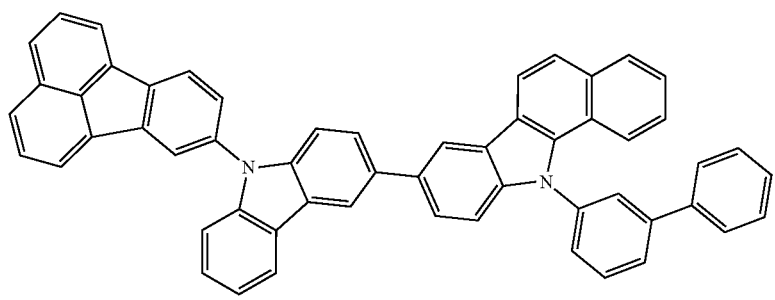
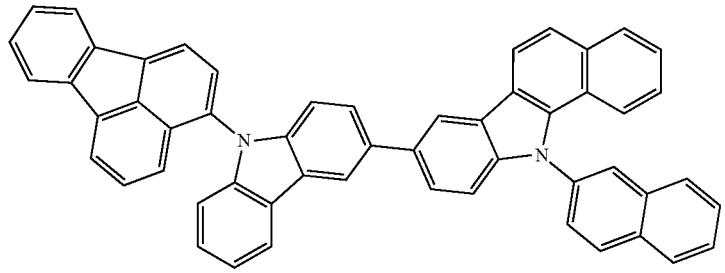

-continued
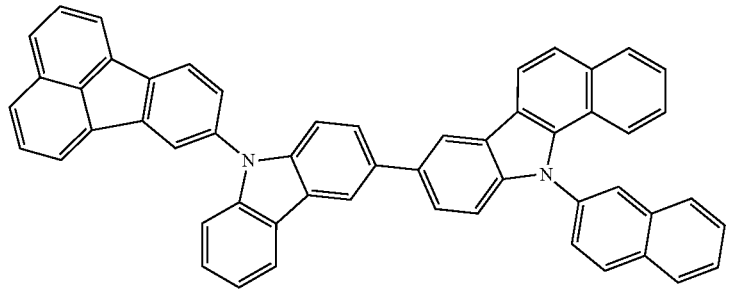
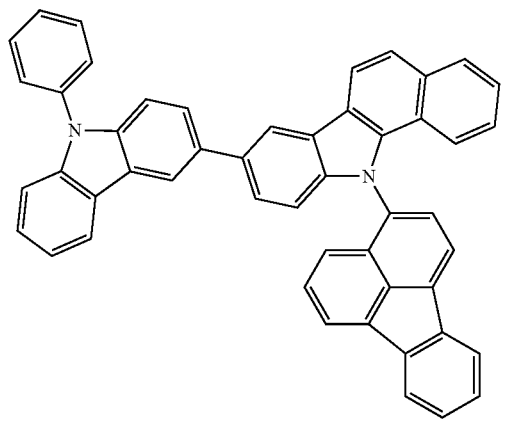
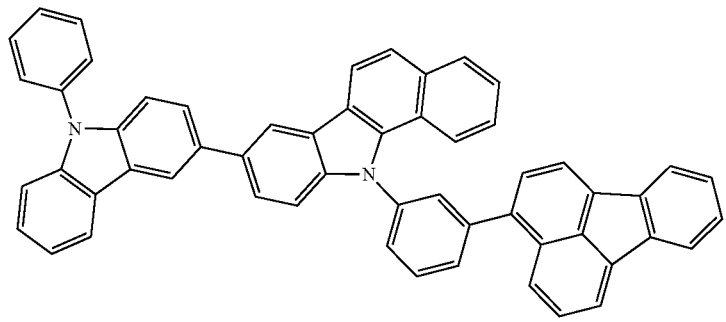
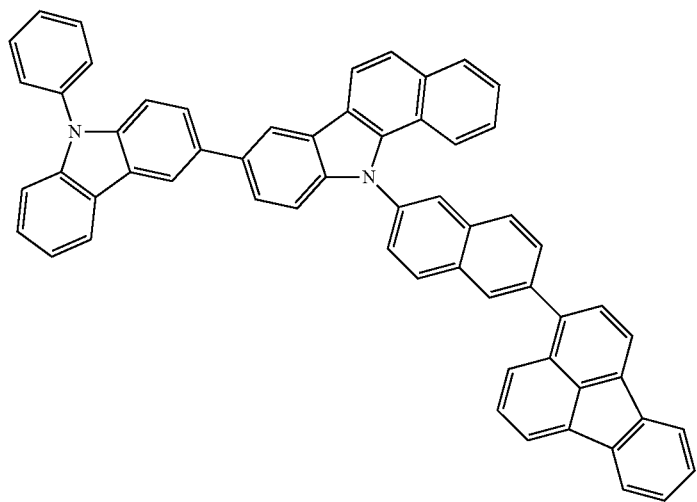

-continued

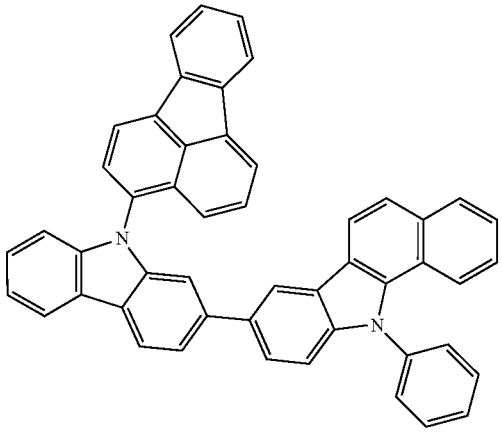

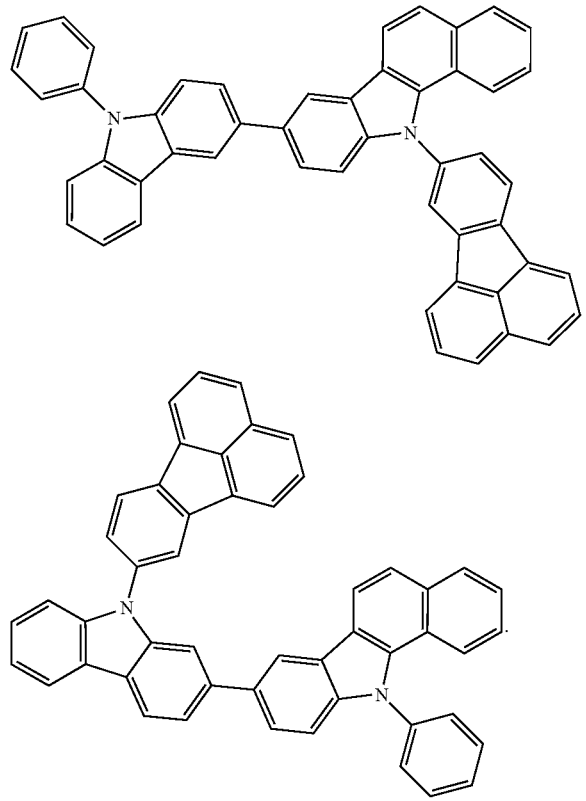

26. An organic electroluminescence device comprising a cathode, an anode, and an organic thin film layer between the cathode and the anode, wherein the organic thin film layer comprises one or more layers, the organic thin film layer comprises a light emitting layer, and at least one layer of the organic thin film layer comprises the compound according to claim 25.

27. The organic electroluminescence device according to claim 26, wherein the light emitting layer comprises a host material and the host material is the compound.

28. An electronic device comprising the organic electroluminescence device according to claim 26.

* * * * *